(12) United States Patent
Field et al.

(10) Patent No.: US 11,553,946 B2
(45) Date of Patent: Jan. 17, 2023

(54) CONVERTIBLE DYNAMIC INTERSPINOUS PROCESS DEVICES AND METHODS FOR SPINAL SURGERY

(71) Applicant: Southern Spine, LLC, Macon, GA (US)

(72) Inventors: David C. Field, Snellville, GA (US); Hugh F. Smisson, III, Macon, GA (US); Donald B. Freeman, Macon, GA (US); Tyler Ovington, Macon, GA (US); Brian Vanhiel, Smyrna, GA (US)

(73) Assignee: Southern Spine, LLC, Macon, GA (US)

( * ) Notice: Subject to any disclaimer, the term of this patent is extended or adjusted under 35 U.S.C. 154(b) by 0 days.

(21) Appl. No.: 16/607,312

(22) PCT Filed: Apr. 24, 2018

(86) PCT No.: PCT/US2018/029204
§ 371 (c)(1),
(2) Date: Oct. 22, 2019

(87) PCT Pub. No.: WO2018/200573
PCT Pub. Date: Nov. 1, 2018

(65) Prior Publication Data
US 2020/0375634 A1    Dec. 3, 2020

Related U.S. Application Data

(60) Provisional application No. 62/488,986, filed on Apr. 24, 2017.

(51) Int. Cl.
*A61B 17/70* (2006.01)
*A61B 17/86* (2006.01)

(52) U.S. Cl.
CPC .......... *A61B 17/7068* (2013.01); *A61B 17/86* (2013.01)

(58) Field of Classification Search
CPC ............. A61B 17/7068; A61B 17/7062; A61F 2/4405; A61F 2/442; A61F 2/4425; A61F 2002/443; A61F 2002/442
(Continued)

(56) References Cited

U.S. PATENT DOCUMENTS 10,022,155 B1 * 7/2018 Crawford ........... A61B 17/7001
2002/0077702 A1   6/2002 Castro
(Continued)

OTHER PUBLICATIONS

PCT International Search Report and Written Opinion for PCT Application No. PCT/US2018/029204 dated Sep. 24, 2018 (14 pages).

*Primary Examiner* — Eduardo C Robert
*Assistant Examiner* — Christina Negrellirodriguez
(74) *Attorney, Agent, or Firm* — Eversheds Sutherland (US) LLP

(57) ABSTRACT

A dynamic interspinous process device for implantation with respect to a first vertebra and an adjacent second vertebra is provided. The dynamic interspinous process device may include a first attachment side and a second attachment side. Each of the first attachment side and second attachment side may include a central portion, a first wing extending from the central portion, a second wing extending from the central portion, and one or more slots extending from an interior side of the respective attachment side to an exterior side of the respective attachment side. The one or more slots of the respective attachment side may be configured to allow the first wing and the second wing to move relative to one another in a direction of a longitudinal axis of the dynamic interspinous process device.

19 Claims, 59 Drawing Sheets

(58) Field of Classification Search
USPC .............. 623/17.11–17.16; 606/246–249
See application file for complete search history.

(56) References Cited

U.S. PATENT DOCUMENTS

| | | | |
|---|---|---|---|
| 2007/0225813 A1* | 9/2007 | Haines ................ | A61F 2/4425 623/17.16 |
| 2008/0281423 A1 | 11/2008 | Sheffer et al. | |
| 2008/0319487 A1* | 12/2008 | Fielding ............ | A61B 17/7053 606/263 |
| 2010/0036419 A1* | 2/2010 | Patel ................ | A61B 17/7068 606/279 |
| 2010/0191287 A1 | 7/2010 | Bucci | |
| 2010/0211102 A1 | 8/2010 | Belliard et al. | |
| 2011/0224731 A1* | 9/2011 | Smisson, III ...... | A61B 17/7067 606/249 |
| 2013/0178903 A1* | 7/2013 | Abdou ................ | A61B 17/70 606/279 |
| 2013/0184753 A1* | 7/2013 | Keiper .............. | A61B 17/7047 606/248 |
| 2013/0296940 A1 | 11/2013 | Northcutt et al. | |
| 2013/0325065 A1* | 12/2013 | Malandain ........ | A61B 17/7062 606/248 |
| 2015/0012040 A1 | 1/2015 | Agarwal et al. | |

\* cited by examiner

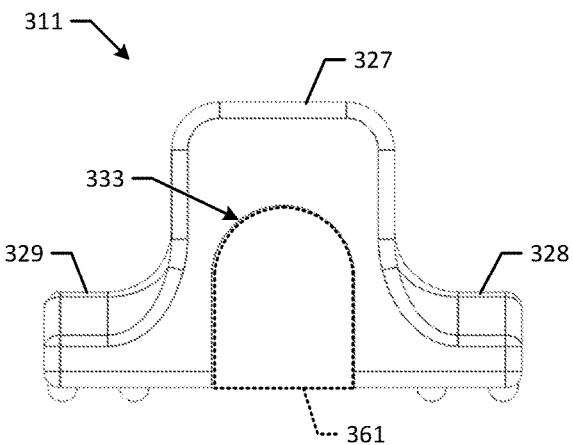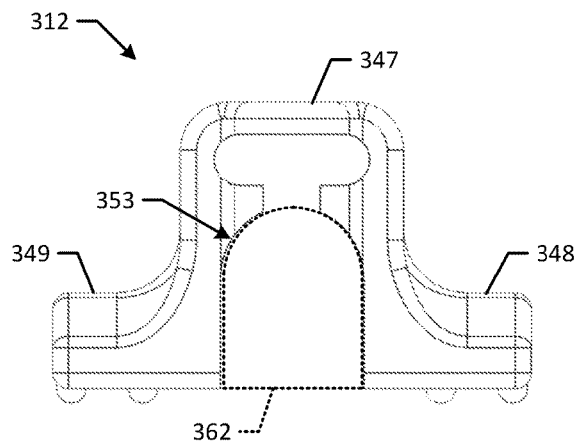
*FIG. 3G*  *FIG. 3H*
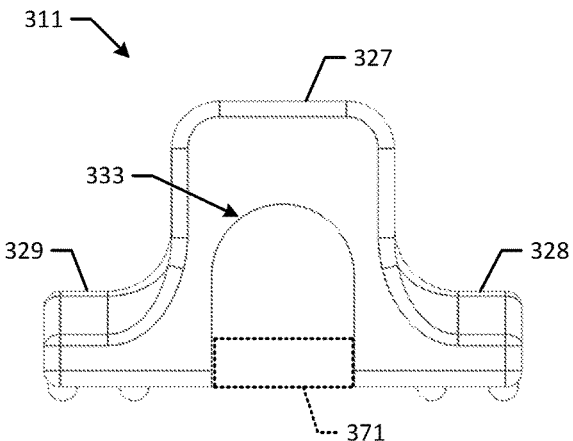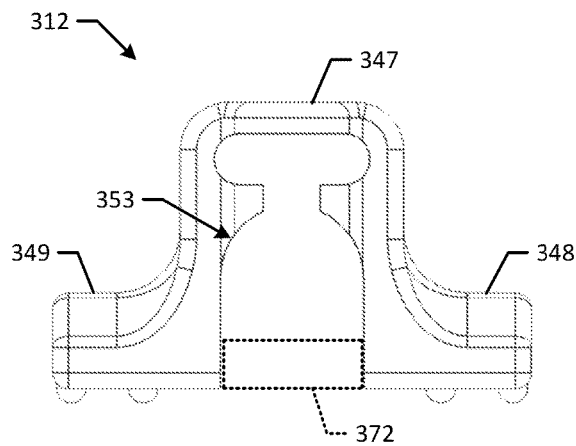
*FIG. 3I*  *FIG. 3J*

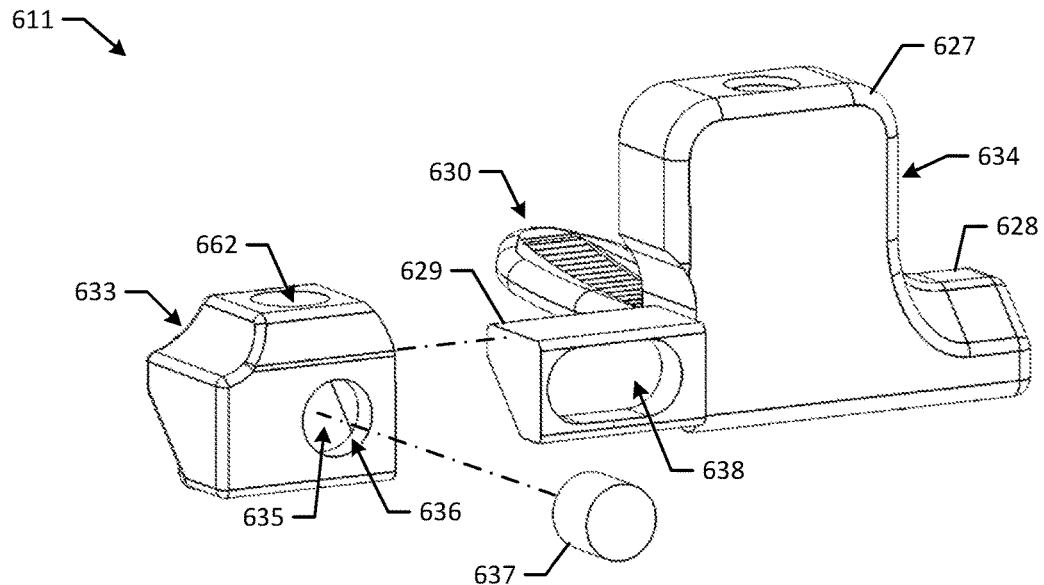
FIG. 6I
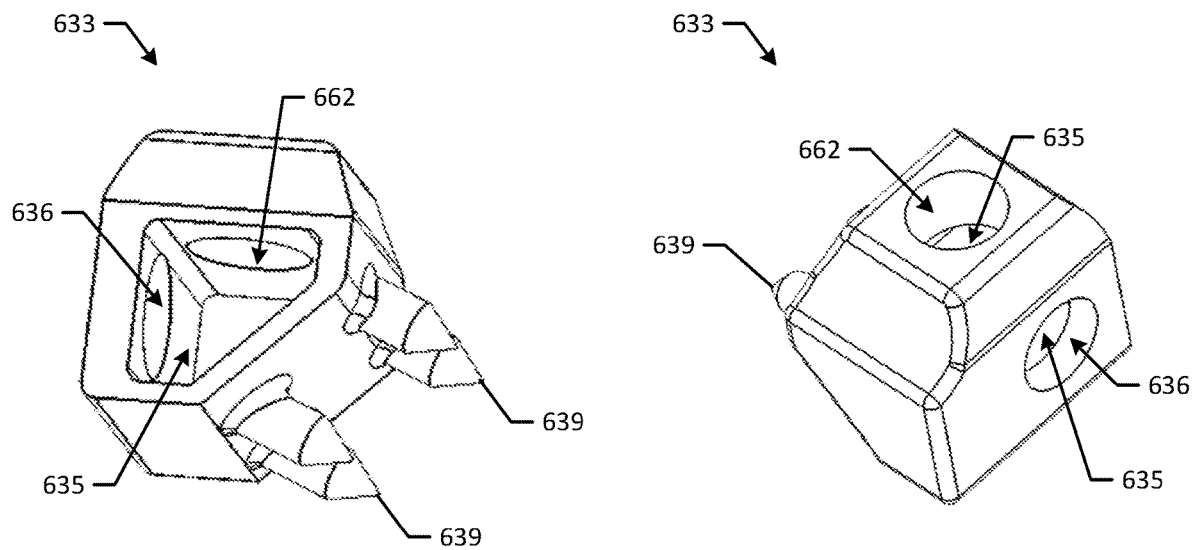
FIG. 6J  FIG. 6K

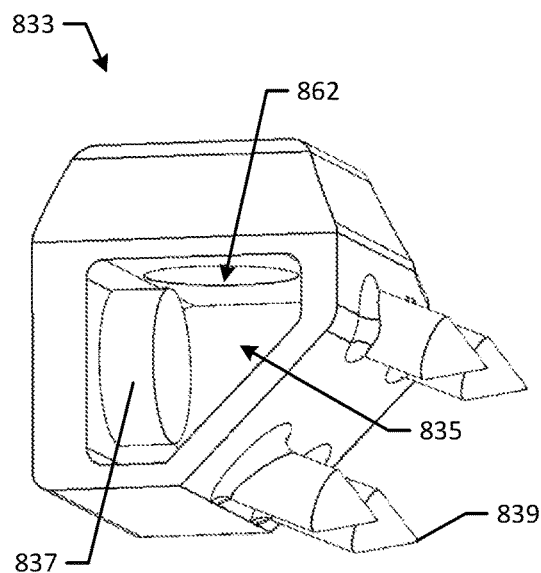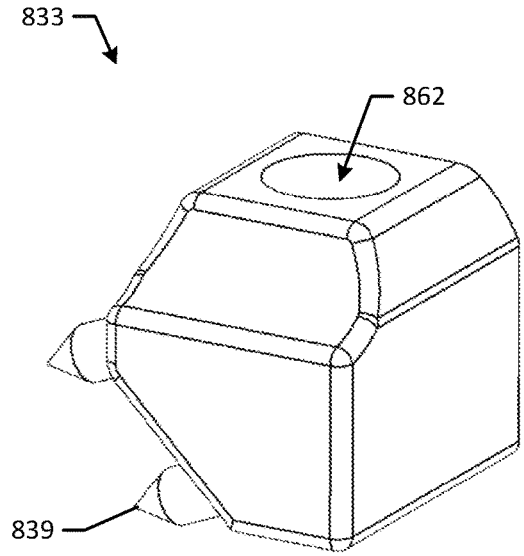
*FIG. 8Q*      *FIG. 8R*
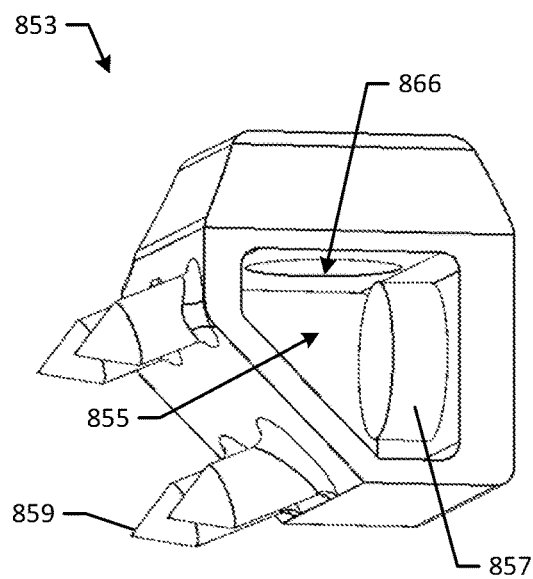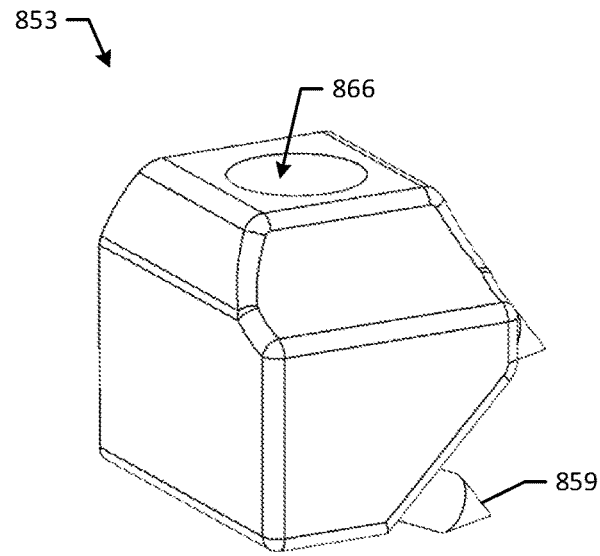
*FIG. 8S*      *FIG. 8T*

CONVERTIBLE DYNAMIC INTERSPINOUS PROCESS DEVICES AND METHODS FOR SPINAL SURGERY

CROSS REFERENCE TO RELATED APPLICATIONS

This application claims the priority benefit of PCT/US2018/029204 filed on Apr. 24, 2018, which claims priority benefit of U.S. Provisional Application No. 62/488,986, filed on Apr. 24, 2017, the entire contents of which are hereby incorporated by reference herein.

FIELD OF THE DISCLOSURE

The present disclosure relates generally to devices and methods for spinal surgery, and more particularly to convertible dynamic interspinous process devices and related methods for using such devices in spinal surgery to selectively allow a degree of relative movement between adjacent vertebrae.

BACKGROUND OF THE DISCLOSURE

Various types of implantable devices for spinal surgery, which generally may be referred to as "spinal devices" or "spinal implants," are commonly used to treat a variety of spinal conditions by stabilizing adjacent vertebrae in an effort to restore and maintain normal spacing and orientation of the treated vertebrae. Certain spinal devices, which may be referred to as "rigid devices" or "fusion devices," are configured to stabilize adjacent vertebrae in a substantially rigid or fixed manner to promote fusion (i.e., bone growth) between the adjacent vertebrae. Rigid devices may effectively fix the relative spacing and orientation of adjacent vertebrae until fusion is achieved, which may be facilitated by bone graft or bone growth promoting substances. Upon fusion, rigid devices may provide a load sharing function in combination with the bone formed between the adjacent vertebrae. Other spinal devices, which may be referred to as "dynamic devices" or "motion devices," are configured to stabilize adjacent vertebrae in a dynamic manner that allows a degree of relative movement between the adjacent vertebrae. As a result, dynamic devices may allow adjacent vertebrae to move relative to one another, such as in flexion, extension, lateral bending, and/or axial rotation of the spine, thereby inhibiting fusion between the adjacent vertebrae. Dynamic devices may provide a load sharing function in combination with the native spinal disc between the adjacent vertebrae or may carry substantially all loads applied to the respective vertebrae in instances where the spinal disc is removed. Rigid devices or dynamic devices may be used in the treatment of various degenerative diseases of the spine, including spondylolisthesis, degenerative disc disease, spinal osteoarthritis, degenerative scoliosis, and recurrent disc herniation, as well traumatic spinal injury. Example spinal devices include pedicle screws, facet screws, rods, plates, interbody cages, artificial discs, and other types of spacers, some of which may be used as stand-alone devices or may be used in combination with one another. Such spinal devices may be configured for rigid or dynamic stabilization, and the selection between rigid or dynamic treatment may depend on the type and/or severity of the spinal disease or traumatic injury to be addressed.

An interspinous process device, which also may be referred to as an "ISP device," is one type of spinal device that may be used for treatment of various spinal conditions. Generally described, an interspinous process device may include a portion that is positioned within an interspinous process space between a pair of adjacent vertebrae (i.e., the space between the spinous process of a first vertebra and the spinous process of an adjacent second vertebra) and one or more additional portions that interface with the spinous processes, the laminae, and/or other portions of the respective vertebrae. In certain instances, interspinous process devices may be used primarily to distract the spinous processes and restrict extension of the treated segment of the spine. Such devices may be referred to as "interspinous distraction devices" and generally may not be fixed to the vertebrae upon implantation thereof. In other instances, interspinous process devices may be used for fixation purposes to facilitate fusion of the treated segment of the spine, although such devices also may function to distract the spinous processes of the respective vertebrae. Such devices may be referred to as "interspinous fixation devices" and generally may be fixed to the respective vertebrae by one or more engagement features.

Certain interspinous process devices, which may be referred to as "rigid devices" or "fusion devices," are configured to stabilize adjacent vertebrae in a substantially rigid or fixed manner to promote fusion (i.e., bone growth) between the adjacent vertebrae. In this manner, such interspinous process devices may prevent or substantially inhibit relative motion of the adjacent vertebrae. Such rigid interspinous process devices generally may include one or more engagement features for fixedly attaching the device to the spinous processes, the laminae, and/or other portions of the respective vertebrae. Other interspinous process devices, which may be referred to as "dynamic devices" or "motion devices," are configured to stabilize adjacent vertebrae in a dynamic manner that allows a degree of movement between the adjacent vertebrae. Accordingly, such interspinous process devices may allow the adjacent vertebrae to move relative to one another, for example, in flexion and extension of the spine, thereby inhibiting fusion of the treated segment of the spine. Such dynamic interspinous process devices may or may not include engagement features for fixedly attaching the device to the spinous processes, the laminae, and/or other portions of the respective vertebrae.

Although existing interspinous process devices may be suitable for use in various applications, such devices may suffer from one or more potential drawbacks. For example, in some applications, certain rigid interspinous process devices may provide desired stabilization of the treated vertebrae but the lack of relative motion between the vertebrae may result in undesirable loads being carried by the rigid devices and may increase the incidence of failure of such devices over time. Additionally, the fixation provided by certain rigid interspinous process devices and subsequent fusion of the treated segment of the spine may cause increased stresses on the adjacent untreated segments and adjacent segment degeneration. With respect to dynamic interspinous process devices that allow for relative movement between the treated vertebrae, certain dynamic devices may not provide the type of controlled motion as may be desired in some applications. For example, the degree of movement allowed by such devices may be greater than or less than desired in some applications. Additionally, the relative movement between the treated vertebrae may not be adequately constrained in the desired anatomical direction(s). Certain dynamic interspinous process devices also may present issues of engagement between the device and the respective vertebrae becoming compromised over time due to the relative movement of the vertebrae. Moreover, certain dynamic interspinous process devices may have complicated designs including numerous components, which may increase the incidence of device failure and/or may result in the implantation and intraoperative assembly of the device being cumbersome and time consuming Finally, certain dynamic interspinous process devices may lack a means for adjusting the degree of relative movement allowed by the device and/or preventing relative movement, as may be desired. For example, it may be desirable to provide a greater degree or a lesser degree of relative movement in different treatment applications. Further, in certain instances, it may be desirable to change a treatment approach to allow a degree of relative movement or to prevent relative movement, during either an initial surgery or a follow-up surgery.

A need therefore exists for improved interspinous process devices and methods that address one or more of the above-described potential drawbacks of existing technology and allow for the use of interspinous process devices in a broader range of treatment options.

SUMMARY OF THE DISCLOSURE

Various embodiments described herein provide interspinous process devices and related methods for use in spinal surgery to restore and maintain normal spacing between adjacent vertebrae. In certain embodiments, the interspinous process devices may allow a desired degree of relative movement between the treated vertebrae and thus may be referred to as "dynamic interspinous process devices." In certain embodiments, such dynamic interspinous process devices may be converted between one or more dynamic configurations and one or more rigid configurations to selectively allow, inhibit, or prevent relative movement between the treated vertebrae and thus may be referred to as "convertible dynamic interspinous process devices."

According to one aspect, a dynamic interspinous process device is provided for implantation between respective spinous processes of a first vertebra and a second vertebra. In one embodiment, the dynamic interspinous process device may include a first attachment side and a second attachment side. The first attachment side may include a central portion, a first wing extending from the central portion, a second wing extending from the central portion, and one or more slots extending from an interior side of the first attachment side to an exterior side of the first attachment side. The one or more slots of the first attachment side may be configured to allow the first wing and the second wing to move relative to one another in a direction of a longitudinal axis of the dynamic interspinous process device. The second attachment side may include a central portion, a first wing extending from the central portion, a second wing extending from the central portion, and one or more slots extending from an interior side of the second attachment side to an exterior side of the second attachment side. The one or more slots of the second attachment side may be configured to allow the first wing and the second wing to move relative to one another in a direction of a longitudinal axis of the dynamic interspinous process device.

According to another aspect, a dynamic interspinous process device is provided for implantation between respective spinous processes of a first vertebra and a second vertebra. In another embodiment, the dynamic interspinous process device may include a first attachment side and a second attachment side. The first attachment side may include a central portion, a first wing extending from the central portion, a second wing extending from the central portion, and a slider movably attached to the second wing. The slider of the first attachment side may be configured to move relative to the second wing between an extended position and a retracted position. The second attachment side may include a central portion, a first wing extending from the central portion, a second wing extending from the central portion, and a slider movably attached to the second wing. The slider of the second attachment side may be configured to move relative to the second wing between an extended position and a retracted position.

These and other aspects and embodiments of the present disclosure will be apparent or will become apparent to one of ordinary skill in the art upon review of the following detailed description when taken in conjunction with the several drawings and the appended claims.

BRIEF DESCRIPTION OF THE DRAWINGS

In describing the various embodiments of the present disclosure, reference is made to the accompanying drawings, which are not necessarily drawn to scale, and wherein:

FIG. 3G is a plan view of the first attachment side and a resistance means of the dynamic interspinous process device of FIG. 3A.

FIG. 3H is a plan view of the second attachment side and a resistance means of the dynamic interspinous process device of FIG. 3A.

FIG. 3I is a plan view of the first attachment side and a fixation means of the dynamic interspinous process device of FIG. 3A.

FIG. 3J is a plan view of the second attachment side and a number of fixation means of the dynamic interspinous process device of FIG. 3A.

FIG. 6I is a perspective view of the first attachment side of the dynamic interspinous process device of FIG. 6A, showing the slider, the main body, and a pin of the first attachment side in a disassembled state.

FIG. 6J is a perspective view of the slider of the first attachment side of the dynamic interspinous process device of FIG. 6A.

FIG. 6K is a perspective view of the slider of the first attachment side of the dynamic interspinous process device of FIG. 6A.

FIG. 8L is a plan view of the second attachment side of the dynamic interspinous process device of FIG. 8A, showing the slider of the second attachment side in a retracted position relative to the main body of the second attachment side.

FIG. 8M is a perspective view of the sheath of the first attachment side of the dynamic interspinous process device of FIG. 8A.

FIG. 8N is a perspective view of the sheath of the first attachment side of the dynamic interspinous process device of FIG. 8A.

FIG. 8O is a perspective view of the sheath of the second attachment side of the dynamic interspinous process device of FIG. 8A.

FIG. 8P is a perspective view of the sheath of the second attachment side of the dynamic interspinous process device of FIG. 8A.

FIG. 8Q is a perspective view of the slider of the first attachment side of the dynamic interspinous process device of FIG. 8A.

FIG. 8R is a perspective view of the slider of the first attachment side of the dynamic interspinous process device of FIG. 8A.

FIG. 8S is a perspective view of the slider of the second attachment side of the dynamic interspinous process device of FIG. 8A.

FIG. 8T is a perspective view of the slider of the second attachment side of the dynamic interspinous process device of FIG. 8A.

FIG. 8U is a perspective view of the dynamic interspinous process device of FIG. 8A, showing the first attachment side and the second attachment side in an assembled state and a pair of slider securing means in a disassembled state.

FIG. 8V is a perspective view of the dynamic interspinous process device of FIG. 8A, showing the first attachment side and the second attachment side in the assembled state and the pair of slider securing means in an assembled state.

FIG. 8W is a side view of the dynamic interspinous process device of FIG. 8A implanted with respect to a first vertebra and a second vertebra in accordance with one or more embodiments of the present disclosure.

Figure 8A:
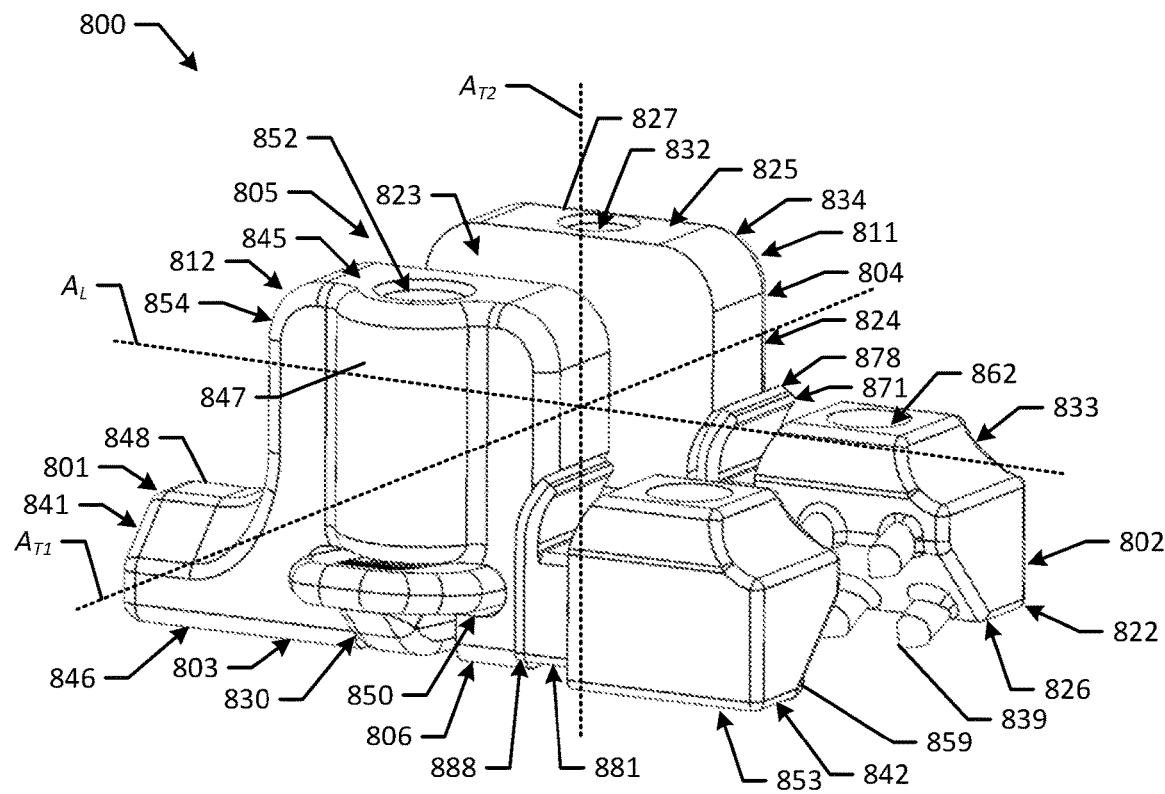
FIG. 8A is a perspective view of a dynamic interspinous process device in accordance with one or more embodiments of the present disclosure, showing a first attachment side and a second attachment side of the dynamic interspinous process device in an assembled state.
Figure 8B:
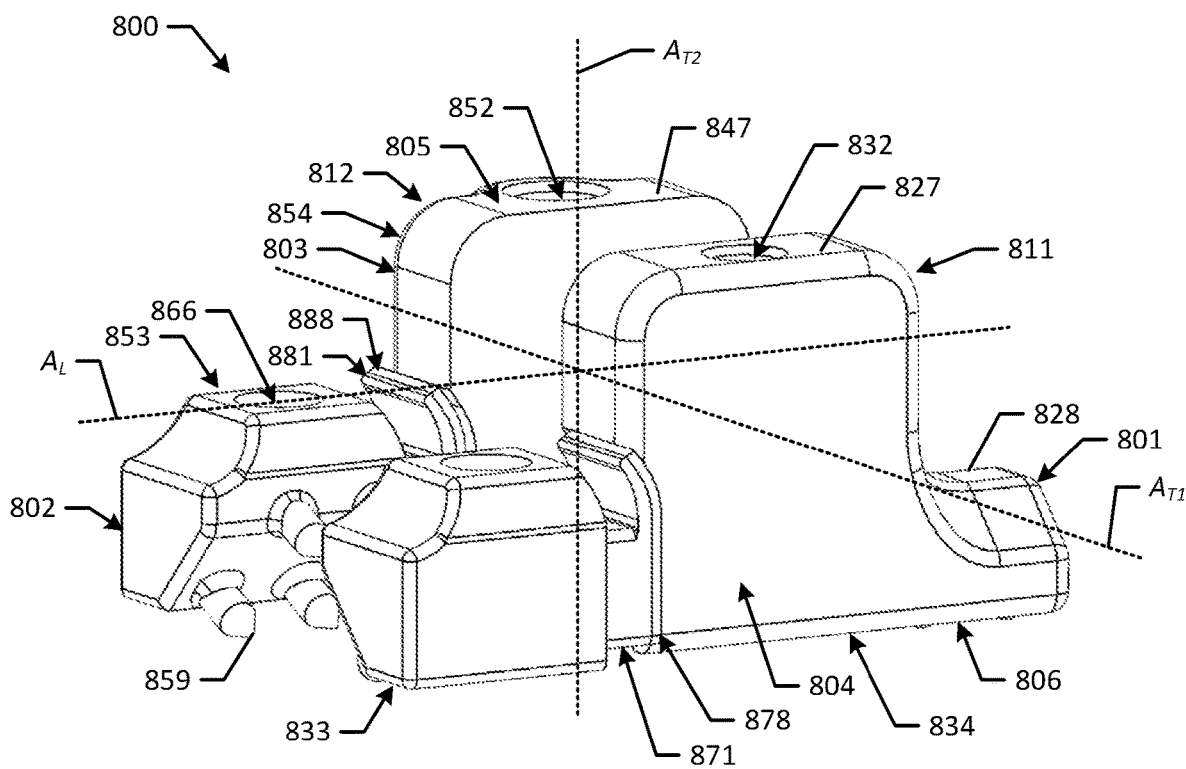
FIG. 8B is a perspective view of the dynamic interspinous process device of FIG. 8A, showing the first attachment side and the second attachment side in the assembled state.
Figure 8C:
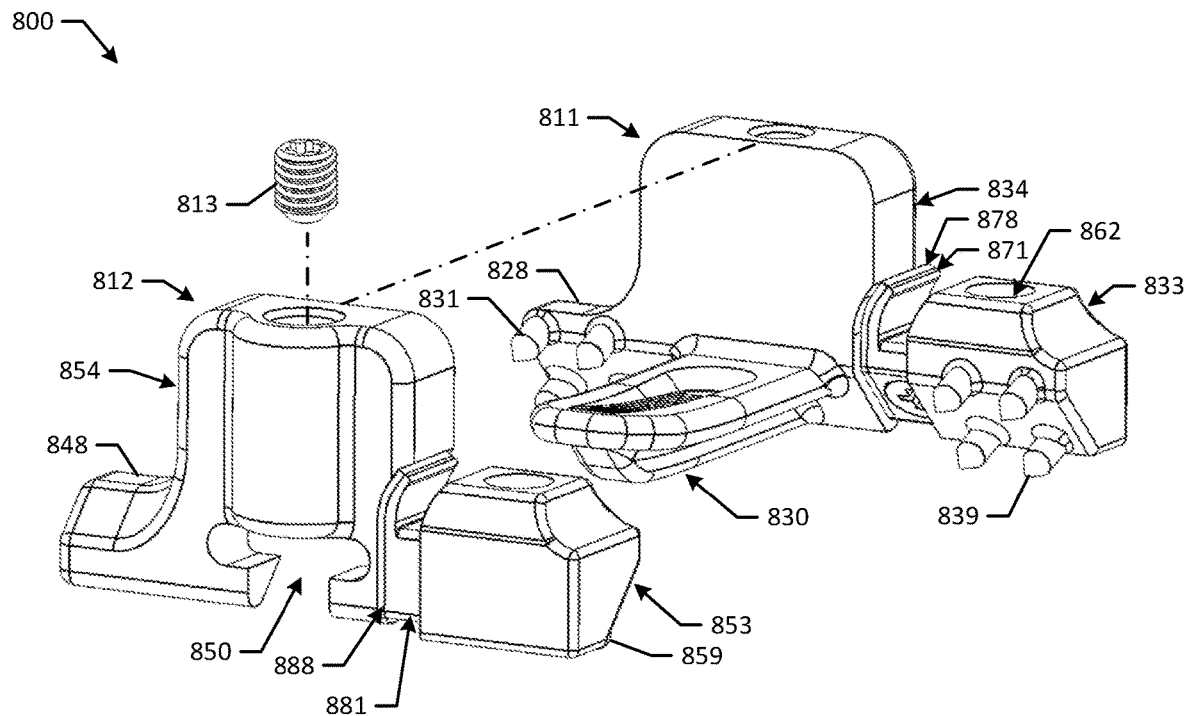
FIG. 8C is a perspective view of the dynamic interspinous process device of FIG. 8A, showing the first attachment side, the second attachment side, and a securing means of the dynamic interspinous process device in a disassembled state.
Figure 8D:
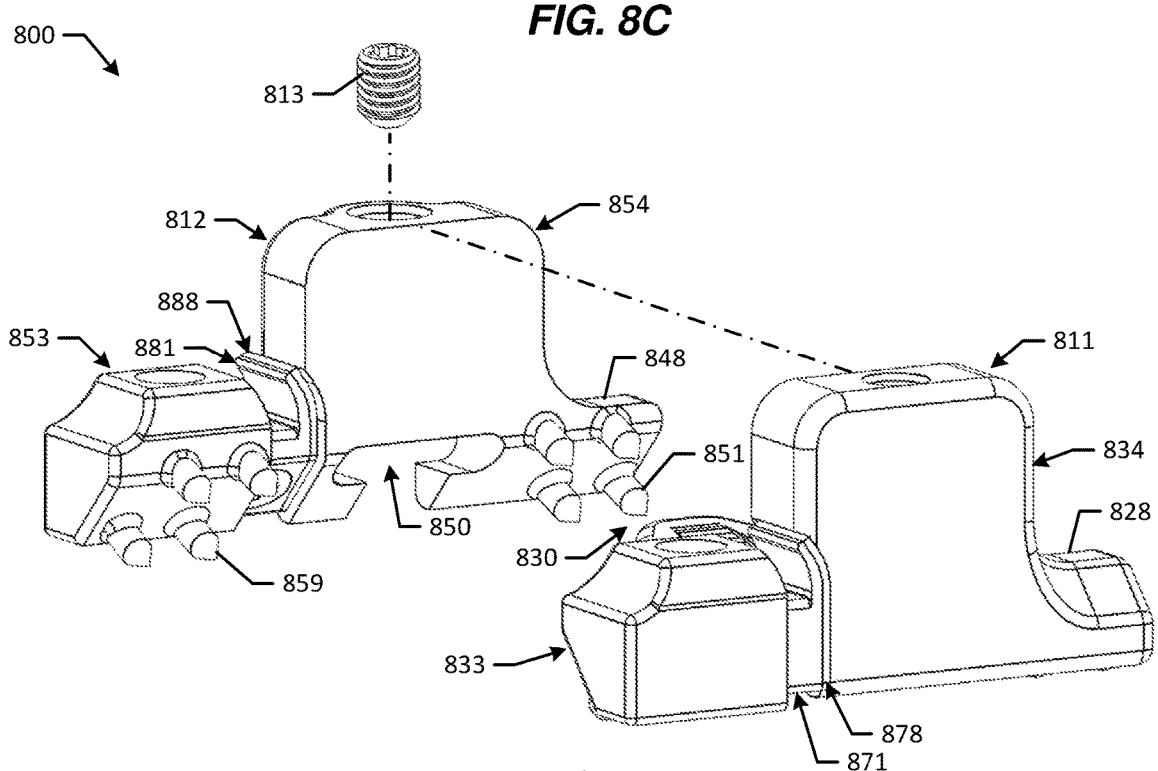
FIG. 8D is a perspective view of the dynamic interspinous process device of FIG. 8A, showing the first attachment side, the second attachment side, and the securing means in the disassembled state.
Figure 8E:
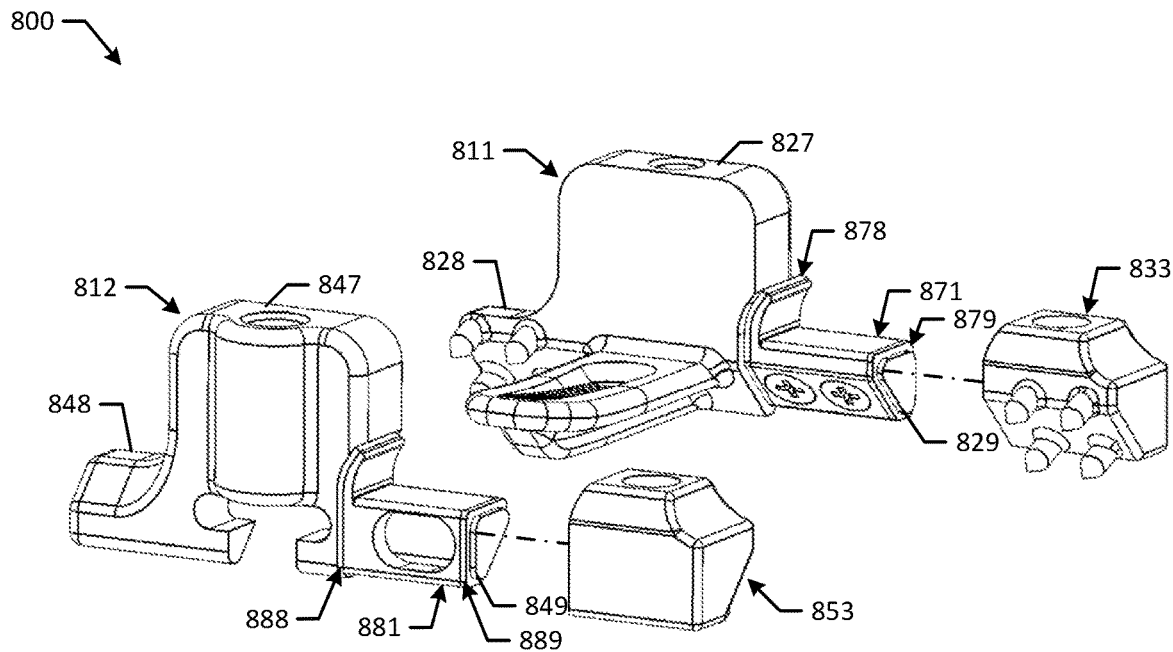
FIG. 8E is a perspective view of the dynamic interspinous process device of FIG. 8A, showing respective sliders of the first attachment side and the second attachment side in a disassembled state.
Figure 8F:
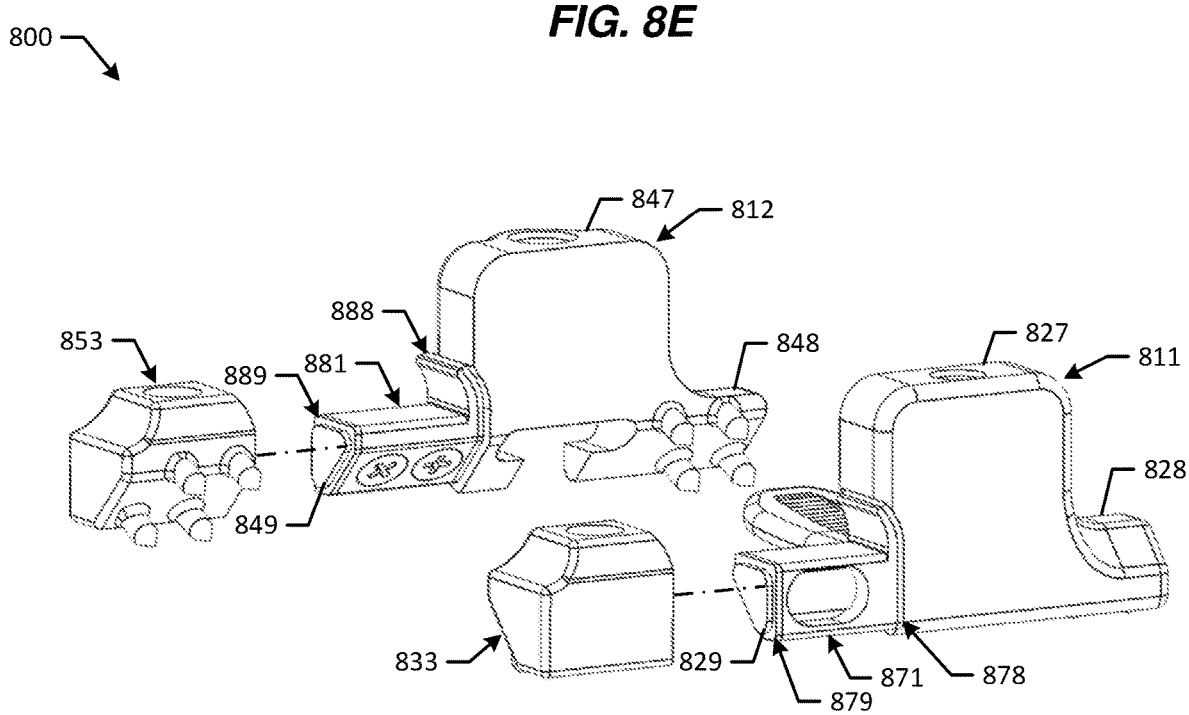
FIG. 8F is a perspective view of the dynamic interspinous process device of FIG. 8A, showing the sliders of the first attachment side and the second attachment side in the disassembled state.
Figure 8G:
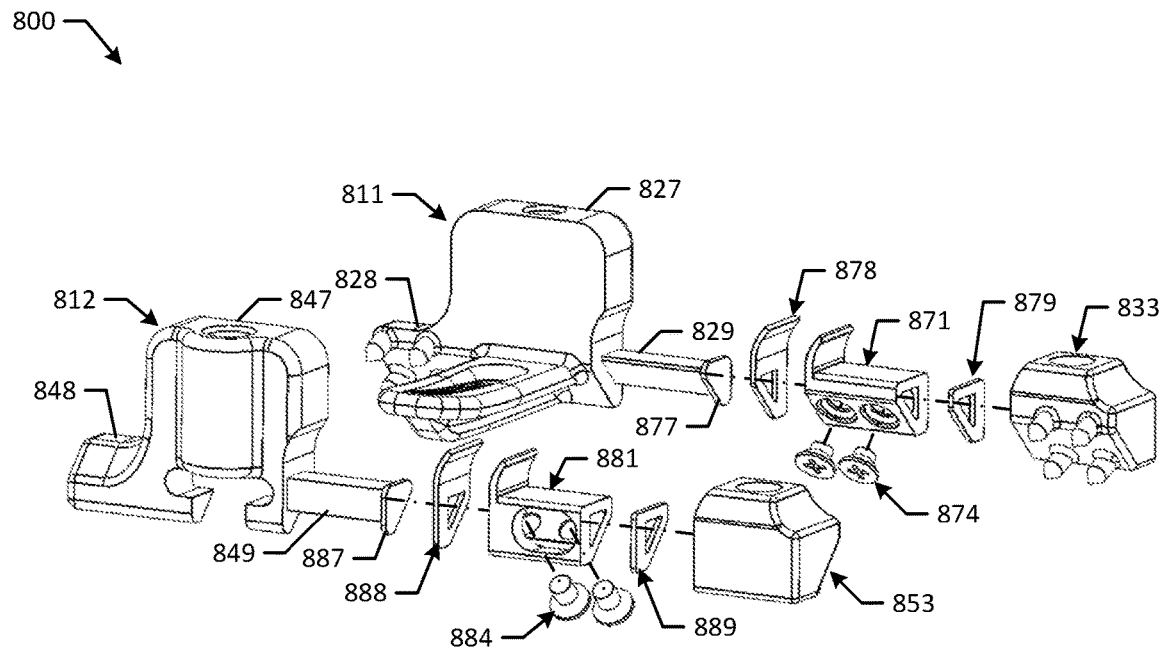
FIG. 8G is a perspective view of the dynamic interspinous process device of FIG. 8A, showing respective sliders, sheaths, and resistance means of the first attachment side and the second attachment side in a disassembled state.
Figure 8H:
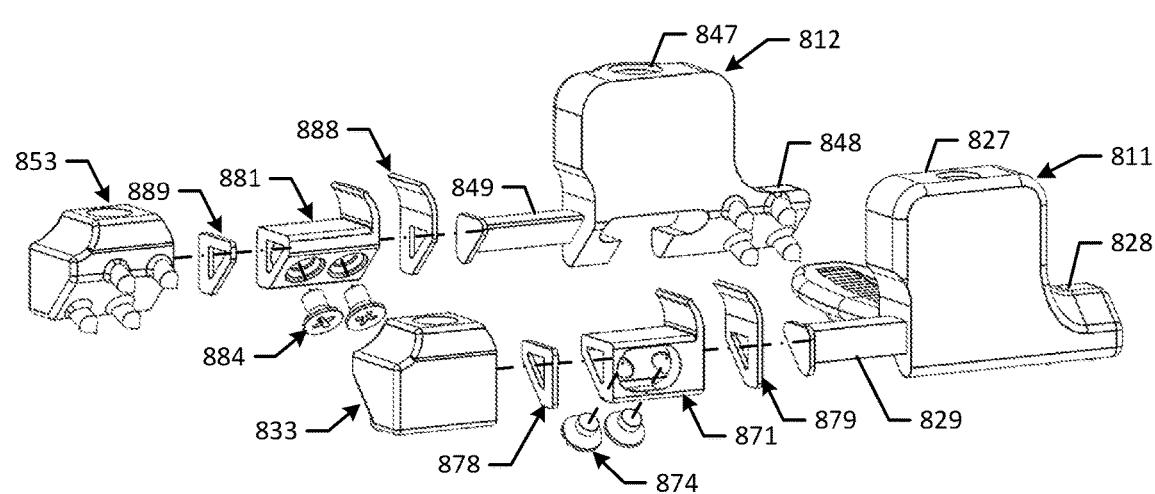
FIG. 8H is a perspective view of the dynamic interspinous process device of FIG. 7A, showing the sliders, the sheaths, and the resistance means of the first attachment side and the second attachment side in the disassembled state.
Figure 8I:
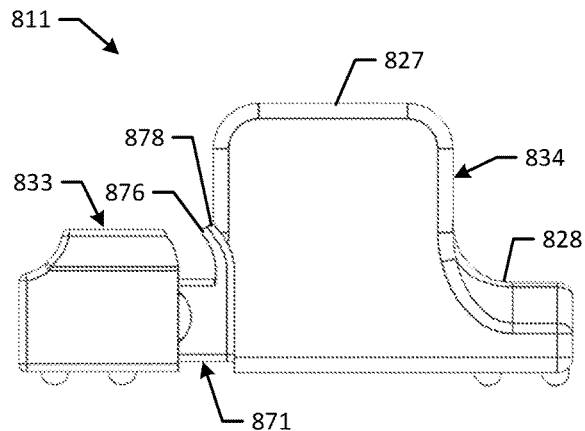
FIG. 8I is a plan view of the first attachment side of the dynamic interspinous process device of FIG. 8A, showing the slider of the first attachment side in an extended position relative to a main body of the first attachment side.
Figure 8J:
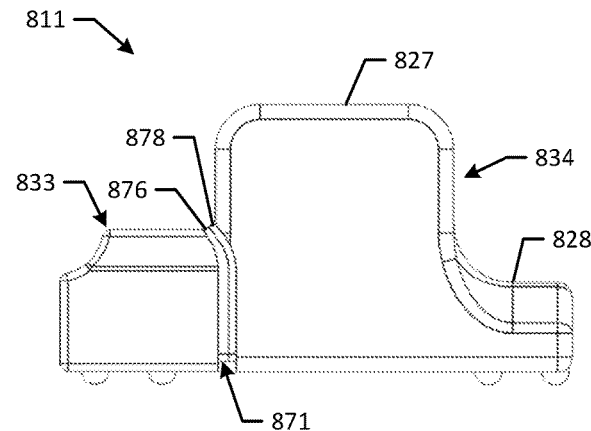
FIG. 8J is a plan view of the first attachment side of the dynamic interspinous process device of FIG. 8A, showing the slider of the first attachment side in a retracted position relative to the main body of the first attachment side.
Figure 8K:
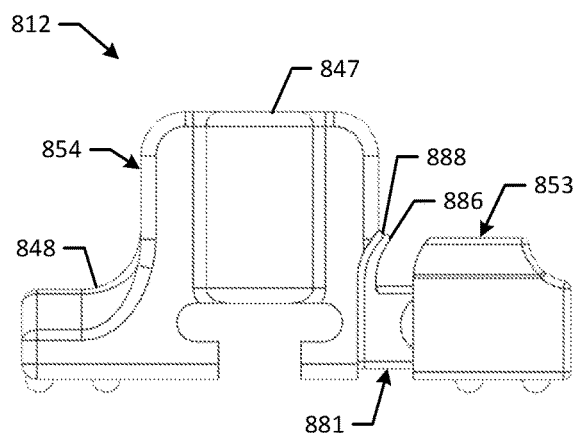
FIG. 8K is a plan view of the second attachment side of the dynamic interspinous process device of FIG. 8A, showing the slider of the second attachment side in an extended position relative to a main body of the second attachment side.
Figure 8L:
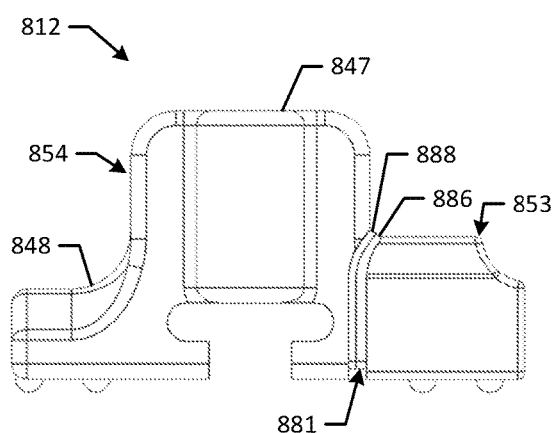
Figure 8M:
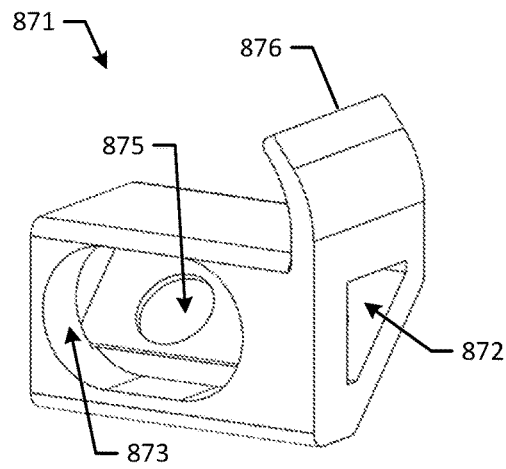
Figure 8N:
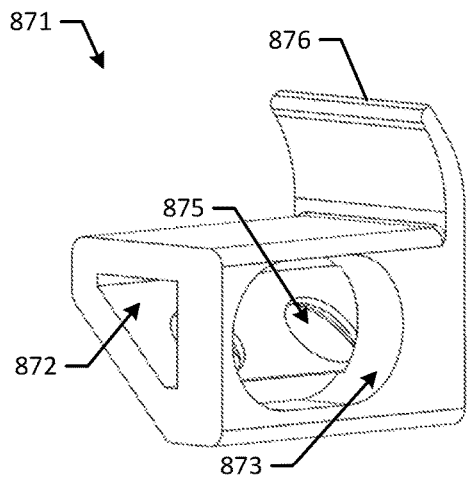
Figure 8O:
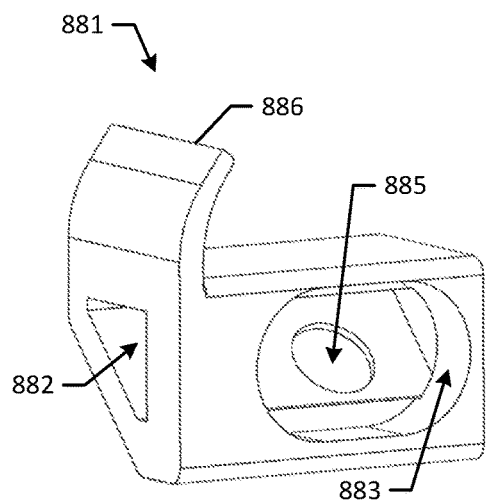
Figure 8P:
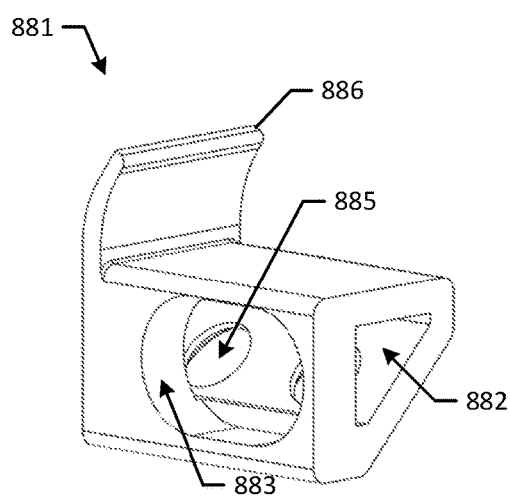
Figure 8U:
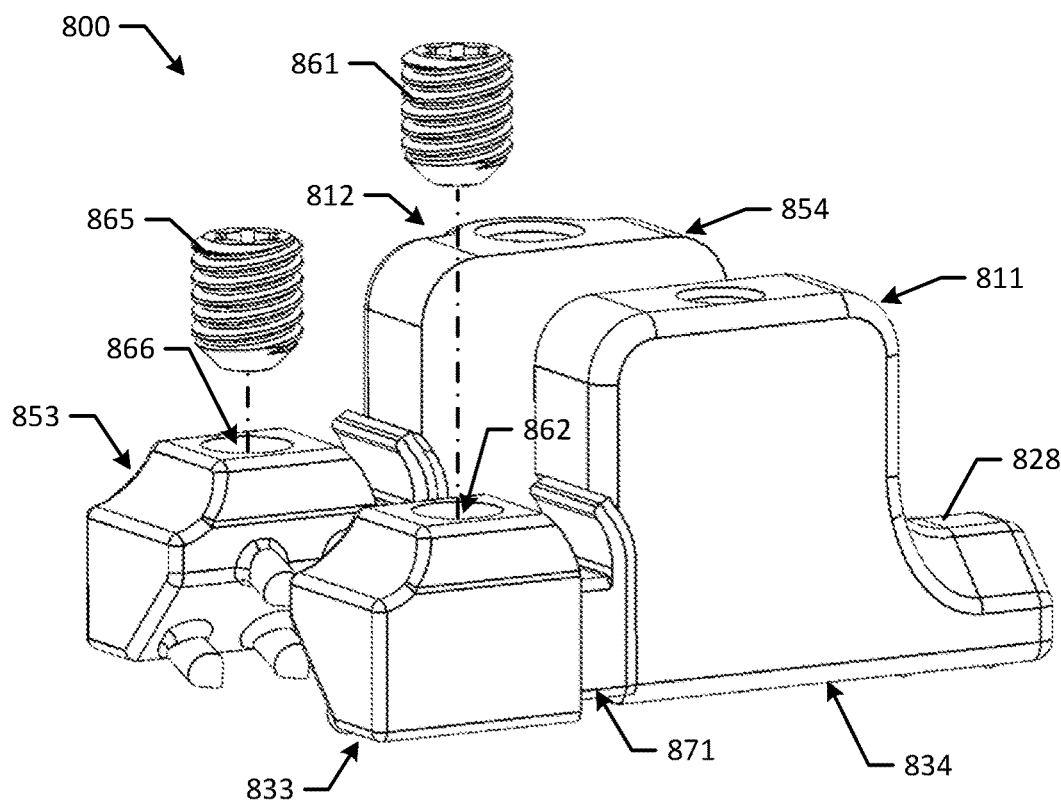
Figure 8V:
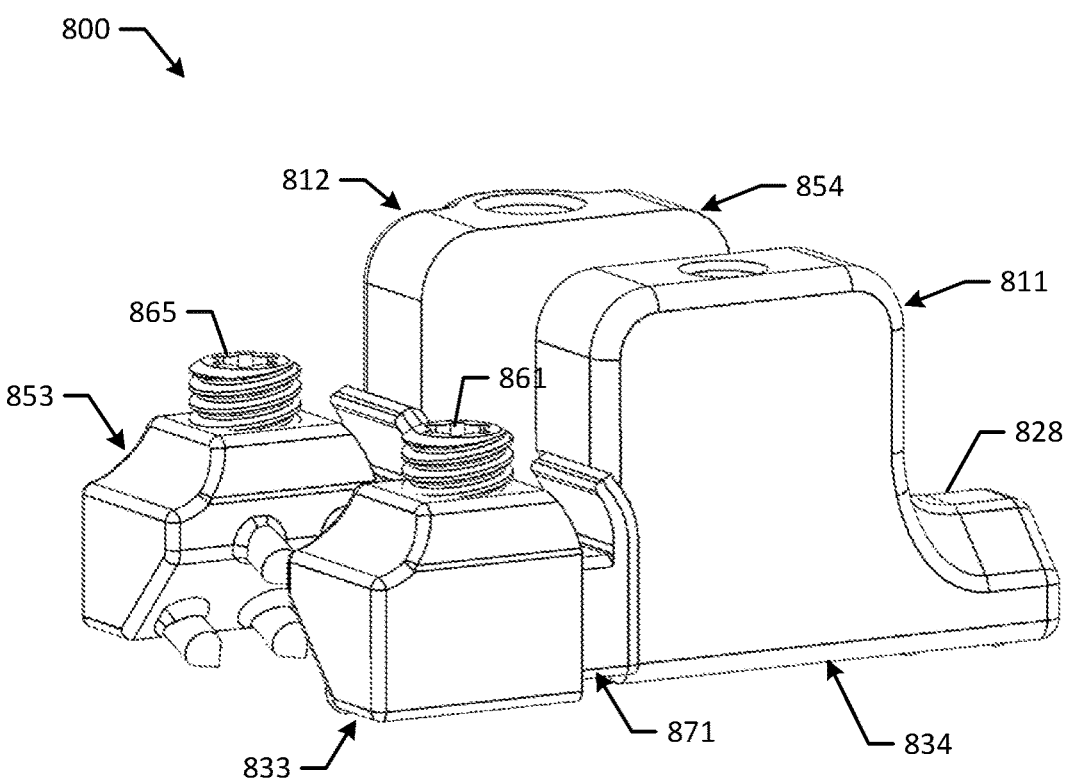
Figure 8W:
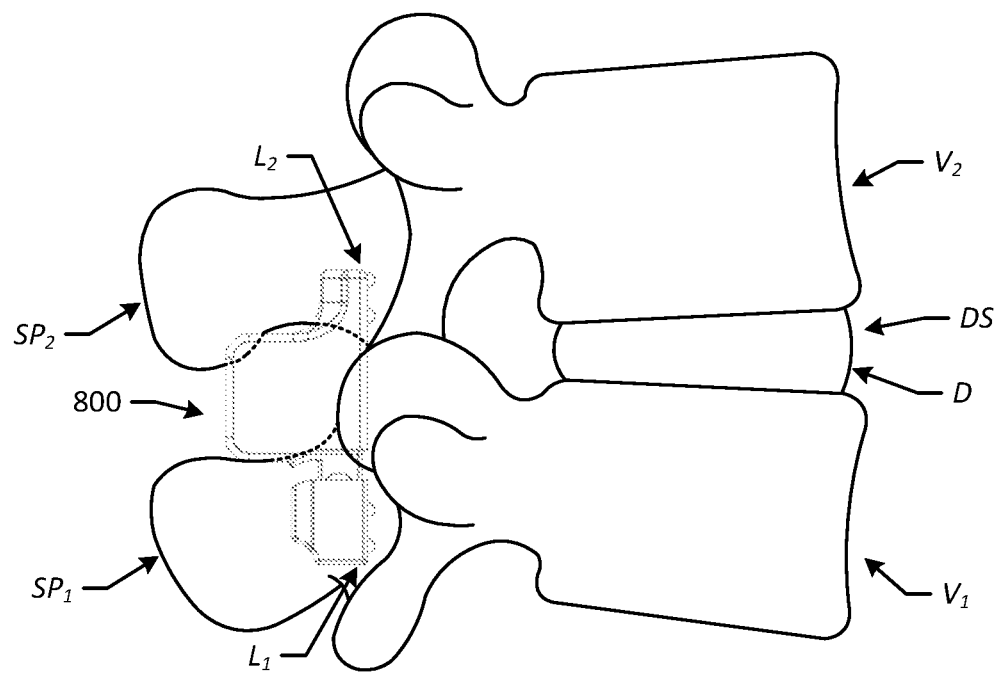
Figure 8X:
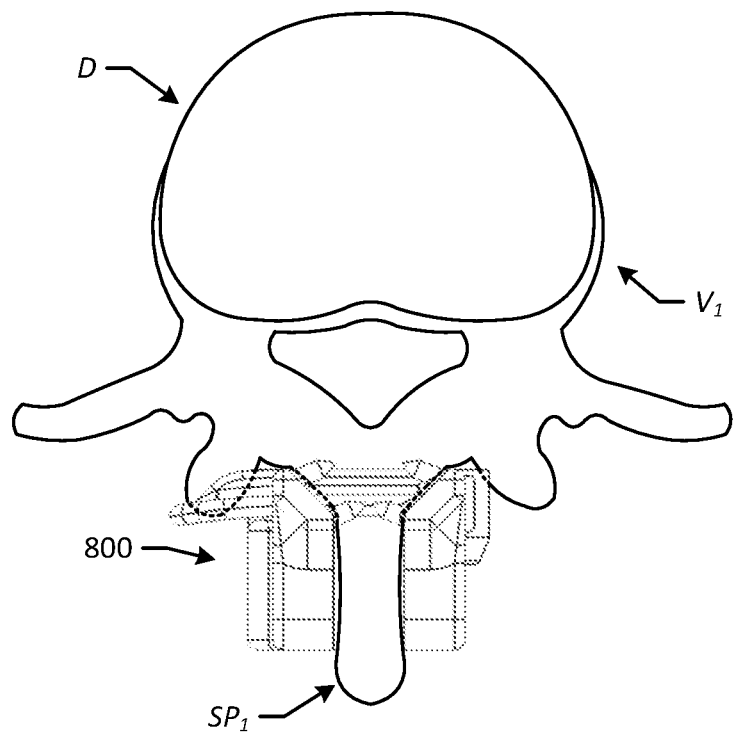

FIG. 8X is a top view of the dynamic interspinous process device of FIG. 8A implanted with respect to the first vertebra, the second vertebra being removed from view for purposes of illustration.

Figure 9A:
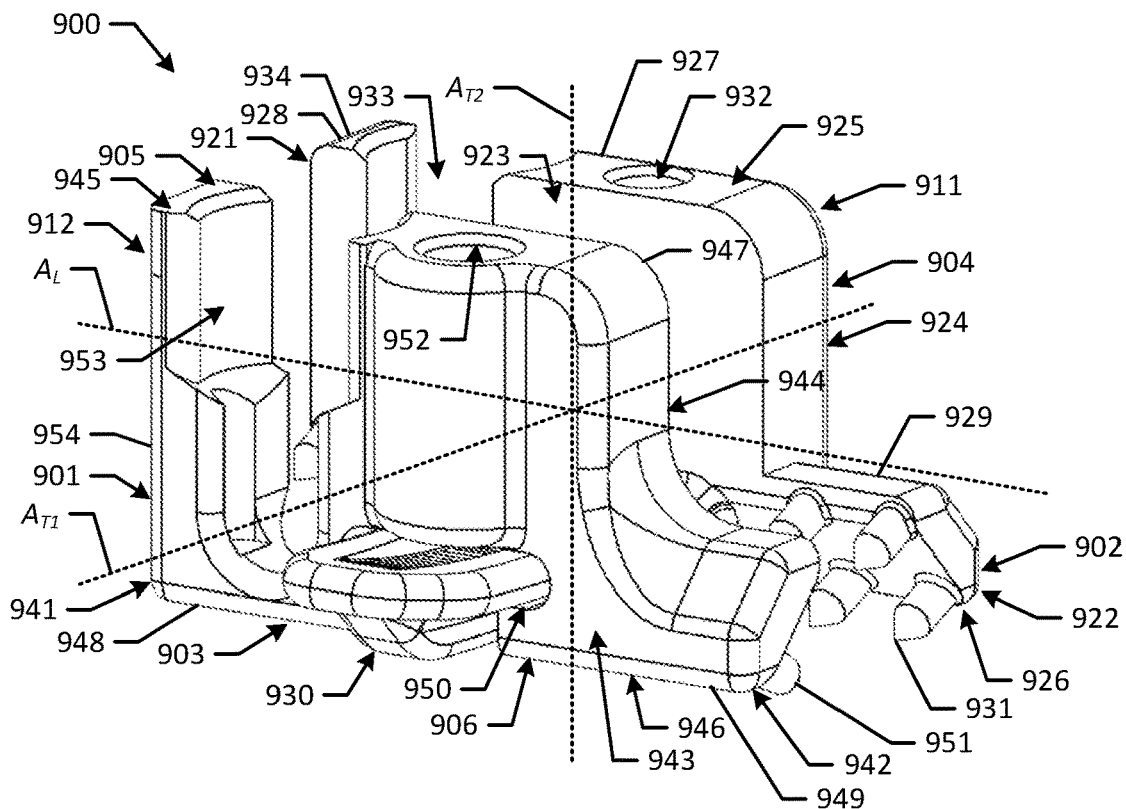

FIG. 9A is a perspective view of a dynamic interspinous process device in accordance with one or more embodiments of the present disclosure, showing a first attachment side and a second attachment side of the dynamic interspinous process device in an assembled state.

Figure 9B:
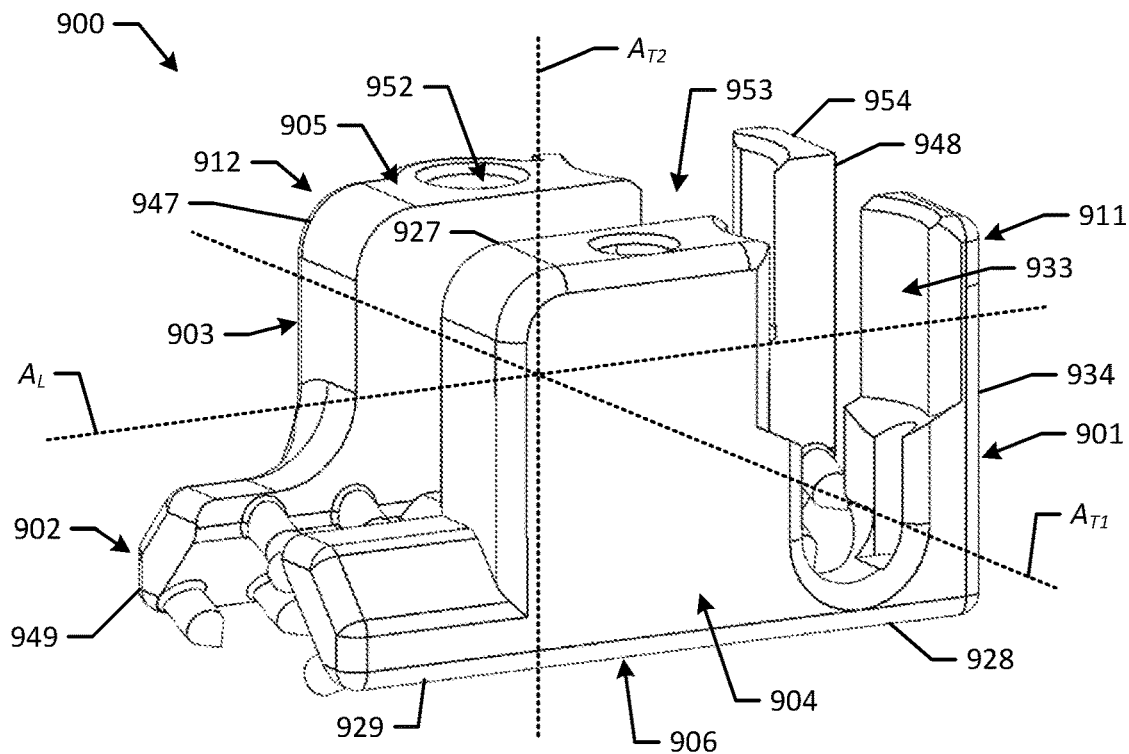

FIG. 9B is a perspective view of the dynamic interspinous process device of FIG. 9A, showing the first attachment side and the second attachment side in the assembled state.

Figure 9C:
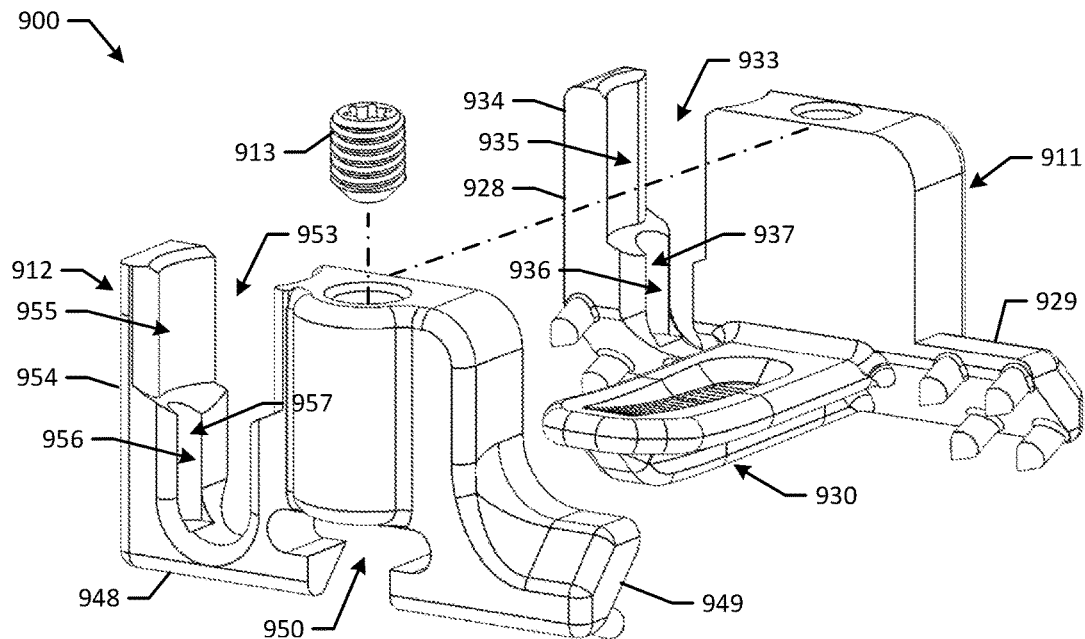

FIG. 9C is a perspective view of the dynamic interspinous process device of FIG. 9A, showing the first attachment side, the second attachment side, and a securing means of the dynamic interspinous process device in a disassembled state.

Figure 9D:
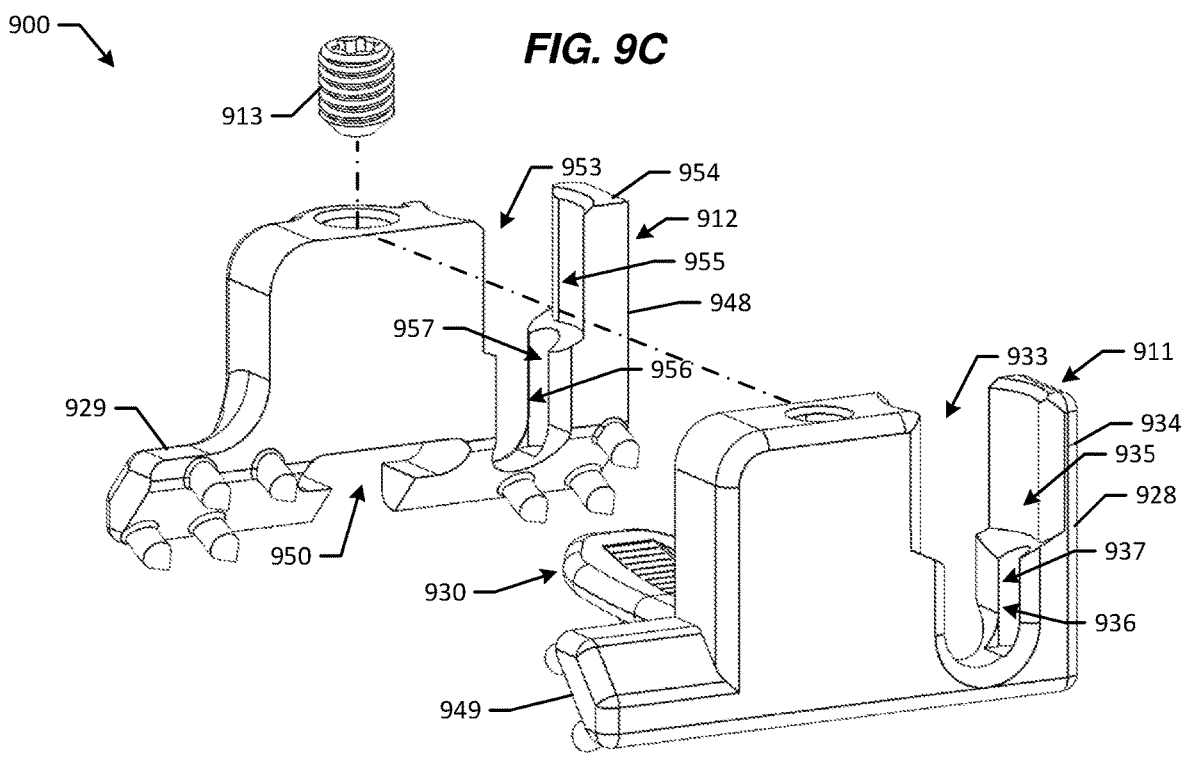

FIG. 9D is a perspective view of the dynamic interspinous process device of FIG. 9A, showing the first attachment side, the second attachment side, and the securing means in the disassembled state.

Figure 9E:
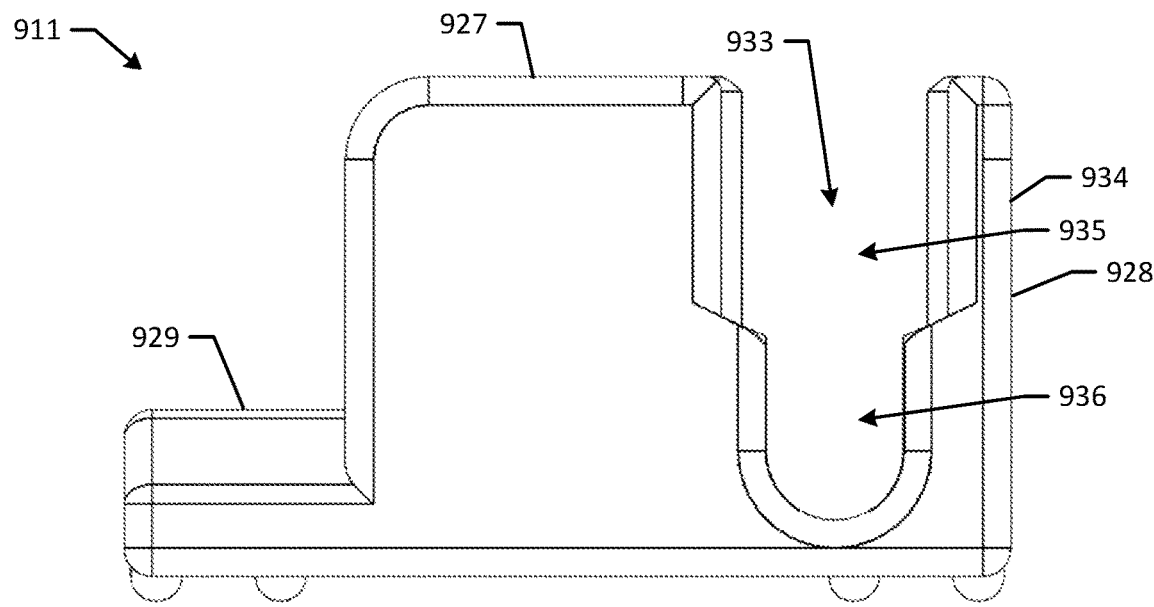

FIG. 9E is a plan view of the first attachment side of the dynamic interspinous process device of FIG. 9A.

Figure 9F:
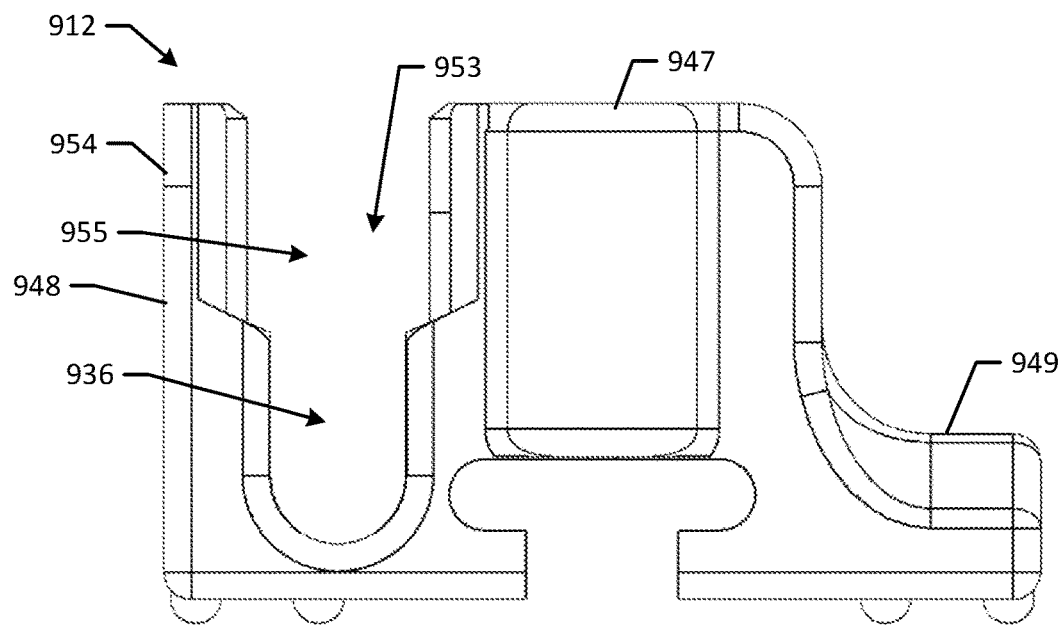

FIG. 9F is a plan view of the second attachment side of the dynamic interspinous process device of FIG. 9A.

Figure 9G:
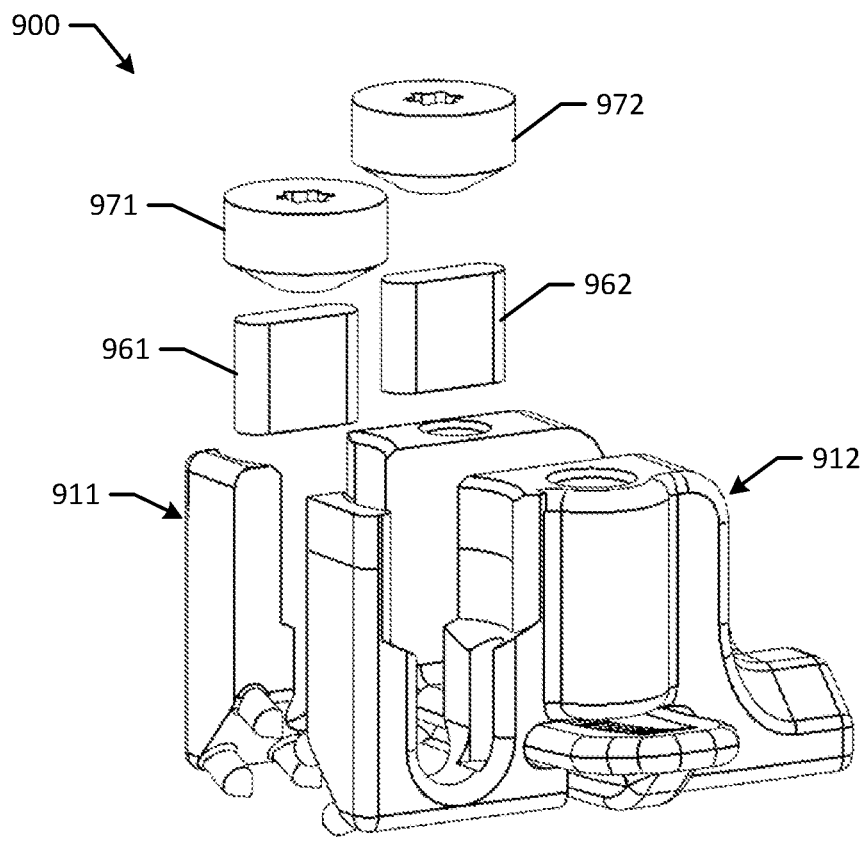

FIG. 9G is a perspective view of the dynamic interspinous process device of FIG. 9A, showing the first attachment side and the second attachment side in the assembled state and a pair of resistance means and a pair of fixation means in a disassembled state.

Figure 9H:
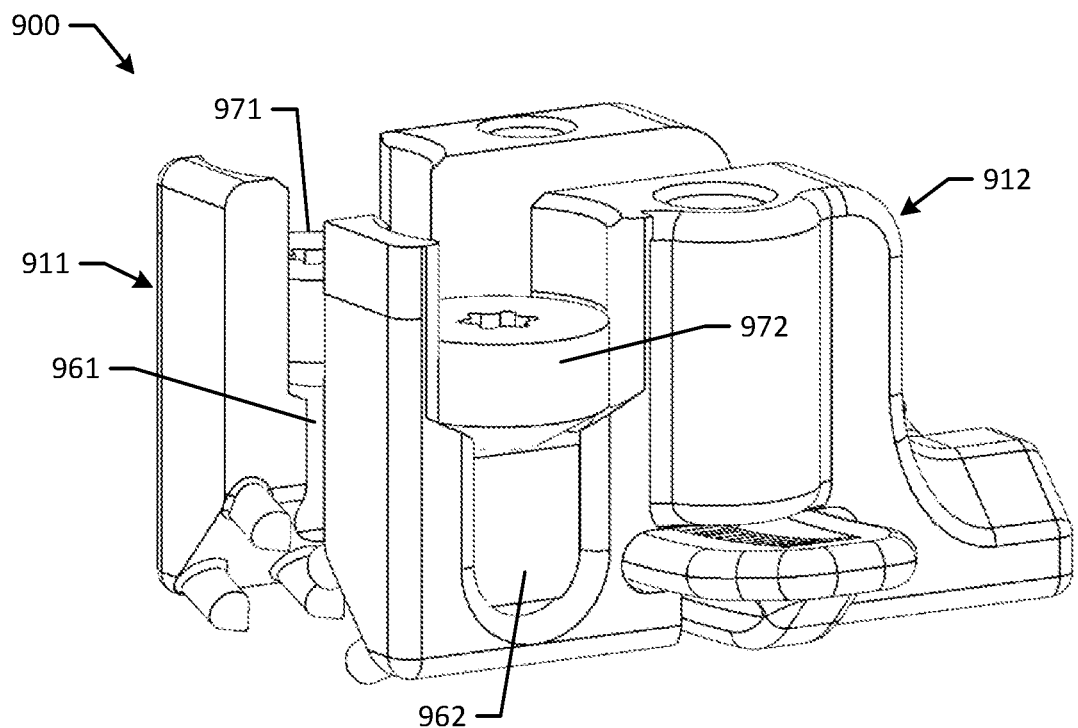

FIG. 9H is a perspective view of the dynamic interspinous process device of FIG. 9A, showing the first attachment side and the second attachment side in the assembled state and the resistance means and the fixation means in an assembled state.

Figures 9I, 9J:
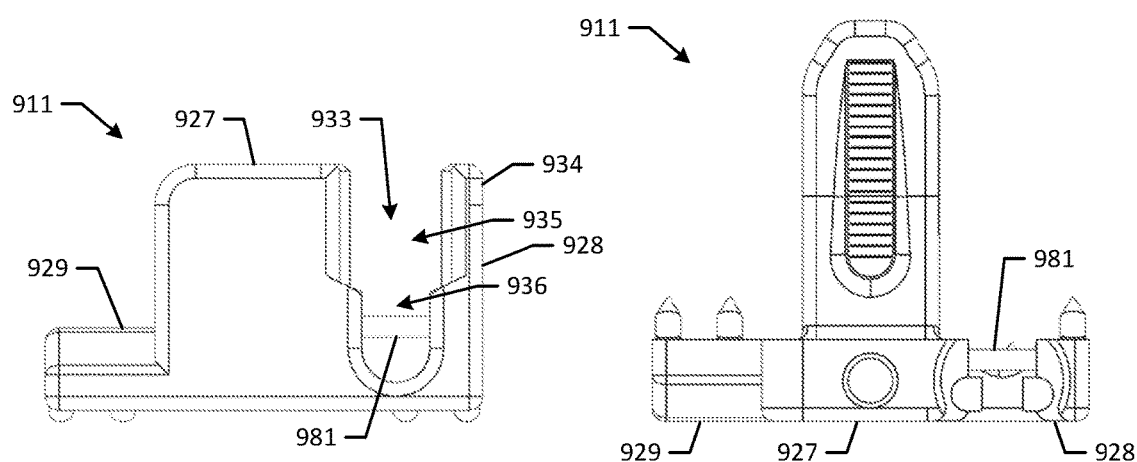

FIG. 9I is a plan view of the first attachment side of the dynamic interspinous process device of FIG. 9A in accordance with one or more embodiments of the present disclosure, showing a resistance means of the first attachment side.

FIG. 9J is a top view of the first attachment side of the dynamic interspinous process device of FIG. 9I, showing the resistance means of the first attachment side.

Figures 9K, 9L:
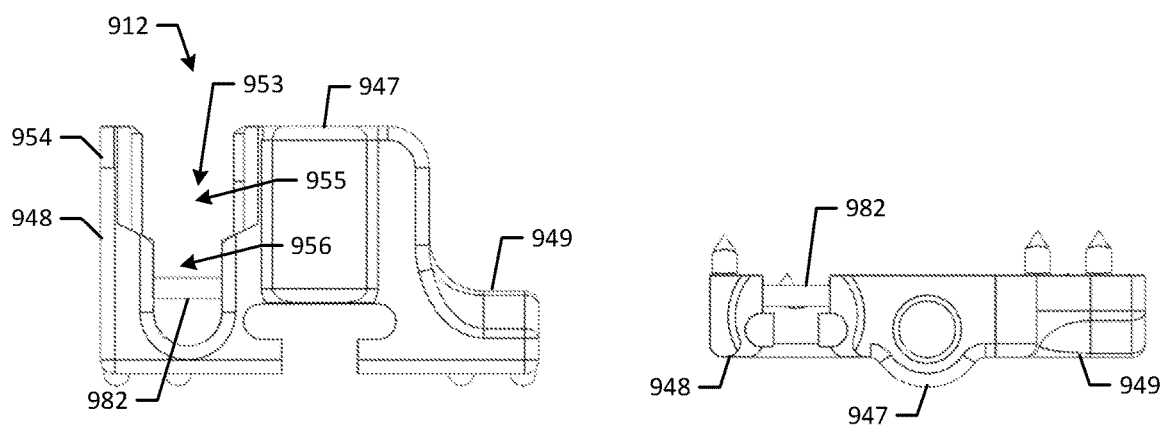

FIG. 9K is a plan view of the second attachment side of the dynamic interspinous process device of FIG. 9A in accordance with one or more embodiments of the present disclosure, showing a resistance means of the second attachment side.

FIG. 9L is a top view of the second attachment side of the dynamic interspinous process device of FIG. 9K, showing the resistance means of the second attachment side.

Figure 9M:
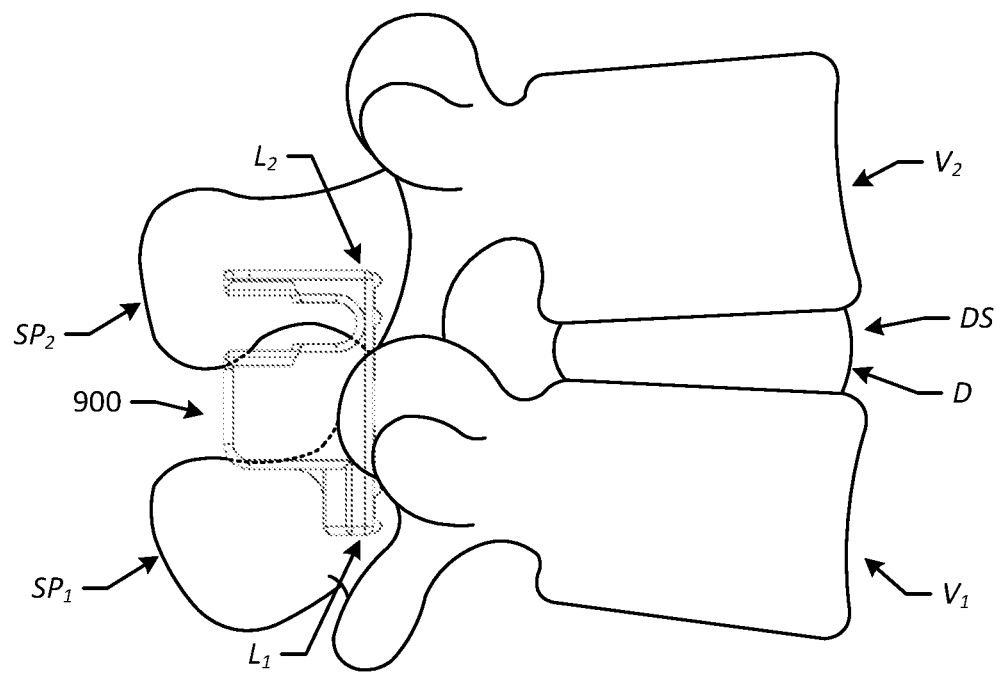

FIG. 9M is a side view of the dynamic interspinous process device of FIG. 9A implanted with respect to a first vertebra and a second vertebra in accordance with one or more embodiments of the present disclosure.

Figure 9N:
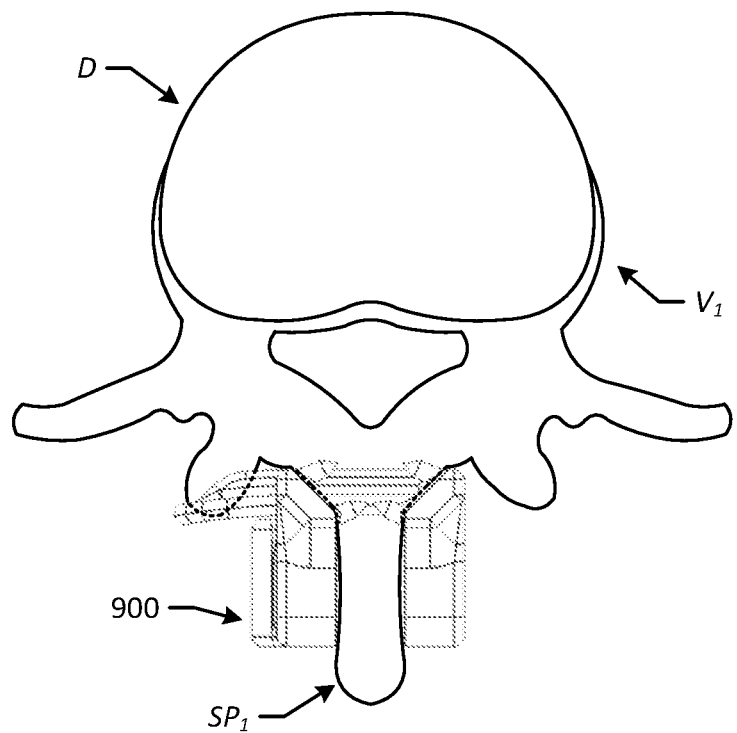

FIG. 9N is a top view of the dynamic interspinous process device of FIG. 9A implanted with respect to the first vertebra, the second vertebra being removed from view for purposes of illustration.

DETAILED DESCRIPTION OF THE DISCLOSURE

Various embodiments of the present disclosure provide improved interspinous process devices and related methods for use in spinal surgery to restore and maintain normal spacing between adjacent vertebrae while also allowing a desired degree of relative movement between the treated vertebrae. Such interspinous process devices and methods may address one or more of the above-described potential drawbacks of existing technology for spinal surgery. In certain embodiments, the interspinous process devices may allow a desired degree of relative movement between the treated vertebrae and thus may be referred to as "dynamic interspinous process devices." In certain embodiments, such dynamic interspinous process devices may be converted between one or more dynamic configurations and one or more rigid configurations to selectively allow, inhibit, or prevent relative movement between the treated vertebrae and thus may be referred to as "convertible dynamic interspinous process devices."

Certain embodiments of the present disclosure may build upon the interspinous process devices and related methods and instruments described in applicant's prior applications, including U.S. patent application Ser. No. 13/047,472 (issued as U.S. Pat. No. 8,591,547) and U.S. patent application Ser. No. 14/713,006 (published as U.S. Patent Application Publication No. 2015/0320456) (collectively, "the Prior Applications"), which are hereby incorporated by reference herein in their entirety. It will be appreciated that certain aspects, features, and/or functionality of the interspinous process devices and methods described herein may correspond to similar or identical aspects, features, and/or functionality of the interspinous process devices and methods described in the Prior Applications, and that similar or identical terminology may be used herein to describe such aspects, features, and/or functionality.

Embodiments of the present disclosure are described herein below with reference to the accompanying drawings, in which some, but not all, embodiments are shown. Indeed, the interspinous process devices and methods disclosed may be embodied in many different forms and should not be construed as limited to the embodiments set forth herein; rather, these embodiments are provided so that this disclosure is thorough and complete and fully conveys the scope of the devices, instruments, and methods to those skilled in the art. Like reference numbers refer to like elements throughout. The singular forms "a," "an," and "the" can refer to plural instances unless the context clearly dictates otherwise or unless explicitly stated.

As described in detail below, the embodiments of the present disclosure provide improved interspinous process devices and related methods for use in spinal surgery to restore and maintain normal spacing between adjacent vertebrae while also allowing a desired degree of relative movement between the treated vertebrae. In particular, the interspinous process devices described herein may be implanted with respect to a first vertebra and an adjacent second vertebra and may function as dynamic devices. In this manner, the interspinous process devices may allow relative movement between the first vertebra and the second vertebra. As described herein, embodiments of the interspinous process devices may provide controlled relative motion of the treated vertebrae as may be desired in certain applications. In particular, the relative motion of the vertebrae provided by embodiments of the interspinous process devices may be constrained in the desired anatomical direction(s), thereby inhibiting undesired movement of the treated vertebrae relative to one another. Some embodiments of the interspinous process devices may include one or more engagement features, such as spikes or other types of bone fasteners, configured for securely attaching the device to the treated vertebrae while still allowing the desired relative movement of the treated vertebrae. Embodiments of the interspinous process devices may include a straightforward configuration including a limited number of components, thereby easing implantation and intraoperative assembly of the device and minimizing incidence of device failure over time. In some embodiments, the interspinous process devices may provide controlled movement of the treated vertebrae by varying resistance to such movement over a range of motion allowed by the device. As described below, some embodiments of the interspinous process devices may include a mechanism for adjusting the degree of relative movement allowed by the device and/or selectively allowing or preventing relative movement, as may be desired in certain applications. In this manner, embodiments of the interspinous process devices may be adjusted to provide a decreased dynamic range of relative movement or an increased dynamic range of relative movement, without the need for removing or replacing the device. Further, embodiments of the interspinous process devices may be adjusted between a dynamic configuration and a rigid configuration, without the need for removing or replacing the device. Such adjustment may be performed prior to implantation of the device, during implantation of the device during an initial surgery, or during a follow-up revision surgery. In this manner, embodiments of the interspinous process devices may provide greater flexibility in tailoring the device for desired performance in different treatment application. Accordingly, the interspinous process devices and methods described herein may address one or more of the above-described potential drawbacks of existing technology for spinal surgery.

Dynamic Interspinous Process Devices

Referring now to the drawings of the present disclosure, FIGS. 1A-1L illustrate an interspinous process device 100 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 100 may be configured for implantation relative to a first vertebra and an adjacent second vertebra, as described below, specifically with reference to FIGS. 1K and 1L. In particular, a portion of the interspinous process device 100 may be positioned between the spinous process of the first vertebra and the spinous process of the second vertebra, while one or more other portions of the interspinous process device 100 engage the spinous processes, the laminae, and/or other portions of the respective vertebra. As described below, the interspinous process device 100 may allow a desired range of relative movement between the treated vertebrae, which may be desirable in certain treatment applications. The interspinous process device 100 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 100, itself or in combination with additional hardware, may provide the structural support necessary to restore and maintain normal spacing and alignment of the treated vertebrae while avoiding certain drawbacks presented by existing interspinous process devices.

The interspinous process device 100 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 100 may include a first end 101 and a second end 102 disposed opposite the first end 101 in the direction of the longitudinal axis $A_L$. As described below, the device 100 may be implanted with the longitudinal axis $A_L$ extending in a direction substantially parallel to the sagittal plane and the coronal plane of the patient and transverse to the transverse plane of the patient. In this manner, depending on the orientation of the device 100 upon implantation thereof, one of the first end 101 and the second end 102 of the device 100 may be referred to as a the "superior end" of the device 100, and the other of the first end 101 and the second end 102 of the device 100 may be referred to as the "inferior end" of the device 100. The device 100 also may include a first side 103 extending from the first end 101 to the second end 102, and a second side 104 disposed opposite the first side 103 in the direction of the first transverse axis $A_{T1}$ and extending from the first end 101 to the second end 102. The device 100 may be implanted with the first transverse axis $A_{T1}$ extending in a direction substantially parallel to the coronal plane and the transverse plane of the patient and transverse to the sagittal plane of the patient. In this manner, depending on the orientation of the device 100 upon implantation thereof, one of the first side 103 and the second side 104 of the device 100 may be referred to as a the "right side" of the device 100, and the other of the first side 103 and the second side 104 of the device 100 may be referred to as the "left side" of the device 100. The device 100 further may include a third side 105 extending from the first end 101 to the second end 102 and from the first side 103 to the second side 104, and a fourth side 106 disposed opposite the third side 105 in the direction of the second transverse axis $A_{T2}$ and extending from the first end 101 to the second end 102 and from the first side 103 to the second side 104. The device 100 may be implanted with the second transverse axis $A_{T2}$ extending in a direction substantially parallel to the sagittal plane and the transverse plane of the patient and transverse to the coronal plane of the patient. As described below, the device 100 may be oriented upon implantation thereof such that the third side 105 faces posteriorly and the fourth side 106 faces anteriorly with respect to the patient. In this manner, the third side 105 may be referred to as the "posterior side" of the device 100, and the fourth side 106 may be referred to as the "anterior side" of the device 100. The device 100 may have an overall "length" extending from the first end 101 to the second end 102 in the direction of the longitudinal axis $A_L$, an overall "width" extending from the first side 103 to the second side 104 in the direction of the first transverse axis $A_{T1}$, and an overall "height" extending from the third side 105 to the fourth side 106 in the direction of the second transverse axis $A_{T2}$. Further, various components and features of the device 100 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 100 may include a first attachment side 111 (which also may be referred to as a "first attachment portion," a "first attachment assembly," or a "first plate") and a second attachment side 112 (which also may be referred to as a "second attachment portion," a "second attachment assembly," or a "second plate") configured for removably attaching to one another via a securing means 113. During use of the device 100, one of the first attachment side 111 and the second attachment side 112 may be disposed, at least partially, along the right side of the patient's spine, and the other of the first attachment side 111 and the second attachment side 112 may be disposed, at least partially, along the right side of the patient's spine. It will be appreciated that the first attachment side 111 and the second attachment side 112 may include corresponding features that are mirror images of one another, although certain differences between the first attachment side 111 and the second attachment side 112 may exist, as described below. In certain embodiments, the first attachment side 111 and the second attachment side 112 may be formed of a metal, such as titanium or stainless steel, although other suitable materials, such as polyether ether ketone (PEEK), other polymers, or composites, may be used.

The first attachment side 111 may have a first end 121, a second end 122 disposed opposite the first end 121, a first side 123 (which also may be referred to as an "interior side"), a second side 124 (which also may be referred to as an "exterior side") disposed opposite the first side 123, a third side 125 (which also may be referred to as an "posterior side"), and a fourth side 126 (which also may be referred to as an "anterior side") disposed opposite the third side 125. As shown, the first attachment side 111 may include a central portion 127 and a pair of wings 128, 129 disposed on opposite sides of the central portion 127. In particular, the first wing 128 may extend from the central portion 127 to the first end 121 of the first attachment side 111, and the second wing 129 may extend from the central portion 127 to the second end 122 of the first attachment side 111. In certain embodiments, as shown, the wings 128, 129 may extend in opposite directions from the central portion 127 and may be formed as mirror images of one another. In other embodiments, the wings 128, 129 may extend in opposite directions from the central portion 127, but the first wing 128 may have a different shape or configuration than the second wing 129 such that the wings 128, 129 are not mirror images of one another. In certain embodiments, the wings 128, 129 may be shaped and configured in a manner similar to any one of the wing embodiments described and/or shown in the Prior Applications. Various other configurations of the wings 128, 129 may be used.

The first attachment side 111 also may include a spacer 130 extending from the first side 123 thereof. During use of the device 100, the spacer 130 may be positioned between the spinous processes of the respective vertebrae. In certain embodiments, as shown, the spacer 130 may extend from the central portion 127 of the first attachment side 111 and be integrally formed therewith. In other embodiments, the spacer 130 may be separately formed from and attached to the central portion 127 via an attachment mechanism. The first attachment side 111 further may include a number of engagement features configured for securely engaging the respective vertebrae. In certain embodiments, as shown, the engagement features may be one or more bone fasteners 131 extending from the first side 123 of the first attachment side 111. The bone fasteners 131 may be formed as spikes or barbs, although other forms and types of bone fasteners 131 may be used for securely engaging the vertebrae. In certain embodiments, one or more of the bone fasteners 131 may extend form the first wing 128, and one or more bone fasteners 131 may extend from the second wing 129. In certain embodiments, the first wing 128 may include a first number of bone fasteners 131 extending therefrom, and the second wing 129 may include a second number of bone fasteners 131 extending therefrom, wherein the first number is different than the second number. In this manner, the degree of engagement between the bone fasteners 131 of the first wing 128 and the corresponding vertebra may be different from the degree of engagement between the bone fasteners 131 of the second wing 129 and the corresponding vertebra. Such an arrangement may facilitate relative movement of the treated vertebrae, while minimizing certain stresses induced in the device 100. In certain embodiments, one of the first wing 128 and the second wing 129 may not include any bone fasteners 131 extending therefrom, and the other of the first wing 128 and the second wing 129 may include one or more of the bone fasteners 131 extending therefrom. Such an arrangement also may facilitate relative movement of the treated vertebrae, while minimizing certain stresses induced in the device 100. Various configurations of the bone fasteners 131 of the first attachment side 111 may be used. In certain embodiments, as shown, the bone fasteners 131 may be configured to engage the laminae of the respective vertebrae. In other embodiments, one or more of the bone fasteners 131 may be configured to engage the spinous processes, the laminae, and/or other portions of the respective vertebrae. As shown, the first attachment side 111 also may include an instrument engagement aperture 132 configured for receiving a portion of and cooperating with an instrument used for positioning the first attachment side 111 during implantation of the device 100. Example instruments for implantation of the device 100 are described in the Prior Applications.

In a similar manner, the second attachment side 112 may have a first end 141, a second end 142 disposed opposite the first end 141, a first side 143 (which also may be referred to as an "exterior side"), a second side 144 (which also may be referred to as an "interior side") disposed opposite the first side 143, a third side 145 (which also may be referred to as an "posterior side"), and a fourth side 146 (which also may be referred to as an "anterior side") disposed opposite the third side 145. As shown, the second attachment side 112 may include a central portion 147 and a pair of wings 148, 149 disposed on opposite sides of the central portion 147. In particular, the first wing 148 may extend from the central portion 147 to the first end 141 of the second attachment side 112, and the second wing 149 may extend from the central portion 147 to the second end 142 of the second attachment side 112. In certain embodiments, as shown, the wings 148, 149 may extend in opposite directions from the central portion 147 and may be formed as mirror images of one another. In other embodiments, the wings 148, 149 may extend in opposite directions from the central portion 147, but the first wing 148 may have a different shape or configuration than the second wing 149 such that the wings 148, 149 are not mirror images of one another. In certain embodiments, the wings 148, 149 may be shaped and configured in a manner similar to any one of the wing embodiments described and/or shown in the Prior Applications. Various other configurations of the wings 148, 149 may be used.

The second attachment side 112 also may include a spacer slot 150 extending through the second attachment side 112 from the first side 143 to the second side 144 thereof. During use of the device 100, the spacer slot 150 may be configured to receive the spacer 130 of the first attachment side 111 therethrough, as shown. In certain embodiments, as shown, the spacer slot 150 may be defined in the central portion 147 of the second attachment side 112 and may extend to the fourth side 146 thereof, although other positions of the spacer slot 150 may be used. The second attachment side 112 further may include a number of engagement features configured for securely engaging the respective vertebrae. In certain embodiments, as shown, the engagement features may be one or more bone fasteners 151 extending from the second side 144 of the second attachment side 112. The bone fasteners 151 may be formed as spikes or barbs, although other forms and types of bone fasteners 151 may be used for securely engaging the vertebrae. In certain embodiments, one or more of the bone fasteners 151 may extend form the first wing 148, and one or more bone fasteners 151 may extend from the second wing 149. In certain embodiments, the first wing 148 may include a first number of bone fasteners 151 extending therefrom, and the second wing 159 may include a second number of bone fasteners 151 extending therefrom, wherein the first number is different than the second number. In this manner, the degree of engagement between the bone fasteners 151 of the first wing 148 and the corresponding vertebra may be different from the degree of engagement between the bone fasteners 151 of the second wing 149 and the corresponding vertebra. Such an arrangement may facilitate relative movement of the treated vertebrae, while minimizing certain stresses induced in the device 100. In certain embodiments, one of the first wing 148 and the second wing 149 may not include any bone fasteners 151 extending therefrom, and the other of the first wing 148 and the second wing 149 may include one or more of the bone fasteners 151 extending therefrom. Such an arrangement also may facilitate relative movement of the treated vertebrae, while minimizing certain stresses induced in the device 100. Various configurations of the bone fasteners 151 of the second attachment side 112 may be used. In certain embodiments, as shown, the bone fasteners 151 may be configured to engage the laminae of the respective vertebrae. In other embodiments, one or more of the bone fasteners 151 may be configured to engage the spinous processes, the laminae, and/or other portions of the respective vertebrae. As shown, the second attachment side 112 also may include a securing aperture 152 configured to receive at least a portion of and cooperate with the securing means 113 for selectively fixing the first attachment side 111 and the second attachment side 112 relative to one another. The securing aperture 152 also may be configured for receiving a portion of and cooperating with an instrument used for positioning the second attachment side 112 during implantation of the device 100. Example instruments for implantation of the device 100 are described in the Prior Applications.

The securing means 113 may be configured for selectively fixing the first attachment side 111 and the second attachment side 112 relative to one another. In certain embodiments, as shown, the securing means 113 may be a fastener, such as a set screw, although other types of fasteners and other types of securing means may be used. As shown, the securing means may be inserted into and at least partially through the securing aperture 152 of the second attachment side 112. In this manner, the securing means 113 may be advanced through the securing aperture 152 until the securing means 113 engages the spacer 130 of the first attachment side 111 positioned within the spacer slot 150 of the second attachment side 112. Upon desired positioning of the first attachment side 111 and the second attachment side 112 with respect to the corresponding vertebrae of the patient, the securing means 113 may be tightened to maintain the spacing and orientation of the first attachment side 111 and the second attachment side 112 relative to one another and relative to the corresponding vertebrae. In certain embodiments, the securing means 113 may be formed of a metal, such as titanium or stainless steel, although other suitable materials, such as polyether ether ketone (PEEK), other polymers, or composites, may be used.

As described above, the device 100 may be configured to allow relative movement of the treated vertebrae upon implantation of the device 100. In particular, the device 100 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 111 and the second attachment side 112 each may include one or more features configured to facilitate such relative movement of the treated vertebrae. In particular, the first attachment side 111 may include one or more slots 133 (which also may be referred to as a "dynamic slot," a "cutout," an "opening," or a "slit") defined therein and configured to allow relative movement of portions of the first attachment side 111. In certain embodiments, as shown, the first attachment side 111 may include a pair of the slots 133 spaced apart from one another in the direction of the longitudinal axis $A_L$ of the device 100. In certain embodiments, as shown, the slots 133 may be formed at least partially, or entirely, within the central portion 127 of the first attachment side 111. Each slot 133 may have an elongated shape extending in the direction of the second transverse axis $A_{T2}$ of the device 100. In certain embodiments, as shown, each slot 133 may extend from the first side 123 to the second side 124 of the first attachment side 111. Further, in certain embodiments, as shown, each slot 133 may extend from the fourth side 126 of the first attachment side 111 toward, but not to, the third side 125 of the first attachment side 111. In other words, the slot 133 may be open along the fourth side 126 and may terminate at a location spaced apart from the third side 125. In certain embodiments, as shown, each slot 133 may have one or more straight portions extending in a linear manner in the direction of the second transverse axis $A_{T2}$ of the device 100 and one or more curved or otherwise contoured portions bending transverse to the second transverse axis $A_{T2}$ in the direction of the longitudinal axis $A_L$ of the device 100. In other embodiments, each slot 133 may be straight or may be contoured along the entire extent of the slot 133. Various other configurations of the slots 133 may be used in other embodiments.

Figure 1A:
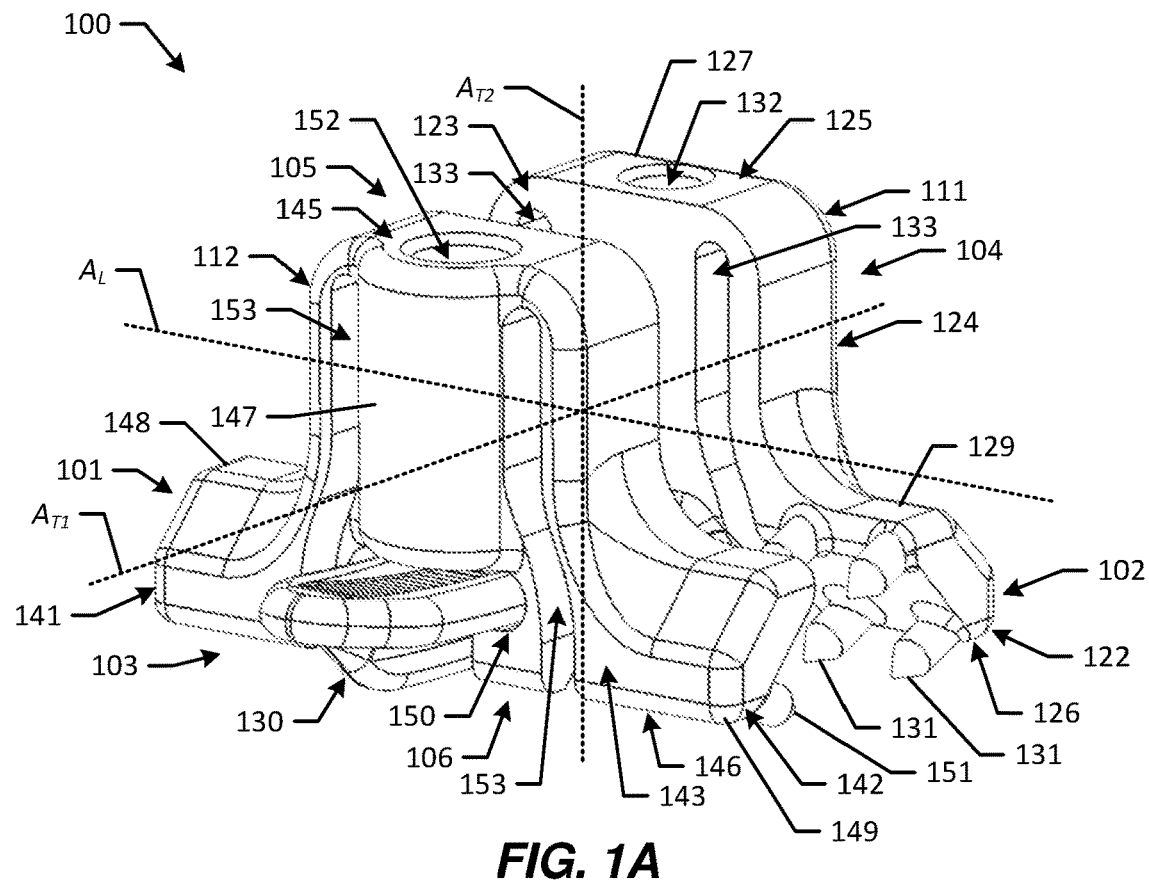
FIG. 1A is a perspective view of a dynamic interspinous process device in accordance with one or more embodiments of the present disclosure, showing a first attachment side and a second attachment side of the dynamic interspinous process device in an assembled state.
Figure 1B:
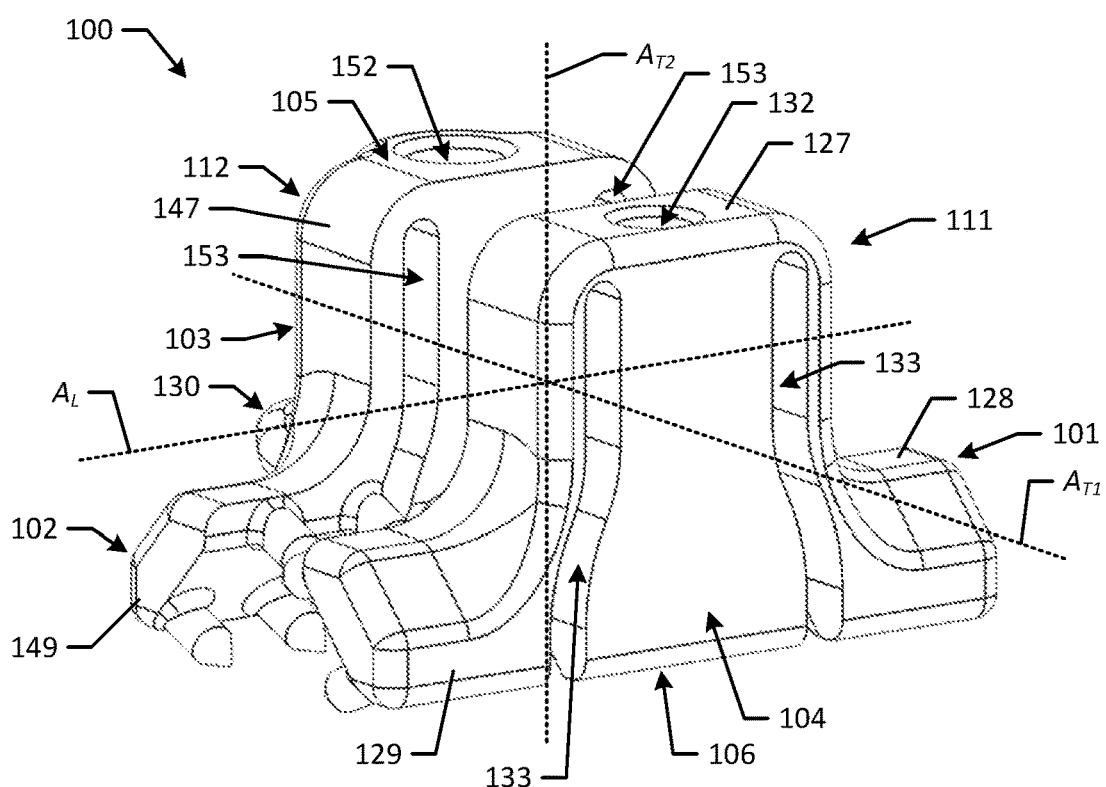
FIG. 1B is a perspective view of the dynamic interspinous process device of FIG. 1A, showing the first attachment side and the second attachment side in the assembled state.
Figure 1C:
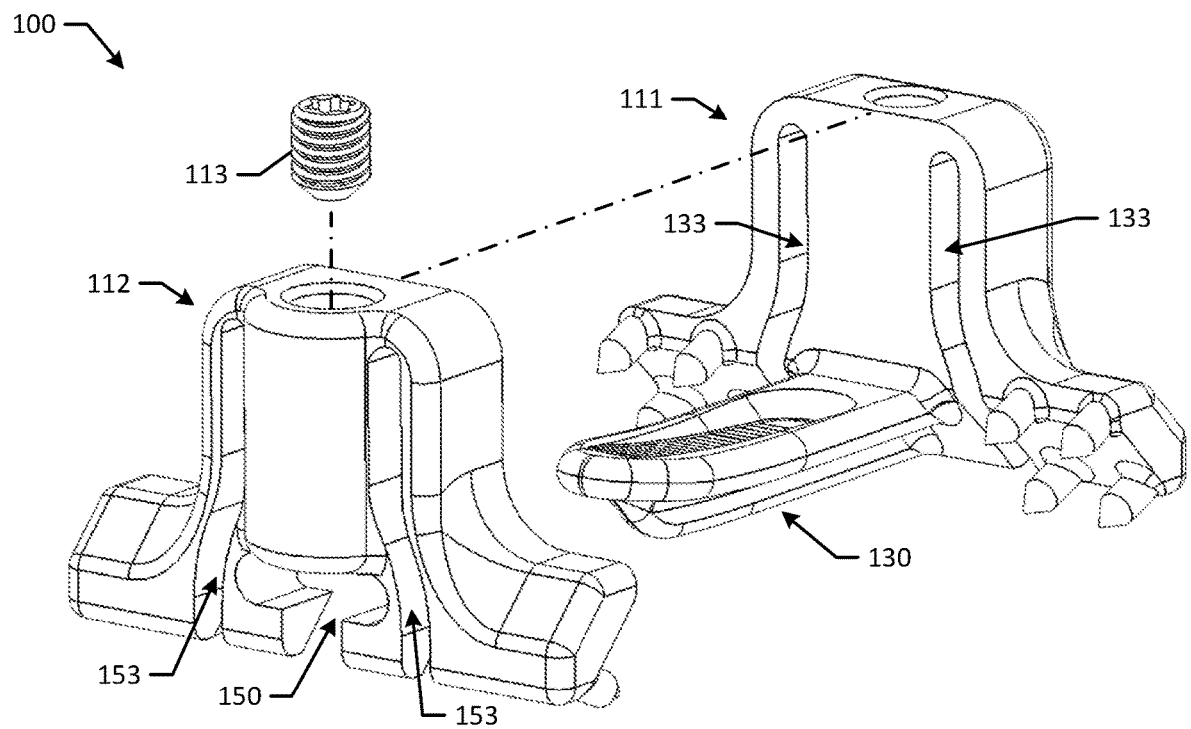
FIG. 1C is a perspective view of the dynamic interspinous process device of FIG. 1A, showing the first attachment side, the second attachment side, and a securing means of the dynamic interspinous process device in a disassembled state.
Figure 1D:
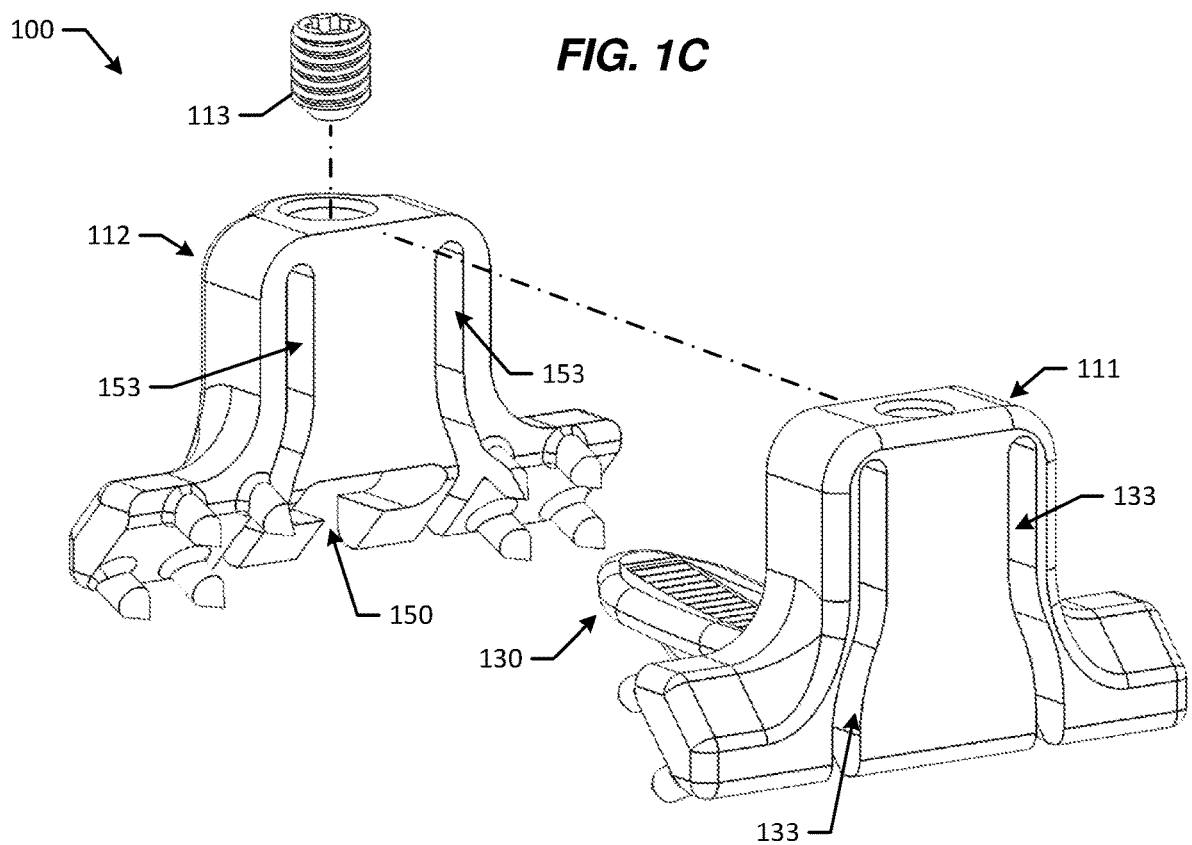
FIG. 1D is a perspective view of the dynamic interspinous process device of FIG. 1A, showing the first attachment side, the second attachment side, and the securing means in the disassembled state.
Figure 1E:
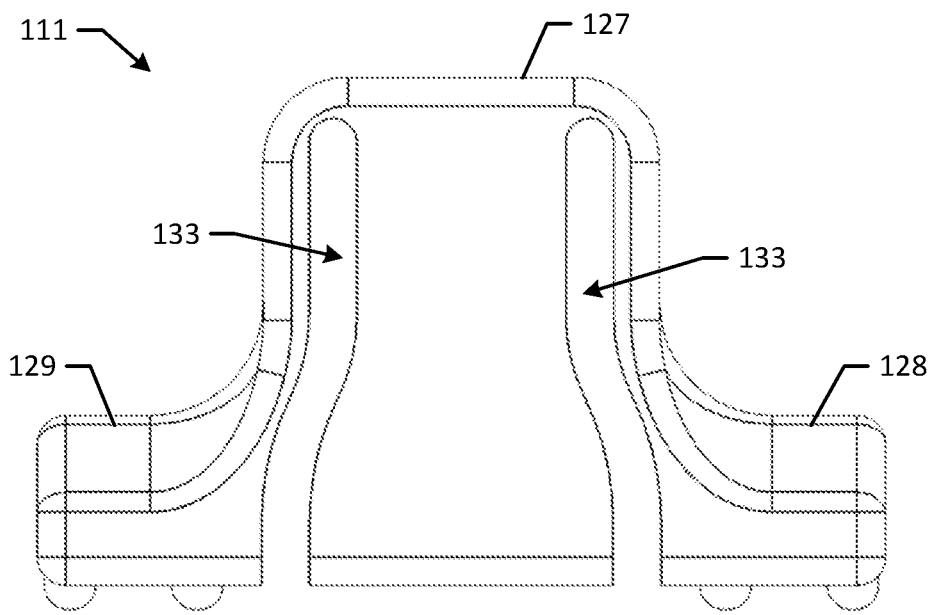
FIG. 1E is a plan view of the first attachment side of the dynamic interspinous process device of FIG. 1A.

It will be appreciated that the slots 133 may be configured to allow portions of the first attachment side 111 to move relative to one another. In particular, one of the slots 133 may be configured to allow the first wing 128 to move toward the central portion 127 and the spacer 130, in the direction of the longitudinal axis $A_L$ of the device 100, as these portions compress the slot 133, and also to allow the first wing 128 to move away from the central portion 127 and the spacer 130, in the direction of the longitudinal axis $A_L$ of the device 100, as these portions expand the slot 133. In a similar manner, the other slot 133 may be configured to allow the second wing 129 to move toward the central portion 127 and the spacer 130, in the direction of the longitudinal axis $A_L$ of the device 100, as these portions compress the slot 133, and also to allow the second wing 129 to move away from the central portion 127 and the spacer 130, in the direction of the longitudinal axis $A_L$ of the device 100, as these portions expand the slot 133. As a result, the first wing 128 and the second wing 129 may be configured to move toward one another as one or both of the slots 133 are compressed, and to move away from one another as one or both of the slots 133 are expanded. In will be appreciated that, during such movement of the wings 128, 129, one or more regions of the first attachment side 111 surrounding the slots 133, such as the regions of the central portion 127 surrounding the terminal ends of the slots 133, may flex or may be compressed to accommodate the compression or expansion of the slots 133. In effect, the slots 133 may cause the first attachment side 111 to function as a spring which may be compressed or extended in the direction of the longitudinal axis $A_L$ of the device 100 but has a natural tendency to return to a natural state as shown in FIG. 1E.

In a similar manner, the second attachment side 112 may include one or more slots 153 (which also may be referred to as a "dynamic slot," a "cutout," an "opening," or a "slit") defined therein and configured to allow relative movement of portions of the second attachment side 112. In certain embodiments, as shown, the second attachment side 112 may include a pair of the slots 153 spaced apart from one another in the direction of the longitudinal axis $A_L$ of the device 100. In certain embodiments, as shown, the slots 153 may be formed at least partially, or entirely, within the central portion 147 of the second attachment side 112. Each slot 153 may have an elongated shape extending in the direction of the second transverse axis $A_{T2}$ of the device 100. In certain embodiments, as shown, each slot 153 may extend from the first side 143 to the second side 144 of the second attachment side 112. Further, in certain embodiments, as shown, each slot 153 may extend from the fourth side 146 of the second attachment side 112 toward, but not to, the third side 145 of the second attachment side 112. In other words, the slot 153 may be open along the fourth side 146 and may terminate at a location spaced apart from the third side 145. In certain embodiments, as shown, each slot 153 may have one or more straight portions extending in a linear manner in the direction of the second transverse axis $A_{T2}$ of the device 100 and one or more curved or otherwise contoured portions bending transverse to the second transverse axis $A_{T2}$ in the direction of the longitudinal axis $A_L$ of the device 100. In other embodiments, each slot 153 may be straight or may be contoured along the entire extent of the slot 153. Various other configurations of the slots 153 may be used in other embodiments.

Figure 1F:
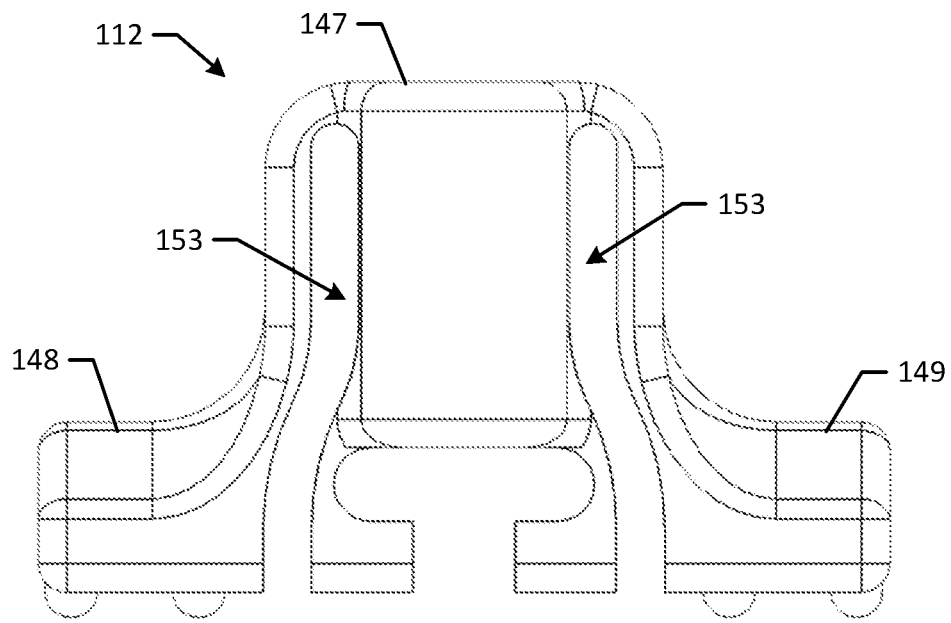
FIG. 1F is a plan view of the second attachment side of the dynamic interspinous process device of FIG. 1A.

It will be appreciated that the slots 153 may be configured to allow portions of the second attachment side 112 to move relative to one another. In particular, one of the slots 153 may be configured to allow the first wing 148 to move toward the central portion 147 and the spacer slot 150, in the direction of the longitudinal axis $A_L$ of the device 100, as these portions compress the slot 153, and also to allow the first wing 148 to move away from the central portion 147 and the spacer slot 150, in the direction of the longitudinal axis $A_L$ of the device 100, as these portions expand the slot 153. In a similar manner, the other slot 153 may be configured to allow the second wing 149 to move toward the central portion 147 and the spacer slot 150, in the direction of the longitudinal axis $A_L$ of the device 100, as these portions compress the slot 153, and also to allow the second wing 149 to move away from the central portion 147 and the spacer slot 150, in the direction of the longitudinal axis $A_L$ of the device 100, as these portions expand the slot 153. As a result, the first wing 148 and the second wing 149 may be configured to move toward one another as one or both of the slots 153 are compressed, and to move away from one another as one or both of the slots 153 are expanded. In will be appreciated that, during such movement of the wings 148, 149, one or more regions of the second attachment side 112 surrounding the slots 153, such as the regions of the central portion 147 surrounding the terminal ends of the slots 153, may flex or may be compressed to accommodate the compression or expansion of the slots 153. In effect, the slots 153 may cause the second attachment side 112 to function as a spring which may be compressed or extended in the direction of the longitudinal axis $A_L$ of the device 100 but has a natural tendency to return to a natural state as shown in FIG. 1F. In certain embodiments, as shown, the slots 133 of the first attachment side 111 may be formed as a mirror image of the slots 153 of the second attachment side 112. In other embodiments, the number, shape, or configuration of the slots 133 of the first attachment side 111 may be different than the number, shape, or configuration of the slots 153 of the second attachment side 112. Various configurations of the slots 133 and the slots 153 may be used to allow for a desired range of movement of the corresponding vertebrae.

Figure 1G:
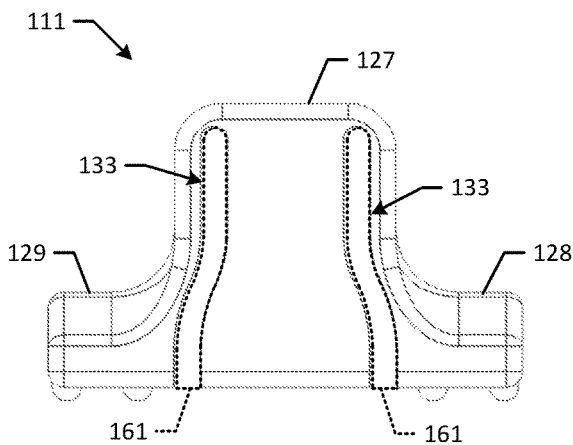
FIG. 1G is a plan view of the first attachment side and a number of resistance means of the dynamic interspinous process device of FIG. 1A.
Figure 1H:
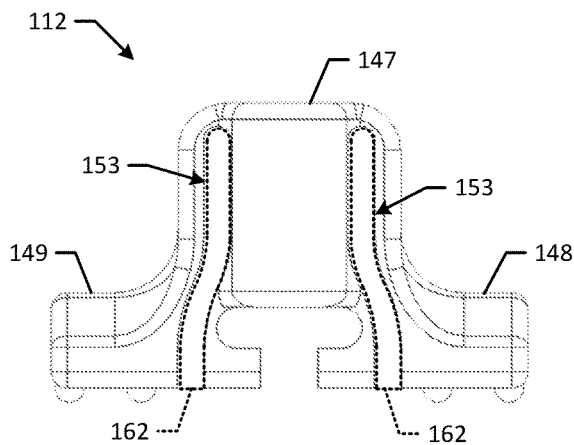
FIG. 1H is a plan view of the second attachment side and a number of resistance means of the dynamic interspinous process device of FIG. 1A.

In certain embodiments, the device 100 may include means for varying resistance to the relative movement between the first wing 128 and the second wing 129 of the first attachment side 111 over at least a portion of the range of motion of the wings 128, 129 and for varying resistance to the relative movement between the first wing 148 and the second wing 149 of the second attachment side 112 over at least a portion of the range of motion of the wings 148, 149. In this manner, the device 100 may vary the resistance to the relative movement between the treated vertebrae over at least a portion of the range of motion of the vertebrae allowed by the device 100. FIGS. 1G and 1H illustrate an embodiment in which the device 100 includes a pair of resistance means for varying resistance to the relative movement between the wings 128, 129 and between the wings 148, 149. As shown, the first attachment side 111 may include a pair of resistance means 161 (which also may be referred to as a "resistance insert," a "resistance member" or a "biasing member") configured for varying resistance to movement of the wings 128, 129 relative to the central portion 127 and relative to one another over at least a portion of the range of motion of these features as may be allowed by the slots 133. In certain embodiments, as shown, each resistance means 161 may be an insert configured to be inserted into and retained within one of the slots 133. In certain embodiments, the resistance means 161 may be removably received within the slots 133, such that the resistance means 161 may be placed therein when resistance is desired and may be removed therefrom when resistance is not desired. In other embodiments, the resistance means 161 may be securely fixed within the slots 133, such that the resistance means 161 are not removable therefrom. In certain embodiments, each resistance means 161 may be formed of a compressible material or a resiliently deformable material, such as a biocompatible polymer or other suitable material, which may be compressed by the relative movement of surrounding portions of the first attachment side 111 but may have a natural tendency to return to a natural state when compression forces are removed. It will be appreciated that a durometer of the compressible material or resiliently deformable material may be selected to provide a desired resistance to the relative movement of surrounding portions of the first attachment side 111. In other embodiments, each resistance means 161 may be formed as a spring, such as a compression spring, which may function similar to the compressible material or resiliently deformable material member. In certain embodiments, as shown, each resistance means 161 may fill or substantially fill the entirety of the respective slot 133. In other embodiments, each resistance means 161 may fill only a portion of the respective slot 133.

According to the illustrated embodiment, each resistance means 161 may be configured to resist movement of one of the wings 128, 129 toward the central portion 127, and thus the pair of resistance means 161 collectively may resist relative movement of the wings 128, 129 toward one another. In particular, as the wings 128, 129 move toward the central portion 127 and toward one another and the slots 133 are compressed, the resistance means 161 may be compressed, thereby resisting, but not preventing, further movement of the wings 128, 129 toward the central portion 127 and toward one another. Further, the resistance means 161 may provide a biasing force acting on the portions of the first attachment side 111 surrounding the slots 133, biasing the wings 128, 129 toward their home or natural position and the slots 133 to their home or natural state.

In a similar manner, the second attachment side 112 may include a pair of resistance means 162 (which also may be referred to as a "resistance insert," a "resistance member" or a "biasing member") configured for varying resistance to movement of the wings 148, 149 relative to the central portion 147 and relative to one another over at least a portion of the range of motion of these features as may be allowed by the slots 153. In certain embodiments, as shown, each resistance means 162 may be an insert configured to be inserted into and retained within one of the slots 153. In certain embodiments, the resistance means 162 may be removably received within the slots 153, such that the resistance means 162 may be placed therein when resistance is desired and may be removed therefrom when resistance is not desired. In other embodiments, the resistance means 162 may be securely fixed within the slots 153, such that the resistance means 162 are not removable therefrom. In certain embodiments, each resistance means 162 may be formed of a compressible material or a resiliently deformable material, such as a biocompatible polymer or other suitable material, which may be compressed by the relative movement of surrounding portions of the second attachment side 112 but may have a natural tendency to return to a natural state when compression forces are removed. It will be appreciated that a durometer of the compressible material or resiliently deformable material may be selected to provide a desired resistance to the relative movement of surrounding portions of the second attachment side 112. In other embodiments, each resistance means 162 may be formed as a spring, such as a compression spring, which may function similar to the compressible material or resiliently deformable material member. In certain embodiments, as shown, each resistance means 162 may fill or substantially fill the entirety of the respective slot 153. In other embodiments, each resistance means 162 may fill only a portion of the respective slot 153.

According to the illustrated embodiment, each resistance means 162 may be configured to resist movement of one of the wings 148, 149 toward the central portion 147, and thus the pair of resistance means 162 collectively may resist relative movement of the wings 148, 149 toward one another. In particular, as the wings 148, 149 move toward the central portion 147 and toward one another and the slots 153 are compressed, the resistance means 162 may be compressed, thereby resisting, but not preventing, further movement of the wings 148, 149 toward the central portion 147 and toward one another. Further, the resistance means 162 may provide a biasing force acting on the portions of the second attachment side 112 surrounding the slots 153, biasing the wings 148, 149 toward their home or natural position and the slots 153 to their home or natural state.

It will be appreciated that the resistance means 161, 162 of the device 100 may be used to vary resistance to the relative movement between the treated vertebrae, when desired. In particular, the resistance means 161, 162 may be used to increase resistance to the relative movement between the treated vertebrae over at least a portion of the range of motion of the vertebrae allowed by the device 100. In this manner, the device 100 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 161, 162 may be selected to provide a desired degree of resistance to the relative motion of the treated vertebrae.

Figure 1I:
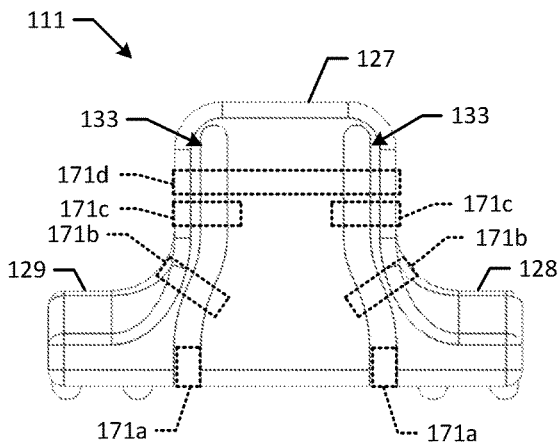
FIG. 1I is a plan view of the first attachment side and a number of fixation means of the dynamic interspinous process device of FIG. 1A.
Figure 1J:
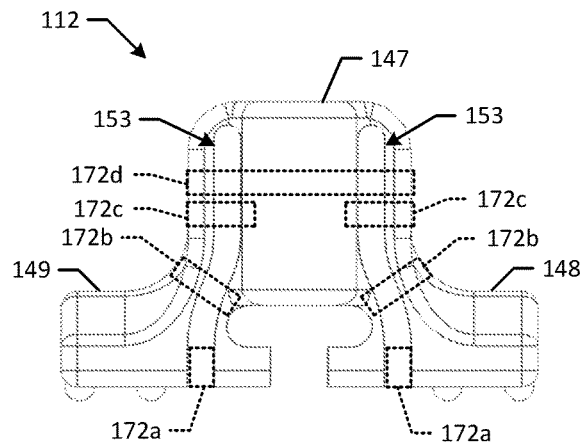
FIG. 1J is a plan view of the second attachment side and a number of fixation means of the dynamic interspinous process device of FIG. 1A.

In certain embodiments, the device 100 may include means for preventing or inhibiting the relative movement between the first wing 128 and the second wing 129 of the first attachment side 111 and for preventing or inhibiting the relative movement between the first wing 148 and the second wing 149 of the second attachment side 112. In this manner, the device 100 may prevent or inhibit the relative movement between the treated vertebrae. FIGS. 1I and 1J illustrate embodiments in which the device 100 includes one or more fixation means for preventing or inhibiting the relative movement between the wings 128, 129 and between the wings 148, 149. As shown, the first attachment side 111 may include one or more fixation means 171 (which also may be referred to as a "fixation insert," a "fixation member," a "fastener," or a "lock") configured for preventing or inhibiting movement of the wings 128, 129 relative to the central portion 127 and relative to one another as may be allowed by the slots 133. In certain embodiments, the fixation means 171 may be removably attached to the central portion 127 and/or one of the wings 128, 129. In other embodiments, the fixation means 171 may be fixedly secured to the central portion 127 and/or one or the wings 128, 129. In certain embodiments, as shown, a pair of the fixation means 171*a* may be configured to be inserted at least partially into and retained within the respective slots 133. Each fixation means 171*a* may engage portions of the first attachment side 111 surrounding the respective slot 133 such that the fixation means 171*a* prevents or inhibits at least a portion of the slot 133 from expanding and/or collapsing. In certain embodiments, each fixation means 171*a* may be a fastener, such as a set screw having a reverse angle thread for threadably engaging and retaining mating threaded portions of the first attachment side 111. In certain embodiments, as shown, each fixation means 171*a* may be inserted, in a direction parallel to the second transverse axis $A_{T2}$ of the device 100, into the open end of the respective slot 133.

In certain embodiments, as shown, a pair of the fixation means 171*b* may be configured to be inserted at least partially into and through the respective slots 133. Each fixation means 171*b* may engage portions of the first attachment side 111 surrounding the respective slot 133 such that the fixation means 171*b* prevents or inhibits at least a portion of the slot 133 from expanding and/or collapsing. In certain embodiments, each fixation means 171*b* may be a fastener, such as a set screw for threadably engaging and retaining mating threaded portions of the first attachment side 111. In certain embodiments, as shown, each fixation means 171*b* may be inserted through a first portion of the first attachment side 111 along one side of the respective slot 133, through a portion of the slot 133, and into a second portion of the first attachment side 111 along an opposite second side of the respective slot 133. In this manner, each fixation means 171*b* may prevent or inhibit compression and expansion of at least a portion of the slot 133 by securely engaging portions of the first attachment side 111 along opposite sides of the slot 133. In other embodiments, each fixation means 171*b* may be inserted through a first portion of the first attachment side 111 along one side of the respective slot 133, through a portion of the slot 133, and may abut a second portion of the first attachment side 111 along an opposite second side of the respective slot 133. In this manner, each fixation means 171*b* may prevent or inhibit compression of at least a portion of the slot 133 while still allowing expansion of the portion of the slot 133. In still other embodiments, each fixation means 171*b* may be inserted through a first portion of the first attachment side 111 along one side of the respective slot 133, into a portion of the slot 133, and may be spaced apart from a second portion of the first attachment side 111 along an opposite second side of the respective slot 133. In this manner, each fixation means 171*b* may allow, but limit, compression of at least a portion of the slot 133 while still allowing expansion of the portion of the slot 133. In certain embodiments, as shown, each fixation means 171*b* may be inserted, in a direction transverse to each of the longitudinal axis $A_L$ and the second transverse axis $A_{T2}$ of the device 100, through an interface of the central portion 127 and one of the wings 128, 129 and through an adjacent portion of the respective slot 133.

In certain embodiments, as shown, a pair of the fixation means 171*c* may be configured to be inserted at least partially into and through the respective slots 133. Each fixation means 171*c* may engage portions of the first attachment side 111 surrounding the respective slot 133 such that the fixation means 171*c* prevents or inhibits at least a portion of the slot 133 from expanding and/or collapsing. In certain embodiments, each fixation means 171*c* may be a fastener, such as a set screw for threadably engaging and retaining mating threaded portions of the first attachment side 111. In certain embodiments, as shown, each fixation means 171*c* may be inserted through a first portion of the first attachment side 111 along one side of the respective slot 133, through a portion of the slot 133, and into a second portion of the first attachment side 111 along an opposite second side of the respective slot 133. In this manner, each fixation means 171*c* may prevent or inhibit compression and expansion of at least a portion of the slot 133 by securely engaging portions of the first attachment side 111 along opposite sides of the slot 133. In other embodiments, each fixation means 171*c* may be inserted through a first portion of the first attachment side 111 along one side of the respective slot 133, through a portion of the slot 133, and may abut a second portion of the first attachment side 111 along an opposite second side of the respective slot 133. In this manner, each fixation means 171*c* may prevent or inhibit compression of at least a portion of the slot 133 while still allowing expansion of the portion of the slot 133. In still other embodiments, each fixation means 171*c* may be inserted through a first portion of the first attachment side 111 along one side of the respective slot 133, into a portion of the slot 133, and may be spaced apart from a second portion of the first attachment side 111 along an opposite second side of the respective slot 133. In this manner, each fixation means 171*c* may allow, but limit, compression of at least a portion of the slot 133 while still allowing expansion of the portion of the slot 133. In certain embodiments, as shown, each fixation means 171*c* may be inserted, in a direction parallel to the longitudinal axis $A_L$ of the device 100, through the central portion 127.

In certain embodiments, as shown, a single fixation means 171*d* may be configured to be inserted at least partially into and through each of the slots 133. The fixation means 171*d* may engage portions of the first attachment side 111 surrounding each of the slots 133 such that the fixation means 171*d* prevents or inhibits at least a portion of each slot 133 from expanding and/or collapsing. In certain embodiments, the fixation means 171*d* may be a fastener, such as a set screw for threadably engaging and retaining mating threaded portions of the first attachment side 111. In certain embodiments, as shown, the fixation means 171*d* may be inserted through a first portion of the first attachment side 111 along one side of a first slot 133, through a portion of the first slot 133, through a second portion of the first attachment side 111 along an opposite second side of the first slot 133, through a third portion of the first attachment side 111 along one side of a second slot 133, through a portion of the second slot 133, and through a fourth portion of the first attachment side 111 along an opposite second side of the second slot 133. In this manner, the fixation means 171*d* may prevent or inhibit compression and expansion of at least a portion of each slot 133 by securely engaging portions of the first attachment side 111 along opposite sides of each slot 133. In certain embodiments, as shown, the fixation means 171*d* may be inserted, in a direction parallel to the longitudinal axis $A_L$ of the device 100, through the central portion 127.

In a similar manner, the second attachment side 112 may include one or more fixation means 172 (which also may be referred to as a "fixation insert," a "fixation member," a "fastener," or a "lock") configured for preventing or inhibiting movement of the wings 148, 149 relative to the central portion 147 and relative to one another as may be allowed by the slots 153. In certain embodiments, the fixation means 172 may be removably attached to the central portion 147 and/or one of the wings 148, 149. In other embodiments, the fixation means 172 may be fixedly secured to the central portion 147 and/or one or the wings 148, 149. In certain embodiments, as shown, a pair of the fixation means 172a may be configured to be inserted at least partially into and retained within the respective slots 153. Each fixation means 172a may engage portions of the second attachment side 112 surrounding the respective slot 153 such that the fixation means 172a prevents or inhibits at least a portion of the slot 153 from expanding and/or collapsing. In certain embodiments, each fixation means 172a may be a fastener, such as a set screw having a reverse angle thread for threadably engaging and retaining mating threaded portions of the second attachment side 112. In certain embodiments, as shown, each fixation means 172a may be inserted, in a direction parallel to the second transverse axis $A_{T2}$ of the device 100, into the open end of the respective slot 153.

In certain embodiments, as shown, a pair of the fixation means 172b may be configured to be inserted at least partially into and through the respective slots 153. Each fixation means 172b may engage portions of the second attachment side 112 surrounding the respective slot 153 such that the fixation means 172b prevents or inhibits at least a portion of the slot 153 from expanding and/or collapsing. In certain embodiments, each fixation means 172b may be a fastener, such as a set screw for threadably engaging and retaining mating threaded portions of the second attachment side 112. In certain embodiments, as shown, each fixation means 172b may be inserted through a first portion of the second attachment side 112 along one side of the respective slot 153, through a portion of the slot 153, and into a second portion of the second attachment side 112 along an opposite second side of the respective slot 153. In this manner, each fixation means 172b may prevent or inhibit compression and expansion of at least a portion of the slot 153 by securely engaging portions of the second attachment side 112 along opposite sides of the slot 153. In other embodiments, each fixation means 172b may be inserted through a first portion of the second attachment side 112 along one side of the respective slot 153, through a portion of the slot 153, and may abut a second portion of the second attachment side 112 along an opposite second side of the respective slot 153. In this manner, each fixation means 172b may prevent or inhibit compression of at least a portion of the slot 153 while still allowing expansion of the portion of the slot 153. In still other embodiments, each fixation means 172b may be inserted through a first portion of the second attachment side 112 along one side of the respective slot 153, into a portion of the slot 153, and may be spaced apart from a second portion of the second attachment side 112 along an opposite second side of the respective slot 153. In this manner, each fixation means 172b may allow, but limit, compression of at least a portion of the slot 153 while still allowing expansion of the portion of the slot 153. In certain embodiments, as shown, each fixation means 172b may be inserted, in a direction transverse to each of the longitudinal axis $A_L$ and the second transverse axis $A_{T2}$ of the device 100, through an interface of the central portion 147 and one of the wings 148, 149 and through an adjacent portion of the respective slot 153.

In certain embodiments, as shown, a pair of the fixation means 172c may be configured to be inserted at least partially into and through the respective slots 153. Each fixation means 172c may engage portions of the second attachment side 112 surrounding the respective slot 153 such that the fixation means 172c prevents or inhibits at least a portion of the slot 153 from expanding and/or collapsing. In certain embodiments, each fixation means 172c may be a fastener, such as a set screw for threadably engaging and retaining mating threaded portions of the second attachment side 112. In certain embodiments, as shown, each fixation means 172c may be inserted through a first portion of the second attachment side 112 along one side of the respective slot 153, through a portion of the slot 153, and into a second portion of the second attachment side 112 along an opposite second side of the respective slot 153. In this manner, each fixation means 172c may prevent or inhibit compression and expansion of at least a portion of the slot 153 by securely engaging portions of the second attachment side 112 along opposite sides of the slot 153. In other embodiments, each fixation means 172c may be inserted through a first portion of the second attachment side 112 along one side of the respective slot 153, through a portion of the slot 153, and may abut a second portion of the second attachment side 112 along an opposite second side of the respective slot 153. In this manner, each fixation means 172c may prevent or inhibit compression of at least a portion of the slot 153 while still allowing expansion of the portion of the slot 153. In still other embodiments, each fixation means 172c may be inserted through a first portion of the second attachment side 112 along one side of the respective slot 153, into a portion of the slot 153, and may be spaced apart from a second portion of the second attachment side 112 along an opposite second side of the respective slot 153. In this manner, each fixation means 172c may allow, but limit, compression of at least a portion of the slot 153 while still allowing expansion of the portion of the slot 153. In certain embodiments, as shown, each fixation means 172c may be inserted, in a direction parallel to the longitudinal axis $A_L$ of the device 100, through the central portion 147.

In certain embodiments, as shown, a single fixation means 172d may be configured to be inserted at least partially into and through each of the slots 153. The fixation means 172d may engage portions of the second attachment side 112 surrounding each of the slots 153 such that the fixation means 172d prevents or inhibits at least a portion of each slot 153 from expanding and/or collapsing. In certain embodiments, the fixation means 172d may be a fastener, such as a set screw for threadably engaging and retaining mating threaded portions of the second attachment side 112. In certain embodiments, as shown, the fixation means 172d may be inserted through a first portion of the second attachment side 112 along one side of a first slot 153, through a portion of the first slot 153, through a second portion of the second attachment side 112 along an opposite second side of the first slot 153, through a third portion of the second attachment side 112 along one side of a second slot 153, through a portion of the second slot 153, and through a fourth portion of the second attachment side 112 along an opposite second side of the second slot 153. In this manner, the fixation means 172d may prevent or inhibit compression and expansion of at least a portion of each slot 153 by securely engaging portions of the second attachment side 112 along opposite sides of each slot 153. In certain embodiments, as shown, the fixation means 172d may be inserted, in a direction parallel to the longitudinal axis $A_L$ of the device 100, through the central portion 147.

It will be appreciated that the fixation means 171, 172 of the device 100 may be used to control the relative movement between the treated vertebrae, when desired. In particular, the fixation means 171, 172 may be used to prevent or inhibit relative movement between the treated vertebrae. In this manner, the device 100 may be used as a dynamic device or a rigid device, with the ability to convert the device 100 between a dynamic configuration and a rigid configuration, as may be desired in certain applications. The fixation means 171, 172 may be used to convert the device 100 between the dynamic configuration and the rigid configuration prior to implantation of the device 100, during initial implantation of the device 100 as a part of an initial surgery, or during a follow-up surgery.

Figure 1K:
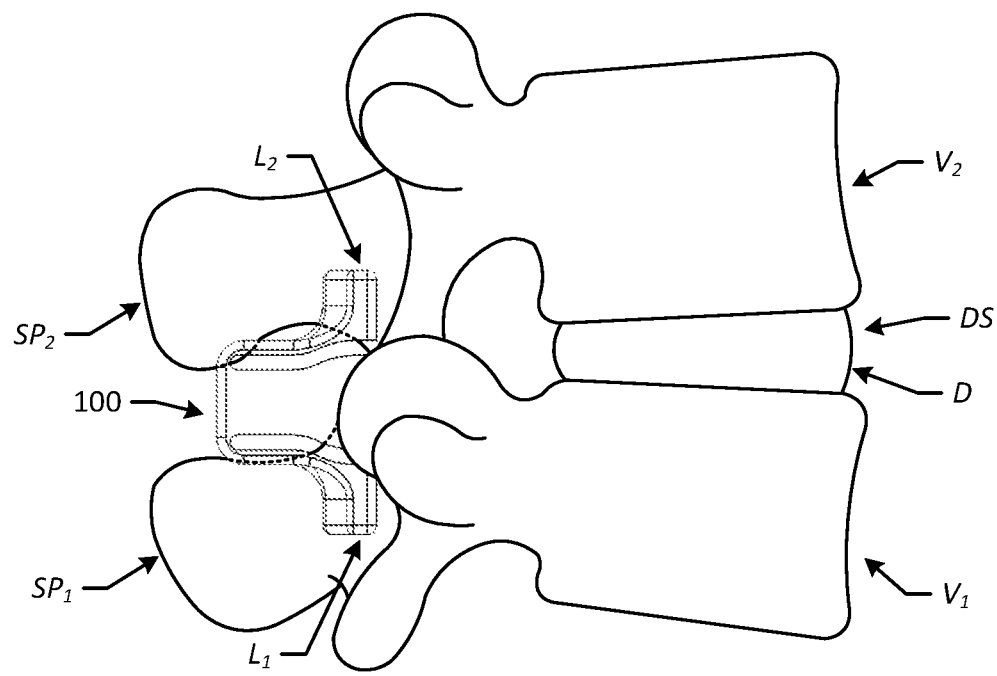
FIG. 1K is a side view of the dynamic interspinous process device of FIG. 1A implanted with respect to a first vertebra and a second vertebra in accordance with one or more embodiments of the present disclosure.
Figure 1L:
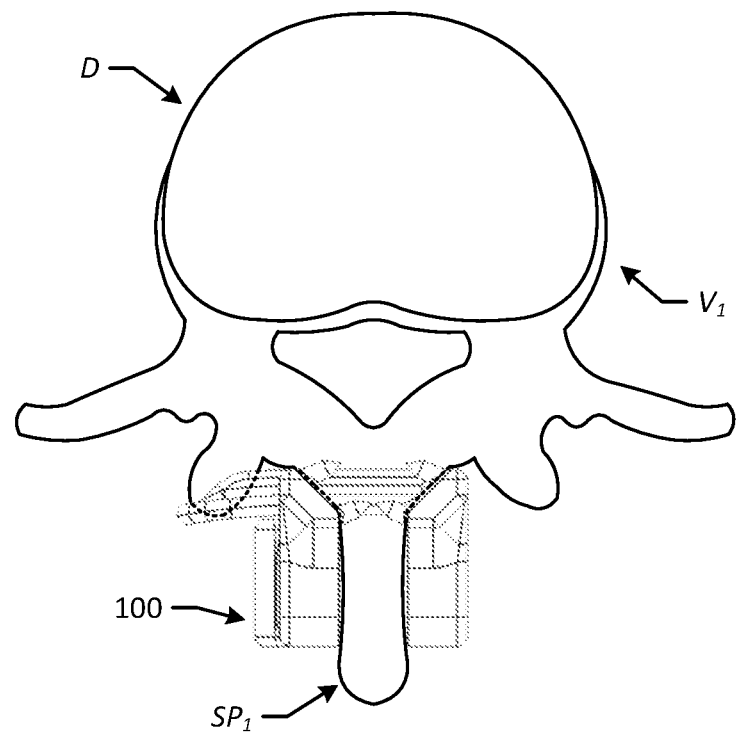
FIG. 1L is a top view of the dynamic interspinous process device of FIG. 1A implanted with respect to the first vertebra, the second vertebra being removed from view for purposes of illustration.

FIGS. 1K and 1L illustrate an example implantation of the device 100 with respect to a first vertebra $V_1$ and an adjacent second vertebra $V_2$. As shown, the first attachment side 111 and the second attachment side 112 may be positioned relative to the vertebrae $V_1$, $V_2$ such that the spacer 130 is positioned between a first spinous process $SP_1$ of the first vertebra $V_1$ and a second spinous process $SP_2$ of the second vertebra $V_2$. In this manner, the spacer 130 may limit a minimum spacing between the spinous processes $SP_1$, $SP_2$. Additionally, the first attachment side 111 and the second attachment side 112 may be positioned relative to the vertebrae $V_1$, $V_2$ such that the respective wings 128, 129 of the first attachment side 111 and the respective wings 148, 149 of the second attachment side 112 engage a first lamina $L_1$ of the first vertebra $V_1$ and a second lamina $L_2$ of the second vertebra $V_2$. In this manner, the respective bone fasteners 131 of the first attachment side 111 and the respective bone fasteners 151 of the second attachment side 112 may penetrate and securely engage the laminae $L_1$, $L_2$. Accordingly, the implanted device 100 may stabilize the vertebrae $V_1$, $V_2$, although the device 100 may allow relative movement of the vertebrae $V_1$, $V_2$. In particular, the slots 133, 153 of the device 100 may allow relative movement of the vertebrae $V_1$, $V_2$ in sagittal plane of the patient, thereby allowing flexion and extension of the treated segment of the spine. It will be appreciated that the configuration of the slots 133, 153 may be varied, for example, by varying the number, size, and/or shape the slots 133, 153 to allow a desired range of motion in the sagittal plane. Further, the material from which the first attachment side 111 and the second attachment side 112 are formed may be selected to achieve the desired range of motion. In certain embodiments, the first attachment side 111 and the second attachment side 112 may be formed of titanium, although other suitable metals, polymers, or other materials may be used in other embodiments. Meanwhile, the device 100 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 100 and the disc D. In other embodiments in which the native disc D is removed, an interbody device, such as a cage or a spacer, may be implanted within the disc space DS (i.e., the intervertebral space) and the loads carried by the treated spinal segment may be shared by the device 100 and the interbody device. As described above, the device 100 may be used in conjunction with other additional hardware, such that the device 100 and the additional hardware collectively stabilize the treated segment of the spine and share loads carried thereby. It will be appreciated that the foregoing description and the corresponding drawings are merely examples of the device 100 and that other configurations and modifications may be made.

FIGS. 2A-2L illustrate an interspinous process device 200 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 200 may be configured for implantation relative to a first vertebra and an adjacent second vertebra, as described below, specifically with reference to FIGS. 2K and 2L. In particular, a portion of the interspinous process device 200 may be positioned between the spinous process of the first vertebra and the spinous process of the second vertebra, while one or more other portions of the interspinous process device 200 engage the spinous processes, the laminae, and/or other portions of the respective vertebra. As described below, the interspinous process device 200 may allow a desired range of relative movement between the treated vertebrae, which may be desirable in certain treatment applications. The interspinous process device 200 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 200, itself or in combination with additional hardware, may provide the structural support necessary to restore and maintain normal spacing and alignment of the treated vertebrae while avoiding certain drawbacks presented by existing interspinous process devices.

The interspinous process device 200 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 200 may include a first end 201 and a second end 202 disposed opposite the first end 201 in the direction of the longitudinal axis $A_L$. As described below, the device 200 may be implanted with the longitudinal axis $A_L$ extending in a direction substantially parallel to the sagittal plane and the coronal plane of the patient and transverse to the transverse plane of the patient. In this manner, depending on the orientation of the device 200 upon implantation thereof, one of the first end 201 and the second end 202 of the device 200 may be referred to as a the "superior end" of the device 200, and the other of the first end 201 and the second end 202 of the device 200 may be referred to as the "inferior end" of the device 200. The device 200 also may include a first side 203 extending from the first end 201 to the second end 202, and a second side 204 disposed opposite the first side 203 in the direction of the first transverse axis $A_{T1}$ and extending from the first end 201 to the second end 202. The device 200 may be implanted with the first transverse axis $A_{T1}$ extending in a direction substantially parallel to the coronal plane and the transverse plane of the patient and transverse to the sagittal plane of the patient. In this manner, depending on the orientation of the device 200 upon implantation thereof, one of the first side 203 and the second side 204 of the device 200 may be referred to as a the "right side" of the device 200, and the other of the first side 203 and the second side 204 of the device 200 may be referred to as the "left side" of the device 200. The device 200 further may include a third side 205 extending from the first end 201 to the second end 202 and from the first side 203 to the second side 204, and a fourth side 206 disposed opposite the third side 205 in the direction of the second transverse axis $A_{T2}$ and extending from the first end 201 to the second end 202 and from the first side 203 to the second side 204. The device 200 may be implanted with the second transverse axis $A_{T2}$ extending in a direction substantially parallel to the sagittal plane and the transverse plane of the patient and transverse to the coronal plane of the patient. As described below, the device 200 may be oriented upon implantation thereof such that the third side 205 faces posteriorly and the fourth side 206 faces anteriorly with respect to the patient. In this manner, the third side 205 may be referred to as the "posterior side" of the device 200, and the fourth side 206 may be referred to as the "anterior side" of the device 200. The device 200 may have an overall "length" extending from the first end 201 to the second end 202 in the direction of the longitudinal axis $A_L$, an overall "width" extending from the first side 203 to the second side 204 in the direction of the first transverse axis $A_{T1}$, and an overall "height" extending from the third side 205 to the fourth side 206 in the direction of the second transverse axis $A_{T2}$. Further, various components and features of the device 200 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 200 may include a first attachment side 211 (which also may be referred to as a "first attachment portion," a "first attachment assembly," or a "first plate") and a second attachment side 212 (which also may be referred to as a "second attachment portion," a "second attachment assembly," or a "second plate") configured for removably attaching to one another via a securing means 213. During use of the device 200, one of the first attachment side 211 and the second attachment side 212 may be disposed, at least partially, along the right side of the patient's spine, and the other of the first attachment side 211 and the second attachment side 212 may be disposed, at least partially, along the right side of the patient's spine. It will be appreciated that the first attachment side 211 and the second attachment side 212 may include corresponding features that are mirror images of one another, although certain differences between the first attachment side 211 and the second attachment side 212 may exist, as described below. In certain embodiments, the first attachment side 211 and the second attachment side 212 may be formed of a metal, such as titanium or stainless steel, although other suitable materials, such as polyether ether ketone (PEEK), other polymers, or composites, may be used.

The first attachment side 211 may have a first end 221, a second end 222 disposed opposite the first end 221, a first side 223 (which also may be referred to as an "interior side"), a second side 224 (which also may be referred to as an "exterior side") disposed opposite the first side 223, a third side 225 (which also may be referred to as an "posterior side"), and a fourth side 226 (which also may be referred to as an "anterior side") disposed opposite the third side 125. As shown, the first attachment side 211 may include a central portion 227 and a pair of wings 228, 229 disposed on opposite sides of the central portion 227. In particular, the first wing 228 may extend from the central portion 227 to the first end 221 of the first attachment side 211, and the second wing 229 may extend from the central portion 227 to the second end 222 of the first attachment side 211. In certain embodiments, as shown, the wings 228, 229 may extend in opposite directions from the central portion 227 and may be formed as mirror images of one another. In other embodiments, the wings 228, 229 may extend in opposite directions from the central portion 227, but the first wing 228 may have a different shape or configuration than the second wing 229 such that the wings 228, 229 are not mirror images of one another. In certain embodiments, the wings 228, 229 may be shaped and configured in a manner similar to any one of the wing embodiments described and/or shown in the Prior Applications. Various other configurations of the wings 228, 229 may be used.

The first attachment side 211 also may include a spacer 230 extending from the first side 223 thereof. During use of the device 200, the spacer 230 may be positioned between the spinous processes of the respective vertebrae. In certain embodiments, as shown, the spacer 230 may extend from the central portion 227 of the first attachment side 211 and be integrally formed therewith. In other embodiments, the spacer 230 may be separately formed from and attached to the central portion 227 via an attachment mechanism. The first attachment side 211 further may include a number of engagement features configured for securely engaging the respective vertebrae. In certain embodiments, as shown, the engagement features may be one or more bone fasteners 231 extending from the first side 223 of the first attachment side 211. The bone fasteners 231 may be formed as spikes or barbs, although other forms and types of bone fasteners 231 may be used for securely engaging the vertebrae. In certain embodiments, one or more of the bone fasteners 231 may extend form the first wing 228, and one or more bone fasteners 231 may extend from the second wing 229. In certain embodiments, the first wing 228 may include a first number of bone fasteners 231 extending therefrom, and the second wing 229 may include a second number of bone fasteners 231 extending therefrom, wherein the first number is different than the second number. In this manner, the degree of engagement between the bone fasteners 231 of the first wing 228 and the corresponding vertebra may be different from the degree of engagement between the bone fasteners 231 of the second wing 229 and the corresponding vertebra. Such an arrangement may facilitate relative movement of the treated vertebrae, while minimizing certain stresses induced in the device 200. In certain embodiments, one of the first wing 228 and the second wing 229 may not include any bone fasteners 231 extending therefrom, and the other of the first wing 228 and the second wing 229 may include one or more of the bone fasteners 231 extending therefrom. Such an arrangement also may facilitate relative movement of the treated vertebrae, while minimizing certain stresses induced in the device 200. Various configurations of the bone fasteners 231 of the first attachment side 211 may be used. In certain embodiments, as shown, the bone fasteners 231 may be configured to engage the laminae of the respective vertebrae. In other embodiments, one or more of the bone fasteners 231 may be configured to engage the spinous processes, the laminae, and/or other portions of the respective vertebrae. As shown, the first attachment side 211 also may include an instrument engagement aperture 232 configured for receiving a portion of and cooperating with an instrument used for positioning the first attachment side 211 during implantation of the device 200. Example instruments for implantation of the device 200 are described in the Prior Applications.

In a similar manner, the second attachment side 212 may have a first end 241, a second end 242 disposed opposite the first end 241, a first side 243 (which also may be referred to as an "exterior side"), a second side 244 (which also may be referred to as an "interior side") disposed opposite the first side 243, a third side 245 (which also may be referred to as an "posterior side"), and a fourth side 246 (which also may be referred to as an "anterior side") disposed opposite the third side 245. As shown, the second attachment side 212 may include a central portion 247 and a pair of wings 248, 249 disposed on opposite sides of the central portion 247. In particular, the first wing 248 may extend from the central portion 247 to the first end 241 of the second attachment side 212, and the second wing 249 may extend from the central portion 247 to the second end 242 of the second attachment side 212. In certain embodiments, as shown, the wings 248, 249 may extend in opposite directions from the central portion 247 and may be formed as mirror images of one another. In other embodiments, the wings 248, 249 may extend in opposite directions from the central portion 247, but the first wing 248 may have a different shape or configuration than the second wing 249 such that the wings 248, 249 are not mirror images of one another. In certain embodiments, the wings 248, 249 may be shaped and configured in a manner similar to any one of the wing embodiments described and/or shown in the Prior Applications. Various other configurations of the wings 248, 249 may be used.

The second attachment side 212 also may include a spacer slot 250 extending through the second attachment side 212 from the first side 243 to the second side 244 thereof. During use of the device 200, the spacer slot 250 may be configured to receive the spacer 230 of the first attachment side 211 therethrough, as shown. In certain embodiments, as shown, the spacer slot 250 may be defined in the central portion 247 of the second attachment side 212 and may extend to the fourth side 246 thereof, although other positions of the spacer slot 250 may be used. The second attachment side 212 further may include a number of engagement features configured for securely engaging the respective vertebrae. In certain embodiments, as shown, the engagement features may be one or more bone fasteners 251 extending from the second side 244 of the second attachment side 212. The bone fasteners 251 may be formed as spikes or barbs, although other forms and types of bone fasteners 251 may be used for securely engaging the vertebrae. In certain embodiments, one or more of the bone fasteners 251 may extend form the first wing 248, and one or more bone fasteners 251 may extend from the second wing 249. In certain embodiments, the first wing 248 may include a first number of bone fasteners 251 extending therefrom, and the second wing 259 may include a second number of bone fasteners 251 extending therefrom, wherein the first number is different than the second number. In this manner, the degree of engagement between the bone fasteners 251 of the first wing 248 and the corresponding vertebra may be different from the degree of engagement between the bone fasteners 251 of the second wing 249 and the corresponding vertebra. Such an arrangement may facilitate relative movement of the treated vertebrae, while minimizing certain stresses induced in the device 200. In certain embodiments, one of the first wing 248 and the second wing 249 may not include any bone fasteners 251 extending therefrom, and the other of the first wing 248 and the second wing 249 may include one or more of the bone fasteners 251 extending therefrom. Such an arrangement also may facilitate relative movement of the treated vertebrae, while minimizing certain stresses induced in the device 200. Various configurations of the bone fasteners 251 of the second attachment side 212 may be used. In certain embodiments, as shown, the bone fasteners 251 may be configured to engage the laminae of the respective vertebrae. In other embodiments, one or more of the bone fasteners 251 may be configured to engage the spinous processes, the laminae, and/or other portions of the respective vertebrae. As shown, the second attachment side 212 also may include a securing aperture 252 configured to receive at least a portion of and cooperate with the securing means 213 for selectively fixing the first attachment side 211 and the second attachment side 212 relative to one another. The securing aperture 252 also may be configured for receiving a portion of and cooperating with an instrument used for positioning the second attachment side 212 during implantation of the device 200. Example instruments for implantation of the device 200 are described in the Prior Applications.

The securing means 213 may be configured for selectively fixing the first attachment side 211 and the second attachment side 212 relative to one another. In certain embodiments, as shown, the securing means 213 may be a fastener, such as a set screw, although other types of fasteners and other types of securing means may be used. As shown, the securing means may be inserted into and at least partially through the securing aperture 252 of the second attachment side 212. In this manner, the securing means 213 may be advanced through the securing aperture 252 until the securing means 213 engages the spacer 230 of the first attachment side 211 positioned within the spacer slot 250 of the second attachment side 212. Upon desired positioning of the first attachment side 211 and the second attachment side 212 with respect to the corresponding vertebrae of the patient, the securing means 213 may be tightened to maintain the spacing and orientation of the first attachment side 211 and the second attachment side 212 relative to one another and relative to the corresponding vertebrae. In certain embodiments, the securing means 213 may be formed of a metal, such as titanium or stainless steel, although other suitable materials, such as polyether ether ketone (PEEK), other polymers, or composites, may be used.

As described above, the device 200 may be configured to allow relative movement of the treated vertebrae upon implantation of the device 200. In particular, the device 200 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 211 and the second attachment side 212 each may include one or more features configured to facilitate such relative movement of the treated vertebrae. In particular, the first attachment side 211 may include one or more slots 233 (which also may be referred to as a "dynamic slot," a "cutout," an "opening," or a "slit") defined therein and configured to allow relative movement of portions of the first attachment side 211. In certain embodiments, as shown, the first attachment side 211 may include a plurality of the slots 233 spaced apart from one another in the direction of the longitudinal axis $A_L$ of the device 200. In certain embodiments, as shown, the slots 233 may be formed at least partially, or entirely, within the central portion 227 of the first attachment side 211. Each slot 233 may have an elongated shape extending in the direction of the second transverse axis $A_{T2}$ of the device 200. In certain embodiments, as shown, each slot 233 may extend from the first side 223 to the second side 224 of the first attachment side 211. Further, in certain embodiments, as shown, one or more of the slots 233 may extend from the fourth side 226 of the first attachment side 211 toward, but not to, the third side 225 of the first attachment side 211. In other words, such slots 233 may be open along the fourth side 226 and may terminate at a location spaced apart from the third side 225. In certain embodiments, as shown, one or more other slots 233 may extend from the third side 225 of the first attachment side 211 toward, but not to, the fourth side 226 of the first attachment side 211. In other words, such slots 233 may be open along the third side 225 and may terminate at a location spaced apart from the fourth side 226. In certain embodiments, as shown, each of the slots 233 may extend at an acute angle relative to the first transverse axis $A_{T1}$ of the device 200. In certain embodiments, as shown each slot 233 may have a straight shape along the entire extent of the slot 233, although the slot 233 may be tapered in the direction from the open end of the slot 233 to the closed end of the slot 233. In certain embodiments, as shown, the all of the slots 233 may be offset from the first transverse axis $A_{T1}$ of the device 200 toward one of the ends 201, 202 of the device in the direction of the longitudinal axis $A_L$ of the device 200. Various other configurations of the slots 233 may be used in other embodiments.

Figure 2A:
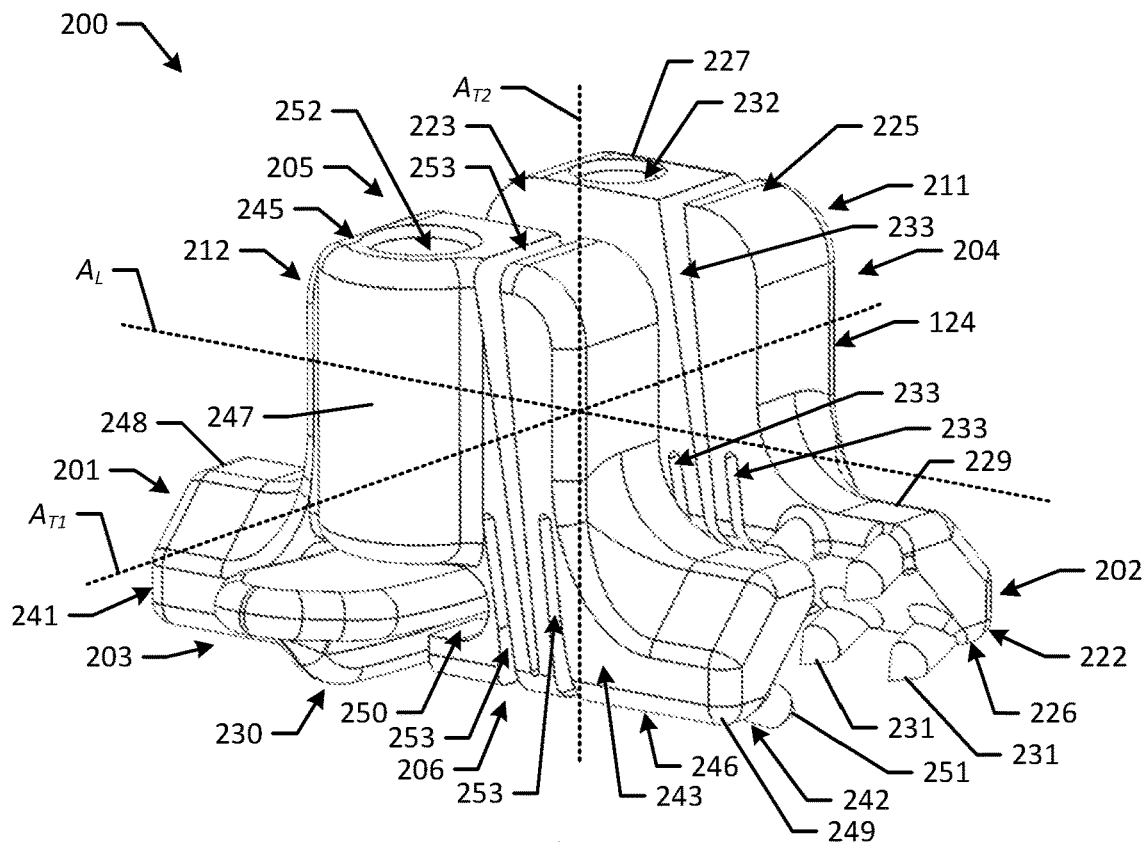
FIG. 2A is a perspective view of a dynamic interspinous process device in accordance with one or more embodiments of the present disclosure, showing a first attachment side and a second attachment side of the dynamic interspinous process device in an assembled state.
Figure 2B:
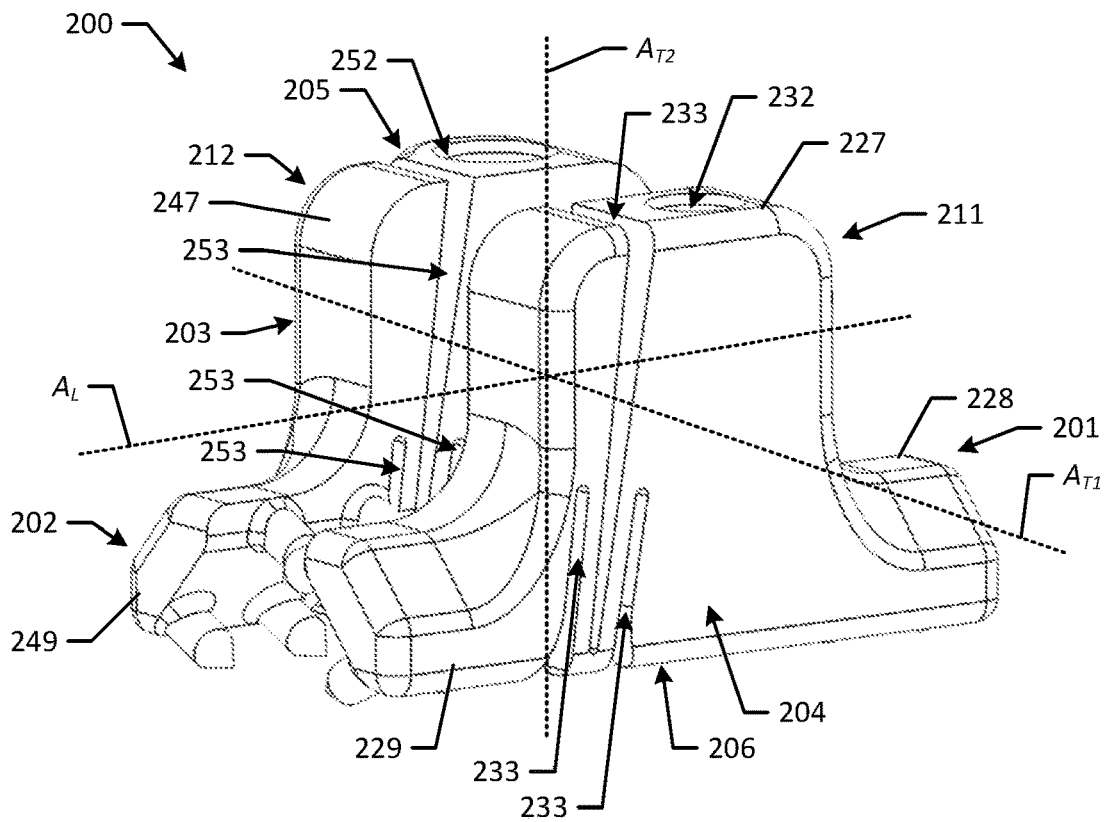
FIG. 2B is a perspective view of the dynamic interspinous process device of FIG. 2A, showing the first attachment side and the second attachment side in the assembled state.
Figure 2C:
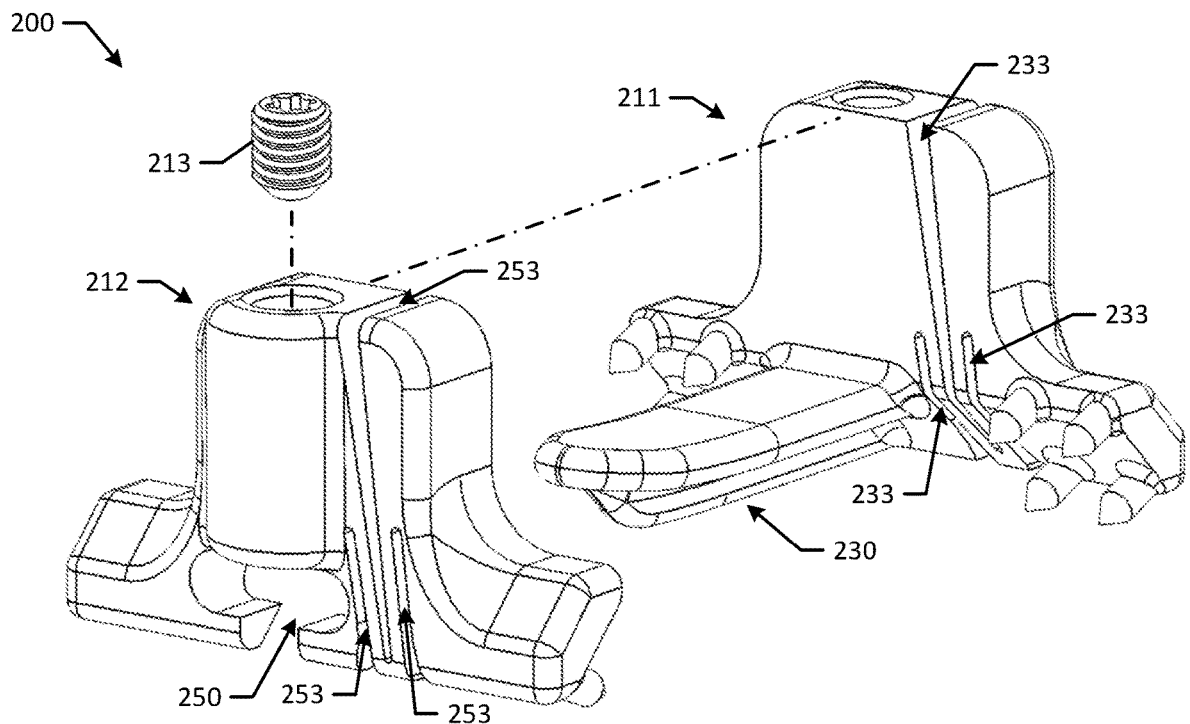
FIG. 2C is a perspective view of the dynamic interspinous process device of FIG. 2A, showing the first attachment side, the second attachment side, and a securing means of the dynamic interspinous process device in a disassembled state.
Figure 2D:
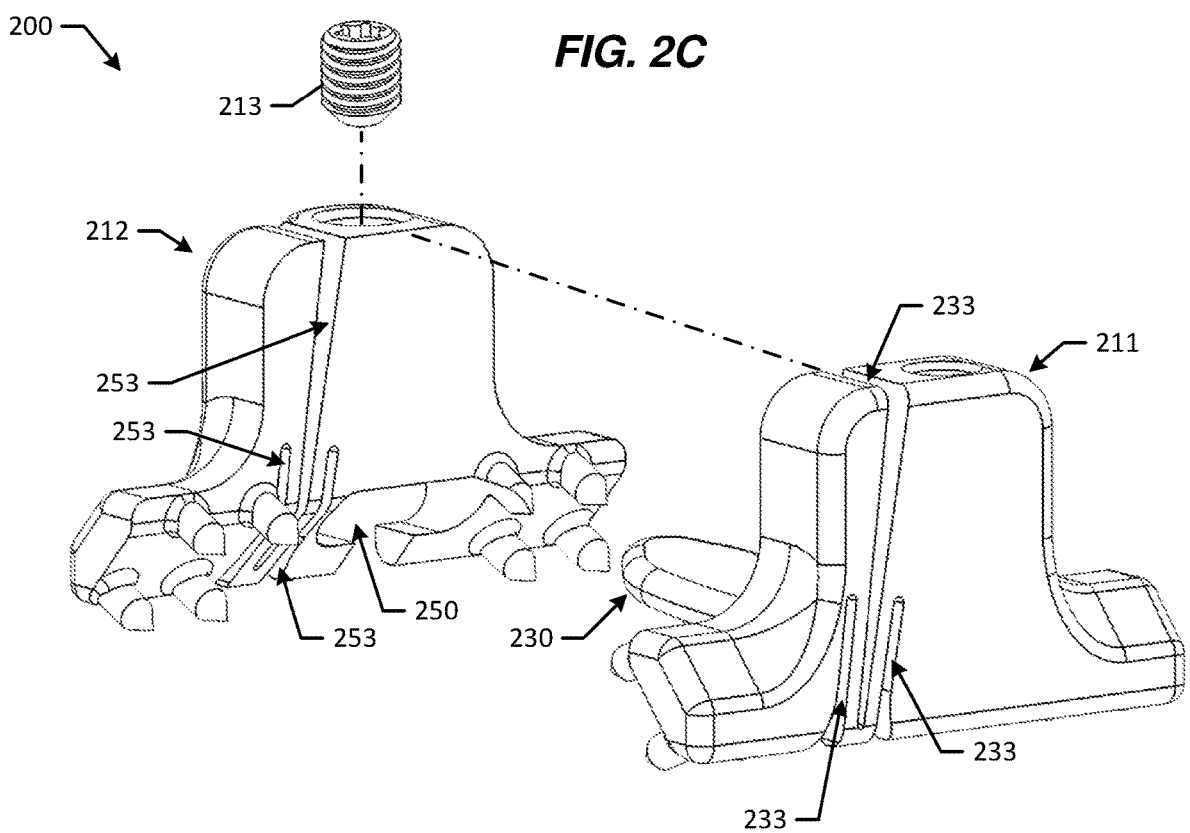
FIG. 2D is a perspective view of the dynamic interspinous process device of FIG. 2A, showing the first attachment side, the second attachment side, and the securing means in the disassembled state.
Figure 2E:
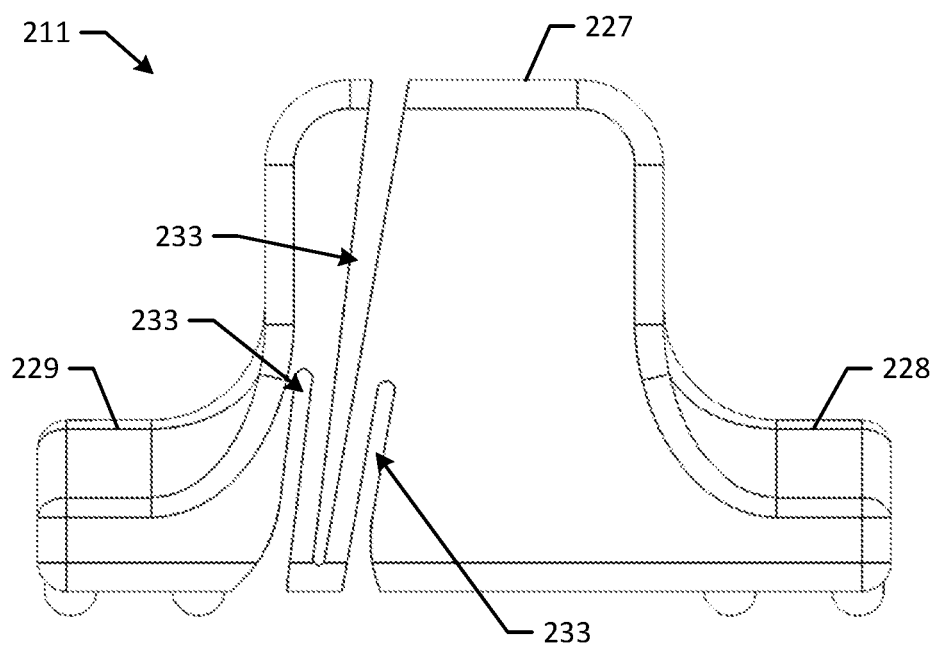
FIG. 2E is a plan view of the first attachment side of the dynamic interspinous process device of FIG. 2A.

It will be appreciated that the slots 233 may be configured to allow portions of the first attachment side 211 to move relative to one another. In particular, as shown, the slots 233 may be configured to allow the second wing 229 to move toward the central portion 227 and the spacer 230, in the direction of the longitudinal axis $A_L$ of the device 200, as these portions compress the slots 233, and also to allow the second wing 229 to move away from the central portion 227 and the spacer 230, in the direction of the longitudinal axis $A_L$ of the device 200, as these portions expand the slots 233. In a similar manner, the slots 233 may be configured to allow the first wing 228 to move toward the central portion 227 and the spacer 230, in the direction of the longitudinal axis $A_L$ of the device 200, as these portions compress the slots 233, and also to allow the first wing 228 to move away from the central portion 227 and the spacer 230, in the direction of the longitudinal axis $A_L$ of the device 200, as these portions expand the slots 233. As a result, the first wing 228 and the second wing 229 may be configured to move toward one another as one or more of the slots 233 are compressed, and to move away from one another as one or more of the slots 233 are expanded. In will be appreciated that, during such movement of the wings 228, 229, one or more regions of the first attachment side 211 surrounding the slots 233, such as the regions of the central portion 227 surrounding the terminal ends of the slots 233, may flex or may be compressed to accommodate the compression or expansion of the slots 233. In effect, the slots 233 may cause the first attachment side 211 to function as a spring which may be compressed or extended in the direction of the longitudinal axis $A_L$ of the device 200 but has a natural tendency to return to a natural state as shown in FIG. 2E.

In a similar manner, the second attachment side 212 may include one or more slots 253 (which also may be referred to as a "dynamic slot," a "cutout," an "opening," or a "slit") defined therein and configured to allow relative movement of portions of the second attachment side 212. In certain embodiments, as shown, the second attachment side 212 may include a plurality of the slots 253 spaced apart from one another in the direction of the longitudinal axis $A_L$ of the device 200. In certain embodiments, as shown, the slots 253 may be formed at least partially, or entirely, within the central portion 247 of the second attachment side 212. Each slot 253 may have an elongated shape extending in the direction of the second transverse axis $A_{T2}$ of the device 200. In certain embodiments, as shown, each slot 253 may extend from the first side 243 to the second side 244 of the second attachment side 212. Further, in certain embodiments, as shown, one or more of the slots 253 may extend from the fourth side 246 of the second attachment side 212 toward, but not to, the third side 245 of the second attachment side 212. In other words, such slots 253 may be open along the fourth side 246 and may terminate at a location spaced apart from the third side 245. In certain embodiments, as shown, one or more other slots 253 may extend from the third side 245 of the second attachment side 212 toward, but not to, the fourth side 246 of the second attachment side 212. In other words, such slots 253 may be open along the third side 245 and may terminate at a location spaced apart from the fourth side 246. In certain embodiments, as shown, each of the slots 253 may extend at an acute angle relative to the first transverse axis $A_{T1}$ of the device 200. In certain embodiments, as shown each slot 253 may have a straight shape along the entire extent of the slot 253, although the slot 253 may be tapered in the direction from the open end of the slot 253 to the closed end of the slot 253. In certain embodiments, as shown, the all of the slots 253 may be offset from the first transverse axis $A_{T1}$ of the device 200 toward one of the ends 201, 202 of the device in the direction of the longitudinal axis $A_L$ of the device 200. Various other configurations of the slots 253 may be used in other embodiments.

Figure 2F:
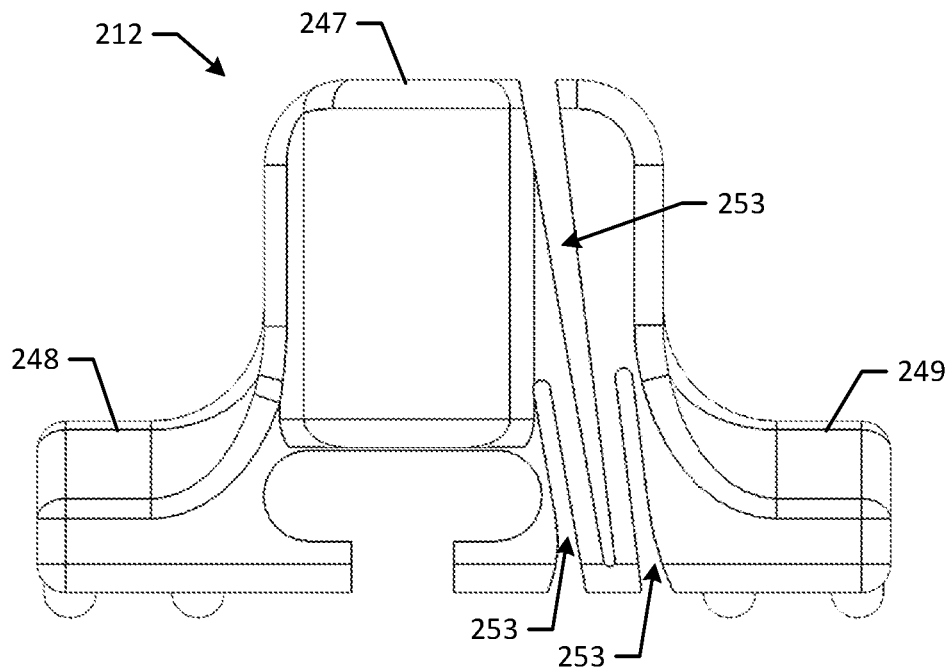
FIG. 2F is a plan view of the second attachment side of the dynamic interspinous process device of FIG. 2A.

It will be appreciated that the slots 253 may be configured to allow portions of the second attachment side 212 to move relative to one another. In particular, as shown, the slots 253 may be configured to allow the second wing 249 to move toward the central portion 247 and the spacer slot 250, in the direction of the longitudinal axis $A_L$ of the device 200, as these portions compress the slots 253, and also to allow the second wing 249 to move away from the central portion 247 and the spacer slot 250, in the direction of the longitudinal axis $A_L$ of the device 200, as these portions expand the slots 253. In a similar manner, the slots 253 may be configured to allow the first wing 248 to move toward the central portion 247 and the spacer slot 250, in the direction of the longitudinal axis $A_L$ of the device 200, as these portions compress the slots 253, and also to allow the first wing 248 to move away from the central portion 247 and the spacer slot 250, in the direction of the longitudinal axis $A_L$ of the device 200, as these portions expand the slots 253. As a result, the first wing 248 and the second wing 249 may be configured to move toward one another as one or more of the slots 253 are compressed, and to move away from one another as one or more of the slots 253 are expanded. In will be appreciated that, during such movement of the wings 248, 249, one or more regions of the second attachment side 212 surrounding the slots 253, such as the regions of the central portion 247 surrounding the terminal ends of the slots 253, may flex or may be compressed to accommodate the compression or expansion of the slots 253. In effect, the slots 253 may cause the second attachment side 212 to function as a spring which may be compressed or extended in the direction of the longitudinal axis $A_L$ of the device 200 but has a natural tendency to return to a natural state as shown in FIG. 2F. In certain embodiments, as shown, the slots 233 of the first attachment side 211 may be formed as a mirror image of the slots 253 of the second attachment side 212. In other embodiments, the number, shape, or configuration of the slots 233 of the first attachment side 211 may be different than the number, shape, or configuration of the slots 253 of the second attachment side 212. Various configurations of the slots 233 and the slots 253 may be used to allow for a desired range of movement of the corresponding vertebrae.

Figure 2G:
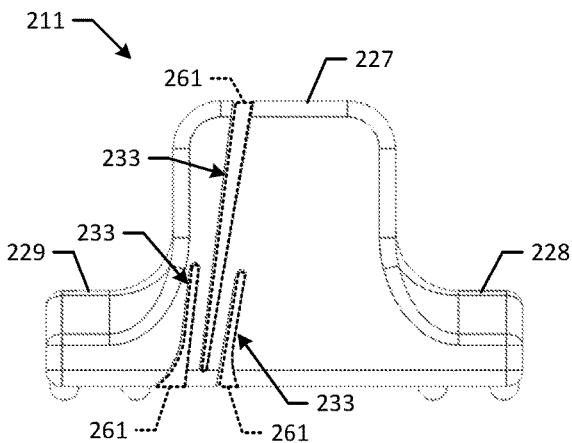
FIG. 2G is a plan view of the first attachment side and a number of resistance means of the dynamic interspinous process device of FIG. 2A.
Figure 2H:
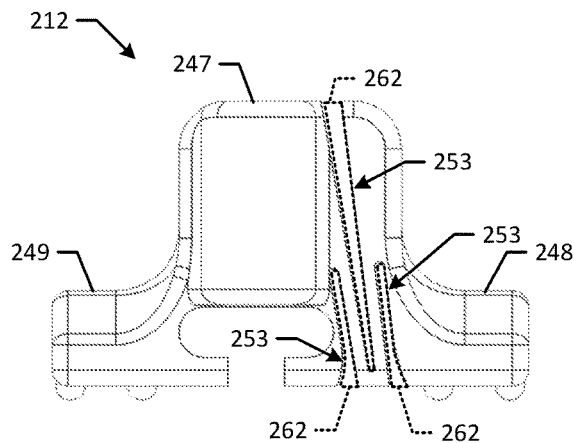
FIG. 2H is a plan view of the second attachment side and a number of resistance means of the dynamic interspinous process device of FIG. 2A.

In certain embodiments, the device 200 may include means for varying resistance to the relative movement between the first wing 228 and the second wing 229 of the first attachment side 211 over at least a portion of the range of motion of the wings 228, 229 and for varying resistance to the relative movement between the first wing 248 and the second wing 249 of the second attachment side 212 over at least a portion of the range of motion of the wings 248, 249. In this manner, the device 200 may vary the resistance to the relative movement between the treated vertebrae over at least a portion of the range of motion of the vertebrae allowed by the device 200. FIGS. 2G and 2H illustrate an embodiment in which the device 200 includes a pair of resistance means for varying resistance to the relative movement between the wings 228, 229 and between the wings 248, 249. As shown, the first attachment side 211 may include a number of resistance means 261 (which also may be referred to as a "resistance insert," a "resistance member" or a "biasing member") configured for varying resistance to movement of the wings 228, 229 relative to the central portion 227 and relative to one another over at least a portion of the range of motion of these features as may be allowed by the slots 233. In certain embodiments, as shown, each resistance means 261 may be an insert configured to be inserted into and retained within one of the slots 233. In certain embodiments, the resistance means 261 may be removably received within the slots 233, such that the resistance means 261 may be placed therein when resistance is desired and may be removed therefrom when resistance is not desired. In other embodiments, the resistance means 261 may be securely fixed within the slots 233, such that the resistance means 261 are not removable therefrom. In certain embodiments, each resistance means 261 may be formed of a compressible material or a resiliently deformable material, such as a biocompatible polymer or other suitable material, which may be compressed by the relative movement of surrounding portions of the first attachment side 211 but may have a natural tendency to return to a natural state when compression forces are removed. It will be appreciated that a durometer of the compressible material or resiliently deformable material may be selected to provide a desired resistance to the relative movement of surrounding portions of the first attachment side 211. In other embodiments, each resistance means 261 may be formed as a spring, such as a compression spring, which may function similar to the compressible material or resiliently deformable material member. In certain embodiments, as shown, each resistance means 261 may fill or substantially fill the entirety of the respective slot 233. In other embodiments, each resistance means 261 may fill only a portion of the respective slot 233.

According to the illustrated embodiment, each resistance means 261 may be configured to resist movement of one of the wings 228, 229 toward the central portion 227, and thus the pair of resistance means 261 collectively may resist relative movement of the wings 228, 229 toward one another. In particular, as the wings 228, 229 move toward the central portion 227 and toward one another and the slots 233 are compressed, the resistance means 261 may be compressed, thereby resisting, but not preventing, further movement of the wings 228, 229 toward the central portion 227 and toward one another. Further, the resistance means 261 may provide a biasing force acting on the portions of the first attachment side 211 surrounding the slots 233, biasing the wings 228, 229 toward their home or natural position and the slots 233 to their home or natural state.

In a similar manner, the second attachment side 212 may include a pair of resistance means 262 (which also may be referred to as a "resistance insert," a "resistance member" or a "biasing member") configured for varying resistance to movement of the wings 248, 249 relative to the central portion 247 and relative to one another over at least a portion of the range of motion of these features as may be allowed by the slots 253. In certain embodiments, as shown, each resistance means 262 may be an insert configured to be inserted into and retained within one of the slots 253. In certain embodiments, the resistance means 262 may be removably received within the slots 253, such that the resistance means 262 may be placed therein when resistance is desired and may be removed therefrom when resistance is not desired. In other embodiments, the resistance means 262 may be securely fixed within the slots 253, such that the resistance means 262 are not removable therefrom. In certain embodiments, each resistance means 262 may be formed of a compressible material or a resiliently deformable material, such as a biocompatible polymer or other suitable material, which may be compressed by the relative movement of surrounding portions of the second attachment side 212 but may have a natural tendency to return to a natural state when compression forces are removed. It will be appreciated that a durometer of the compressible material or resiliently deformable material may be selected to provide a desired resistance to the relative movement of surrounding portions of the second attachment side 212. In other embodiments, each resistance means 262 may be formed as a spring, such as a compression spring, which may function similar to the compressible material or resiliently deformable material member. In certain embodiments, as shown, each resistance means 262 may fill or substantially fill the entirety of the respective slot 253. In other embodiments, each resistance means 262 may fill only a portion of the respective slot 253.

According to the illustrated embodiment, each resistance means 262 may be configured to resist movement of one of the wings 248, 249 toward the central portion 247, and thus the pair of resistance means 262 collectively may resist relative movement of the wings 248, 249 toward one another. In particular, as the wings 248, 249 move toward the central portion 247 and toward one another and the slots 253 are compressed, the resistance means 262 may be compressed, thereby resisting, but not preventing, further movement of the wings 248, 249 toward the central portion 247 and toward one another. Further, the resistance means 262 may provide a biasing force acting on the portions of the second attachment side 212 surrounding the slots 253, biasing the wings 248, 249 toward their home or natural position and the slots 253 to their home or natural state.

It will be appreciated that the resistance means 261, 262 of the device 200 may be used to vary resistance to the relative movement between the treated vertebrae, when desired. In particular, the resistance means 261, 262 may be used to increase resistance to the relative movement between the treated vertebrae over at least a portion of the range of motion of the vertebrae allowed by the device 200. In this manner, the device 200 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 261, 262 may be selected to provide a desired degree of resistance to the relative motion of the treated vertebrae.

Figure 2I:
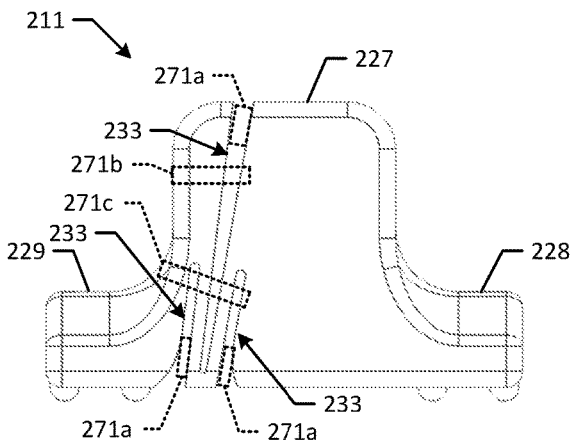
FIG. 2I is a plan view of the first attachment side and a number of fixation means of the dynamic interspinous process device of FIG. 2A.
Figure 2J:
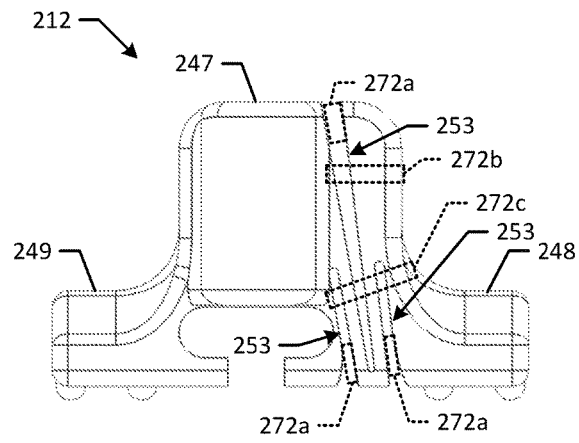
FIG. 2J is a plan view of the second attachment side and a number of fixation means of the dynamic interspinous process device of FIG. 2A.

In certain embodiments, the device 200 may include means for preventing or inhibiting the relative movement between the first wing 228 and the second wing 229 of the first attachment side 211 and for preventing or inhibiting the relative movement between the first wing 248 and the second wing 249 of the second attachment side 212. In this manner, the device 200 may prevent or inhibit the relative movement between the treated vertebrae. FIGS. 2I and 2J illustrate embodiments in which the device 200 includes one or more fixation means for preventing or inhibiting the relative movement between the wings 228, 229 and between the wings 248, 249. As shown, the first attachment side 211 may include one or more fixation means 271 (which also may be referred to as a "fixation insert," a "fixation member," a "fastener," or a "lock") configured for preventing or inhibiting movement of the wings 228, 229 relative to the central portion 227 and relative to one another as may be allowed by the slots 233. In certain embodiments, the fixation means 271 may be removably attached to the central portion 227 and/or one of the wings 228, 229. In other embodiments, the fixation means 271 may be fixedly secured to the central portion 227 and/or one or the wings 228, 229. In certain embodiments, as shown, three of the fixation means 271a may be configured to be inserted at least partially into and retained within the respective slots 233. Each fixation means 271a may engage portions of the first attachment side 211 surrounding the respective slot 233 such that the fixation means 271a prevents or inhibits at least a portion of the slot 233 from expanding and/or collapsing. In certain embodiments, each fixation means 271a may be a fastener, such as a set screw having a reverse angle thread for threadably engaging and retaining mating threaded portions of the first attachment side 211. In certain embodiments, as shown, each fixation means 271a may be inserted, in a direction transverse to the longitudinal axis $A_L$ and the second transverse axis $A_{T2}$ of the device 200, into the open end of the respective slot 233.

In certain embodiments, as shown, a single fixation means 271b may be configured to be inserted at least partially into and through one of the slots 233. The fixation means 271b may engage portions of the first attachment side 211 surrounding the respective slot 233 such that the fixation means 271b prevents or inhibits at least a portion of the slot 233 from expanding and/or collapsing. In certain embodiments, the fixation means 271b may be a fastener, such as a set screw for threadably engaging and retaining mating threaded portions of the first attachment side 211. In certain embodiments, as shown, the fixation means 271b may be inserted through a first portion of the first attachment side 211 along one side of the respective slot 233, through a portion of the slot 233, and into a second portion of the first attachment side 211 along an opposite second side of the respective slot 233. In this manner, the fixation means 271b may prevent or inhibit compression and expansion of at least a portion of the slot 233 by securely engaging portions of the first attachment side 211 along opposite sides of the slot 233. In other embodiments, the fixation means 271b may be inserted through a first portion of the first attachment side 211 along one side of the respective slot 233, through a portion of the slot 233, and may abut a second portion of the first attachment side 211 along an opposite second side of the respective slot 233. In this manner, the fixation means 271b may prevent or inhibit compression of at least a portion of the slot 233 while still allowing expansion of the portion of the slot 233. In still other embodiments, the fixation means 271b may be inserted through a first portion of the first attachment side 211 along one side of the respective slot 233, into a portion of the slot 233, and may be spaced apart from a second portion of the first attachment side 211 along an opposite second side of the respective slot 233. In this manner, the fixation means 271b may allow, but limit, compression of at least a portion of the slot 233 while still allowing expansion of the portion of the slot 233. In certain embodiments, as shown, the fixation means 271b may be inserted, in a direction parallel to the longitudinal axis $A_L$ of the device 200, through the central portion 227.

In certain embodiments, as shown, a single fixation means 271c may be configured to be inserted at least partially into and through each of the slots 233. The fixation means 271c may engage portions of the first attachment side 211 surrounding each of the slots 233 such that the fixation means 271c prevents or inhibits at least a portion of each slot 233 from expanding and/or collapsing. In certain embodiments, the fixation means 271c may be a fastener, such as a set screw for threadably engaging and retaining mating threaded portions of the first attachment side 211. In certain embodiments, as shown, the fixation means 271c may be inserted through a first portion of the first attachment side 211 along one side of a first slot 233, through a portion of the first slot 233, through a second portion of the first attachment side 211 along an opposite second side of the first slot 233, through a third portion of the first attachment side 211 along one side of a second slot 233, through a portion of the second slot 233, through a fourth portion of the first attachment side 211 along an opposite second side of the second slot 233, through a fifth portion of the first attachment side 211 along one side of a third slot 233, through a portion of the third slot 233, and through a sixth portion of the first attachment side 211 along an opposite second side of the third slot 233. In this manner, the fixation means 271c may prevent or inhibit compression and expansion of at least a portion of each slot 233 by securely engaging portions of the first attachment side 211 along opposite sides of each slot 233. In certain embodiments, as shown, the fixation means 271c may be inserted, in a direction transverse to each of the longitudinal axis $A_L$ and the second transverse axis $A_{T2}$ of the device 200, through an interface of the central portion 227 and one of the wings 228, 229 and through adjacent portions of the respective slots 233.

In a similar manner, the second attachment side 212 may include one or more fixation means 272 (which also may be referred to as a "fixation insert," a "fixation member," a "fastener," or a "lock") configured for preventing or inhibiting movement of the wings 248, 249 relative to the central portion 247 and relative to one another as may be allowed by the slots 253. In certain embodiments, the fixation means 272 may be removably attached to the central portion 247 and/or one of the wings 248, 249. In other embodiments, the fixation means 272 may be fixedly secured to the central portion 247 and/or one or the wings 248, 249. In certain embodiments, as shown, three of the fixation means 272a may be configured to be inserted at least partially into and retained within the respective slots 253. Each fixation means 272a may engage portions of the second attachment side 212 surrounding the respective slot 253 such that the fixation means 272a prevents or inhibits at least a portion of the slot 253 from expanding and/or collapsing. In certain embodiments, each fixation means 272a may be a fastener, such as a set screw having a reverse angle thread for threadably engaging and retaining mating threaded portions of the second attachment side 212. In certain embodiments, as shown, each fixation means 272a may be inserted, in a direction transverse to the longitudinal axis $A_L$ and the second transverse axis $A_{T2}$ of the device 200, into the open end of the respective slot 253.

In certain embodiments, as shown, a single fixation means 272b may be configured to be inserted at least partially into and through one of the slots 253. The fixation means 272b may engage portions of the second attachment side 212 surrounding the respective slot 253 such that the fixation means 272b prevents or inhibits at least a portion of the slot 253 from expanding and/or collapsing. In certain embodiments, the fixation means 272b may be a fastener, such as a set screw for threadably engaging and retaining mating threaded portions of the second attachment side 212. In certain embodiments, as shown, the fixation means 272b may be inserted through a first portion of the second attachment side 212 along one side of the respective slot 253, through a portion of the slot 253, and into a second portion of the second attachment side 212 along an opposite second side of the respective slot 253. In this manner, the fixation means 272b may prevent or inhibit compression and expansion of at least a portion of the slot 253 by securely engaging portions of the second attachment side 212 along opposite sides of the slot 253. In other embodiments, the fixation means 272b may be inserted through a first portion of the second attachment side 212 along one side of the respective slot 253, through a portion of the slot 253, and may abut a second portion of the second attachment side 212 along an opposite second side of the respective slot 253. In this manner, the fixation means 272b may prevent or inhibit compression of at least a portion of the slot 253 while still allowing expansion of the portion of the slot 253. In still other embodiments, the fixation means 272b may be inserted through a first portion of the second attachment side 212 along one side of the respective slot 253, into a portion of the slot 253, and may be spaced apart from a second portion of the second attachment side 212 along an opposite second side of the respective slot 253. In this manner, the fixation means 272b may allow, but limit, compression of at least a portion of the slot 253 while still allowing expansion of the portion of the slot 253. In certain embodiments, as shown, the fixation means 272b may be inserted, in a direction parallel to the longitudinal axis $A_L$ of the device 200, through the central portion 247.

In certain embodiments, as shown, a single fixation means 272c may be configured to be inserted at least partially into and through each of the slots 253. The fixation means 272c may engage portions of the second attachment side 212 surrounding each of the slots 253 such that the fixation means 272c prevents or inhibits at least a portion of each slot 253 from expanding and/or collapsing. In certain embodiments, the fixation means 272c may be a fastener, such as a set screw for threadably engaging and retaining mating threaded portions of the second attachment side 212. In certain embodiments, as shown, the fixation means 272c may be inserted through a first portion of the second attachment side 212 along one side of a first slot 253, through a portion of the first slot 253, through a second portion of the second attachment side 212 along an opposite second side of the first slot 253, through a third portion of the second attachment side 212 along one side of a second slot 253, through a portion of the second slot 253, through a fourth portion of the second attachment side 212 along an opposite second side of the second slot 253, through a fifth portion of the second attachment side 212 along one side of a third slot 253, through a portion of the third slot 253, and through a sixth portion of the second attachment side 212 along an opposite second side of the third slot 253. In this manner, the fixation means 272c may prevent or inhibit compression and expansion of at least a portion of each slot 253 by securely engaging portions of the second attachment side 212 along opposite sides of each slot 253. In certain embodiments, as shown, the fixation means 272c may be inserted, in a direction transverse to each of the longitudinal axis $A_L$ and the second transverse axis $A_{T2}$ of the device 200, through an interface of the central portion 247 and one of the wings 248, 249 and through adjacent portions of the respective slots 253.

It will be appreciated that the fixation means 271, 272 of the device 200 may be used to control the relative movement between the treated vertebrae, when desired. In particular, the fixation means 271, 272 may be used to prevent or inhibit relative movement between the treated vertebrae. In this manner, the device 200 may be used as a dynamic device or a rigid device, with the ability to convert the device 200 between a dynamic configuration and a rigid configuration, as may be desired in certain applications. The fixation means 271, 272 may be used to convert the device 200 between the dynamic configuration and the rigid configuration prior to implantation of the device 200, during initial implantation of the device 200 as a part of an initial surgery, or during a follow-up surgery.

Figure 2K:
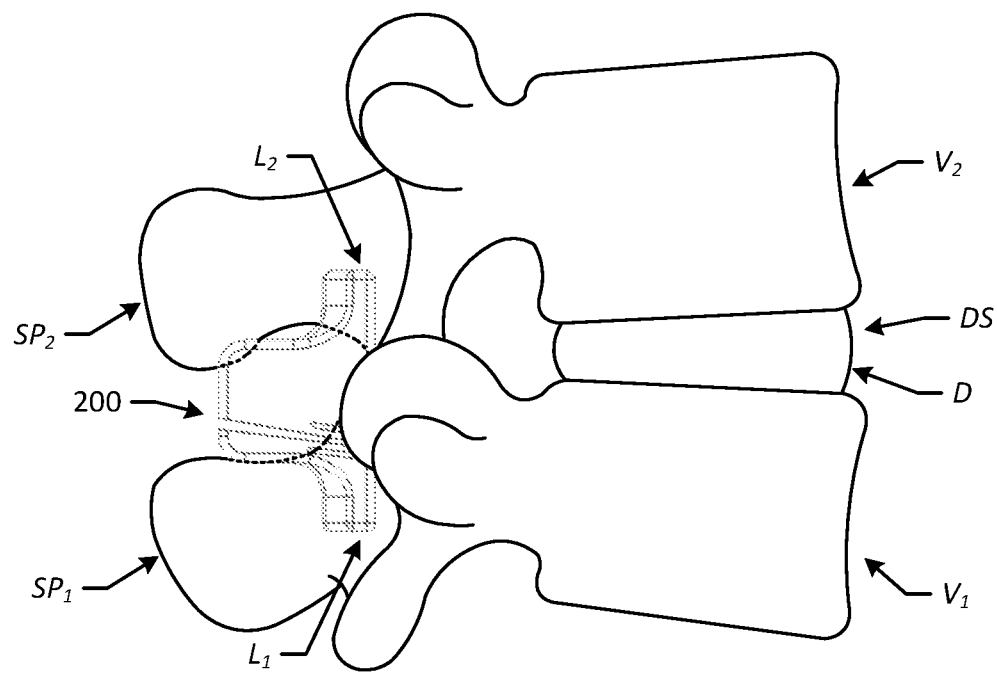
FIG. 2K is a side view of the dynamic interspinous process device of FIG. 2A implanted with respect to a first vertebra and a second vertebra in accordance with one or more embodiments of the present disclosure.
Figure 2L:
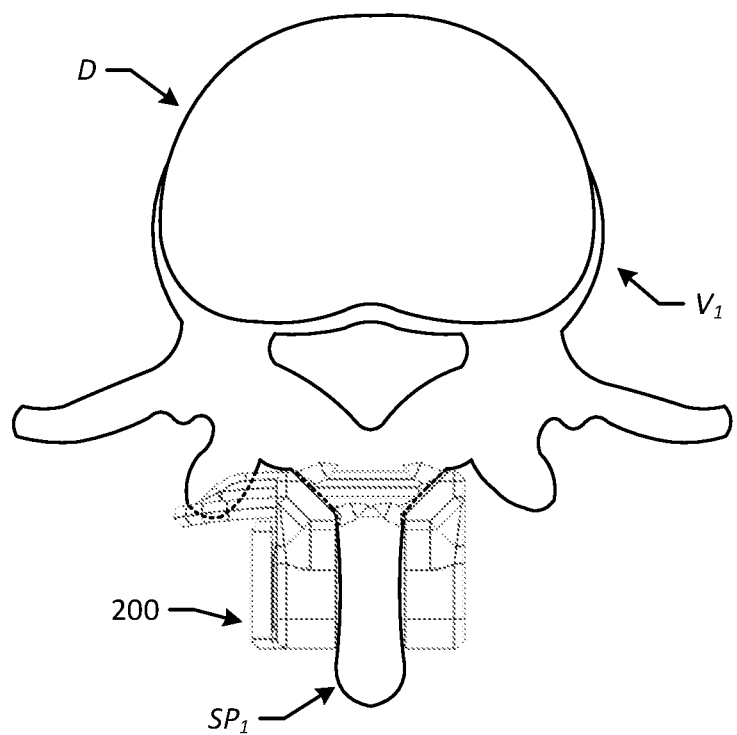
FIG. 2L is a top view of the dynamic interspinous process device of FIG. 2A implanted with respect to the first vertebra, the second vertebra being removed from view for purposes of illustration.

FIGS. 2K and 2L illustrate an example implantation of the device 200 with respect to a first vertebra $V_1$ and an adjacent second vertebra $V_2$. As shown, the first attachment side 211 and the second attachment side 212 may be positioned relative to the vertebrae $V_1$, $V_2$ such that the spacer 230 is positioned between a first spinous process $SP_1$ of the first vertebra $V_1$ and a second spinous process $SP_2$ of the second vertebra $V_2$. In this manner, the spacer 230 may limit a minimum spacing between the spinous processes $SP_1$, $SP_2$. Additionally, the first attachment side 211 and the second attachment side 212 may be positioned relative to the vertebrae $V_1$, $V_2$ such that the respective wings 228, 229 of the first attachment side 211 and the respective wings 248, 249 of the second attachment side 212 engage a first lamina $L_1$ of the first vertebra $V_1$ and a second lamina $L_2$ of the second vertebra $V_2$. In this manner, the respective bone fasteners 231 of the first attachment side 211 and the respective bone fasteners 251 of the second attachment side 212 may penetrate and securely engage the laminae $L_1$, $L_2$. Accordingly, the implanted device 200 may stabilize the vertebrae $V_1$, $V_2$, although the device 200 may allow relative movement of the vertebrae $V_1$, $V_2$. In particular, the slots 233, 253 of the device 200 may allow relative movement of the vertebrae $V_1$, $V_2$ in sagittal plane of the patient, thereby allowing flexion and extension of the treated segment of the spine. It will be appreciated that the configuration of the slots 233, 253 may be varied, for example, by varying the number, size, and/or shape the slots 233, 253 to allow a desired range of motion in the sagittal plane. Further, the material from which the first attachment side 211 and the second attachment side 212 are formed may be selected to achieve the desired range of motion. In certain embodiments, the first attachment side 211 and the second attachment side 212 may be formed of titanium, although other suitable metals, polymers, or other materials may be used in other embodiments. Meanwhile, the device 200 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 200 and the disc D. In other embodiments in which the native disc D is removed, an interbody device, such as a cage or a spacer, may be implanted within the disc space DS (i.e., the intervertebral space) and the loads carried by the treated spinal segment may be shared by the device 200 and the interbody device. As described above, the device 200 may be used in conjunction with other additional hardware, such that the device 200 and the additional hardware collectively stabilize the treated segment of the spine and share loads carried thereby. It will be appreciated that the foregoing description and the corresponding drawings are merely examples of the device 200 and that other configurations and modifications may be made.

FIGS. 3A-3H illustrate an interspinous process device 300 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 300 may be configured for implantation relative to a first vertebra and an adjacent second vertebra, as described below, specifically with reference to FIGS. 3G and 3H. In particular, a portion of the interspinous process device 300 may be positioned between the spinous process of the first vertebra and the spinous process of the second vertebra, while one or more other portions of the interspinous process device 300 engage the spinous processes, the laminae, and/or other portions of the respective vertebra. As described below, the interspinous process device 300 may allow a desired range of relative movement between the treated vertebrae, which may be desirable in certain treatment applications. The interspinous process device 300 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 300, itself or in combination with additional hardware, may provide the structural support necessary to restore and maintain normal spacing and alignment of the treated vertebrae while avoiding certain drawbacks presented by existing interspinous process devices.

The interspinous process device 300 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 300 may include a first end 301 and a second end 302 disposed opposite the first end 301 in the direction of the longitudinal axis $A_L$. As described below, the device 300 may be implanted with the longitudinal axis $A_L$ extending in a direction substantially parallel to the sagittal plane and the coronal plane of the patient and transverse to the transverse plane of the patient. In this manner, depending on the orientation of the device 300 upon implantation thereof, one of the first end 301 and the second end 302 of the device 300 may be referred to as a the "superior end" of the device 300, and the other of the first end 301 and the second end 302 of the device 300 may be referred to as the "inferior end" of the device 300. The device 300 also may include a first side 303 extending from the first end 301 to the second end 302, and a second side 304 disposed opposite the first side 303 in the direction of the first transverse axis $A_{T1}$ and extending from the first end 301 to the second end 302. The device 300 may be implanted with the first transverse axis $A_{T1}$ extending in a direction substantially parallel to the coronal plane and the transverse plane of the patient and transverse to the sagittal plane of the patient. In this manner, depending on the orientation of the device 300 upon implantation thereof, one of the first side 303 and the second side 304 of the device 300 may be referred to as the "right side" of the device 300, and the other of the first side 303 and the second side 304 of the device 300 may be referred to as the "left side" of the device 300. The device 300 further may include a third side 305 extending from the first end 301 to the second end 302 and from the first side 303 to the second side 304, and a fourth side 306 disposed opposite the third side 305 in the direction of the second transverse axis $A_{T2}$ and extending from the first end 301 to the second end 302 and from the first side 303 to the second side 304. The device 300 may be implanted with the second transverse axis $A_{T2}$ extending in a direction substantially parallel to the sagittal plane and the transverse plane of the patient and transverse to the coronal plane of the patient. As described below, the device 300 may be oriented upon implantation thereof such that the third side 305 faces posteriorly and the fourth side 306 faces anteriorly with respect to the patient. In this manner, the third side 305 may be referred to as the "posterior side" of the device 300, and the fourth side 306 may be referred to as the "anterior side" of the device 300. The device 300 may have an overall "length" extending from the first end 301 to the second end 302 in the direction of the longitudinal axis $A_L$, an overall "width" extending from the first side 303 to the second side 304 in the direction of the first transverse axis $A_{T1}$, and an overall "height" extending from the third side 305 to the fourth side 306 in the direction of the second transverse axis $A_{T2}$. Further, various components and features of the device 300 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 300 may include a first attachment side 311 (which also may be referred to as a "first attachment portion," a "first attachment assembly," or a "first plate") and a second attachment side 312 (which also may be referred to as a "second attachment portion," a "second attachment assembly," or a "second plate") configured for removably attaching to one another via a securing means 313. During use of the device 300, one of the first attachment side 311 and the second attachment side 312 may be disposed, at least partially, along the right side of the patient's spine, and the other of the first attachment side 311 and the second attachment side 312 may be disposed, at least partially, along the right side of the patient's spine. It will be appreciated that the first attachment side 311 and the second attachment side 312 may include corresponding features that are mirror images of one another, although certain differences between the first attachment side 311 and the second attachment side 312 may exist, as described below. In certain embodiments, the first attachment side 311 and the second attachment side 312 may be formed of a metal, such as titanium or stainless steel, although other suitable materials, such as polyether ether ketone (PEEK), other polymers, or composites, may be used.

The first attachment side 311 may have a first end 321, a second end 322 disposed opposite the first end 321, a first side 323 (which also may be referred to as an "interior side"), a second side 324 (which also may be referred to as an "exterior side") disposed opposite the first side 323, a third side 325 (which also may be referred to as an "posterior side"), and a fourth side 326 (which also may be referred to as an "anterior side") disposed opposite the third side 325. As shown, the first attachment side 311 may include a central portion 327 and a pair of wings 328, 329 disposed on opposite sides of the central portion 327. In particular, the first wing 328 may extend from the central portion 327 to the first end 321 of the first attachment side 311, and the second wing 329 may extend from the central portion 327 to the second end 322 of the first attachment side 311. In certain embodiments, as shown, the wings 328, 329 may extend in opposite directions from the central portion 327 and may be formed as mirror images of one another. In other embodiments, the wings 328, 329 may extend in opposite directions from the central portion 327, but the first wing 328 may have a different shape or configuration than the second wing 329 such that the wings 328, 329 are not mirror images of one another. In certain embodiments, the wings 328, 329 may be shaped and configured in a manner similar to any one of the wing embodiments described and/or shown in the Prior Applications. Various other configurations of the wings 328, 329 may be used.

The first attachment side 311 also may include a spacer 330 extending from the first side 323 thereof. During use of the device 300, the spacer 330 may be positioned between the spinous processes of the respective vertebrae. In certain embodiments, as shown, the spacer 330 may extend from the central portion 327 of the first attachment side 311 and be integrally formed therewith. In other embodiments, the spacer 330 may be separately formed from and attached to the central portion 327 via an attachment mechanism. The first attachment side 311 further may include a number of engagement features configured for securely engaging the respective vertebrae. In certain embodiments, as shown, the engagement features may be one or more bone fasteners 331 extending from the first side 323 of the first attachment side 311. The bone fasteners 331 may be formed as spikes or barbs, although other forms and types of bone fasteners 331 may be used for securely engaging the vertebrae. In certain embodiments, one or more of the bone fasteners 331 may extend form the first wing 328, and one or more bone fasteners 331 may extend from the second wing 329. In certain embodiments, the first wing 328 may include a first number of bone fasteners 331 extending therefrom, and the second wing 329 may include a second number of bone fasteners 331 extending therefrom, wherein the first number is different than the second number. In this manner, the degree of engagement between the bone fasteners 331 of the first wing 328 and the corresponding vertebra may be different from the degree of engagement between the bone fasteners 331 of the second wing 329 and the corresponding vertebra. Such an arrangement may facilitate relative movement of the treated vertebrae, while minimizing certain stresses induced in the device 300. In certain embodiments, one of the first wing 328 and the second wing 329 may not include any bone fasteners 331 extending therefrom, and the other of the first wing 328 and the second wing 329 may include one or more of the bone fasteners 331 extending therefrom. Such an arrangement also may facilitate relative movement of the treated vertebrae, while minimizing certain stresses induced in the device 300. Various configurations of the bone fasteners 331 of the first attachment side 311 may be used. In certain embodiments, as shown, the bone fasteners 331 may be configured to engage the laminae of the respective vertebrae. In other embodiments, one or more of the bone fasteners 331 may be configured to engage the spinous processes, the laminae, and/or other portions of the respective vertebrae. As shown, the first attachment side 311 also may include an instrument engagement aperture 332 configured for receiving a portion of and cooperating with an instrument used for positioning the first attachment side 311 during implantation of the device 300. Example instruments for implantation of the device 300 are described in the Prior Applications.

In a similar manner, the second attachment side 312 may have a first end 341, a second end 342 disposed opposite the first end 341, a first side 343 (which also may be referred to as an "exterior side"), a second side 344 (which also may be referred to as an "interior side") disposed opposite the first side 343, a third side 345 (which also may be referred to as an "posterior side"), and a fourth side 346 (which also may be referred to as an "anterior side") disposed opposite the third side 345. As shown, the second attachment side 312 may include a central portion 347 and a pair of wings 348, 349 disposed on opposite sides of the central portion 347. In particular, the first wing 348 may extend from the central portion 347 to the first end 341 of the second attachment side 312, and the second wing 349 may extend from the central portion 347 to the second end 342 of the second attachment side 312. In certain embodiments, as shown, the wings 348, 349 may extend in opposite directions from the central portion 347 and may be formed as mirror images of one another. In other embodiments, the wings 348, 349 may extend in opposite directions from the central portion 347, but the first wing 348 may have a different shape or configuration than the second wing 349 such that the wings 348, 349 are not mirror images of one another. In certain embodiments, the wings 348, 349 may be shaped and configured in a manner similar to any one of the wing embodiments described and/or shown in the Prior Applications. Various other configurations of the wings 348, 349 may be used.

The second attachment side 312 also may include a spacer slot 350 extending through the second attachment side 312 from the first side 343 to the second side 344 thereof. During use of the device 300, the spacer slot 350 may be configured to receive the spacer 330 of the first attachment side 311 therethrough, as shown. In certain embodiments, as shown, the spacer slot 350 may be defined in the central portion 347 of the second attachment side 312, although other positions of the spacer slot 350 may be used. The second attachment side 312 further may include a number of engagement features configured for securely engaging the respective vertebrae. In certain embodiments, as shown, the engagement features may be one or more bone fasteners 351 extending from the second side 344 of the second attachment side 312. The bone fasteners 351 may be formed as spikes or barbs, although other forms and types of bone fasteners 351 may be used for securely engaging the vertebrae. In certain embodiments, one or more of the bone fasteners 351 may extend form the first wing 348, and one or more bone fasteners 351 may extend from the second wing 349. In certain embodiments, the first wing 348 may include a first number of bone fasteners 351 extending therefrom, and the second wing 359 may include a second number of bone fasteners 351 extending therefrom, wherein the first number is different than the second number. In this manner, the degree of engagement between the bone fasteners 351 of the first wing 348 and the corresponding vertebra may be different from the degree of engagement between the bone fasteners 351 of the second wing 349 and the corresponding vertebra. Such an arrangement may facilitate relative movement of the treated vertebrae, while minimizing certain stresses induced in the device 300. In certain embodiments, one of the first wing 348 and the second wing 349 may not include any bone fasteners 351 extending therefrom, and the other of the first wing 348 and the second wing 349 may include one or more of the bone fasteners 351 extending therefrom. Such an arrangement also may facilitate relative movement of the treated vertebrae, while minimizing certain stresses induced in the device 300. Various configurations of the bone fasteners 351 of the second attachment side 312 may be used. In certain embodiments, as shown, the bone fasteners 351 may be configured to engage the laminae of the respective vertebrae. In other embodiments, one or more of the bone fasteners 351 may be configured to engage the spinous processes, the laminae, and/or other portions of the respective vertebrae. As shown, the second attachment side 312 also may include a securing aperture 352 configured to receive at least a portion of and cooperate with the securing means 313 for selectively fixing the first attachment side 311 and the second attachment side 312 relative to one another. The securing aperture 352 also may be configured for receiving a portion of and cooperating with an instrument used for positioning the second attachment side 312 during implantation of the device 300. Example instruments for implantation of the device 300 are described in the Prior Applications.

The securing means 313 may be configured for selectively fixing the first attachment side 311 and the second attachment side 312 relative to one another. In certain embodiments, as shown, the securing means 313 may be a fastener, such as a set screw, although other types of fasteners and other types of securing means may be used. As shown, the securing means may be inserted into and at least partially through the securing aperture 352 of the second attachment side 312. In this manner, the securing means 313 may be advanced through the securing aperture 352 until the securing means 313 engages the spacer 330 of the first attachment side 311 positioned within the spacer slot 350 of the second attachment side 312. Upon desired positioning of the first attachment side 311 and the second attachment side 312 with respect to the corresponding vertebrae of the patient, the securing means 313 may be tightened to maintain the spacing and orientation of the first attachment side 311 and the second attachment side 312 relative to one another and relative to the corresponding vertebrae. In certain embodiments, the securing means 313 may be formed of a metal, such as titanium or stainless steel, although other suitable materials, such as polyether ether ketone (PEEK), other polymers, or composites, may be used.

As described above, the device 300 may be configured to allow relative movement of the treated vertebrae upon implantation of the device 300. In particular, the device 300 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 311 and the second attachment side 312 each may include one or more features configured to facilitate such relative movement of the treated vertebrae. In particular, the first attachment side 311 may include one or more slots 333 (which also may be referred to as a "dynamic slot," a "cutout," an "opening," or a "slit") defined therein and configured to allow relative movement of portions of the first attachment side 311. In certain embodiments, as shown, the first attachment side 311 may include a single slot 333 formed at a central location in the direction of the longitudinal axis $A_L$ of the device 300. In certain embodiments, as shown, the slot 333 may be formed at least partially, or entirely, within the central portion 327 of the first attachment side 311. The slot 333 may have an elongated shape extending in the direction of the second transverse axis $A_{T2}$ of the device 300. In certain embodiments, as shown, the slot 333 may extend from the first side 323 to the second side 324 of the first attachment side 311. Further, in certain embodiments, as shown, the slot 333 may extend from the fourth side 326 of the first attachment side 311 toward, but not to, the third side 325 of the first attachment side 311. In other words, the slot 333 may be open along the fourth side 326 and may terminate at a location spaced apart from the third side 325. In certain embodiments, as shown, the slot 333 may have a straight portion extending in a linear manner in the direction of the second transverse axis $A_{T2}$ of the device 300 and a rounded portion positioned at the terminal end of the slot 333. In other embodiments, the slot 333 may be curved or otherwise contoured along one or more portions of or along the entire extend of the slot 333. Various other configurations of the slot 333 may be used in other embodiments.

Figure 3A:
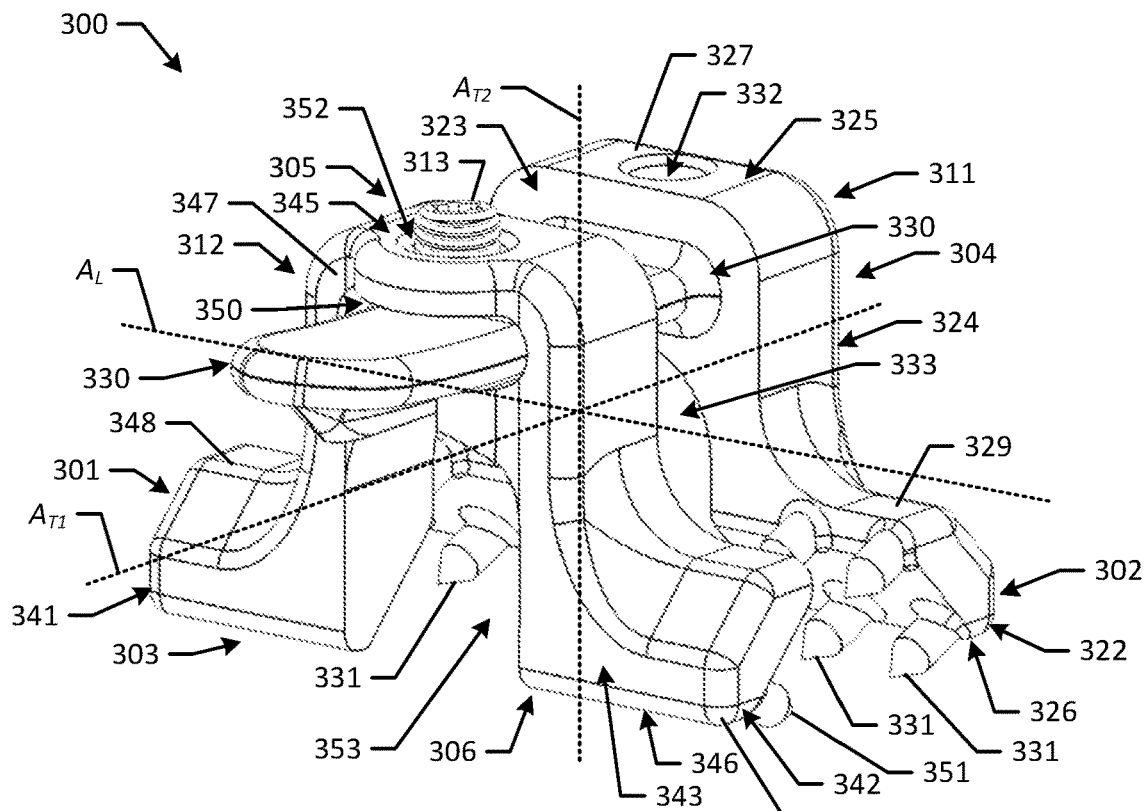
FIG. 3A is a perspective view of a dynamic interspinous process device in accordance with one or more embodiments of the present disclosure, showing a first attachment side, a second attachment side, and a securing means of the dynamic interspinous process device in an assembled state.
Figure 3B:
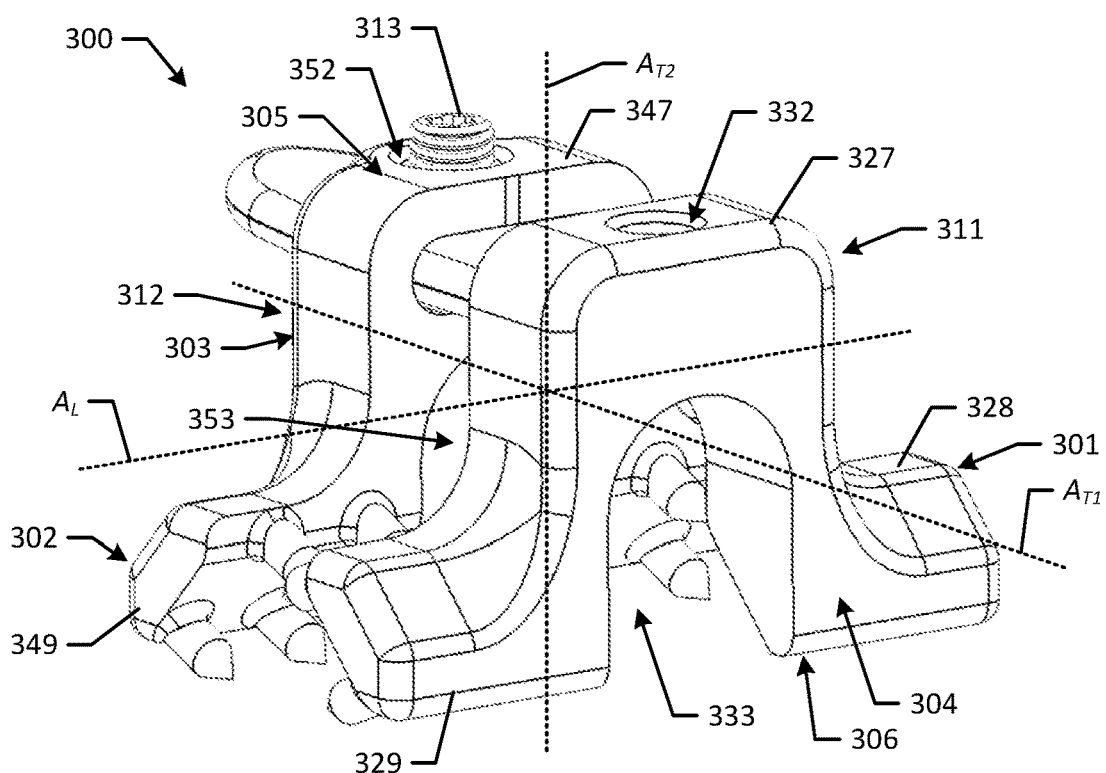
FIG. 3B is a perspective view of the dynamic interspinous process device of FIG. 3A, showing the first attachment side, the second attachment side, and the securing means in the assembled state.
Figure 3C:
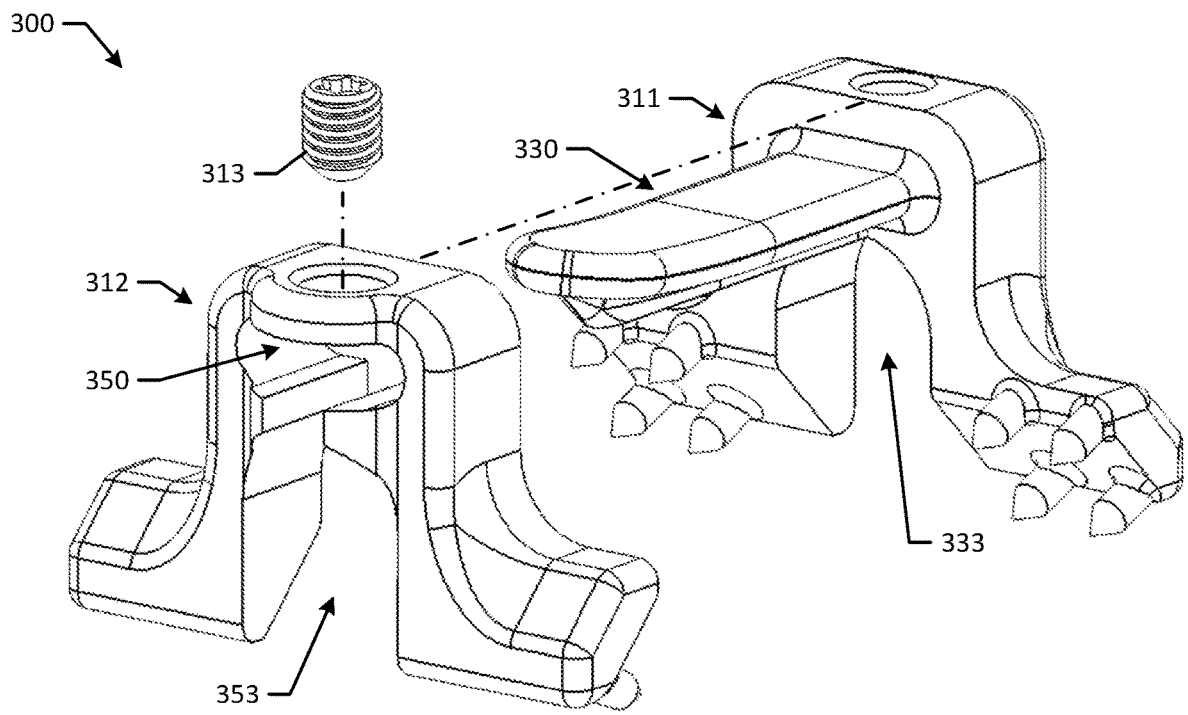
FIG. 3C is a perspective view of the dynamic interspinous process device of FIG. 3A, showing the first attachment side, the second attachment side, and the securing means in a disassembled state.
Figure 3D:
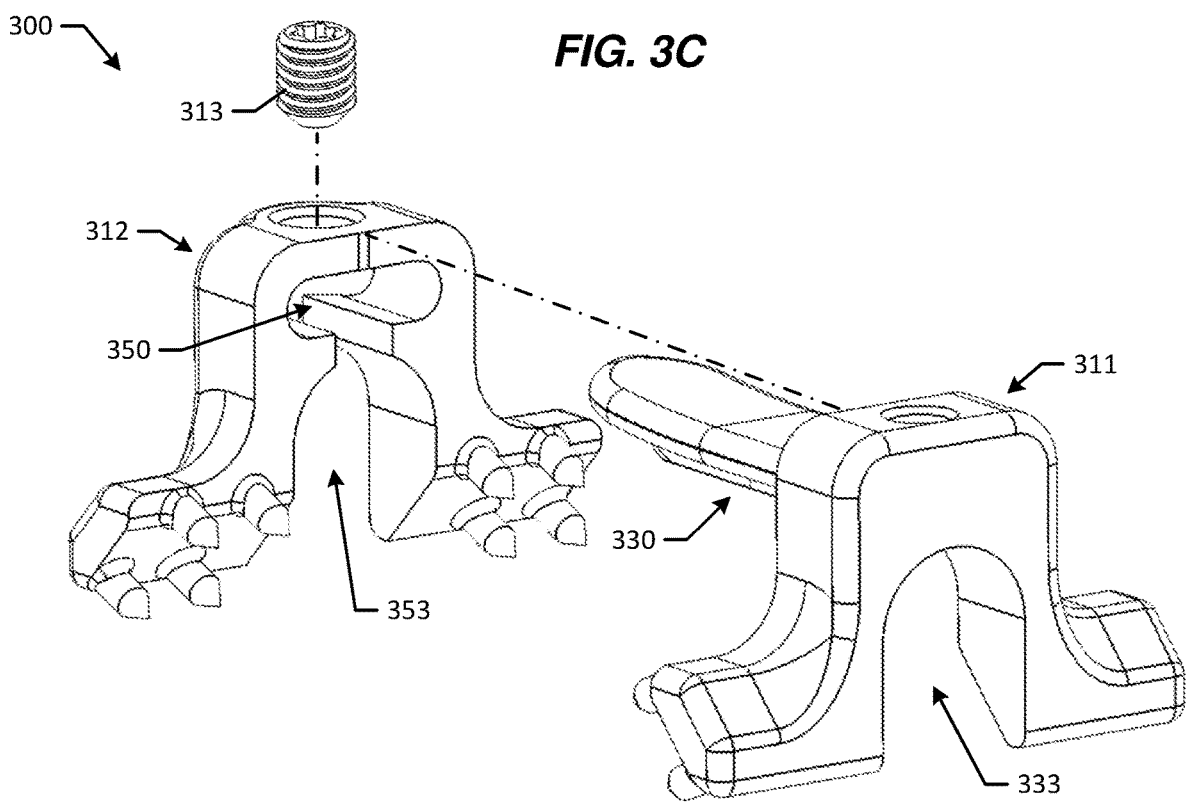
FIG. 3D is a perspective view of the dynamic interspinous process device of FIG. 3A, showing the first attachment side, the second attachment side, and the securing means in the disassembled state.
Figure 3E:
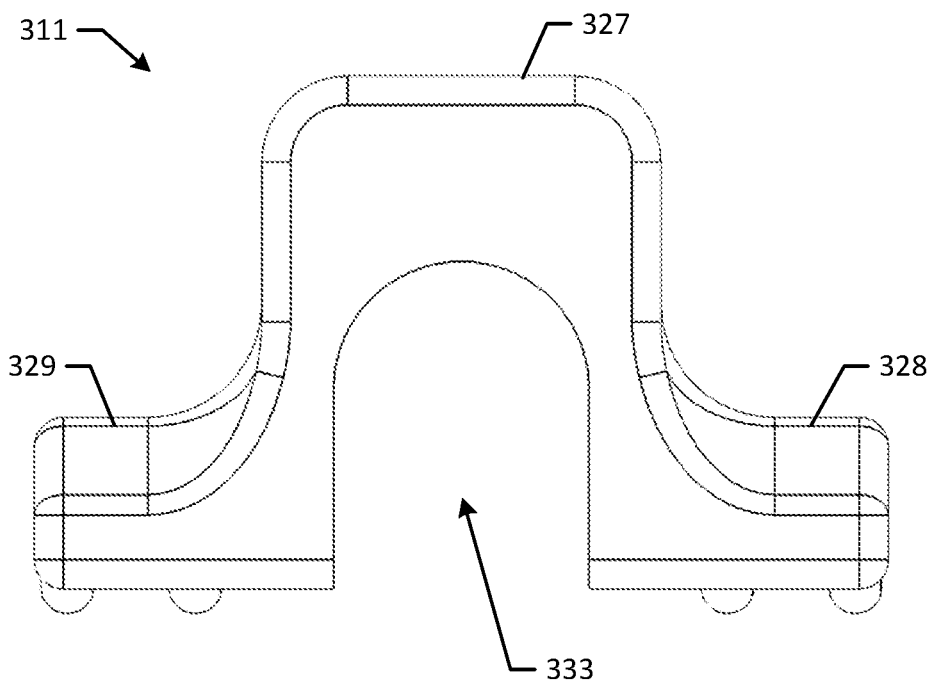
FIG. 3E is a plan view of the first attachment side of the dynamic interspinous process device of FIG. 3A.

It will be appreciated that the slot 333 may be configured to allow portions of the first attachment side 311 to move relative to one another. In particular, the slot 333 may be configured to allow the first wing 328 to move toward the spacer 330, in the direction of the longitudinal axis $A_L$ of the device 300, as the slot 333 is compressed, and also to allow the first wing 328 to move away from the spacer 330, in the direction of the longitudinal axis $A_L$ of the device 300, as the slot 333 is expanded. In a similar manner, the slot 333 may be configured to allow the second wing 329 to move toward the spacer 330, in the direction of the longitudinal axis $A_L$ of the device 300, as the slot 333 is compressed, and also to allow the second wing 329 to move away from the spacer 330, in the direction of the longitudinal axis $A_L$ of the device 300, as the slot 333 is expanded. As a result, the first wing 328 and the second wing 329 may be configured to move toward one another as the slot 333 is compressed, and to move away from one another as the slot 333 is expanded. In will be appreciated that, during such movement of the wings 328, 329, one or more regions of the first attachment side 311 surrounding the slot 333, such as the regions of the central portion 327 surrounding the terminal end of the slot 333, may flex or may be compressed to accommodate the compression or expansion of the slot 333. In effect, the slot 333 may cause the first attachment side 311 to function as a spring which may be compressed or extended in the direction of the longitudinal axis $A_L$ of the device 300 but has a natural tendency to return to a natural state as shown in FIG. 3E.

In a similar manner, the second attachment side 312 may include one or more slots 353 (which also may be referred to as a "dynamic slot," a "cutout," an "opening," or a "slit") defined therein and configured to allow relative movement of portions of the second attachment side 312. In certain embodiments, as shown, the second attachment side 312 may include a single slot 353 formed at a central location in the direction of the longitudinal axis $A_L$ of the device 300. In certain embodiments, as shown, the slot 353 may be formed at least partially, or entirely, within the central portion 347 of the second attachment side 312. The slot 353 may have an elongated shape extending in the direction of the second transverse axis $A_{T2}$ of the device 300. In certain embodiments, as shown, the slot 353 may extend from the first side 343 to the second side 344 of the second attachment side 312. Further, in certain embodiments, as shown, the slot 353 may extend from the fourth side 346 of the second attachment side 312 toward, but not to, the third side 345 of the second attachment side 312. In other words, the slot 353 may be open along the fourth side 346 and may terminate at a location spaced apart from the third side 345. In certain embodiments, as shown, the slot 353 may extend from the fourth side 346 to the spacer slot 350. In certain embodiments, as shown, the slot 353 may have a straight portion extending in a linear manner in the direction of the second transverse axis $A_{T2}$ of the device 300 and a rounded portion positioned at the terminal end of the slot 353. In other embodiments, the slot 353 may be curved or otherwise contoured along one or more portions of or along the entire extent of the slot 353. Various other configurations of the slot 353 may be used in other embodiments.

Figure 3F:
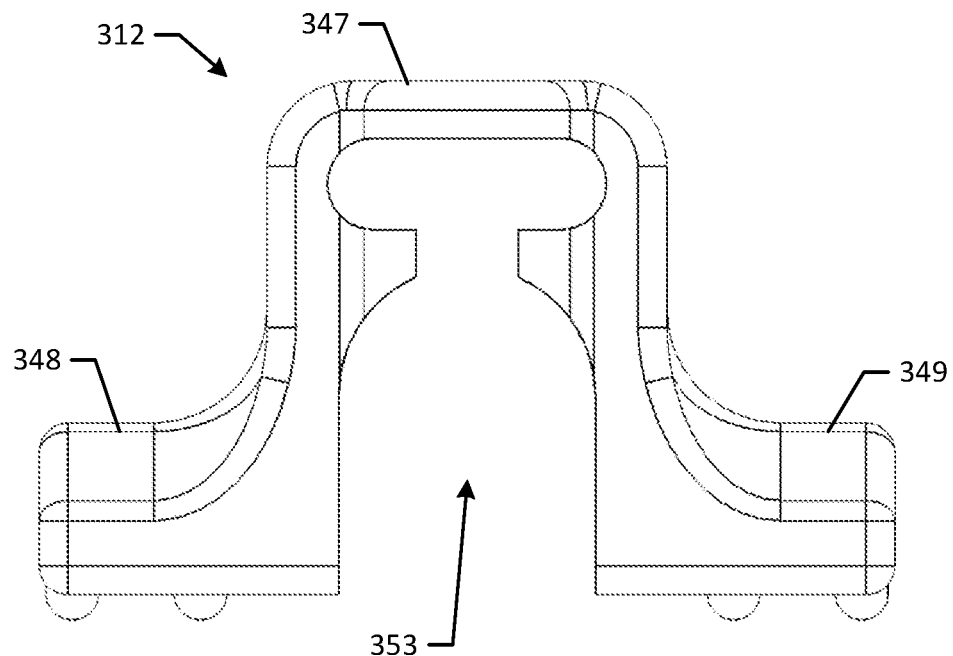
FIG. 3F is a plan view of the second attachment side of the dynamic interspinous process device of FIG. 3A.

It will be appreciated that the slot 353 may be configured to allow portions of the second attachment side 312 to move relative to one another. In particular, the slot 353 may be configured to allow the first wing 348 to move toward the spacer slot 350, in the direction of the longitudinal axis $A_L$ of the device 300, as the slot 353 is compressed, and also to allow the first wing 348 to move away from the spacer slot 350, in the direction of the longitudinal axis $A_L$ of the device 300, as the slot 353 is expanded. In a similar manner, the slot 353 may be configured to allow the second wing 349 to move toward the spacer slot 350, in the direction of the longitudinal axis $A_L$ of the device 300, as the slot 353 is compressed, and also to allow the second wing 349 to move away from the spacer slot 350, in the direction of the longitudinal axis $A_L$ of the device 300, as the slot 353 is expanded. As a result, the first wing 348 and the second wing 349 may be configured to move toward one another as the slot 353 is compressed, and to move away from one another as the slot 353 is expanded. In will be appreciated that, during such movement of the wings 348, 349, one or more regions of the second attachment side 312 surrounding the slot 353, such as the regions of the central portion 347 surrounding the terminal end of the slot 353, may flex or may be compressed to accommodate the compression or expansion of the slot 353. In effect, the slot 353 may cause the second attachment side 312 to function as a spring which may be compressed or extended in the direction of the longitudinal axis $A_L$ of the device 300 but has a natural tendency to return to a natural state as shown in FIG. 3F. In certain embodiments, as shown, the slot 333 of the first attachment side 311 may be formed as a mirror image of the slot 353 of the second attachment side 312. In other embodiments, the shape or configuration of the slot 333 of the first attachment side 311 may be different than the shape or configuration of the slot 353 of the second attachment side 312. Various configurations of the slot 333 and the slot 353 may be used to allow for a desired range of movement of the corresponding vertebrae.

In certain embodiments, the device 300 may include means for varying resistance to the relative movement between the first wing 328 and the second wing 329 of the first attachment side 311 over at least a portion of the range of motion of the wings 328, 329 and for varying resistance to the relative movement between the first wing 348 and the second wing 349 of the second attachment side 312 over at least a portion of the range of motion of the wings 348, 349. In this manner, the device 300 may vary the resistance to the relative movement between the treated vertebrae over at least a portion of the range of motion of the vertebrae allowed by the device 300. FIGS. 3G and 3H illustrate an embodiment in which the device 300 includes a resistance means for varying resistance to the relative movement between the wings 328, 329 and between the wings 348, 349. As shown, the first attachment side 311 may include a single resistance means 361 (which also may be referred to as a "resistance insert," a "resistance member" or a "biasing member") configured for varying resistance to movement of the wings 328, 329 relative to the central portion 327 and relative to one another over at least a portion of the range of motion of these features as may be allowed by the slot 333. In certain embodiments, as shown, the resistance means 361 may be an insert configured to be inserted into and retained within the slots 333. In certain embodiments, the resistance means 361 may be removably received within the slot 333, such that the resistance means 361 may be placed therein when resistance is desired and may be removed therefrom when resistance is not desired. In other embodiments, the resistance means 361 may be securely fixed within the slot 333, such that the resistance means 361 is not removable therefrom. In certain embodiments, the resistance means 361 may be formed of a compressible material or a resiliently deformable material, such as a biocompatible polymer or other suitable material, which may be compressed by the relative movement of surrounding portions of the first attachment side 311 but may have a natural tendency to return to a natural state when compression forces are removed. It will be appreciated that a durometer of the compressible material or resiliently deformable material may be selected to provide a desired resistance to the relative movement of surrounding portions of the first attachment side 311. In other embodiments, the resistance means 361 may be formed as a spring, such as a compression spring, which may function similar to the compressible material or resiliently deformable material member. In certain embodiments, as shown, the resistance means 361 may fill or substantially fill the entirety of the slot 333. In other embodiments, the resistance means 361 may fill only a portion of the slot 333.

According to the illustrated embodiment, the resistance means 361 may be configured to resist movement of the wings 328, 329 toward the central portion 327, and thus the resistance means 361 also may resist relative movement of the wings 328, 329 toward one another. In particular, as the wings 328, 329 move toward the central portion 327 and toward one another and the slot 333 is compressed, the resistance means 361 may be compressed, thereby resisting, but not preventing, further movement of the wings 328, 329 toward the central portion 327 and toward one another. Further, the resistance means 361 may provide a biasing force acting on the portions of the first attachment side 311 surrounding the slot 333, biasing the wings 328, 329 toward their home or natural position and the slot 333 to its home or natural state.

In a similar manner, the second attachment side 312 may include a resistance means 362 (which also may be referred to as a "resistance insert," a "resistance member" or a "biasing member") configured for varying resistance to movement of the wings 348, 349 relative to the central portion 347 and relative to one another over at least a portion of the range of motion of these features as may be allowed by the slot 353. In certain embodiments, as shown, the resistance means 362 may be an insert configured to be inserted into and retained within the slot 353. In certain embodiments, the resistance means 362 may be removably received within the slot 353, such that the resistance means 362 may be placed therein when resistance is desired and may be removed therefrom when resistance is not desired. In other embodiments, the resistance means 362 may be securely fixed within the slot 353, such that the resistance means 362 is not removable therefrom. In certain embodiments, the resistance means 362 may be formed of a compressible material or a resiliently deformable material, such as a biocompatible polymer or other suitable material, which may be compressed by the relative movement of surrounding portions of the second attachment side 312 but may have a natural tendency to return to a natural state when compression forces are removed. It will be appreciated that a durometer of the compressible material or resiliently deformable material may be selected to provide a desired resistance to the relative movement of surrounding portions of the second attachment side 312. In other embodiments, the resistance means 362 may be formed as a spring, such as a compression spring, which may function similar to the compressible material or resiliently deformable material member. In certain embodiments, as shown, the resistance means 362 may fill or substantially fill the entirety of the slot 353. In other embodiments, the resistance means 362 may fill only a portion of the slot 353.

According to the illustrated embodiment, the resistance means 362 may be configured to resist movement of one of the wings 348, 349 toward the central portion 347, and thus the resistance means 362 also may resist relative movement of the wings 348, 349 toward one another. In particular, as the wings 348, 349 move toward the central portion 347 and toward one another and the slot 353 is compressed, the resistance means 362 may be compressed, thereby resisting, but not preventing, further movement of the wings 348, 349 toward the central portion 347 and toward one another. Further, the resistance means 362 may provide a biasing force acting on the portions of the second attachment side 312 surrounding the slot 353, biasing the wings 348, 349 toward their home or natural position and the slot 353 to its home or natural state.

It will be appreciated that the resistance means 361, 362 of the device 300 may be used to vary resistance to the relative movement between the treated vertebrae, when desired. In particular, the resistance means 361, 362 may be used to increase resistance to the relative movement between the treated vertebrae over at least a portion of the range of motion of the vertebrae allowed by the device 300. In this manner, the device 300 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 361, 362 may be selected to provide a desired degree of resistance to the relative motion of the treated vertebrae.

In certain embodiments, the device 300 may include means for preventing or inhibiting the relative movement between the first wing 328 and the second wing 329 of the first attachment side 311 and for preventing or inhibiting the relative movement between the first wing 348 and the second wing 349 of the second attachment side 312. In this manner, the device 300 may prevent or inhibit the relative movement between the treated vertebrae. FIGS. 3I and 3J illustrate embodiments in which the device 300 includes one or more fixation means for preventing or inhibiting the relative movement between the wings 328, 329 and between the wings 348, 349. As shown, the first attachment side 311 may include one or more fixation means 371 (which also may be referred to as a "fixation insert," a "fixation member," a "fastener," or a "lock") configured for preventing or inhibiting movement of the wings 328, 329 relative to the central portion 327 and relative to one another as may be allowed by the slot 333. In certain embodiments, the fixation means 371 may be removably attached to the central portion 327 and/or one of the wings 328, 329. In other embodiments, the fixation means 371 may be fixedly secured to the central portion 327 and/or one or the wings 328, 329. In certain embodiments, as shown, the fixation means 371 may be configured to be inserted at least partially into and retained within the slot 333. The fixation means 371 may engage portions of the first attachment side 311 surrounding the slot 333 such that the fixation means 371 prevents or inhibits at least a portion of the slot 333 from expanding and/or collapsing. In certain embodiments, the fixation means 371 may be a fastener, such as a set screw having a reverse angle thread for threadably engaging and retaining mating threaded portions of the first attachment side 311. In certain embodiments, as shown, the fixation means 371 may be inserted, in a direction parallel to the second transverse axis $A_{T2}$ of the device 300, into the open end of the slot 333.

In a similar manner, the second attachment side 312 may include one or more fixation means 372 (which also may be referred to as a "fixation insert," a "fixation member," a "fastener," or a "lock") configured for preventing or inhibiting movement of the wings 348, 349 relative to the central portion 347 and relative to one another as may be allowed by the slot 353. In certain embodiments, the fixation means 372 may be removably attached to the central portion 347 and/or one of the wings 348, 349. In other embodiments, the fixation means 372 may be fixedly secured to the central portion 347 and/or one or the wings 348, 349. In certain embodiments, as shown, a single fixation means 372 may be configured to be inserted at least partially into and retained within the slot 353. The fixation means 372 may engage portions of the second attachment side 312 surrounding the slot 353 such that the fixation means 372 prevents or inhibits at least a portion of the slot 353 from expanding and/or collapsing. In certain embodiments, the fixation means 372 may be a fastener, such as a set screw having a reverse angle thread for threadably engaging and retaining mating threaded portions of the second attachment side 312. In certain embodiments, as shown, the fixation means 372 may be inserted, in a direction parallel to the second transverse axis $A_{T2}$ of the device 300, into the open end of the slot 353.

It will be appreciated that the fixation means 371, 372 of the device 300 may be used to control the relative movement between the treated vertebrae, when desired. In particular, the fixation means 371, 372 may be used to prevent or inhibit relative movement between the treated vertebrae. In this manner, the device 300 may be used as a dynamic device or a rigid device, with the ability to convert the device 300 between a dynamic configuration and a rigid configuration, as may be desired in certain applications. The fixation means 371, 372 may be used to convert the device 300 between the dynamic configuration and the rigid configuration prior to implantation of the device 300, during initial implantation of the device 300 as a part of an initial surgery, or during a follow-up surgery.

Figure 3K:
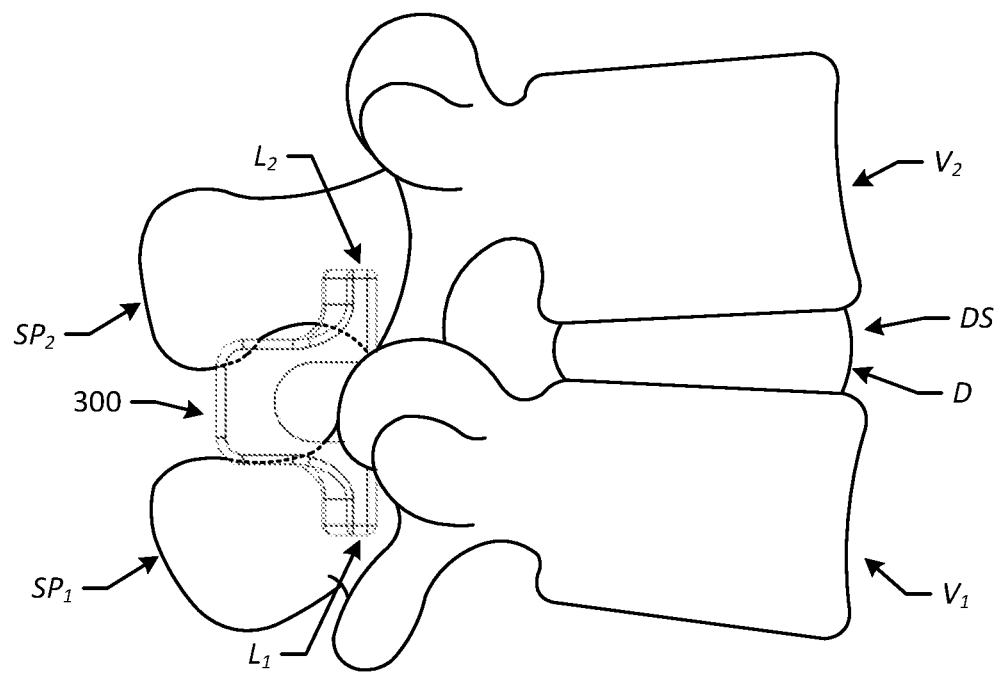
FIG. 3K is a side view of the dynamic interspinous process device of FIG. 3A implanted with respect to a first vertebra and a second vertebra in accordance with one or more embodiments of the present disclosure.
Figure 3L:
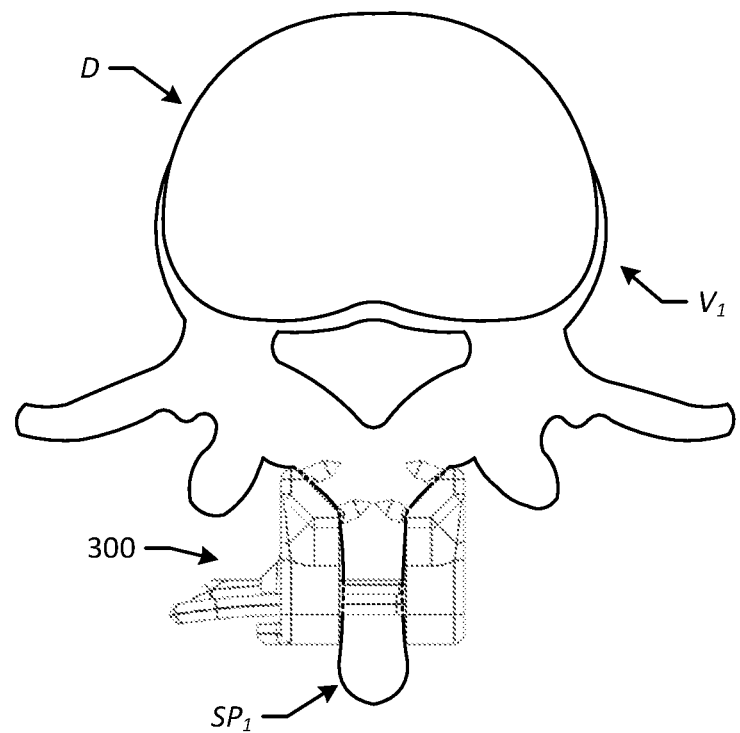
FIG. 3L is a top view of the dynamic interspinous process device of FIG. 3A implanted with respect to the first vertebra, the second vertebra being removed from view for purposes of illustration.

FIGS. 3K and 3L illustrate an example implantation of the device 300 with respect to a first vertebra $V_1$ and an adjacent second vertebra $V_2$. As shown, the first attachment side 311 and the second attachment side 312 may be positioned relative to the vertebrae $V_1$, $V_2$ such that the spacer 330 is positioned between a first spinous process $SP_1$ of the first vertebra $V_1$ and a second spinous process $SP_2$ of the second vertebra $V_2$. In this manner, the spacer 330 may limit a minimum spacing between the spinous processes $SP_1$, $SP_2$. Additionally, the first attachment side 311 and the second attachment side 312 may be positioned relative to the vertebrae $V_1$, $V_2$ such that the respective wings 328, 329 of the first attachment side 311 and the respective wings 348, 349 of the second attachment side 312 engage a first lamina $L_1$ of the first vertebra $V_1$ and a second lamina $L_2$ of the second vertebra $V_2$. In this manner, the respective bone fasteners 331 of the first attachment side 311 and the respective bone fasteners 351 of the second attachment side 312 may penetrate and securely engage the laminae $L_1$, $L_2$. Accordingly, the implanted device 300 may stabilize the vertebrae $V_1$, $V_2$, although the device 300 may allow relative movement of the vertebrae $V_1$, $V_2$. In particular, the slots 333, 353 of the device 300 may allow relative movement of the vertebrae $V_1$, $V_2$ in sagittal plane of the patient, thereby allowing flexion and extension of the treated segment of the spine. It will be appreciated that the configuration of the slots 333, 353 may be varied, for example, by varying the number, size, and/or shape the slots 333, 353 to allow a desired range of motion in the sagittal plane. Further, the material from which the first attachment side 311 and the second attachment side 312 are formed may be selected to achieve the desired range of motion. In certain embodiments, the first attachment side 311 and the second attachment side 312 may be formed of titanium, although other suitable metals, polymers, or other materials may be used in other embodiments. Meanwhile, the device 300 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 300 and the disc D. In other embodiments in which the native disc D is removed, an interbody device, such as a cage or a spacer, may be implanted within the disc space DS (i.e., the intervertebral space) and the loads carried by the treated spinal segment may be shared by the device 300 and the interbody device. As described above, the device 300 may be used in conjunction with other additional hardware, such that the device 300 and the additional hardware collectively stabilize the treated segment of the spine and share loads carried thereby. It will be appreciated that the foregoing description and the corresponding drawings are merely examples of the device 300 and that other configurations and modifications may be made.

FIGS. 4A-4L illustrate an interspinous process device 400 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 400 may be configured for implantation relative to a first vertebra and an adjacent second vertebra, as described below, specifically with reference to FIGS. 4K and 4L. In particular, a portion of the interspinous process device 400 may be positioned between the spinous process of the first vertebra and the spinous process of the second vertebra, while one or more other portions of the interspinous process device 400 engage the spinous processes, the laminae, and/or other portions of the respective vertebra. As described below, the interspinous process device 400 may allow a desired range of relative movement between the treated vertebrae, which may be desirable in certain treatment applications. The interspinous process device 400 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 400, itself or in combination with additional hardware, may provide the structural support necessary to restore and maintain normal spacing and alignment of the treated vertebrae while avoiding certain drawbacks presented by existing interspinous process devices.

The interspinous process device 400 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 400 may include a first end 401 and a second end 402 disposed opposite the first end 401 in the direction of the longitudinal axis $A_L$. As described below, the device 400 may be implanted with the longitudinal axis $A_L$ extending in a direction substantially parallel to the sagittal plane and the coronal plane of the patient and transverse to the transverse plane of the patient. In this manner, depending on the orientation of the device 400 upon implantation thereof, one of the first end 401 and the second end 402 of the device 400 may be referred to as a the "superior end" of the device 400, and the other of the first end 401 and the second end 402 of the device 400 may be referred to as the "inferior end" of the device 400. The device 400 also may include a first side 403 extending from the first end 401 to the second end 402, and a second side 404 disposed opposite the first side 403 in the direction of the first transverse axis $A_{T1}$ and extending from the first end 401 to the second end 402. The device 400 may be implanted with the first transverse axis $A_{T1}$ extending in a direction substantially parallel to the coronal plane and the transverse plane of the patient and transverse to the sagittal plane of the patient. In this manner, depending on the orientation of the device 400 upon implantation thereof, one of the first side 403 and the second side 404 of the device 400 may be referred to as a the "right side" of the device 400, and the other of the first side 403 and the second side 404 of the device 400 may be referred to as the "left side" of the device 400. The device 400 further may include a third side 405 extending from the first end 401 to the second end 402 and from the first side 403 to the second side 404, and a fourth side 406 disposed opposite the third side 405 in the direction of the second transverse axis $A_{T2}$ and extending from the first end 401 to the second end 402 and from the first side 403 to the second side 404. The device 400 may be implanted with the second transverse axis $A_{T2}$ extending in a direction substantially parallel to the sagittal plane and the transverse plane of the patient and transverse to the coronal plane of the patient. As described below, the device 400 may be oriented upon implantation thereof such that the third side 405 faces posteriorly and the fourth side 406 faces anteriorly with respect to the patient. In this manner, the third side 405 may be referred to as the "posterior side" of the device 400, and the fourth side 406 may be referred to as the "anterior side" of the device 400. The device 400 may have an overall "length" extending from the first end 401 to the second end 402 in the direction of the longitudinal axis $A_L$, an overall "width" extending from the first side 403 to the second side 404 in the direction of the first transverse axis $A_{T1}$, and an overall "height" extending from the third side 405 to the fourth side 406 in the direction of the second transverse axis $A_{T2}$. Further, various components and features of the device 400 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 400 may include a first attachment side 411 (which also may be referred to as a "first attachment portion," a "first attachment assembly," or a "first plate") and a second attachment side 412 (which also may be referred to as a "second attachment portion," a "second attachment assembly," or a "second plate") configured for removably attaching to one another via a securing means 413. During use of the device 400, one of the first attachment side 411 and the second attachment side 412 may be disposed, at least partially, along the right side of the patient's spine, and the other of the first attachment side 411 and the second attachment side 412 may be disposed, at least partially, along the right side of the patient's spine. It will be appreciated that the first attachment side 411 and the second attachment side 412 may include corresponding features that are mirror images of one another, although certain differences between the first attachment side 411 and the second attachment side 412 may exist, as described below. In certain embodiments, the first attachment side 411 and the second attachment side 412 may be formed of a metal, such as titanium or stainless steel, although other suitable materials, such as polyether ether ketone (PEEK), other polymers, or composites, may be used.

The first attachment side 411 may have a first end 421, a second end 422 disposed opposite the first end 421, a first side 423 (which also may be referred to as an "interior side"), a second side 424 (which also may be referred to as an "exterior side") disposed opposite the first side 423, a third side 425 (which also may be referred to as an "posterior side"), and a fourth side 426 (which also may be referred to as an "anterior side") disposed opposite the third side 425. As shown, the first attachment side 411 may include a central portion 427 and a pair of wings 428, 429 disposed on opposite sides of the central portion 427. In particular, the first wing 428 may extend from the central portion 427 to the first end 421 of the first attachment side 411, and the second wing 429 may extend from the central portion 427 to the second end 422 of the first attachment side 411. In certain embodiments, as shown, the wings 428, 429 may extend in opposite directions from the central portion 427 and may be formed as mirror images of one another. In other embodiments, the wings 428, 429 may extend in opposite directions from the central portion 427, but the first wing 428 may have a different shape or configuration than the second wing 429 such that the wings 428, 429 are not mirror images of one another. In certain embodiments, the wings 428, 429 may be shaped and configured in a manner similar to any one of the wing embodiments described and/or shown in the Prior Applications. Various other configurations of the wings 428, 429 may be used.

The first attachment side 411 also may include a spacer 430 extending from the first side 423 thereof. During use of the device 400, the spacer 430 may be positioned between the spinous processes of the respective vertebrae. In certain embodiments, as shown, the spacer 430 may extend from the central portion 427 of the first attachment side 411 and be integrally formed therewith. In other embodiments, the spacer 430 may be separately formed from and attached to the central portion 427 via an attachment mechanism. The first attachment side 411 further may include a number of engagement features configured for securely engaging the respective vertebrae. In certain embodiments, as shown, the engagement features may be one or more bone fasteners 431 extending from the first side 423 of the first attachment side 411. The bone fasteners 431 may be formed as spikes or barbs, although other forms and types of bone fasteners 431 may be used for securely engaging the vertebrae. In certain embodiments, one or more of the bone fasteners 431 may extend form the first wing 428, and one or more bone fasteners 431 may extend from the second wing 429. In certain embodiments, the first wing 428 may include a first number of bone fasteners 431 extending therefrom, and the second wing 429 may include a second number of bone fasteners 431 extending therefrom, wherein the first number is different than the second number. In this manner, the degree of engagement between the bone fasteners 431 of the first wing 428 and the corresponding vertebra may be different from the degree of engagement between the bone fasteners 431 of the second wing 429 and the corresponding vertebra. Such an arrangement may facilitate relative movement of the treated vertebrae, while minimizing certain stresses induced in the device 400. In certain embodiments, one of the first wing 428 and the second wing 429 may not include any bone fasteners 431 extending therefrom, and the other of the first wing 428 and the second wing 429 may include one or more of the bone fasteners 431 extending therefrom. Such an arrangement also may facilitate relative movement of the treated vertebrae, while minimizing certain stresses induced in the device 400. Various configurations of the bone fasteners 431 of the first attachment side 411 may be used. In certain embodiments, as shown, the bone fasteners 431 may be configured to engage the laminae of the respective vertebrae. In other embodiments, one or more of the bone fasteners 431 may be configured to engage the spinous processes, the laminae, and/or other portions of the respective vertebrae. As shown, the first attachment side 411 also may include an instrument engagement aperture 432 configured for receiving a portion of and cooperating with an instrument used for positioning the first attachment side 411 during implantation of the device 400. Example instruments for implantation of the device 400 are described in the Prior Applications.

In a similar manner, the second attachment side 412 may have a first end 441, a second end 442 disposed opposite the first end 441, a first side 443 (which also may be referred to as an "exterior side"), a second side 444 (which also may be referred to as an "interior side") disposed opposite the first side 443, a third side 445 (which also may be referred to as an "posterior side"), and a fourth side 446 (which also may be referred to as an "anterior side") disposed opposite the third side 445. As shown, the second attachment side 412 may include a central portion 447 and a pair of wings 448, 449 disposed on opposite sides of the central portion 447. In particular, the first wing 448 may extend from the central portion 447 to the first end 441 of the second attachment side 412, and the second wing 449 may extend from the central portion 447 to the second end 442 of the second attachment side 412. In certain embodiments, as shown, the wings 448, 449 may extend in opposite directions from the central portion 447 and may be formed as mirror images of one another. In other embodiments, the wings 448, 449 may extend in opposite directions from the central portion 447, but the first wing 448 may have a different shape or configuration than the second wing 449 such that the wings 448, 449 are not mirror images of one another. In certain embodiments, the wings 448, 449 may be shaped and configured in a manner similar to any one of the wing embodiments described and/or shown in the Prior Applications. Various other configurations of the wings 448, 449 may be used.

The second attachment side 412 also may include a spacer slot 450 extending through the second attachment side 412 from the first side 443 to the second side 444 thereof. During use of the device 400, the spacer slot 450 may be configured to receive the spacer 430 of the first attachment side 411 therethrough, as shown. In certain embodiments, as shown, the spacer slot 450 may be defined in the central portion 447 of the second attachment side 412 and may extend to the fourth side 446 thereof, although other positions of the spacer slot 450 may be used. The second attachment side 412 further may include a number of engagement features configured for securely engaging the respective vertebrae. In certain embodiments, as shown, the engagement features may be one or more bone fasteners 451 extending from the second side 444 of the second attachment side 412. The bone fasteners 451 may be formed as spikes or barbs, although other forms and types of bone fasteners 451 may be used for securely engaging the vertebrae. In certain embodiments, one or more of the bone fasteners 451 may extend form the first wing 448, and one or more bone fasteners 451 may extend from the second wing 449. In certain embodiments, the first wing 448 may include a first number of bone fasteners 451 extending therefrom, and the second wing 449 may include a second number of bone fasteners 451 extending therefrom, wherein the first number is different than the second number. In this manner, the degree of engagement between the bone fasteners 451 of the first wing 448 and the corresponding vertebra may be different from the degree of engagement between the bone fasteners 451 of the second wing 449 and the corresponding vertebra. Such an arrangement may facilitate relative movement of the treated vertebrae, while minimizing certain stresses induced in the device 400. In certain embodiments, one of the first wing 448 and the second wing 449 may not include any bone fasteners 451 extending therefrom, and the other of the first wing 448 and the second wing 449 may include one or more of the bone fasteners 451 extending therefrom. Such an arrangement also may facilitate relative movement of the treated vertebrae, while minimizing certain stresses induced in the device 400. Various configurations of the bone fasteners 451 of the second attachment side 412 may be used. In certain embodiments, as shown, the bone fasteners 451 may be configured to engage the laminae of the respective vertebrae. In other embodiments, one or more of the bone fasteners 451 may be configured to engage the spinous processes, the laminae, and/or other portions of the respective vertebrae. As shown, the second attachment side 412 also may include a securing aperture 452 configured to receive at least a portion of and cooperate with the securing means 413 for selectively fixing the first attachment side 411 and the second attachment side 412 relative to one another. The securing aperture 452 also may be configured for receiving a portion of and cooperating with an instrument used for positioning the second attachment side 412 during implantation of the device 400. Example instruments for implantation of the device 400 are described in the Prior Applications.

The securing means 413 may be configured for selectively fixing the first attachment side 411 and the second attachment side 412 relative to one another. In certain embodiments, as shown, the securing means 413 may be a fastener, such as a set screw, although other types of fasteners and other types of securing means may be used. As shown, the securing means may be inserted into and at least partially through the securing aperture 452 of the second attachment side 412. In this manner, the securing means 413 may be advanced through the securing aperture 452 until the securing means 413 engages the spacer 430 of the first attachment side 411 positioned within the spacer slot 450 of the second attachment side 412. Upon desired positioning of the first attachment side 411 and the second attachment side 412 with respect to the corresponding vertebrae of the patient, the securing means 413 may be tightened to maintain the spacing and orientation of the first attachment side 411 and the second attachment side 412 relative to one another and relative to the corresponding vertebrae. In certain embodiments, the securing means 413 may be formed of a metal, such as titanium or stainless steel, although other suitable materials, such as polyether ether ketone (PEEK), other polymers, or composites, may be used.

As described above, the device 400 may be configured to allow relative movement of the treated vertebrae upon implantation of the device 400. In particular, the device 400 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 411 and the second attachment side 412 each may include one or more features configured to facilitate such relative movement of the treated vertebrae. In particular, the first attachment side 411 may include one or more slots 433 (which also may be referred to as a "dynamic slot," a "cutout," an "opening," or a "slit") defined therein and configured to allow relative movement of portions of the first attachment side 411. In certain embodiments, as shown, the first attachment side 411 may include a pair of the slots 433 spaced apart from one another in the direction of the longitudinal axis $A_L$ of the device 400. In certain embodiments, as shown, the slots 433 may be formed at least partially within the central portion 427 of the first attachment side 411. Each slot 433 may have an elongated shape extending partially in the direction of the second transverse axis $A_{T2}$ of the device 400 and partially in the direction of the longitudinal axis $A_L$ of the device 400. In certain embodiments, as shown, each slot 433 may extend at an acute angle relative to the second transverse axis $A_{T2}$ and at an acute angle relative to the longitudinal axis $A_L$ of the device 400. In certain embodiments, as shown, one of the slots 433 may be positioned at an intersection of the central portion 427 and the first wing 428, and the other slot 433 may be positioned at an intersection of the central portion 427 and the second wing 429. In certain embodiments, as shown, each slot 433 may extend from the first side 423 to the second side 424 of the first attachment side 411. Further, in certain embodiments, as shown, each slot 133 may extend from an outer surface along the respective intersection of the central portion 427 and the first wing 428 or the second wing 429 toward, but not to, the spacer 430 of the first attachment side 411. In other words, the slot 433 may be open along the respective intersection of the central portion 427 and the first wing 428 or the second wing 429 and may terminate at a location spaced apart from the spacer 430. In certain embodiments, as shown, each slot 433 may have a straight shape, although the slot 433 may taper in the direction from the open end of the slot 433 to the closed end of the slot 433. In other embodiments, each slot 433 may be include one or more curved or otherwise contoured portions or may be contoured along the entire extent of the slot 433. Various other configurations of the slots 433 may be used in other embodiments.

Figure 4A:
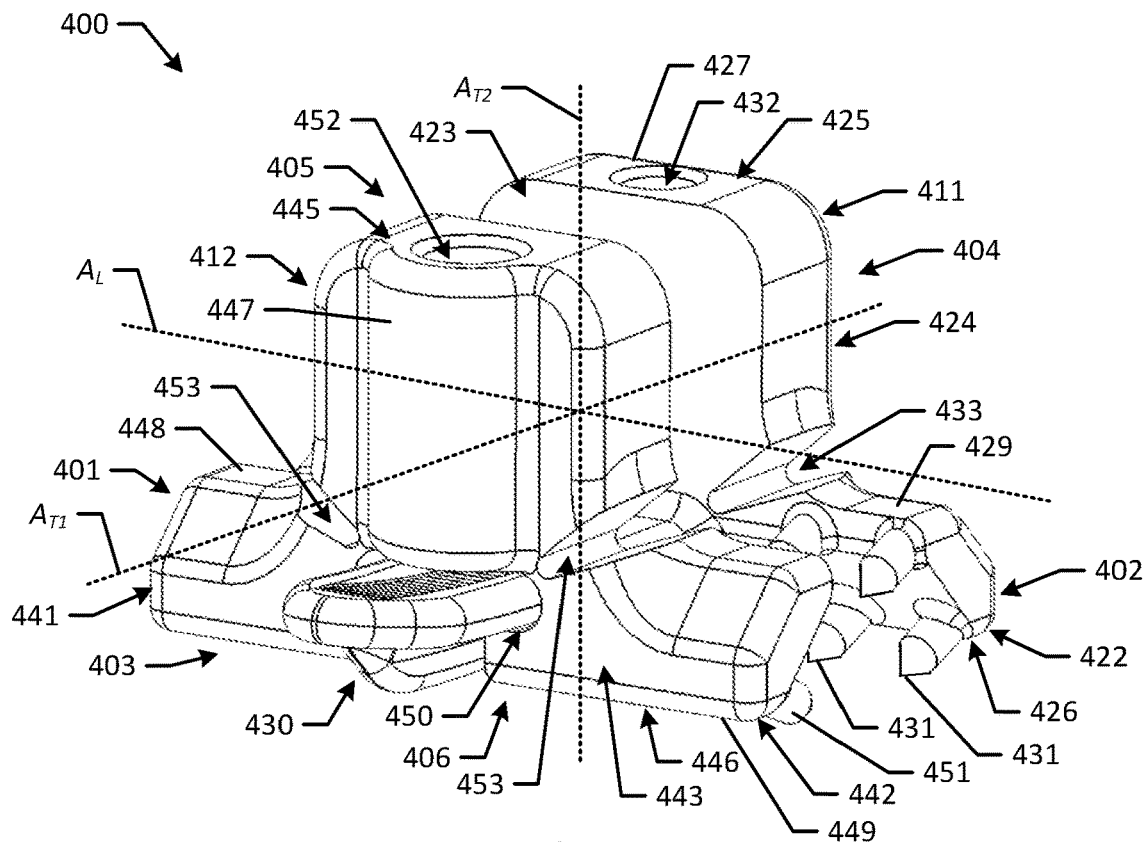
FIG. 4A is a perspective view of a dynamic interspinous process device in accordance with one or more embodiments of the present disclosure, showing a first attachment side and a second attachment side of the dynamic interspinous process device in an assembled state.
Figure 4B:
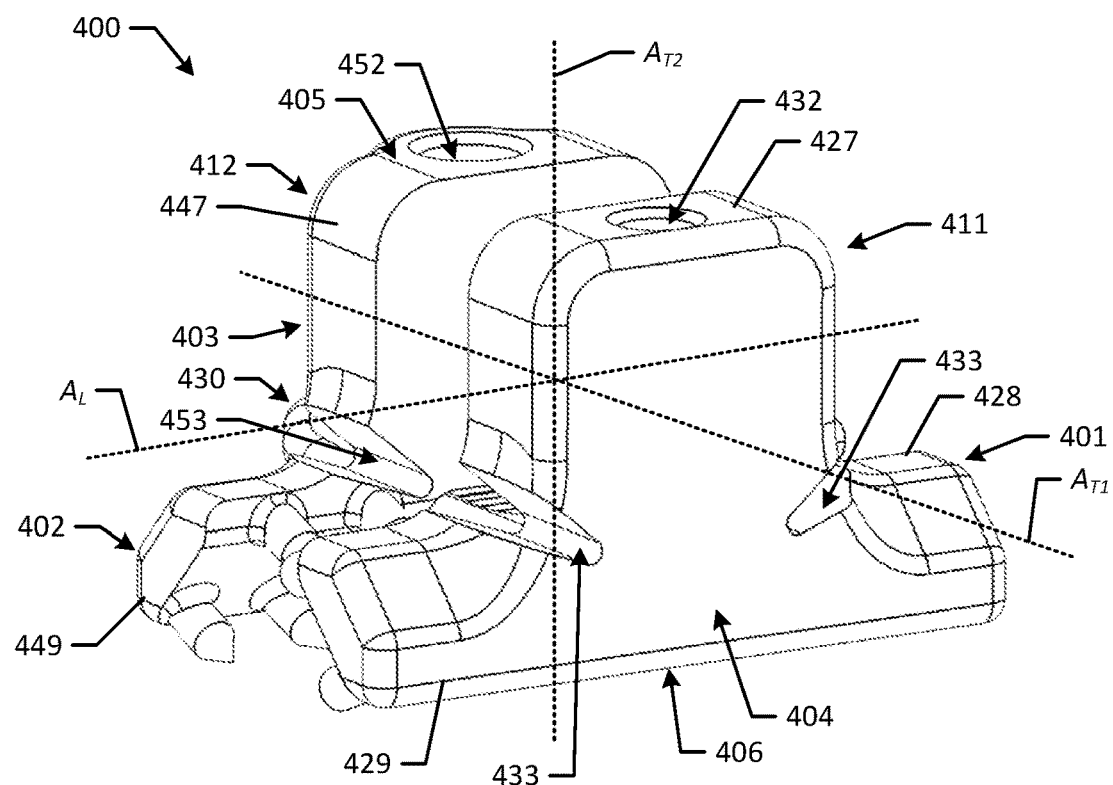
FIG. 4B is a perspective view of the dynamic interspinous process device of FIG. 4A, showing the first attachment side and the second attachment side in the assembled state.
Figure 4C:
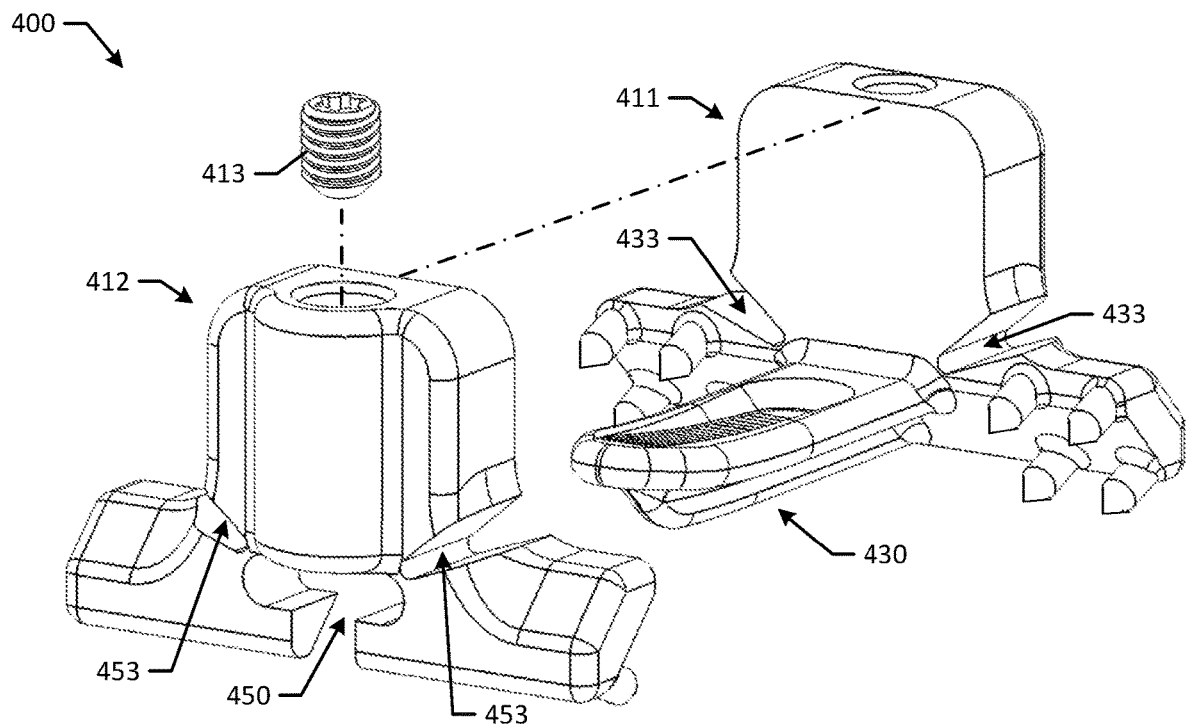
FIG. 4C is a perspective view of the dynamic interspinous process device of FIG. 4A, showing the first attachment side, the second attachment side, and a securing means of the dynamic interspinous process device in a disassembled state.
Figure 4D:
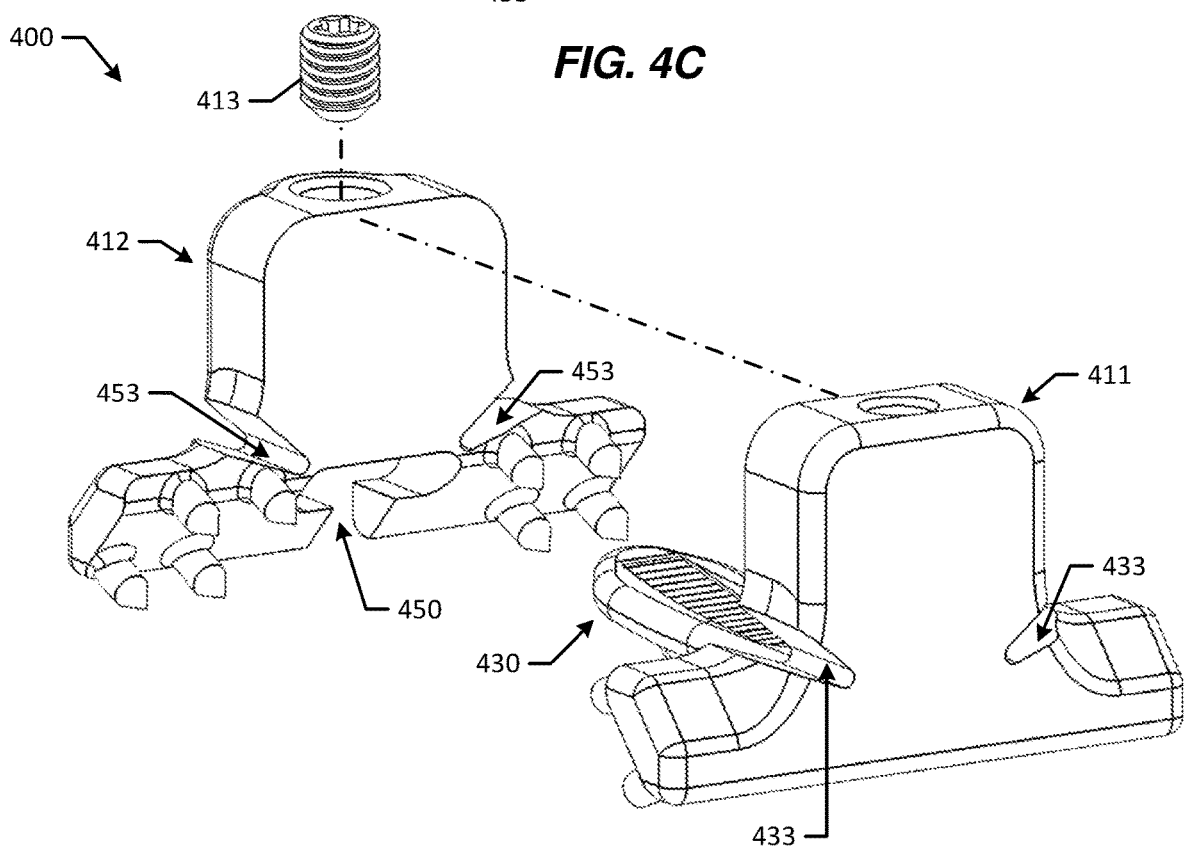
FIG. 4D is a perspective view of the dynamic interspinous process device of FIG. 4A, showing the first attachment side, the second attachment side, and the securing means in the disassembled state.
Figure 4E:
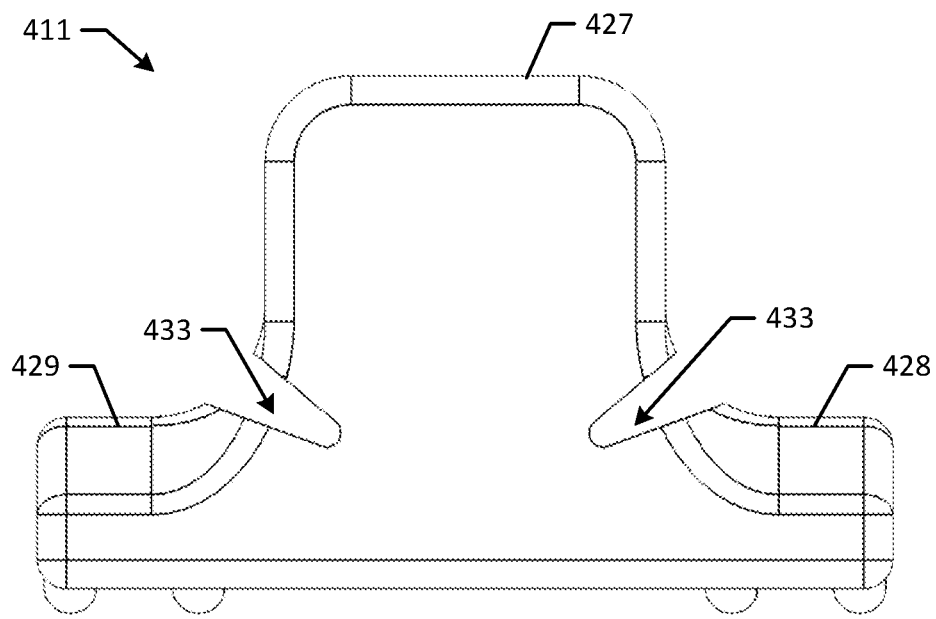
FIG. 4E is a plan view of the first attachment side of the dynamic interspinous process device of FIG. 4A.

It will be appreciated that the slots 433 may be configured to allow portions of the first attachment side 411 to move relative to one another. In particular, one of the slots 433 may be configured to allow the first wing 428 to move toward the central portion 427 and the spacer 430, in the direction of the longitudinal axis $A_L$ of the device 400, as these portions compress the slot 433, and also to allow the first wing 428 to move away from the central portion 427 and the spacer 430, in the direction of the longitudinal axis $A_L$ of the device 400, as these portions expand the slot 433. In a similar manner, the other slot 433 may be configured to allow the second wing 429 to move toward the central portion 427 and the spacer 430, in the direction of the longitudinal axis $A_L$ of the device 400, as these portions compress the slot 433, and also to allow the second wing 429 to move away from the central portion 427 and the spacer 430, in the direction of the longitudinal axis $A_L$ of the device 400, as these portions expand the slot 433. As a result, the first wing 428 and the second wing 429 may be configured to move toward one another as one or both of the slots 433 are compressed, and to move away from one another as one or both of the slots 433 are expanded. In will be appreciated that, during such movement of the wings 428, 429, one or more regions of the first attachment side 411 surrounding the slots 433, such as the regions of the central portion 427 and the respective wing 428, 429 surrounding the terminal ends of the slots 433, may flex or may be compressed to accommodate the compression or expansion of the slots 433. In effect, the slots 433 may cause the first attachment side 411 to function as a spring which may be compressed or extended in the direction of the longitudinal axis $A_L$ of the device 400 but has a natural tendency to return to a natural state as shown in FIG. 4E.

In a similar manner, the second attachment side 412 may include one or more slots 453 (which also may be referred to as a "dynamic slot," a "cutout," an "opening," or a "slit") defined therein and configured to allow relative movement of portions of the second attachment side 412. In certain embodiments, as shown, the second attachment side 412 may include a pair of the slots 453 spaced apart from one another in the direction of the longitudinal axis $A_L$ of the device 400. In certain embodiments, as shown, the slots 453 may be formed at least partially within the central portion 447 of the second attachment side 412. Each slot 453 may have an elongated shape extending partially in the direction of the second transverse axis $A_{T2}$ of the device 400 and partially in the direction of the longitudinal axis $A_L$ of the device 400. In certain embodiments, as shown, each slot 453 may extend at an acute angle relative to the second transverse axis $A_{T2}$ and at an acute angle relative to the longitudinal axis $A_L$ of the device 400. In certain embodiments, as shown, one of the slots 453 may be positioned at an intersection of the central portion 447 and the first wing 448, and the other slot 453 may be positioned at an intersection of the central portion 447 and the second wing 449. In certain embodiments, as shown, each slot 453 may extend from the first side 443 to the second side 444 of the second attachment side 412. Further, in certain embodiments, as shown, each slot 453 may extend from an outer surface along the respective intersection of the central portion 447 and the first wing 448 or the second wing 449 toward, but not to, the spacer slot 450 of the second attachment side 412. In other words, the slot 453 may be open along the respective intersection of the central portion 447 and the first wing 448 or the second wing 449 and may terminate at a location spaced apart from the spacer slot 450. In certain embodiments, as shown, each slot 453 may have a straight shape, although the slot 453 may taper in the direction from the open end of the slot 453 to the closed end of the slot 453. In other embodiments, each slot 453 may be include one or more curved or otherwise contoured portions or may be contoured along the entire extent of the slot 453. Various other configurations of the slots 453 may be used in other embodiments.

Figure 4F:
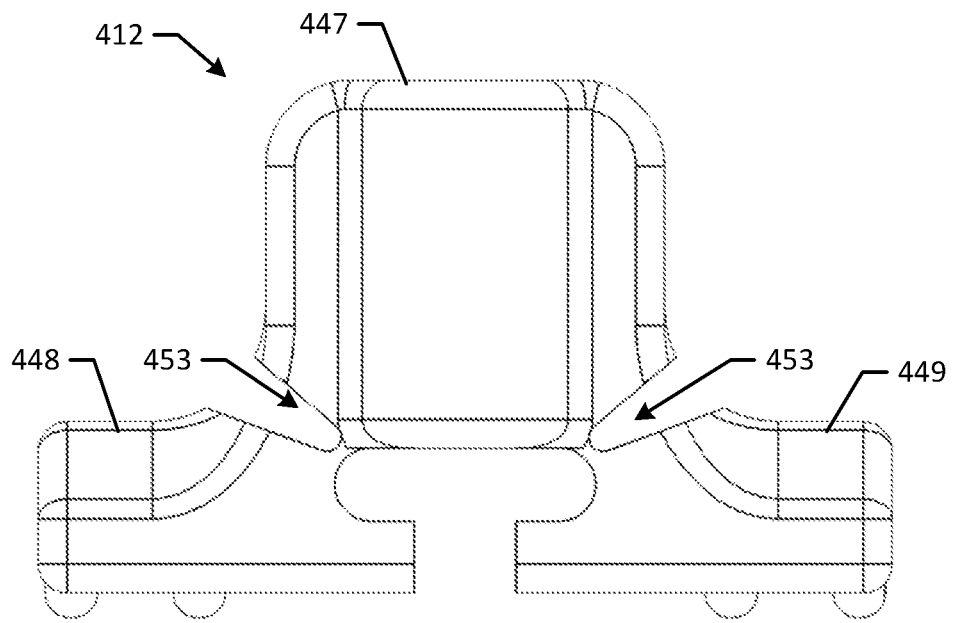
FIG. 4F is a plan view of the second attachment side of the dynamic interspinous process device of FIG. 4A.

It will be appreciated that the slots 453 may be configured to allow portions of the second attachment side 412 to move relative to one another. In particular, one of the slots 453 may be configured to allow the first wing 448 to move toward the central portion 447 and the spacer slot 450, in the direction of the longitudinal axis $A_L$ of the device 400, as these portions compress the slot 453, and also to allow the first wing 448 to move away from the central portion 447 and the spacer slot 450, in the direction of the longitudinal axis $A_L$ of the device 400, as these portions expand the slot 453. In a similar manner, the other slot 453 may be configured to allow the second wing 449 to move toward the central portion 447 and the spacer slot 450, in the direction of the longitudinal axis $A_L$ of the device 400, as these portions compress the slot 453, and also to allow the second wing 449 to move away from the central portion 447 and the spacer slot 450, in the direction of the longitudinal axis $A_L$ of the device 400, as these portions expand the slot 453. As a result, the first wing 448 and the second wing 449 may be configured to move toward one another as one or both of the slots 443 are compressed, and to move away from one another as one or both of the slots 453 are expanded. In will be appreciated that, during such movement of the wings 448, 449, one or more regions of the second attachment side 412 surrounding the slots 453, such as the regions of the central portion 447 and the respective wing 448, 449 surrounding the terminal ends of the slots 453, may flex or may be compressed to accommodate the compression or expansion of the slots 453. In effect, the slots 453 may cause the second attachment side 412 to function as a spring which may be compressed or extended in the direction of the longitudinal axis $A_L$ of the device 400 but has a natural tendency to return to a natural state as shown in FIG. 4F. In certain embodiments, as shown, the slots 433 of the first attachment side 411 may be formed as a mirror image of the slots 453 of the second attachment side 412. In other embodiments, the number, shape, or configuration of the slots 433 of the first attachment side 411 may be different than the number, shape, or configuration of the slots 453 of the second attachment side 412. Various configurations of the slots 433 and the slots 453 may be used to allow for a desired range of movement of the corresponding vertebrae.

Figure 4G:
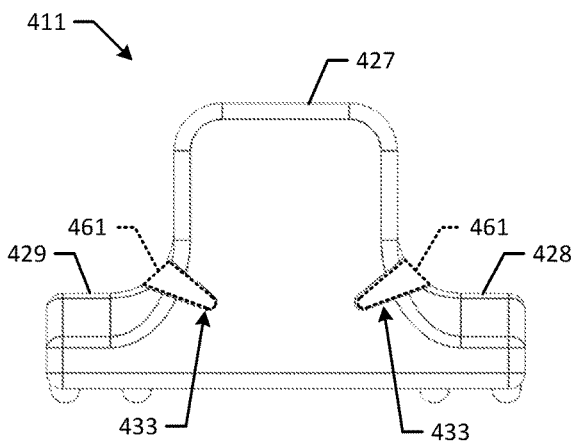
FIG. 4G is a plan view of the first attachment side and a number of resistance means of the dynamic interspinous process device of FIG. 4A.
Figure 4H:
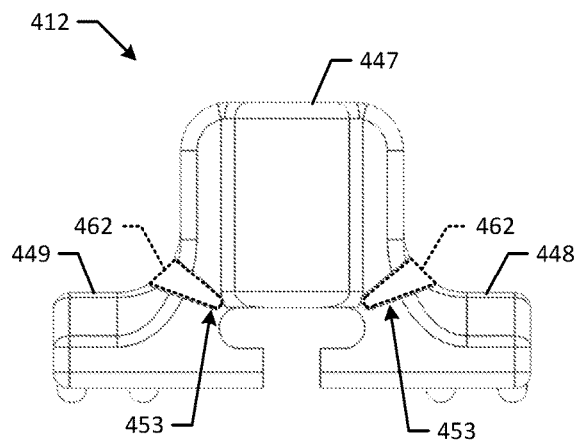
FIG. 4H is a plan view of the second attachment side and a number of resistance means of the dynamic interspinous process device of FIG. 4A.
Figure 4I:
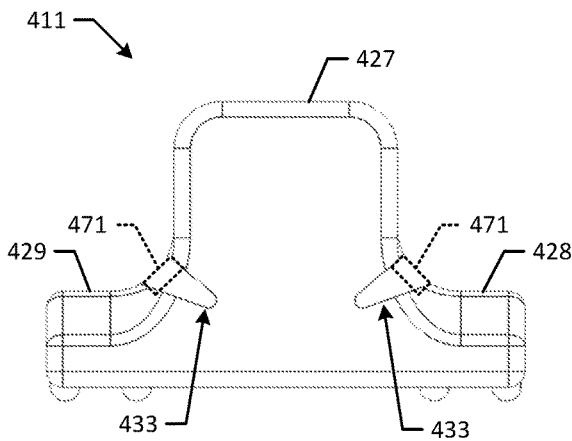
FIG. 4I is a plan view of the first attachment side and a number of fixation means of the dynamic interspinous process device of FIG. 4A.

In certain embodiments, the device 400 may include means for varying resistance to the relative movement between the first wing 428 and the second wing 429 of the first attachment side 411 over at least a portion of the range of motion of the wings 428, 429 and for varying resistance to the relative movement between the first wing 448 and the second wing 449 of the second attachment side 412 over at least a portion of the range of motion of the wings 448, 449. In this manner, the device 400 may vary the resistance to the relative movement between the treated vertebrae over at least a portion of the range of motion of the vertebrae allowed by the device 400. FIGS. 4G and 4H illustrate an embodiment in which the device 400 includes a pair of resistance means for varying resistance to the relative movement between the wings 428, 429 and between the wings 448, 449. As shown, the first attachment side 411 may include a pair of resistance means 461 (which also may be referred to as a "resistance insert," a "resistance member" or a "biasing member") configured for varying resistance to movement of the wings 428, 429 relative to the central portion 427 and relative to one another over at least a portion of the range of motion of these features as may be allowed by the slots 433. In certain embodiments, as shown, each resistance means 461 may be an insert configured to be inserted into and retained within one of the slots 433. In certain embodiments, the resistance means 461 may be removably received within the slots 433, such that the resistance means 461 may be placed therein when resistance is desired and may be removed therefrom when resistance is not desired. In other embodiments, the resistance means 461 may be securely fixed within the slots 433, such that the resistance means 461 are not removable therefrom. In certain embodiments, each resistance means 461 may be formed of a compressible material or a resiliently deformable material, such as a biocompatible polymer or other suitable material, which may be compressed by the relative movement of surrounding portions of the first attachment side 411 but may have a natural tendency to return to a natural state when compression forces are removed. It will be appreciated that a durometer of the compressible material or resiliently deformable material may be selected to provide a desired resistance to the relative movement of surrounding portions of the first attachment side 411. In other embodiments, each resistance means 461 may be formed as a spring, such as a compression spring, which may function similar to the compressible material or resiliently deformable material member. In certain embodiments, as shown, each resistance means 461 may fill or substantially fill the entirety of the respective slot 433. In other embodiments, each resistance means 461 may fill only a portion of the respective slot 433.

According to the illustrated embodiment, each resistance means 461 may be configured to resist movement of one of the wings 428, 429 toward the central portion 427, and thus the pair of resistance means 461 collectively may resist relative movement of the wings 428, 429 toward one another. In particular, as the wings 428, 429 move toward the central portion 427 and toward one another and the slots 433 are compressed, the resistance means 461 may be compressed, thereby resisting, but not preventing, further movement of the wings 428, 429 toward the central portion 427 and toward one another. Further, the resistance means 461 may provide a biasing force acting on the portions of the first attachment side 411 surrounding the slots 433, biasing the wings 428, 429 toward their home or natural position and the slots 433 to their home or natural state.

In a similar manner, the second attachment side 412 may include a pair of resistance means 462 (which also may be referred to as a "resistance insert," a "resistance member" or a "biasing member") configured for varying resistance to movement of the wings 448, 449 relative to the central portion 447 and relative to one another over at least a portion of the range of motion of these features as may be allowed by the slots 453. In certain embodiments, as shown, each resistance means 462 may be an insert configured to be inserted into and retained within one of the slots 453. In certain embodiments, the resistance means 462 may be removably received within the slots 453, such that the resistance means 462 may be placed therein when resistance is desired and may be removed therefrom when resistance is not desired. In other embodiments, the resistance means 462 may be securely fixed within the slots 453, such that the resistance means 462 are not removable therefrom. In certain embodiments, each resistance means 462 may be formed of a compressible material or a resiliently deformable material, such as a biocompatible polymer or other suitable material, which may be compressed by the relative movement of surrounding portions of the second attachment side 412 but may have a natural tendency to return to a natural state when compression forces are removed. It will be appreciated that a durometer of the compressible material or resiliently deformable material may be selected to provide a desired resistance to the relative movement of surrounding portions of the second attachment side 412. In other embodiments, each resistance means 462 may be formed as a spring, such as a compression spring, which may function similar to the compressible material or resiliently deformable material member. In certain embodiments, as shown, each resistance means 462 may fill or substantially fill the entirety of the respective slot 453. In other embodiments, each resistance means 462 may fill only a portion of the respective slot 453.

According to the illustrated embodiment, each resistance means 462 may be configured to resist movement of one of the wings 448, 449 toward the central portion 447, and thus the pair of resistance means 462 collectively may resist relative movement of the wings 448, 449 toward one another. In particular, as the wings 448, 449 move toward the central portion 447 and toward one another and the slots 453 are compressed, the resistance means 462 may be compressed, thereby resisting, but not preventing, further movement of the wings 448, 449 toward the central portion 447 and toward one another. Further, the resistance means 462 may provide a biasing force acting on the portions of the second attachment side 412 surrounding the slots 453, biasing the wings 448, 449 toward their home or natural position and the slots 453 to their home or natural state.

It will be appreciated that the resistance means 461, 462 of the device 400 may be used to vary resistance to the relative movement between the treated vertebrae, when desired. In particular, the resistance means 461, 462 may be used to increase resistance to the relative movement between the treated vertebrae over at least a portion of the range of motion of the vertebrae allowed by the device 400. In this manner, the device 400 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 461, 462 may be selected to provide a desired degree of resistance to the relative motion of the treated vertebrae.

Figure 4J:
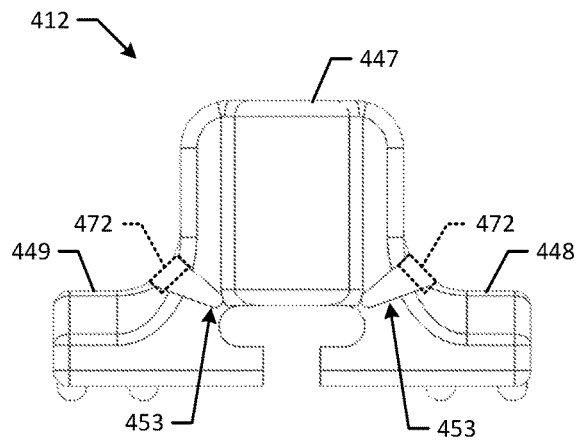
FIG. 4J is a plan view of the second attachment side and a number of fixation means of the dynamic interspinous process device of FIG. 4A.

In certain embodiments, the device 400 may include means for preventing or inhibiting the relative movement between the first wing 428 and the second wing 429 of the first attachment side 411 and for preventing or inhibiting the relative movement between the first wing 448 and the second wing 449 of the second attachment side 412. In this manner, the device 400 may prevent or inhibit the relative movement between the treated vertebrae. FIGS. 41 and 4J illustrate embodiments in which the device 400 includes one or more fixation means for preventing or inhibiting the relative movement between the wings 428, 429 and between the wings 448, 449. As shown, the first attachment side 411 may include one or more fixation means 471 (which also may be referred to as a "fixation insert," a "fixation member," a "fastener," or a "lock") configured for preventing or inhibiting movement of the wings 428, 429 relative to the central portion 427 and relative to one another as may be allowed by the slots 433. In certain embodiments, the fixation means 471 may be removably attached to the central portion 427 and/or one of the wings 428, 429. In other embodiments, the fixation means 471 may be fixedly secured to the central portion 427 and/or one or the wings 428, 429. In certain embodiments, as shown, a pair of the fixation means 471 may be configured to be inserted at least partially into and retained within the respective slots 433. Each fixation means 471 may engage portions of the first attachment side 411 surrounding the respective slot 433 such that the fixation means 471 prevents or inhibits at least a portion of the slot 433 from expanding and/or collapsing. In certain embodiments, each fixation means 471 may be a fastener, such as a set screw having a reverse angle thread for threadably engaging and retaining mating threaded portions of the first attachment side 411. In certain embodiments, as shown, each fixation means 471 may be inserted, in a direction transverse to the longitudinal axis $A_{T2}$ and the second transverse axis $A_{T2}$ of the device 400, into the open end of the respective slot 433.

In a similar manner, the second attachment side 412 may include one or more fixation means 472 (which also may be referred to as a "fixation insert," a "fixation member," a "fastener," or a "lock") configured for preventing or inhibiting movement of the wings 448, 449 relative to the central portion 447 and relative to one another as may be allowed by the slots 453. In certain embodiments, the fixation means 472 may be removably attached to the central portion 447 and/or one of the wings 448, 449. In other embodiments, the fixation means 472 may be fixedly secured to the central portion 447 and/or one or the wings 448, 449. In certain embodiments, as shown, a pair of the fixation means 472 may be configured to be inserted at least partially into and retained within the respective slots 453. Each fixation means 472 may engage portions of the second attachment side 412 surrounding the respective slot 453 such that the fixation means 472 prevents or inhibits at least a portion of the slot 453 from expanding and/or collapsing. In certain embodiments, each fixation means 472 may be a fastener, such as a set screw having a reverse angle thread for threadably engaging and retaining mating threaded portions of the second attachment side 412. In certain embodiments, as shown, each fixation means 472 may be inserted, in a direction transverse to the longitudinal axis $A_{T2}$ and the second transverse axis $A_{T2}$ of the device 400, into the open end of the respective slot 453.

It will be appreciated that the fixation means 471, 472 of the device 400 may be used to control the relative movement between the treated vertebrae, when desired. In particular, the fixation means 471, 472 may be used to prevent or inhibit relative movement between the treated vertebrae. In this manner, the device 400 may be used as a dynamic device or a rigid device, with the ability to convert the device 400 between a dynamic configuration and a rigid configuration, as may be desired in certain applications. The fixation means 471, 472 may be used to convert the device 400 between the dynamic configuration and the rigid configuration prior to implantation of the device 400, during initial implantation of the device 400 as a part of an initial surgery, or during a follow-up surgery.

Figure 4K:
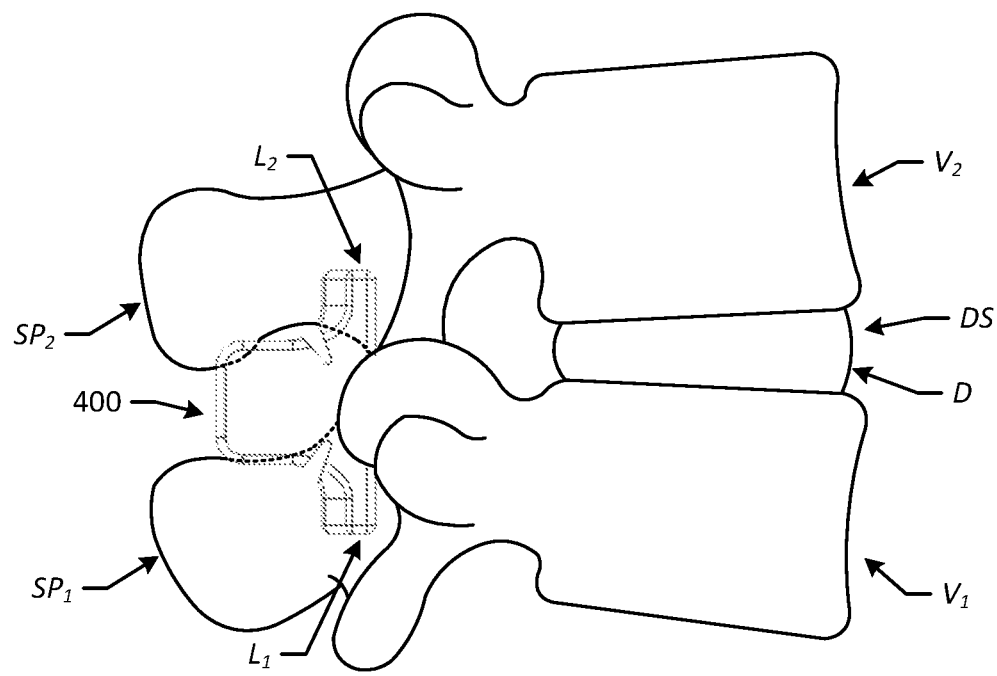
FIG. 4K is a side view of the dynamic interspinous process device of FIG. 4A implanted with respect to a first vertebra and a second vertebra in accordance with one or more embodiments of the present disclosure.
Figure 4L:
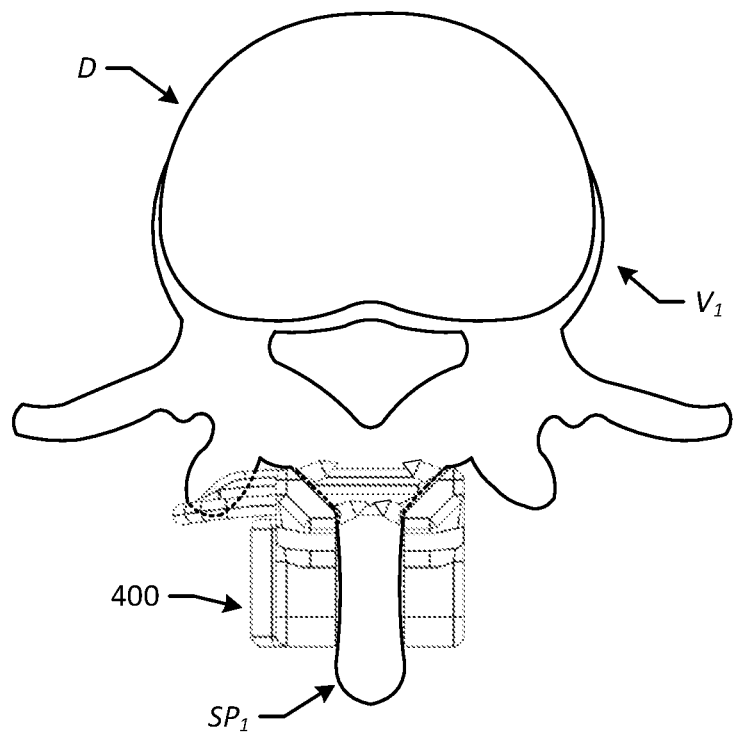
FIG. 4L is a top view of the dynamic interspinous process device of FIG. 4A implanted with respect to the first vertebra, the second vertebra being removed from view for purposes of illustration.

FIGS. 4K and 4L illustrate an example implantation of the device 400 with respect to a first vertebra $V_1$ and an adjacent second vertebra $V_2$. As shown, the first attachment side 411 and the second attachment side 412 may be positioned relative to the vertebrae $V_1$, $V_2$ such that the spacer 430 is positioned between a first spinous process $SP_1$ of the first vertebra $V_1$ and a second spinous process $SP_2$ of the second vertebra $V_2$. In this manner, the spacer 430 may limit a minimum spacing between the spinous processes $SP_1$, $SP_2$. Additionally, the first attachment side 411 and the second attachment side 412 may be positioned relative to the vertebrae $V_1$, $V_2$ such that the respective wings 428, 429 of the first attachment side 411 and the respective wings 448, 449 of the second attachment side 412 engage a first lamina $L_1$ of the first vertebra $V_1$ and a second lamina $L_2$ of the second vertebra $V_2$. In this manner, the respective bone fasteners 431 of the first attachment side 411 and the respective bone fasteners 451 of the second attachment side 412 may penetrate and securely engage the laminae $L_1$, $L_2$. Accordingly, the implanted device 400 may stabilize the vertebrae $V_1$, $V_2$, although the device 400 may allow relative movement of the vertebrae $V_1$, $V_2$. In particular, the slots 433, 453 of the device 400 may allow relative movement of the vertebrae $V_1$, $V_2$ in sagittal plane of the patient, thereby allowing flexion and extension of the treated segment of the spine. It will be appreciated that the configuration of the slots 433, 453 may be varied, for example, by varying the number, size, and/or shape the slots 433, 453 to allow a desired range of motion in the sagittal plane. Further, the material from which the first attachment side 411 and the second attachment side 412 are formed may be selected to achieve the desired range of motion. In certain embodiments, the first attachment side 411 and the second attachment side 412 may be formed of titanium, although other suitable metals, polymers, or other materials may be used in other embodiments. Meanwhile, the device 400 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 400 and the disc D. In other embodiments in which the native disc D is removed, an interbody device, such as a cage or a spacer, may be implanted within the disc space DS (i.e., the intervertebral space) and the loads carried by the treated spinal segment may be shared by the device 400 and the interbody device. As described above, the device 400 may be used in conjunction with other additional hardware, such that the device 400 and the additional hardware collectively stabilize the treated segment of the spine and share loads carried thereby. It will be appreciated that the foregoing description and the corresponding drawings are merely examples of the device 400 and that other configurations and modifications may be made.

FIGS. 5A-5L illustrate an interspinous process device 500 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 500 may be configured for implantation relative to a first vertebra and an adjacent second vertebra, as described below, specifically with reference to FIGS. 5K and 5L. In particular, a portion of the interspinous process device 500 may be positioned between the spinous process of the first vertebra and the spinous process of the second vertebra, while one or more other portions of the interspinous process device 500 engage the spinous processes, the laminae, and/or other portions of the respective vertebra. As described below, the interspinous process device 500 may allow a desired range of relative movement between the treated vertebrae, which may be desirable in certain treatment applications. The interspinous process device 500 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 500, itself or in combination with additional hardware, may provide the structural support necessary to restore and maintain normal spacing and alignment of the treated vertebrae while avoiding certain drawbacks presented by existing interspinous process devices.

The interspinous process device 500 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 500 may include a first end 501 and a second end 502 disposed opposite the first end 501 in the direction of the longitudinal axis $A_L$. As described below, the device 500 may be implanted with the longitudinal axis $A_L$ extending in a direction substantially parallel to the sagittal plane and the coronal plane of the patient and transverse to the transverse plane of the patient. In this manner, depending on the orientation of the device 500 upon implantation thereof, one of the first end 501 and the second end 502 of the device 500 may be referred to as a the "superior end" of the device 500, and the other of the first end 501 and the second end 502 of the device 500 may be referred to as the "inferior end" of the device 500. The device 500 also may include a first side 503 extending from the first end 501 to the second end 502, and a second side 504 disposed opposite the first side 503 in the direction of the first transverse axis $A_{T1}$ and extending from the first end 501 to the second end 502. The device 500 may be implanted with the first transverse axis $A_{T1}$ extending in a direction substantially parallel to the coronal plane and the transverse plane of the patient and transverse to the sagittal plane of the patient. In this manner, depending on the orientation of the device 500 upon implantation thereof, one of the first side 503 and the second side 504 of the device 500 may be referred to as a the "right side" of the device 500, and the other of the first side 503 and the second side 504 of the device 500 may be referred to as the "left side" of the device 500. The device 500 further may include a third side 505 extending from the first end 501 to the second end 502 and from the first side 503 to the second side 504, and a fourth side 506 disposed opposite the third side 505 in the direction of the second transverse axis $A_{T2}$ and extending from the first end 501 to the second end 502 and from the first side 503 to the second side 504. The device 500 may be implanted with the second transverse axis $A_{T2}$ extending in a direction substantially parallel to the sagittal plane and the transverse plane of the patient and transverse to the coronal plane of the patient. As described below, the device 500 may be oriented upon implantation thereof such that the third side 505 faces posteriorly and the fourth side 506 faces anteriorly with respect to the patient. In this manner, the third side 505 may be referred to as the "posterior side" of the device 500, and the fourth side 506 may be referred to as the "anterior side" of the device 500. The device 500 may have an overall "length" extending from the first end 501 to the second end 502 in the direction of the longitudinal axis $A_L$, an overall "width" extending from the first side 503 to the second side 504 in the direction of the first transverse axis $A_{T1}$, and an overall "height" extending from the third side 505 to the fourth side 506 in the direction of the second transverse axis $A_{T2}$. Further, various components and features of the device 500 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 500 may include a first attachment side 511 (which also may be referred to as a "first attachment portion," a "first attachment assembly," or a "first plate") and a second attachment side 512 (which also may be referred to as a "second attachment portion," a "second attachment assembly," or a "second plate") configured for removably attaching to one another via a securing means 513. During use of the device 500, one of the first attachment side 511 and the second attachment side 512 may be disposed, at least partially, along the right side of the patient's spine, and the other of the first attachment side 511 and the second attachment side 512 may be disposed, at least partially, along the right side of the patient's spine. It will be appreciated that the first attachment side 511 and the second attachment side 512 may include corresponding features that are mirror images of one another, although certain differences between the first attachment side 511 and the second attachment side 512 may exist, as described below. In certain embodiments, the first attachment side 511 and the second attachment side 512 may be formed of a metal, such as titanium or stainless steel, although other suitable materials, such as polyether ether ketone (PEEK), other polymers, or composites, may be used.

The first attachment side 511 may have a first end 521, a second end 522 disposed opposite the first end 521, a first side 523 (which also may be referred to as an "interior side"), a second side 524 (which also may be referred to as an "exterior side") disposed opposite the first side 523, a third side 525 (which also may be referred to as an "posterior side"), and a fourth side 526 (which also may be referred to as an "anterior side") disposed opposite the third side 525. As shown, the first attachment side 511 may include a central portion 527 and a pair of wings 528, 529 disposed on opposite sides of the central portion 527. In particular, the first wing 528 may extend from the central portion 527 to the first end 521 of the first attachment side 511, and the second wing 529 may extend from the central portion 527 to the second end 522 of the first attachment side 511. In certain embodiments, as shown, the wings 528, 529 may extend in opposite directions from the central portion 527 and may be formed as mirror images of one another. In other embodiments, the wings 528, 529 may extend in opposite directions from the central portion 527, but the first wing 528 may have a different shape or configuration than the second wing 529 such that the wings 528, 529 are not mirror images of one another. In certain embodiments, the wings 528, 529 may be shaped and configured in a manner similar to any one of the wing embodiments described and/or shown in the Prior Applications. Various other configurations of the wings 528, 529 may be used.

The first attachment side 511 also may include a spacer 530 extending from the first side 523 thereof. During use of the device 500, the spacer 530 may be positioned between the spinous processes of the respective vertebrae. In certain embodiments, as shown, the spacer 530 may extend from the central portion 527 of the first attachment side 511 and be integrally formed therewith. In other embodiments, the spacer 530 may be separately formed from and attached to the central portion 527 via an attachment mechanism. The first attachment side 511 further may include a number of engagement features configured for securely engaging the respective vertebrae. In certain embodiments, as shown, the engagement features may be one or more bone fasteners 531 extending from the first side 523 of the first attachment side 511. The bone fasteners 531 may be formed as spikes or barbs, although other forms and types of bone fasteners 531 may be used for securely engaging the vertebrae. In certain embodiments, one or more of the bone fasteners 531 may extend form the first wing 528, and one or more bone fasteners 531 may extend from the second wing 529. In certain embodiments, the first wing 528 may include a first number of bone fasteners 531 extending therefrom, and the second wing 529 may include a second number of bone fasteners 531 extending therefrom, wherein the first number is different than the second number. In this manner, the degree of engagement between the bone fasteners 531 of the first wing 528 and the corresponding vertebra may be different from the degree of engagement between the bone fasteners 531 of the second wing 529 and the corresponding vertebra. Such an arrangement may facilitate relative movement of the treated vertebrae, while minimizing certain stresses induced in the device 500. In certain embodiments, one of the first wing 528 and the second wing 529 may not include any bone fasteners 531 extending therefrom, and the other of the first wing 528 and the second wing 529 may include one or more of the bone fasteners 531 extending therefrom. Such an arrangement also may facilitate relative movement of the treated vertebrae, while minimizing certain stresses induced in the device 500. Various configurations of the bone fasteners 531 of the first attachment side 511 may be used. In certain embodiments, as shown, the bone fasteners 531 may be configured to engage the laminae of the respective vertebrae. In other embodiments, one or more of the bone fasteners 531 may be configured to engage the spinous processes, the laminae, and/or other portions of the respective vertebrae. As shown, the first attachment side 511 also may include an instrument engagement aperture 532 configured for receiving a portion of and cooperating with an instrument used for positioning the first attachment side 511 during implantation of the device 500. Example instruments for implantation of the device 500 are described in the Prior Applications.

In a similar manner, the second attachment side 512 may have a first end 541, a second end 542 disposed opposite the first end 541, a first side 543 (which also may be referred to as an "exterior side"), a second side 544 (which also may be referred to as an "interior side") disposed opposite the first side 543, a third side 545 (which also may be referred to as an "posterior side"), and a fourth side 546 (which also may be referred to as an "anterior side") disposed opposite the third side 545. As shown, the second attachment side 512 may include a central portion 547 and a pair of wings 548, 549 disposed on opposite sides of the central portion 547. In particular, the first wing 548 may extend from the central portion 547 to the first end 541 of the second attachment side 512, and the second wing 549 may extend from the central portion 547 to the second end 542 of the second attachment side 512. In certain embodiments, as shown, the wings 548, 549 may extend in opposite directions from the central portion 547 and may be formed as mirror images of one another, although other configurations of the wings 548, 549 may be used.

The second attachment side 512 also may include a spacer slot 550 extending through the second attachment side 512 from the first side 543 to the second side 544 thereof. During use of the device 500, the spacer slot 550 may be configured to receive the spacer 530 of the first attachment side 511 therethrough, as shown. In certain embodiments, as shown, the spacer slot 550 may be defined in the central portion 547 of the second attachment side 512, although other positions of the spacer slot 550 may be used. The second attachment side 512 further may include a number of engagement features configured for securely engaging the respective vertebrae. In certain embodiments, as shown, the engagement features may be one or more bone fasteners 551 extending from the second side 544 of the second attachment side 512. The bone fasteners 551 may be formed as spikes or barbs, although other forms and types of bone fasteners 551 may be used for securely engaging the vertebrae. In certain embodiments, one or more of the bone fasteners 551 may extend form the first wing 548, and one or more bone fasteners 551 may extend from the second wing 549. In certain embodiments, the first wing 548 may include a first number of bone fasteners 551 extending therefrom, and the second wing 559 may include a second number of bone fasteners 551 extending therefrom, wherein the first number is different than the second number. In this manner, the degree of engagement between the bone fasteners 551 of the first wing 548 and the corresponding vertebra may be different from the degree of engagement between the bone fasteners 551 of the second wing 549 and the corresponding vertebra. Such an arrangement may facilitate relative movement of the treated vertebrae, while minimizing certain stresses induced in the device 500. In certain embodiments, one of the first wing 548 and the second wing 549 may not include any bone fasteners 551 extending therefrom, and the other of the first wing 548 and the second wing 549 may include one or more of the bone fasteners 551 extending therefrom. Such an arrangement also may facilitate relative movement of the treated vertebrae, while minimizing certain stresses induced in the device 500. Various configurations of the bone fasteners 551 of the second attachment side 512 may be used. In certain embodiments, as shown, the bone fasteners 551 may be configured to engage the laminae of the respective vertebrae. In other embodiments, one or more of the bone fasteners 551 may be configured to engage the spinous processes, the laminae, and/or other portions of the respective vertebrae. As shown, the second attachment side 512 also may include a securing aperture 552 configured to receive at least a portion of and cooperate with the securing means 513 for selectively fixing the first attachment side 511 and the second attachment side 512 relative to one another. The securing aperture 552 also may be configured for receiving a portion of and cooperating with an instrument used for positioning the second attachment side 512 during implantation of the device 500. Example instruments for implantation of the device 500 are described in the Prior Applications.

The securing means 513 may be configured for selectively fixing the first attachment side 511 and the second attachment side 512 relative to one another. In certain embodiments, as shown, the securing means 513 may be a fastener, such as a set screw, although other types of fasteners and other types of securing means may be used. As shown, the securing means may be inserted into and at least partially through the securing aperture 552 of the second attachment side 512. In this manner, the securing means 513 may be advanced through the securing aperture 552 until the securing means 513 engages the spacer 530 of the first attachment side 511 positioned within the spacer slot 550 of the second attachment side 512. Upon desired positioning of the first attachment side 511 and the second attachment side 512 with respect to the corresponding vertebra of the patient, the securing means 513 may be tightened to maintain the spacing and orientation of the first attachment side 511 and the second attachment side 512 relative to one another and relative to the corresponding vertebra. In certain embodiments, the securing means 513 may be formed of a metal, such as titanium or stainless steel, although other suitable materials, such as polyether ether ketone (PEEK), other polymers, or composites, may be used.

As described above, the device 500 may be configured to allow relative movement of the treated vertebrae upon implantation of the device 500. In particular, the device 500 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 511 and the second attachment side 512 each may include one or more features configured to facilitate such relative movement of the treated vertebrae. In particular, the first attachment side 511 may include one or more first slots 533 (which also may be referred to as a "dynamic slot," a "cutout," an "opening," or a "slit") and one or more second slots 534 (which also may be referred to as a "dynamic slot," a "cutout," an "opening," or a "slit") defined therein and configured to allow relative movement of portions of the first attachment side 511. In certain embodiments, as shown, the first attachment side 511 may include a single first slot 533 formed at a substantially central location in the direction of the longitudinal axis $A_L$ of the device 500. In certain embodiments, as shown, the first slot 533 may be formed at least partially, or entirely, within the central portion 527 of the first attachment side 511. The first slot 533 may have an elongated shape extending in the direction of the longitudinal axis $A_L$ of the device 500. In certain embodiments, as shown, the first slot 533 may extend from the first side 523 to the second side 524 of the first attachment side 511. Further, in certain embodiments, as shown, the first slot 533 may extend from an intersection of the central portion 527 and one of the first wing 528 or the second wing 529 toward, but not to an intersection of the central portion 527 and the other of the first wing 528 and the second wing 529. The first slot 533 also may extend downward toward the fourth side 526 and the spacer 530, as shown. The first slot 533 may be open along the intersection of the central portion 527 and the one of the first wing 528 or the second wing 529 and may terminate at a location spaced apart from the intersection of the central portion 527 and the other of the first wing 528 and the second wing 529. In certain embodiments, as shown, the first attachment side 511 may include a pair of the second slots 534 spaced apart from one another in the direction of the longitudinal axis $A_L$ of the device 500. In certain embodiments, as shown, the second slots 534 may be formed at least partially, or entirely, within the central portion 527 of the first attachment side 511. Each second slot 534 may have an elongated shape extending in the direction of the first transverse axis $A_{T1}$ of the device 500. In certain embodiments, as shown, each second slot 534 may extend from the first side 523 to the second side 524 of the first attachment side 511. Further, in certain embodiments, as shown, each second slot 534 may extend from the fourth side 526 toward, but not to, the third side 525 of the first attachment side 511. In other words, each second slot 534 may be open along the fourth side 526 and may terminate at a location spaced apart from the third side 525. In certain embodiments, as shown, each second slot 534 may have a straight portion extending in a linear manner in the direction of the second transverse axis $A_{T2}$ of the device 500 and a rounded portion positioned at the terminal end of the slot 534. In other embodiments, each second slot 534 may be curved or otherwise contoured along one or more portions of or along the entire extent of the slot 534. Various other configurations of the slots 533, 534 may be used in other embodiments.

Figure 5A:
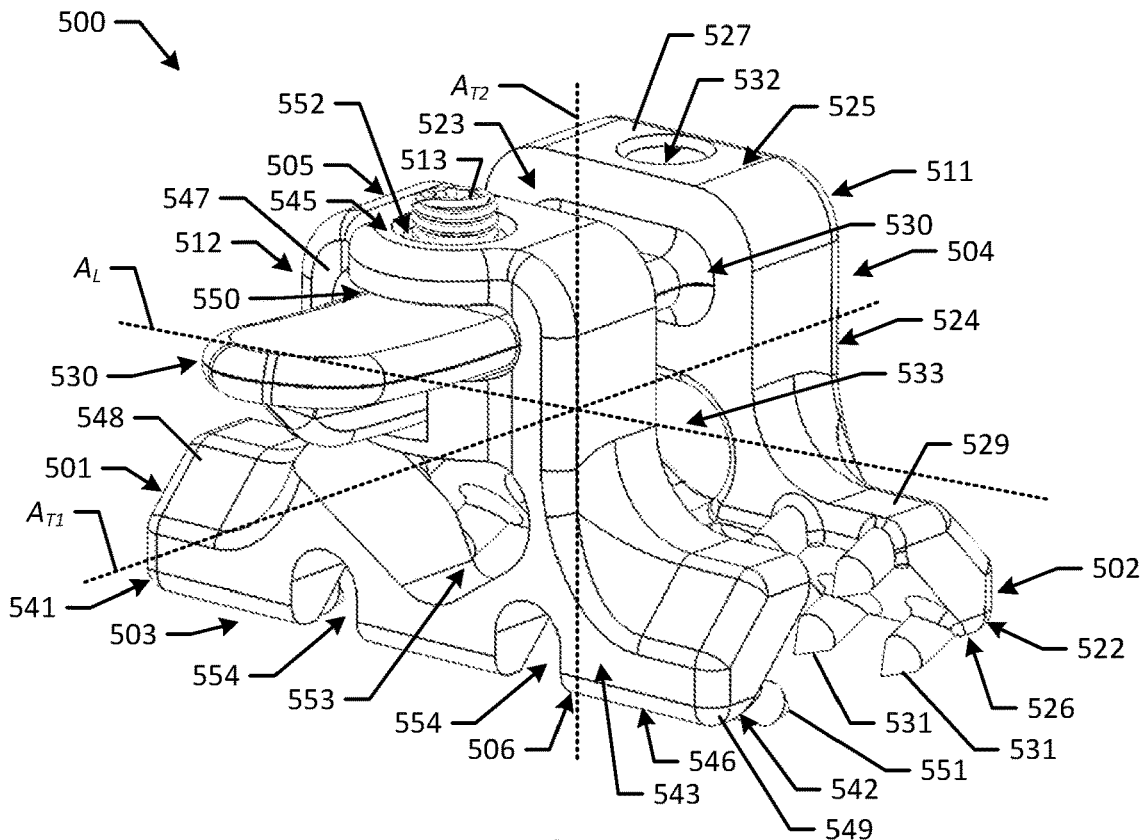
FIG. 5A is a perspective view of a dynamic interspinous process device in accordance with one or more embodiments of the present disclosure, showing a first attachment side, a second attachment side, and a securing means of the dynamic interspinous process device in an assembled state.
Figure 5B:
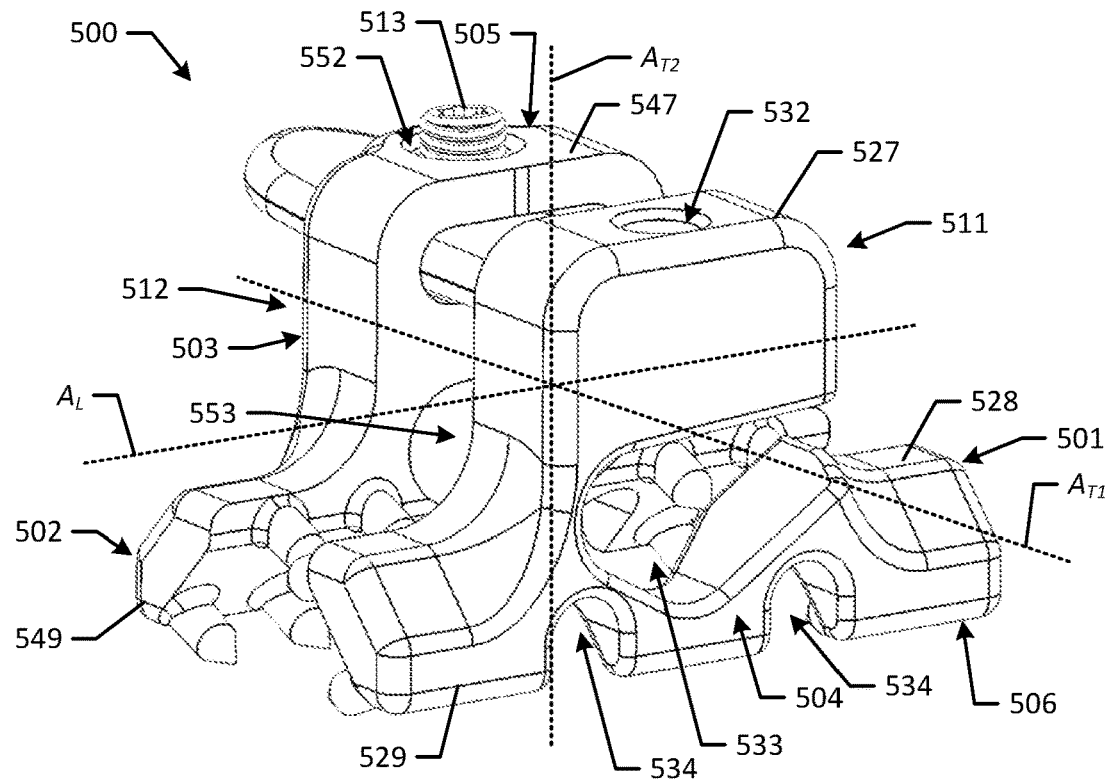
FIG. 5B is a perspective view of the dynamic interspinous process device of FIG. 5A, showing the first attachment side, the second attachment side, and the securing means in the assembled state.
Figure 5C:
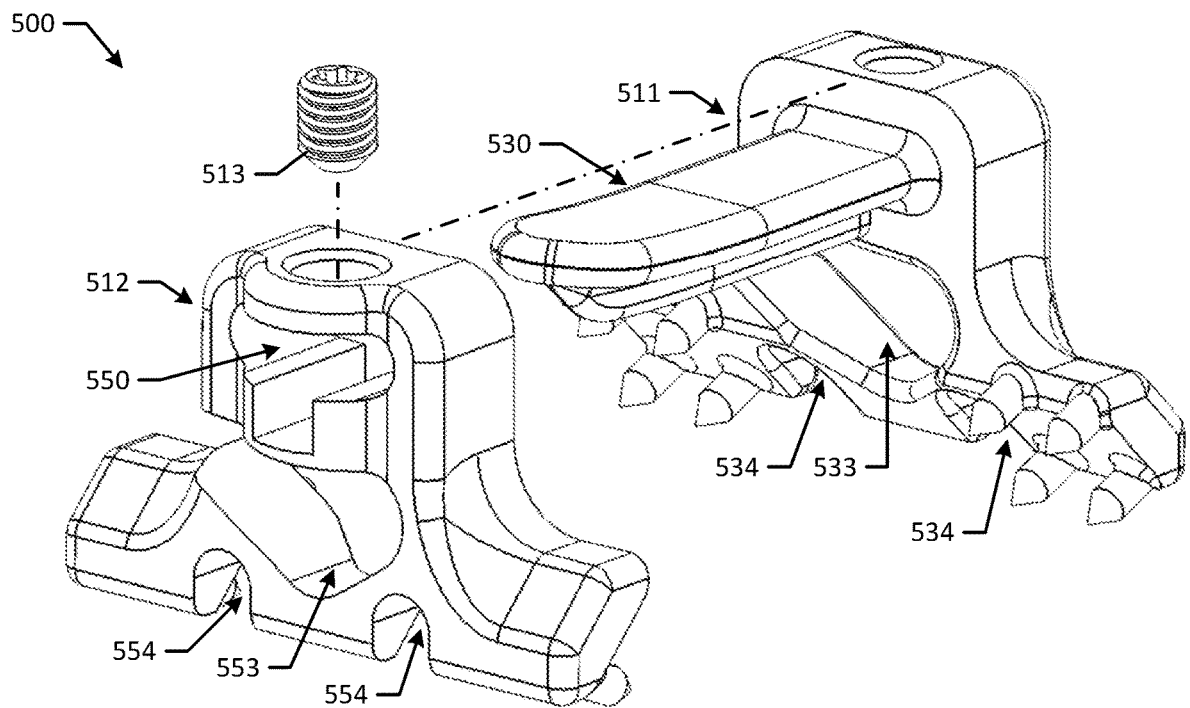
FIG. 5C is a perspective view of the dynamic interspinous process device of FIG. 5A, showing the first attachment side, the second attachment side, and the securing means in a disassembled state.
Figure 5D:
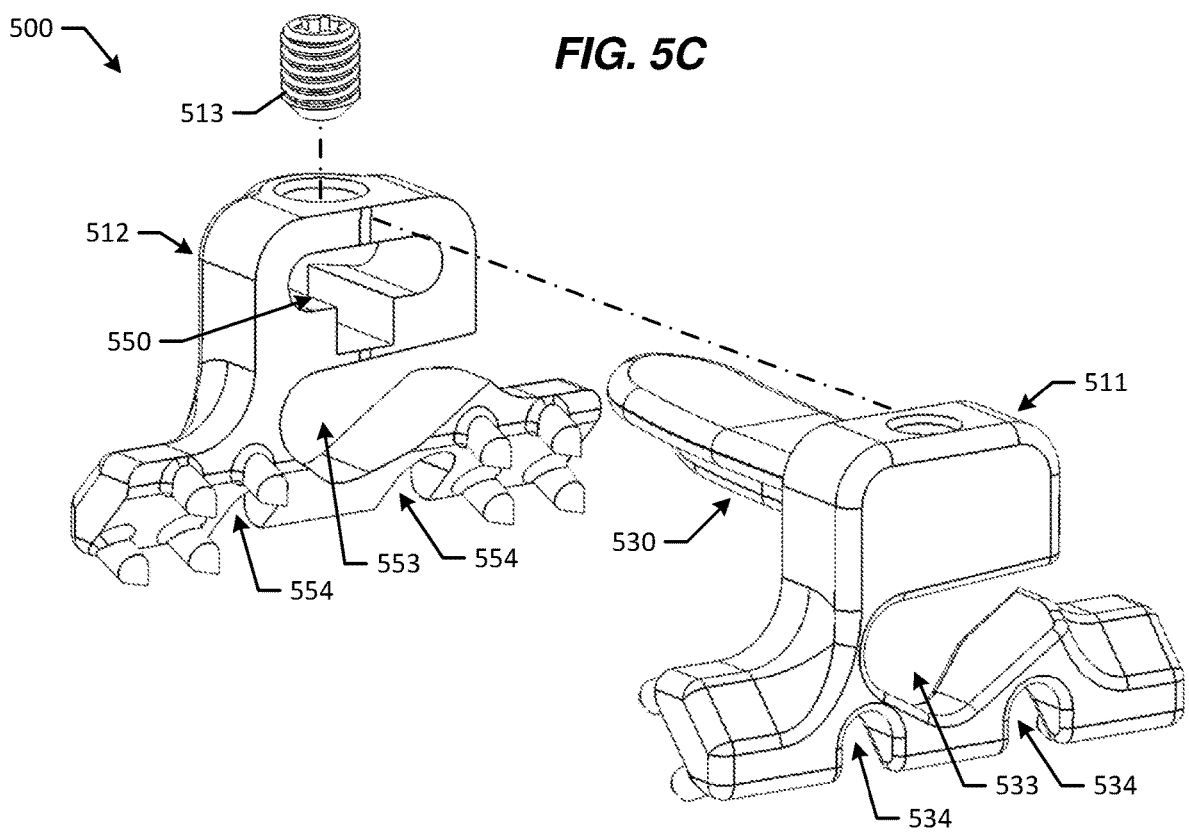
FIG. 5D is a perspective view of the dynamic interspinous process device of FIG. 5A, showing the first attachment side, the second attachment side, and the securing means in the disassembled state.
Figure 5E:
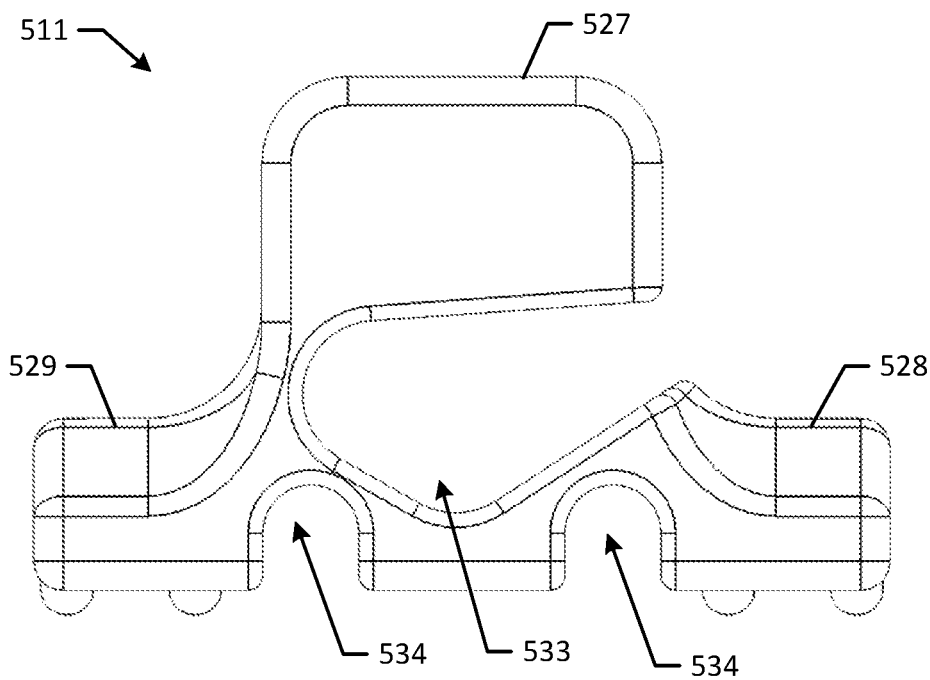
FIG. 5E is a plan view of the first attachment side of the dynamic interspinous process device of FIG. 5A.

It will be appreciated that the slots 533, 534 may be configured to allow portions of the first attachment side 511 to move relative to one another. In particular, the slots 533, 534 may be configured to allow the first wing 528 to move toward the spacer 530, in the direction of the longitudinal axis $A_L$ of the device 500, as on or more of the slots 533, 534 are compressed, and also to allow the first wing 528 to move away from the spacer 530, in the direction of the longitudinal axis $A_L$ of the device 500, as one or more of the slots 533, 534 are expanded. In a similar manner, the slots 533, 534 may be configured to allow the second wing 529 to move toward the spacer 530, in the direction of the longitudinal axis $A_L$ of the device 500, as one or more of the slots 533, 534 are compressed, and also to allow the second wing 529 to move away from the spacer 530, in the direction of the longitudinal axis $A_L$ of the device 500, as one or more of the slots 533, 534 are expanded. As a result, the first wing 528 and the second wing 529 may be configured to move toward one another as one or more of the slots 533, 534 are compressed, and to move away from one another as one or more of the slots 533, 534 are expanded. It will be appreciated that, during such movement of the wings 528, 529, one or more regions of the first attachment side 511 surrounding the slots 533, 534, such as the regions of the central portion 527 surrounding the terminal ends of the slots 533, 534, may flex or may be compressed to accommodate the compression or expansion of the slots 533, 534. In effect, the slots 533, 534 may cause the first attachment side 511 to function as a spring which may be compressed or extended in the direction of the longitudinal axis $A_L$ of the device 500 but has a natural tendency to return to a natural state as shown in FIG. 5E.

In a similar manner, the second attachment side 512 may include one or more first slots 553 (which also may be referred to as a "dynamic slot," a "cutout," an "opening," or a "slit") and one or more second slots 554 (which also may be referred to as a "dynamic slot," a "cutout," an "opening," or a "slit") defined therein and configured to allow relative movement of portions of the second attachment side 512. In certain embodiments, as shown, the second attachment side 512 may include a single first slot 553 formed at a substantially central location in the direction of the longitudinal axis $A_L$ of the device 500. In certain embodiments, as shown, the first slot 553 may be formed at least partially, or entirely, within the central portion 547 of the second attachment side 512. The first slot 553 may have an elongated shape extending in the direction of the longitudinal axis $A_L$ of the device 500. In certain embodiments, as shown, the first slot 553 may extend from the first side 543 to the second side 544 of the second attachment side 512. Further, in certain embodiments, as shown, the first slot 553 may extend from an intersection of the central portion 547 and one of the first wing 548 or the second wing 549 toward, but not to an intersection of the central portion 547 and the other of the first wing 548 and the second wing 549. The first slot 553 also may extend downward toward the fourth side 546 and the spacer 530, as shown. The first slot 553 may be open along the intersection of the central portion 547 and the one of the first wing 548 or the second wing 549 and may terminate at a location spaced apart from the intersection of the central portion 547 and the other of the first wing 548 and the second wing 549. In certain embodiments, as shown, the second attachment side 512 may include a pair of the second slots 554 spaced apart from one another in the direction of the longitudinal axis $A_L$ of the device 500. In certain embodiments, as shown, the second slots 554 may be formed at least partially, or entirely, within the central portion 547 of the first attachment side 511. Each second slot 554 may have an elongated shape extending in the direction of the first transverse axis $A_{T1}$ of the device 500. In certain embodiments, as shown, each second slot 554 may extend from the first side 543 to the second side 544 of the second attachment side 512. Further, in certain embodiments, as shown, each second slot 554 may extend from the fourth side 546 toward, but not to, the third side 545 of the second attachment side 512. In other words, each second slot 554 may be open along the fourth side 546 and may terminate at a location spaced apart from the third side 545. In certain embodiments, as shown, each second slot 554 may have a straight portion extending in a linear manner in the direction of the second transverse axis $A_{T2}$ of the device 500 and a rounded portion positioned at the terminal end of the slot 554. In other embodiments, each second slot 554 may be curved or otherwise contoured along one or more portions of or along the entire extent of the slot 554. Various other configurations of the slots 553, 554 may be used in other embodiments.

Figure 5F:
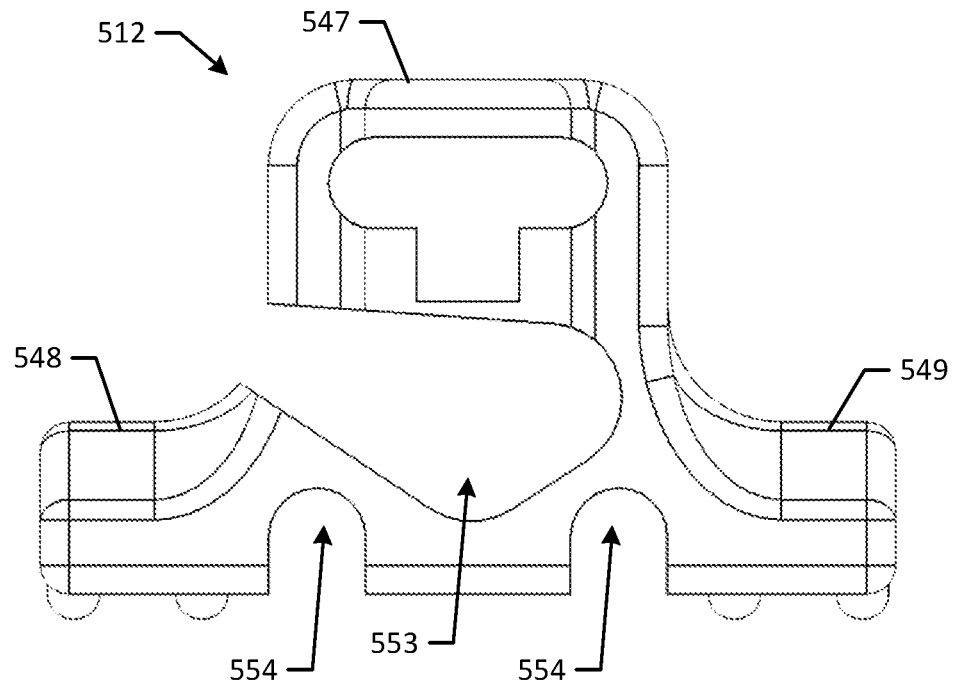
FIG. 5F is a plan view of the second attachment side of the dynamic interspinous process device of FIG. 5A.

It will be appreciated that the slots 553, 554 may be configured to allow portions of the second attachment side 512 to move relative to one another. In particular, the slots 553, 554 may be configured to allow the first wing 548 to move toward the spacer slot 550, in the direction of the longitudinal axis $A_L$ of the device 500, as one or more of the slots 553, 554 are compressed, and also to allow the first wing 548 to move away from the spacer slot 550, in the direction of the longitudinal axis $A_L$ of the device 500, as one or more of the slots 553, 554 are expanded. In a similar manner, the slots 553, 554 may be configured to allow the second wing 549 to move toward the spacer slot 550, in the direction of the longitudinal axis $A_L$ of the device 500, as one or more of the slots 553, 554 are compressed, and also to allow the second wing 549 to move away from the spacer slot 550, in the direction of the longitudinal axis $A_L$ of the device 500, as one or more of the slots 553, 554 are expanded. As a result, the first wing 548 and the second wing 549 may be configured to move toward one another as one or more of the slots 553, 554 are compressed, and to move away from one another as one or more of the slots 553, 554 are expanded. It will be appreciated that, during such movement of the wings 548, 549, one or more regions of the second attachment side 512 surrounding the slots 553, 554, such as the regions of the central portion 547 surrounding the terminal ends of the slots 553, 554, may flex or may be compressed to accommodate the compression or expansion of the slots 553, 554. In effect, the slots 553, 554 may cause the second attachment side 512 to function as a spring which may be compressed or extended in the direction of the longitudinal axis $A_L$ of the device 500 but has a natural tendency to return to a natural state as shown in FIG. 5F. In certain embodiments, as shown, the slots 533, 534 of the first attachment side 511 may be formed as a mirror image of the slots 553, 554 of the second attachment side 512. In other embodiments, the shape or configuration of the slots 533, 534 of the first attachment side 511 may be different than the shape or configuration of the slots 553, 554 of the second attachment side 512. Various configurations of the slots 533, 534 and the slots 553, 554 may be used to allow for a desired range of movement of the corresponding vertebrae.

Figure 5G:
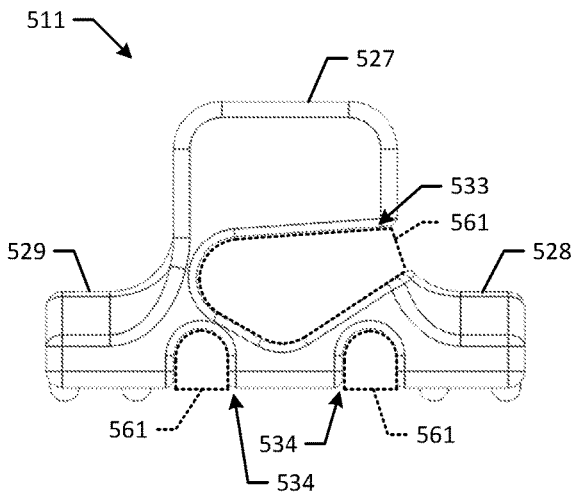
FIG. 5G is a plan view of the first attachment side and a number of resistance means of the dynamic interspinous process device of FIG. 5A.
Figure 5H:
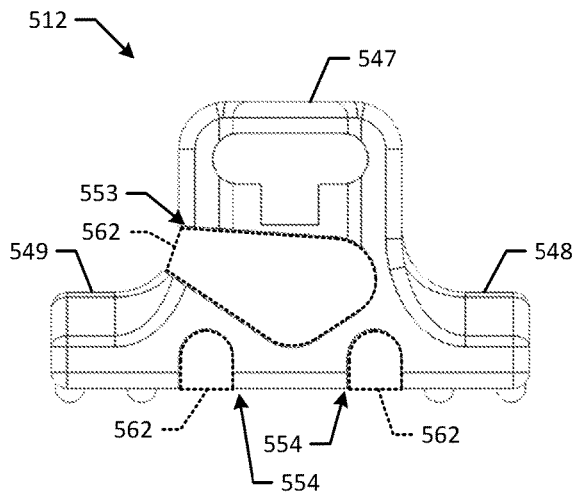
FIG. 5H is a plan view of the second attachment side and a number of resistance means of the dynamic interspinous process device of FIG. 5A.

In certain embodiments, the device 500 may include means for varying resistance to the relative movement between the first wing 528 and the second wing 529 of the first attachment side 511 over at least a portion of the range of motion of the wings 528, 529 and for varying resistance to the relative movement between the first wing 548 and the second wing 549 of the second attachment side 512 over at least a portion of the range of motion of the wings 548, 549. In this manner, the device 500 may vary the resistance to the relative movement between the treated vertebrae over at least a portion of the range of motion of the vertebrae allowed by the device 500. FIGS. 5G and 5H illustrate an embodiment in which the device 500 includes a pair of resistance means for varying resistance to the relative movement between the wings 528, 529 and between the wings 548, 549. As shown, the first attachment side 511 may include a plurality of resistance means 561 (which also may be referred to as a "resistance insert," a "resistance member" or a "biasing member") configured for varying resistance to movement of the wings 528, 529 relative to the central portion 527 and relative to one another over at least a portion of the range of motion of these features as may be allowed by the slots 533, 534. In certain embodiments, as shown, each resistance means 561 may be an insert configured to be inserted into and retained within one of the slots 533. In certain embodiments, the resistance means 561 may be removably received within the slots 533, 534, such that the resistance means 561 may be placed therein when resistance is desired and may be removed therefrom when resistance is not desired. In other embodiments, the resistance means 561 may be securely fixed within the slots 533, 534, such that the resistance means 561 are not removable therefrom. In certain embodiments, each resistance means 561 may be formed of a compressible material or a resiliently deformable material, such as a biocompatible polymer or other suitable material, which may be compressed by the relative movement of surrounding portions of the first attachment side 511 but may have a natural tendency to return to a natural state when compression forces are removed. It will be appreciated that a durometer of the compressible material or resiliently deformable material may be selected to provide a desired resistance to the relative movement of surrounding portions of the first attachment side 511. In other embodiments, each resistance means 561 may be formed as a spring, such as a compression spring, which may function similar to the compressible material or resiliently deformable material member. In certain embodiments, as shown, each resistance means 561 may fill or substantially fill the entirety of the respective slot 533, 534. In other embodiments, each resistance means 561 may fill only a portion of the respective slot 533, 534.

According to the illustrated embodiment, each resistance means 561 may be configured to resist movement of one of the wings 528, 529 toward the central portion 527, and thus the pair of resistance means 561 collectively may resist relative movement of the wings 528, 529 toward one another. In particular, as the wings 528, 529 move toward the central portion 527 and toward one another and the slots 533, 534 are compressed, the resistance means 561 may be compressed, thereby resisting, but not preventing, further movement of the wings 528, 529 toward the central portion 527 and toward one another. Further, the resistance means 561 may provide a biasing force acting on the portions of the first attachment side 511 surrounding the slots 533, 534, biasing the wings 528, 529 toward their home or natural position and the slots 533, 534 to their home or natural state.

In a similar manner, the second attachment side 512 may include a plurality of resistance means 562 (which also may be referred to as a "resistance insert," a "resistance member" or a "biasing member") configured for varying resistance to movement of the wings 548, 549 relative to the central portion 547 and relative to one another over at least a portion of the range of motion of these features as may be allowed by the slots 553, 554. In certain embodiments, as shown, each resistance means 562 may be an insert configured to be inserted into and retained within one of the slots 553, 554. In certain embodiments, the resistance means 562 may be removably received within the slots 553, 554, such that the resistance means 562 may be placed therein when resistance is desired and may be removed therefrom when resistance is not desired. In other embodiments, the resistance means 562 may be securely fixed within the slots 553, 554, such that the resistance means 562 are not removable therefrom. In certain embodiments, each resistance means 562 may be formed of a compressible material or a resiliently deformable material, such as a biocompatible polymer or other suitable material, which may be compressed by the relative movement of surrounding portions of the second attachment side 512 but may have a natural tendency to return to a natural state when compression forces are removed. It will be appreciated that a durometer of the compressible material or resiliently deformable material may be selected to provide a desired resistance to the relative movement of surrounding portions of the second attachment side 512. In other embodiments, each resistance means 562 may be formed as a spring, such as a compression spring, which may function similar to the compressible material or resiliently deformable material member. In certain embodiments, as shown, each resistance means 562 may fill or substantially fill the entirety of the respective slot 553, 554. In other embodiments, each resistance means 562 may fill only a portion of the respective slot 553, 554.

According to the illustrated embodiment, each resistance means 562 may be configured to resist movement of one of the wings 548, 549 toward the central portion 547, and thus the pair of resistance means 562 collectively may resist relative movement of the wings 548, 549 toward one another. In particular, as the wings 548, 549 move toward the central portion 547 and toward one another and the slots 553, 554 are compressed, the resistance means 562 may be compressed, thereby resisting, but not preventing, further movement of the wings 548, 549 toward the central portion 547 and toward one another. Further, the resistance means 562 may provide a biasing force acting on the portions of the second attachment side 512 surrounding the slots 553, 554, biasing the wings 548, 549 toward their home or natural position and the slots 553, 554 to their home or natural state.

It will be appreciated that the resistance means 561, 562 of the device 500 may be used to vary resistance to the relative movement between the treated vertebrae, when desired. In particular, the resistance means 561, 562 may be used to increase resistance to the relative movement between the treated vertebrae over at least a portion of the range of motion of the vertebrae allowed by the device 500. In this manner, the device 500 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 561, 562 may be selected to provide a desired degree of resistance to the relative motion of the treated vertebrae.

Figure 5I:
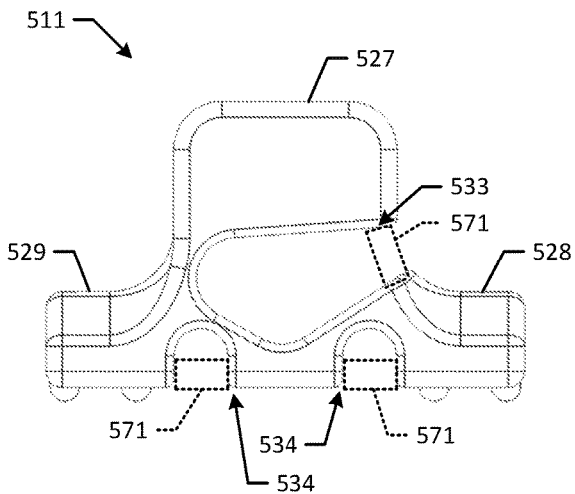
FIG. 5I is a plan view of the first attachment side and a number of fixation means of the dynamic interspinous process device of FIG. 5A.
Figure 5J:
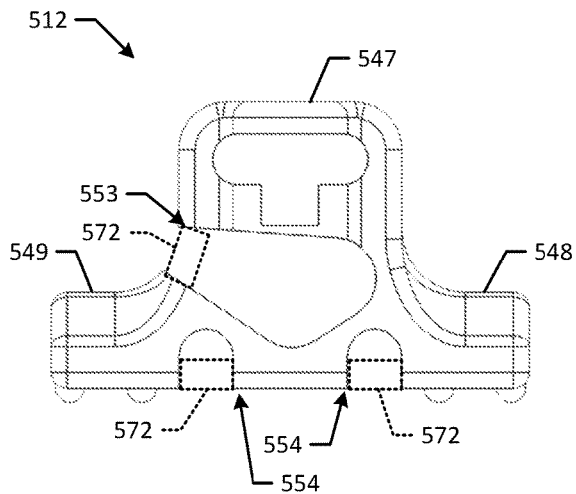
FIG. 5J is a plan view of the second attachment side and a number of fixation means of the dynamic interspinous process device of FIG. 5A.

In certain embodiments, the device 500 may include means for preventing or inhibiting the relative movement between the first wing 528 and the second wing 529 of the first attachment side 511 and for preventing or inhibiting the relative movement between the first wing 548 and the second wing 549 of the second attachment side 512. In this manner, the device 500 may prevent or inhibit the relative movement between the treated vertebrae. FIGS. 5I and 5J illustrate embodiments in which the device 500 includes one or more fixation means for preventing or inhibiting the relative movement between the wings 528, 529 and between the wings 548, 549. As shown, the first attachment side 511 may include one or more fixation means 571 (which also may be referred to as a "fixation insert," a "fixation member," a "fastener," or a "lock") configured for preventing or inhibiting movement of the wings 528, 529 relative to the central portion 527 and relative to one another as may be allowed by the slots 533, 534. In certain embodiments, the fixation means 571 may be removably attached to the central portion 527 and/or one of the wings 528, 529. In other embodiments, the fixation means 571 may be fixedly secured to the central portion 527 and/or one or the wings 528, 529. In certain embodiments, as shown, three of the fixation means 571 may be configured to be inserted at least partially into and retained within the respective slots 533, 534. Each fixation means 571 may engage portions of the first attachment side 511 surrounding the respective slot 533, 534 such that the fixation means 571 prevents or inhibits at least a portion of the slot 533, 534 from expanding and/or collapsing. In certain embodiments, each fixation means 571 may be a fastener, such as a set screw having a reverse angle thread for threadably engaging and retaining mating threaded portions of the first attachment side 511. In certain embodiments, as shown, each fixation means 571 may be inserted, in a direction transverse to the longitudinal axis $A_L$ and either transverse or parallel to the second transverse axis $A_{T2}$ of the device 500, into the open end of the respective slot 533, 534.

In a similar manner, the second attachment side 512 may include one or more fixation means 572 (which also may be referred to as a "fixation insert," a "fixation member," a "fastener," or a "lock") configured for preventing or inhibiting movement of the wings 548, 549 relative to the central portion 547 and relative to one another as may be allowed by the slots 553, 554. In certain embodiments, the fixation means 572 may be removably attached to the central portion 547 and/or one of the wings 548, 549. In other embodiments, the fixation means 572 may be fixedly secured to the central portion 547 and/or one or the wings 548, 549. In certain embodiments, as shown, a pair of the fixation means 572 may be configured to be inserted at least partially into and retained within the respective slots 553, 554. Each fixation means 572 may engage portions of the second attachment side 512 surrounding the respective slot 553, 554 such that the fixation means 572 prevents or inhibits at least a portion of the slot 553, 554 from expanding and/or collapsing. In certain embodiments, each fixation means 572 may be a fastener, such as a set screw having a reverse angle thread for threadably engaging and retaining mating threaded portions of the second attachment side 512. In certain embodiments, as shown, each fixation means 572 may be inserted, in a direction transverse to the longitudinal axis $A_L$ and either transverse or parallel to the second transverse axis $A_{T2}$ of the device 500, into the open end of the respective slot 553, 554.

It will be appreciated that the fixation means 571, 572 of the device 500 may be used to control the relative movement between the treated vertebrae, when desired. In particular, the fixation means 571, 572 may be used to prevent or inhibit relative movement between the treated vertebrae. In this manner, the device 500 may be used as a dynamic device or a rigid device, with the ability to convert the device 500 between a dynamic configuration and a rigid configuration, as may be desired in certain applications. The fixation means 571, 572 may be used to convert the device 500 between the dynamic configuration and the rigid configuration prior to implantation of the device 500, during initial implantation of the device 500 as a part of an initial surgery, or during a follow-up surgery.

Figure 5K:
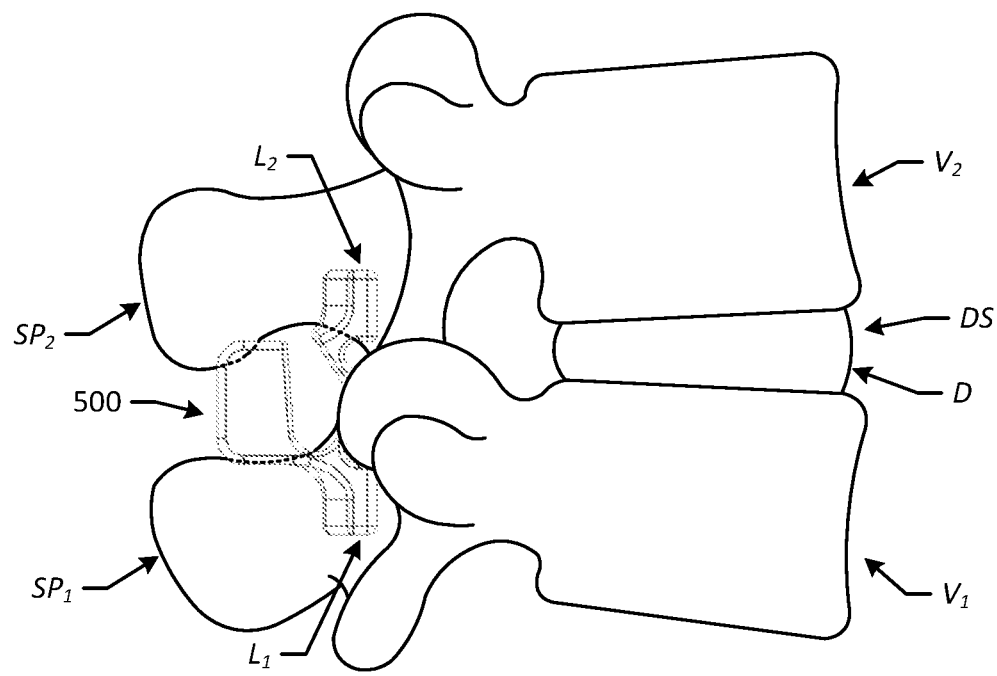
FIG. 5K is a side view of the dynamic interspinous process device of FIG. 5A implanted with respect to a first vertebra and a second vertebra in accordance with one or more embodiments of the present disclosure.
Figure 5L:
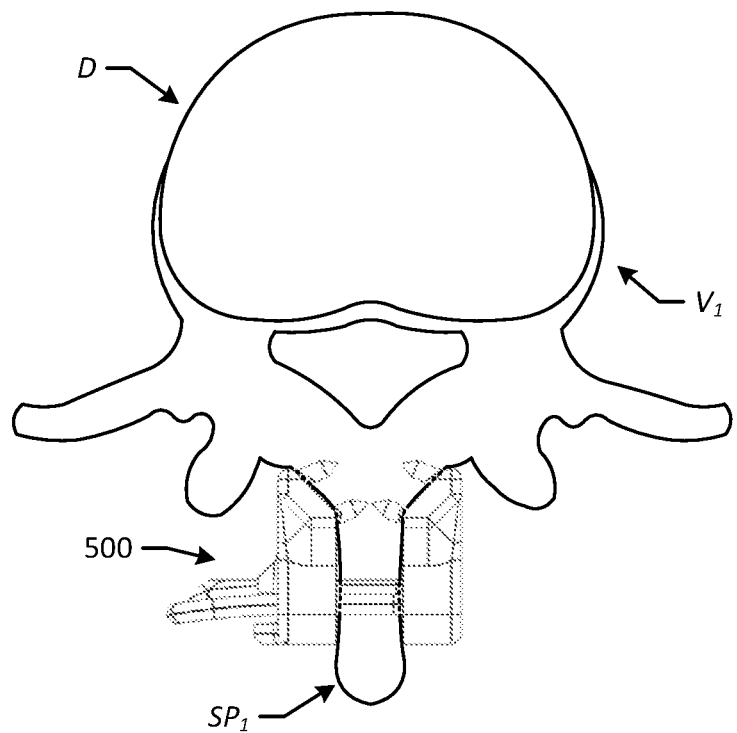
FIG. 5L is a top view of the dynamic interspinous process device of FIG. 5A implanted with respect to the first vertebra, the second vertebra being removed from view for purposes of illustration.

FIGS. 5K and 5L illustrate an example implantation of the device 500 with respect to a first vertebra $V_1$ and an adjacent second vertebra $V_2$. As shown, the first attachment side 511 and the second attachment side 512 may be positioned relative to the vertebrae $V_1$, $V_2$ such that the spacer 530 is positioned between a first spinous process $SP_1$ of the first vertebra $V_1$ and a second spinous process $SP_2$ of the second vertebra $V_2$. In this manner, the spacer 530 may limit a minimum spacing between the spinous processes $SP_1$, $SP_2$.

Additionally, the first attachment side 511 and the second attachment side 512 may be positioned relative to the vertebrae $V_1$, $V_2$ such that the respective wings 528, 529 of the first attachment side 511 and the respective wings 548, 549 of the second attachment side 512 engage a first lamina $L_1$ of the first vertebra $V_1$ and a second lamina $L_2$ of the second vertebra $V_2$. In this manner, the respective bone fasteners 531 of the first attachment side 511 and the respective bone fasteners 551 of the second attachment side 512 may penetrate and securely engage the laminae $L_1$, $L_2$. Accordingly, the implanted device 500 may stabilize the vertebrae $V_1$, $V_2$, although the device 500 may allow relative movement of the vertebrae $V_1$, $V_2$. In particular, the slots 533, 534, 553, 554 of the device 500 may allow relative movement of the vertebrae $V_1$, $V_2$ in sagittal plane of the patient, thereby allowing flexion and extension of the treated segment of the spine. It will be appreciated that the configuration of the slots 533, 534, 553, 554 may be varied, for example, by varying the number, size, and/or shape the slots 533, 534, 553, 554 to allow a desired range of motion in the sagittal plane. Further, the material from which the first attachment side 511 and the second attachment side 512 are formed may be selected to achieve the desired range of motion. In certain embodiments, the first attachment side 511 and the second attachment side 512 may be formed of titanium, although other suitable metals, polymers, or other materials may be used in other embodiments. Meanwhile, the device 500 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 500 and the disc D. In other embodiments in which the native disc D is removed, an interbody device, such as a cage or a spacer, may be implanted within the disc space DS (i.e., the intervertebral space) and the loads carried by the treated spinal segment may be shared by the device 500 and the interbody device. As described above, the device 500 may be used in conjunction with other additional hardware, such that the device 500 and the additional hardware collectively stabilize the treated segment of the spine and share loads carried thereby. It will be appreciated that the foregoing description and the corresponding drawings are merely examples of the device 500 and that other configurations and modifications may be made.

Figure 6A:
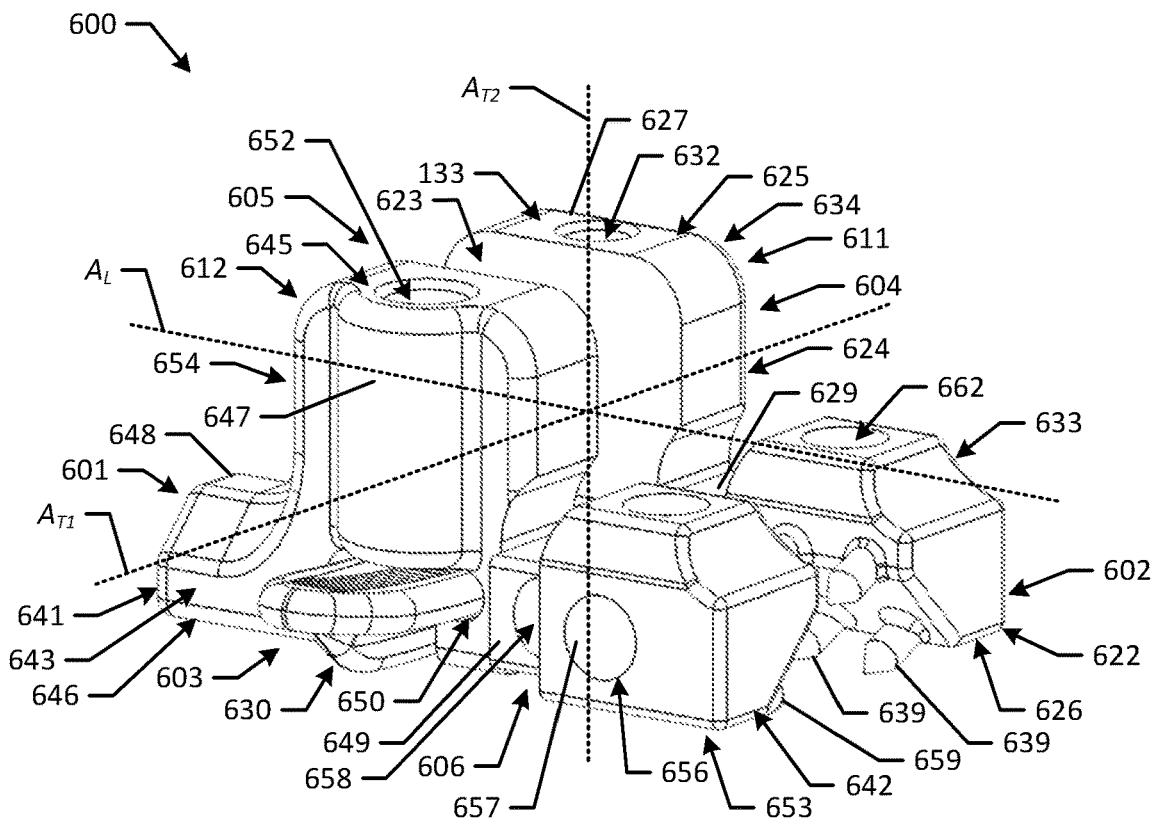
FIG. 6A is a perspective view of a dynamic interspinous process device in accordance with one or more embodiments of the present disclosure, showing a first attachment side and a second attachment side of the dynamic interspinous process device in an assembled state.
Figure 6B:
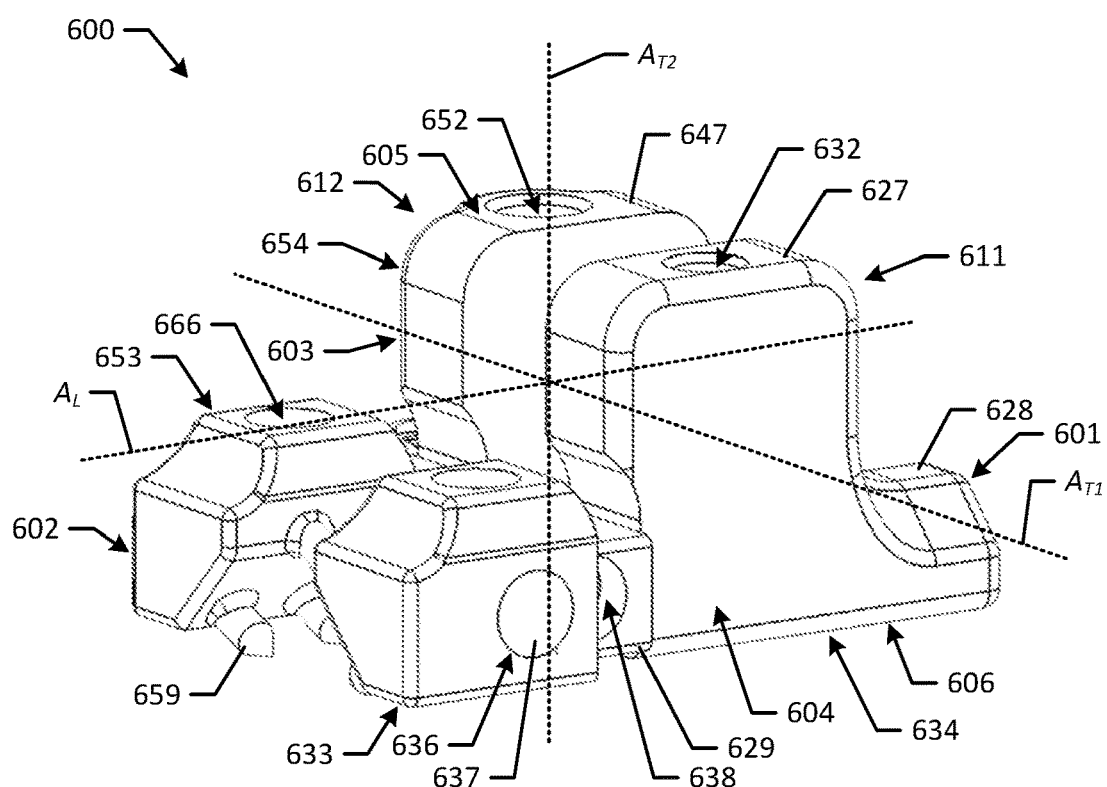
FIG. 6B is a perspective view of the dynamic interspinous process device of FIG. 6A, showing the first attachment side and the second attachment side in the assembled state.
Figure 6C:
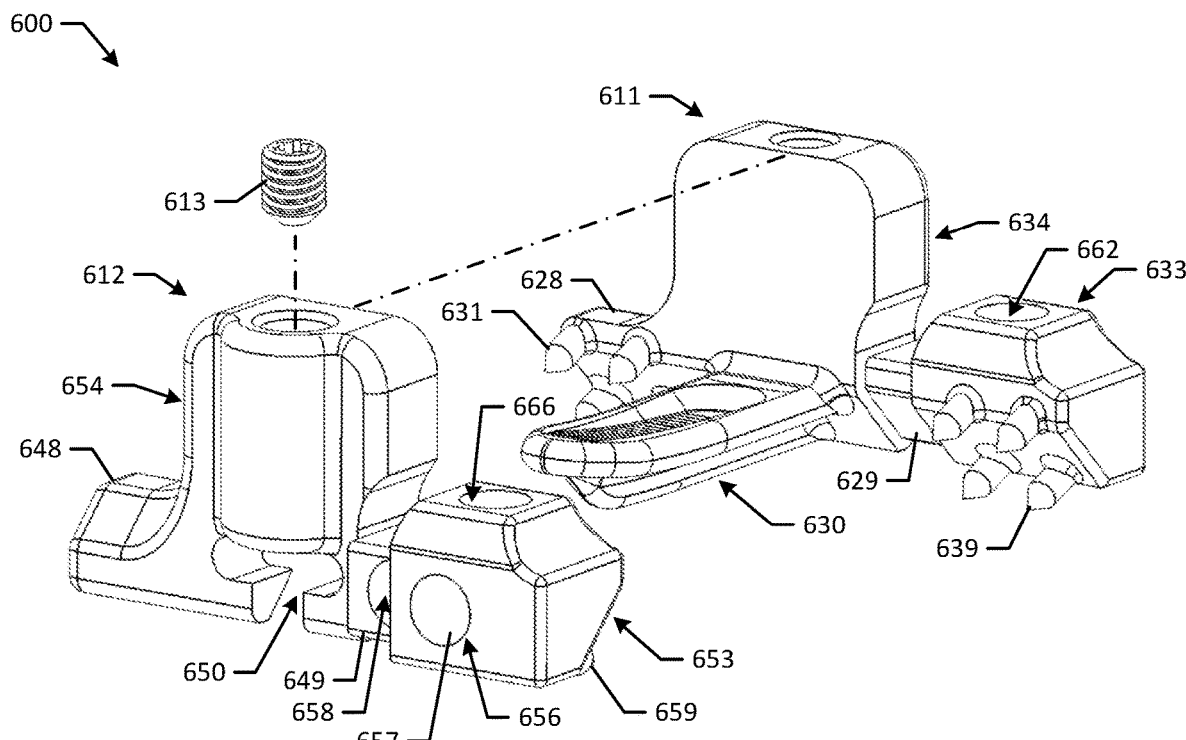
FIG. 6C is a perspective view of the dynamic interspinous process device of FIG. 6A, showing the first attachment side, the second attachment side, and a securing means of the dynamic interspinous process device in a disassembled state.
Figure 6D:
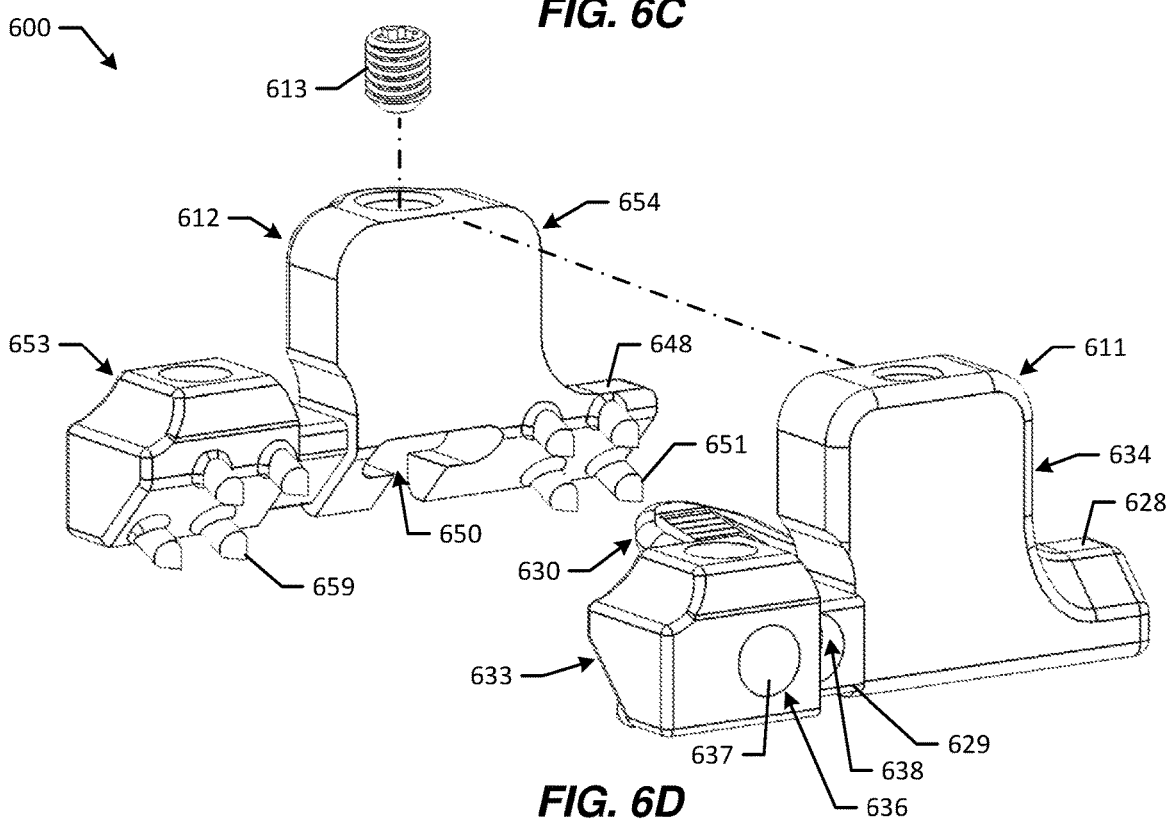
FIG. 6D is a perspective view of the dynamic interspinous process device of FIG. 6A, showing the first attachment side, the second attachment side, and the securing means in the disassembled state.
Figure 6E:
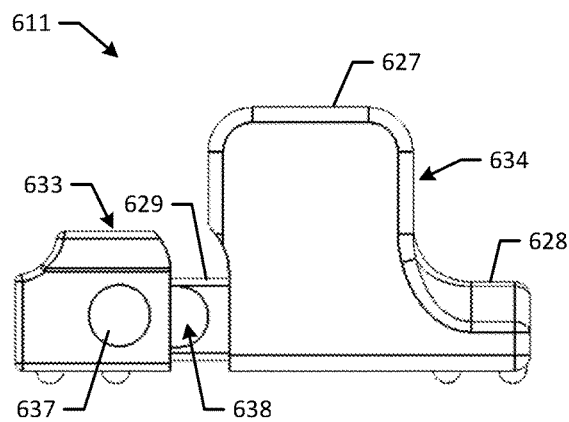
FIG. 6E is a plan view of the first attachment side of the dynamic interspinous process device of FIG. 6A, showing a slider of the first attachment side in an extended position relative to a main body of the first attachment side.
Figure 6F:
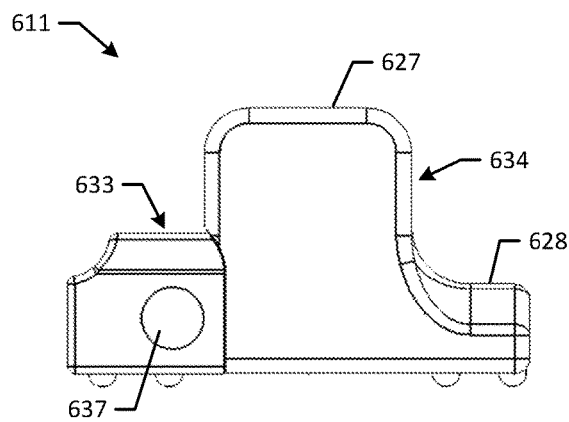
FIG. 6F is a plan view of the first attachment side of the dynamic interspinous process device of FIG. 6A, showing the slider of the first attachment side in a retracted position relative to the main body of the first attachment side.
Figure 6G:
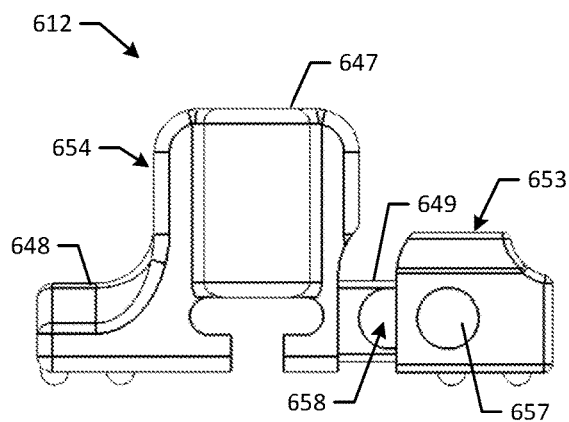
FIG. 6G is a plan view of the second attachment side of the dynamic interspinous process device of FIG. 6A, showing a slider of the second attachment side in an extended position relative to a main body of the second attachment side.
Figure 6H:
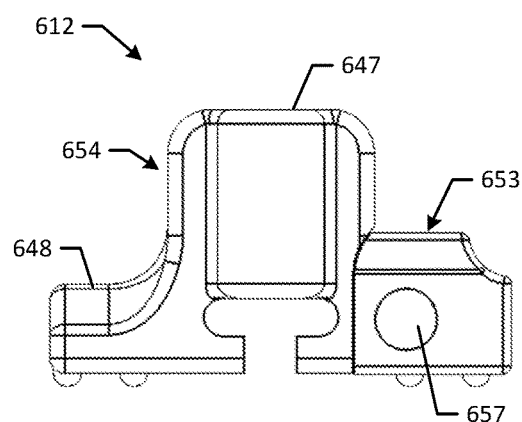
FIG. 6H is a plan view of the second attachment side of the dynamic interspinous process device of FIG. 6A, showing the slider of the second attachment side in a retracted position relative to the main body of the second attachment side.
Figure 6L:
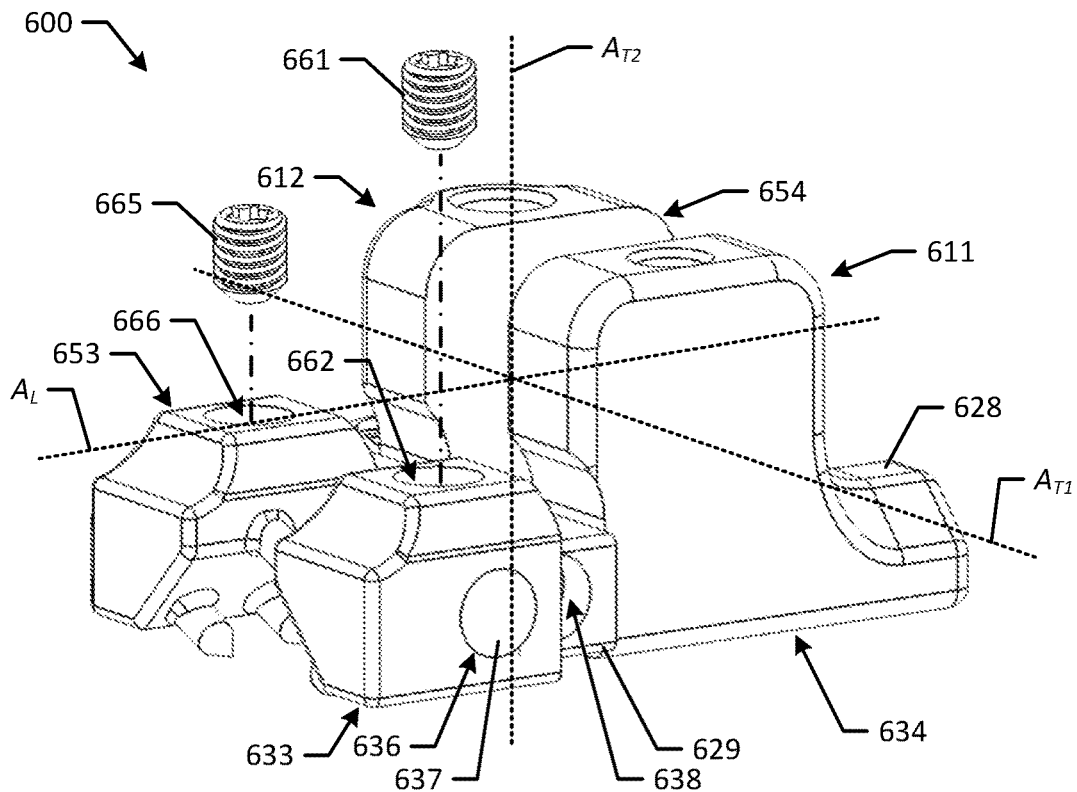
FIG. 6L is a perspective view of the dynamic interspinous process device of FIG. 6A, showing the first attachment side and the second attachment side in an assembled state and a pair of slider securing means in a disassembled state.
Figure 6M:
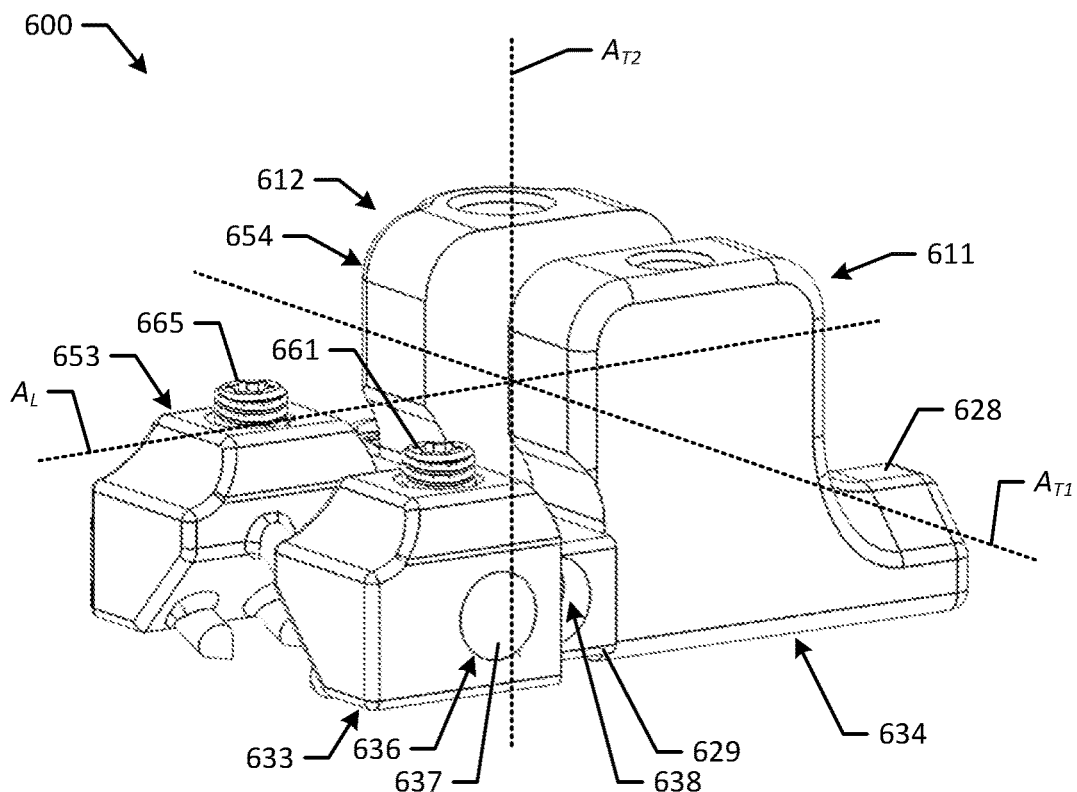
FIG. 6M is a perspective view of the dynamic interspinous process device of FIG. 6A, showing the first attachment side and the second attachment side in the assembled state and the pair of slider securing means in an assembled state.
Figure 6N:
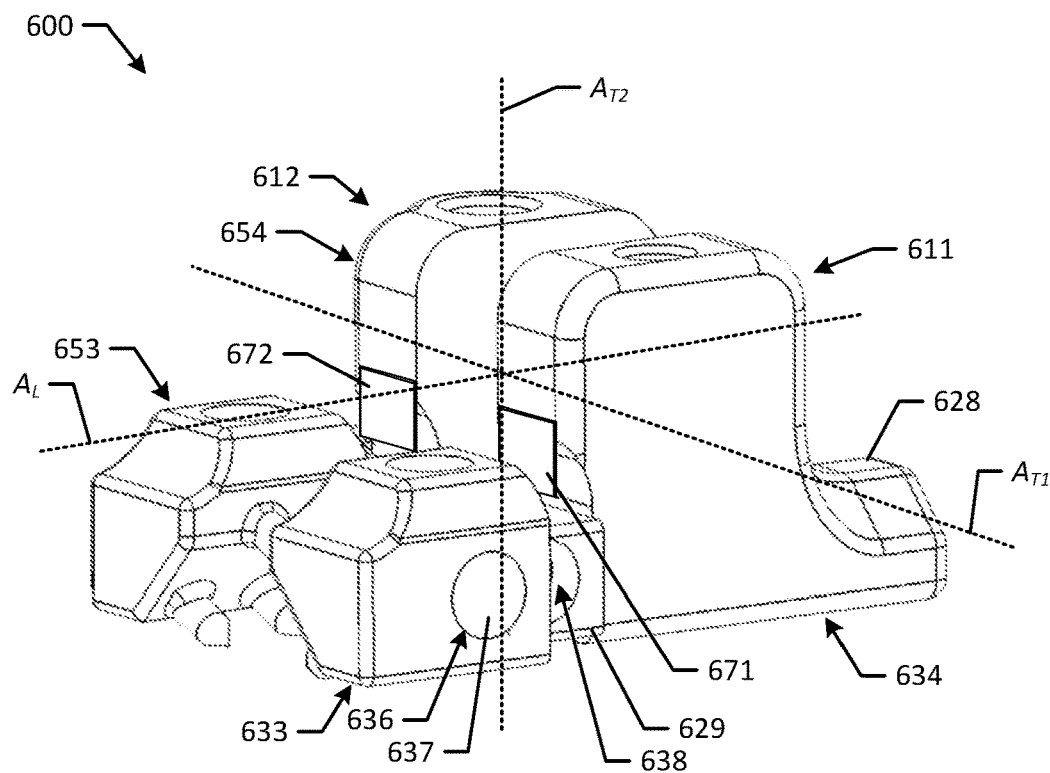
FIG. 6N is a perspective view of the dynamic interspinous process device of FIG. 6A in accordance with one or more embodiments of the present disclosure, showing the first attachment side and the second attachment side in the assembled state and a pair of resistance means of the dynamic interspinous process device in a natural state.
Figure 6O:
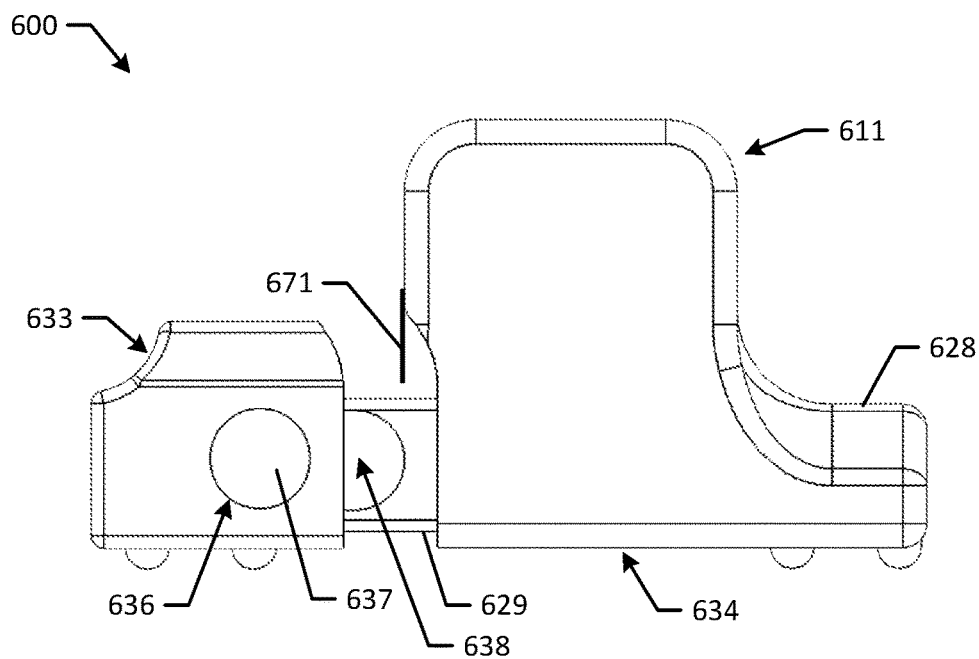
FIG. 6O is a plan view of the first attachment side of the dynamic interspinous process device of FIG. 6N, showing the slider of the first attachment side in the extended position relative to the main body of the first attachment side and the resistance means of the first attachment side in the natural state.
Figure 6P:
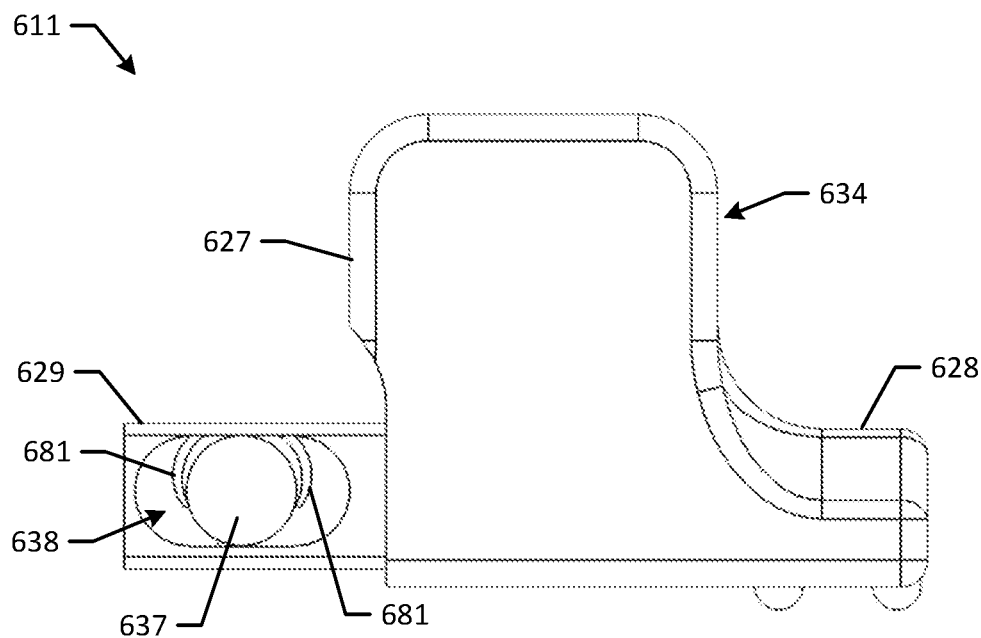
FIG. 6P is a plan view of the first attachment side of the dynamic interspinous process device of FIG. 6A in accordance with one or more embodiments of the present disclosure, showing a pair of resistance means of the first attachment side in a home state and the pin of the first attachment side in a home position.
Figure 6Q:
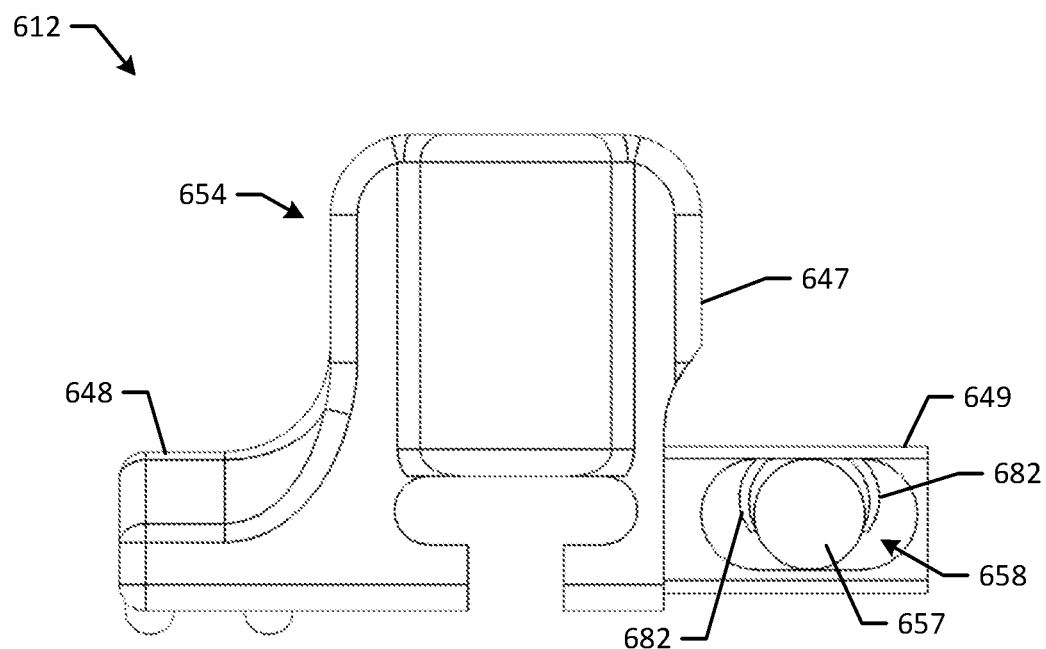
FIG. 6Q is a plan view of the second attachment side of the dynamic interspinous process device of FIG. 6A in accordance with one or more embodiments of the present disclosure, showing a pair of resistance means of the second attachment side in a home state and the pin of the first attachment side in a home position.
Figure 6R:
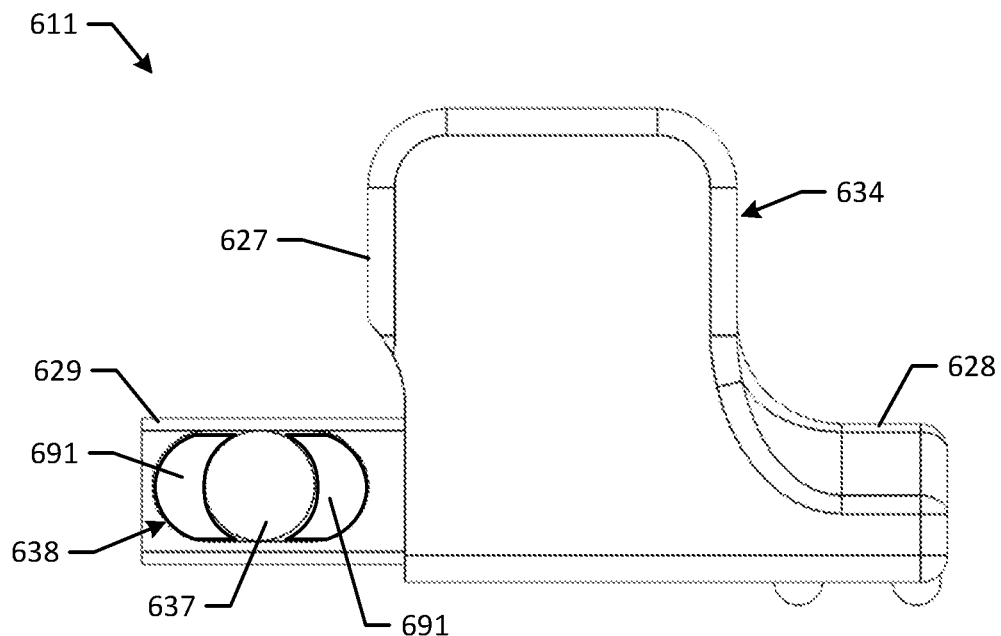
FIG. 6R is a plan view of the first attachment side of the dynamic interspinous process device of FIG. 6A in accordance with one or more embodiments of the present disclosure, showing a pair of resistance means of the first attachment side in a home state and the pin of the first attachment side in a home position.
Figure 6S:
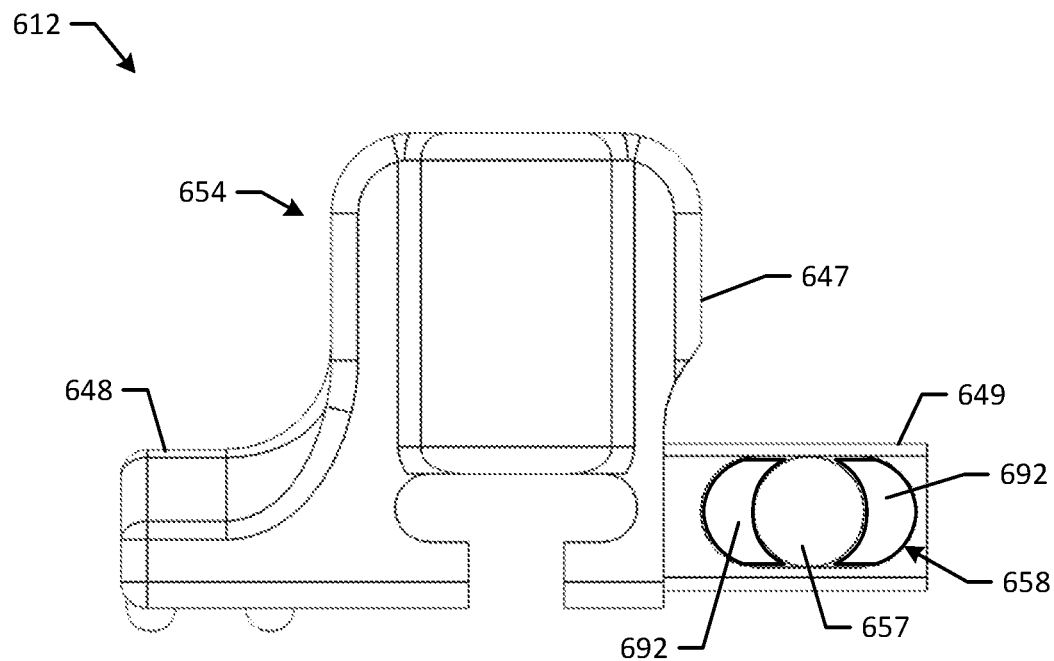
FIG. 6S is a plan view of the second attachment side of the dynamic interspinous process device of FIG. 6A in accordance with one or more embodiments of the present disclosure, showing a pair of resistance means of the second attachment side in a home state and the pin of the first attachment side in a home position.
Figure 6T:
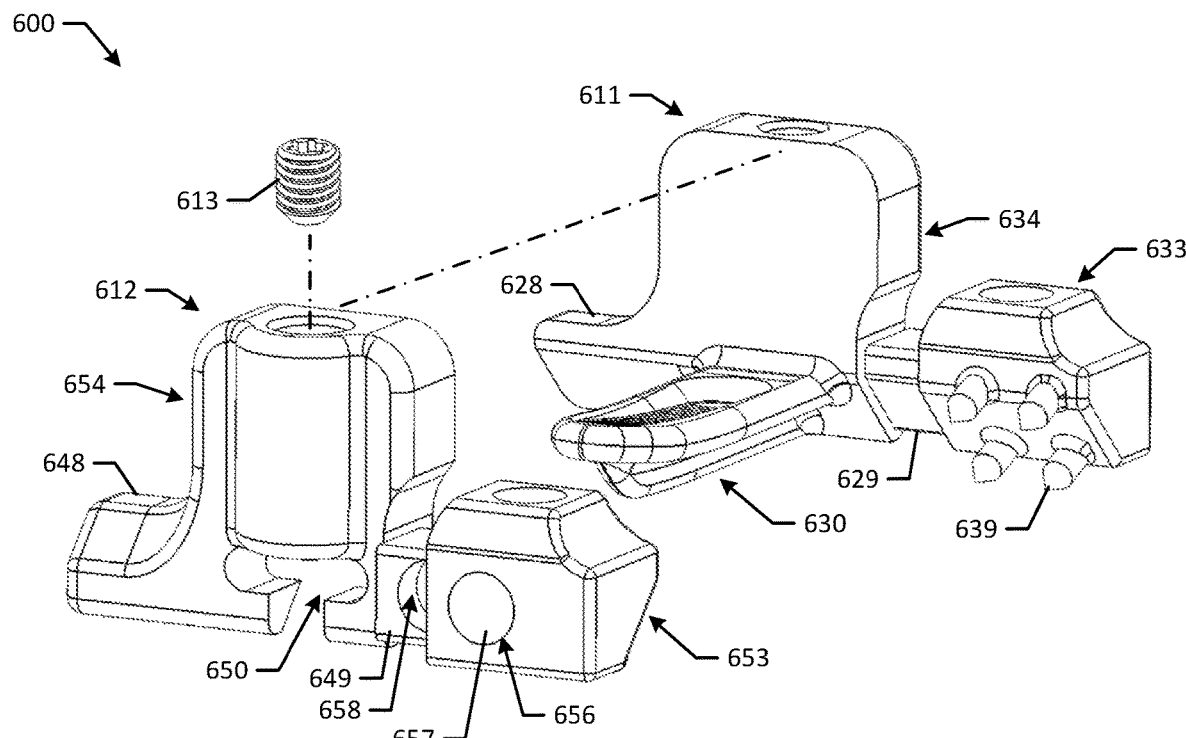
FIG. 6T is a perspective view of the dynamic interspinous process device of FIG. 6A, showing the first attachment side, the second attachment side, and the securing means of the dynamic interspinous process device in a disassembled state.
Figure 6U:
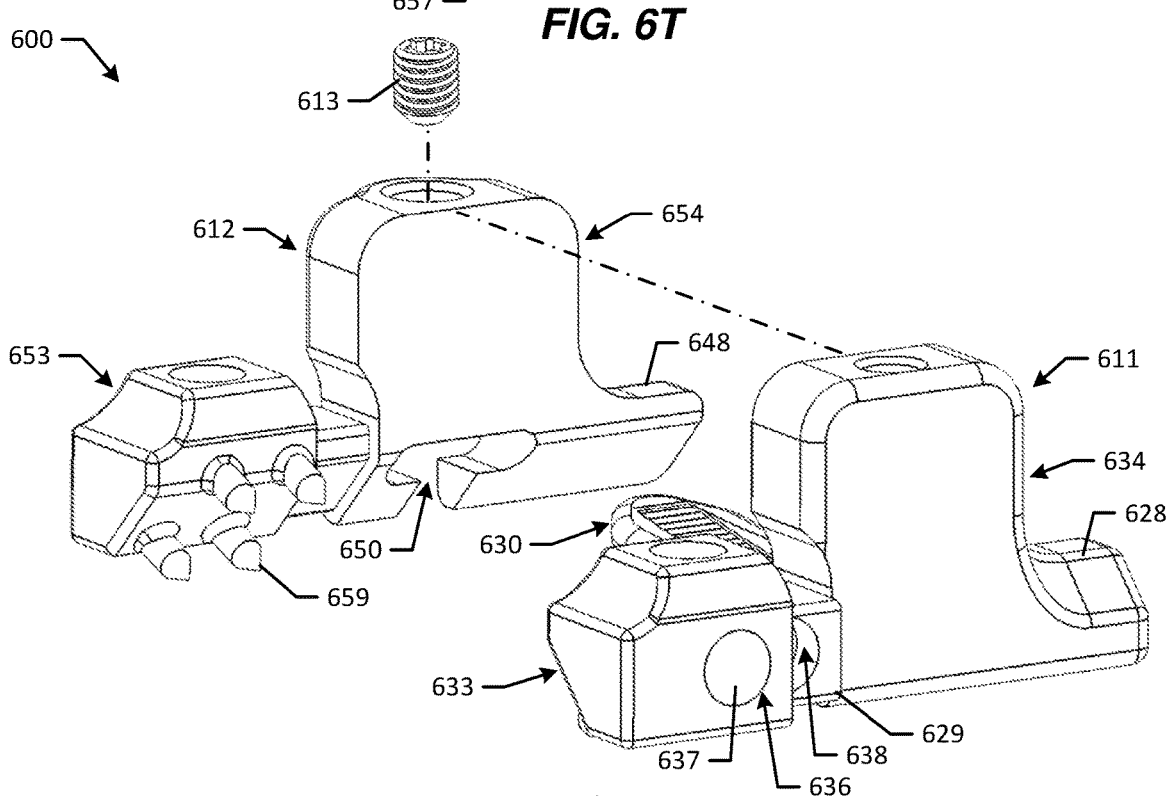
FIG. 6U is a perspective view of the dynamic interspinous process device of FIG. 6A, showing the first attachment side, the second attachment side, and the securing means in the disassembled state.
Figure 6V:
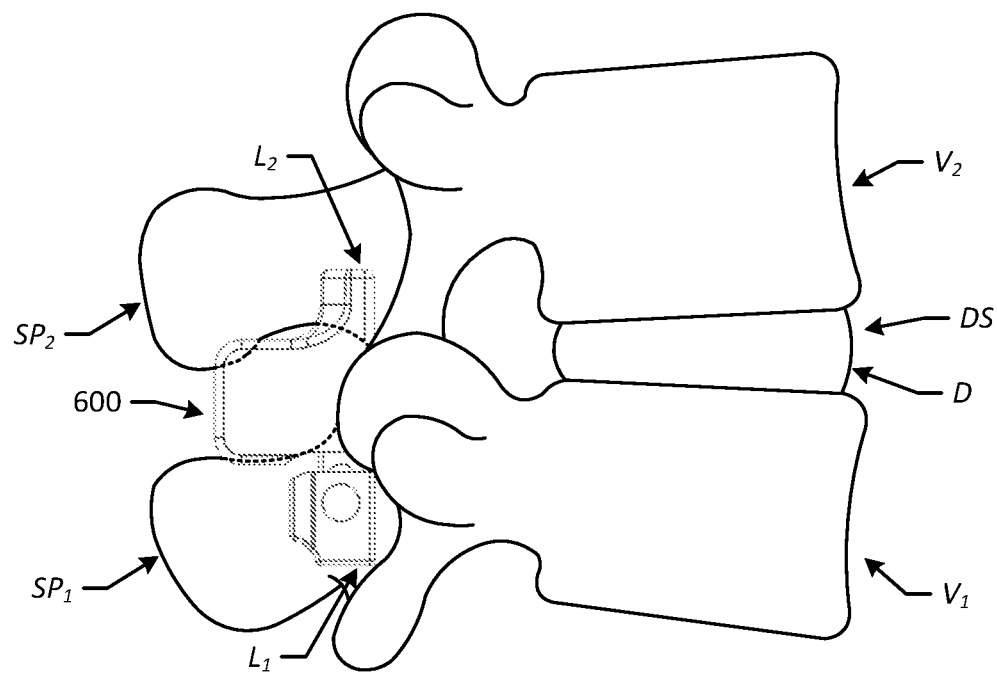
FIG. 6V is a side view of the dynamic interspinous process device of FIG. 6A implanted with respect to a first vertebra and a second vertebra in accordance with one or more embodiments of the present disclosure.
Figure 6W:
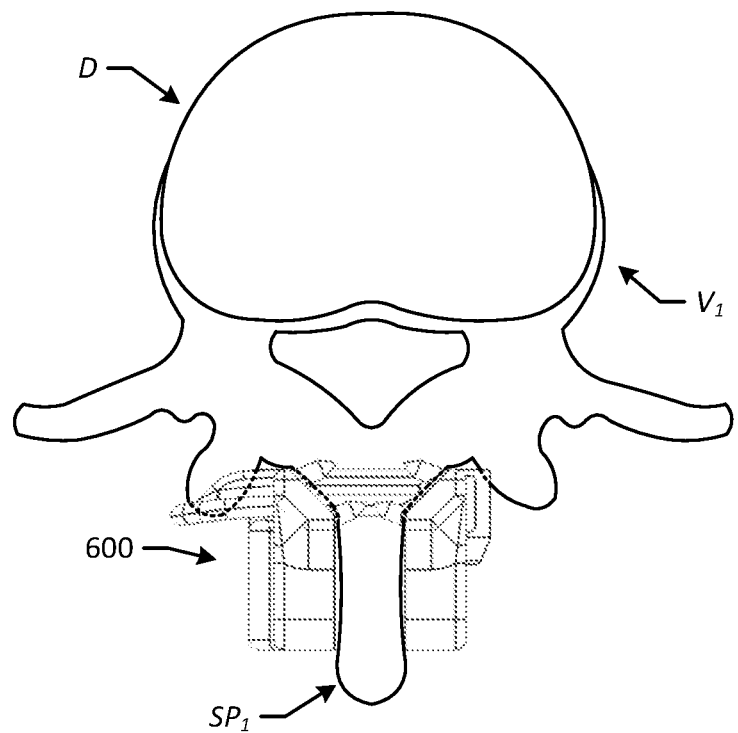
FIG. 6W is a top view of the dynamic interspinous process device of FIG. 6A implanted with respect to the first vertebra, the second vertebra being removed from view for purposes of illustration.

FIGS. 6A-6W illustrate an interspinous process device 600 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 600 may be configured for implantation relative to a first vertebra and an adjacent second vertebra, as described below, specifically with reference to FIGS. 6V and 6W. In particular, a portion of the interspinous process device 600 may be positioned between the spinous process of the first vertebra and the spinous process of the second vertebra, while one or more other portions of the interspinous process device 600 engage the spinous processes, the laminae, and/or other portions of the respective vertebra. As described below, the interspinous process device 600 may allow a desired range of relative movement between the treated vertebrae, which may be desirable in certain treatment applications. Additionally, the interspinous process device 600 may be converted between a dynamic configuration, in which the device 600 allows relative movement between the treated vertebrae, and a rigid configuration, in which the device 600 prevents or substantially inhibits such relative movement. In this manner, the interspinous process device 600 may be adjusted to allow relative motion, when desired, and to inhibit relative motion, when desired, without having to remove or replace the device 600. The interspinous process device 600 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 600, itself or in combination with additional hardware, may provide the structural support necessary to restore and maintain normal spacing and alignment of the treated vertebrae while avoiding certain drawbacks presented by existing interspinous process devices.

The interspinous process device 600 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 600 may include a first end 601 and a second end 602 disposed opposite the first end 601 in the direction of the longitudinal axis $A_L$. As described below, the device 600 may be implanted with the longitudinal axis $A_L$ extending in a direction substantially parallel to the sagittal plane and the coronal plane of the patient and transverse to the transverse plane of the patient. In this manner, depending on the orientation of the device 600 upon implantation thereof, one of the first end 601 and the second end 602 of the device 600 may be referred to as a the "superior end" of the device 600, and the other of the first end 601 and the second end 602 of the device 600 may be referred to as the "inferior end" of the device 600. The device 600 also may include a first side 603 extending from the first end 601 to the second end 602, and a second side 604 disposed opposite the first side 603 in the direction of the first transverse axis $A_{T1}$ and extending from the first end 601 to the second end 602. The device 600 may be implanted with the first transverse axis $A_{T1}$ extending in a direction substantially parallel to the coronal plane and the transverse plane of the patient and transverse to the sagittal plane of the patient. In this manner, depending on the orientation of the device 600 upon implantation thereof, one of the first side 603 and the second side 604 of the device 600 may be referred to as a the "right side" of the device 600, and the other of the first side 603 and the second side 604 of the device 600 may be referred to as the "left side" of the device 600. The device 600 further may include a third side 605 extending from the first end 601 to the second end 602 and from the first side 603 to the second side 604, and a fourth side 606 disposed opposite the third side 605 in the direction of the second transverse axis $A_{T2}$ and extending from the first end 601 to the second end 602 and from the first side 603 to the second side 604. The device 600 may be implanted with the second transverse axis $A_{T2}$ extending in a direction substantially parallel to the sagittal plane and the transverse plane of the patient and transverse to the coronal plane of the patient. As described below, the device 600 may be oriented upon implantation thereof such that the third side 605 faces posteriorly and the fourth side 606 faces anteriorly with respect to the patient. In this manner, the third side 605 may be referred to as the "posterior side" of the device 600, and the fourth side 606 may be referred to as the "anterior side"

of the device 600. The device 600 may have an overall "length" extending from the first end 601 to the second end 602 in the direction of the longitudinal axis $A_L$, an overall "width" extending from the first side 603 to the second side 604 in the direction of the first transverse axis $A_{T1}$, and an overall "height" extending from the third side 605 to the fourth side 606 in the direction of the second transverse axis $A_{T2}$. Further, various components and features of the device 600 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 600 may include a first attachment side 611 (which also may be referred to as a "first attachment portion," a "first attachment assembly," or a "first plate") and a second attachment side 612 (which also may be referred to as a "second attachment portion," a "second attachment assembly," or a "second plate") configured for removably attaching to one another via a securing means 613. During use of the device 600, one of the first attachment side 611 and the second attachment side 612 may be disposed, at least partially, along the right side of the patient's spine, and the other of the first attachment side 611 and the second attachment side 612 may be disposed, at least partially, along the right side of the patient's spine. It will be appreciated that the first attachment side 611 and the second attachment side 612 may include corresponding features that are mirror images of one another, although certain differences between the first attachment side 611 and the second attachment side 612 may exist, as described below. In certain embodiments, the first attachment side 611 and the second attachment side 612 may be formed of a metal, such as titanium or stainless steel, although other suitable materials, such as polyether ether ketone (PEEK), other polymers, or composites, may be used.

The first attachment side 611 may have a first end 621, a second end 622 disposed opposite the first end 621, a first side 623 (which also may be referred to as an "interior side"), a second side 624 (which also may be referred to as an "exterior side") disposed opposite the first side 623, a third side 625 (which also may be referred to as an "posterior side"), and a fourth side 626 (which also may be referred to as an "anterior side") disposed opposite the third side 625. As shown, the first attachment side 611 may include a central portion 627 and a pair of wings 628, 629 disposed on opposite sides of the central portion 627. In particular, the first wing 628 may extend from the central portion 627 to the first end 621 of the first attachment side 611, and the second wing 629 may extend from the central portion 627 toward the second end 622 of the first attachment side 611. In certain embodiments, as shown, the wings 628, 629 may extend in opposite directions from the central portion 627, although other configurations of the wings 628, 629 may be used. In certain embodiments, the wings 628, 629 may be shaped and configured in a manner similar to any one of the wing embodiments described and/or shown in the Prior Applications. Further details regarding the configurations of the wings 628, 629 and differences between the first wing 628 and the second wing 629 are described below.

The first attachment side 611 also may include a spacer 630 extending from the first side 623 thereof. During use of the device 600, the spacer 630 may be positioned between the spinous processes of the respective vertebrae. In certain embodiments, as shown, the spacer 630 may extend from the central portion 627 of the first attachment side 611 and be integrally formed therewith. In other embodiments, the spacer 630 may be separately formed from and attached to the central portion 627 via an attachment mechanism. The first attachment side 611 further may include a number of engagement features configured for securely engaging the respective vertebrae. In certain embodiments, as shown, the engagement features may be one or more bone fasteners 631 extending from the first side 623 of the first attachment side 611. The bone fasteners 631 may be formed as spikes or barbs, although other forms and types of bone fasteners 631 may be used for securely engaging the vertebrae. In certain embodiments, one or more of the bone fasteners 631 may extend form the first wing 628, as shown. Various configurations of the bone fasteners 631 of the first attachment side 611 may be used. In certain embodiments, as shown, the bone fasteners 631 may be configured to engage the laminae of the respective vertebrae. In other embodiments, one or more of the bone fasteners 631 may be configured to engage the spinous processes, the laminae, and/or other portions of the respective vertebrae. As shown, the first attachment side 611 also may include an instrument engagement aperture 632 configured for receiving a portion of and cooperating with an instrument used for positioning the first attachment side 611 during implantation of the device 600. Example instruments for implantation of the device 600 are described in the Prior Applications.

In a similar manner, the second attachment side 612 may have a first end 641, a second end 642 disposed opposite the first end 641, a first side 643 (which also may be referred to as an "exterior side"), a second side 644 (which also may be referred to as an "interior side") disposed opposite the first side 643, a third side 645 (which also may be referred to as an "posterior side"), and a fourth side 646 (which also may be referred to as an "anterior side") disposed opposite the third side 645. As shown, the second attachment side 612 may include a central portion 647 and a pair of wings 648, 649 disposed on opposite sides of the central portion 647. In particular, the first wing 648 may extend from the central portion 647 to the first end 641 of the second attachment side 612, and the second wing 649 may extend from the central portion 647 toward the second end 642 of the second attachment side 612. In certain embodiments, as shown, the wings 648, 649 may extend in opposite directions from the central portion 647, although other configurations of the wings 648, 649 may be used. In certain embodiments, the wings 648, 649 may be shaped and configured in a manner similar to any one of the wing embodiments described and/or shown in the Prior Applications. Further details regarding the configurations of the wings 648, 649 and differences between the first wing 648 and the second wing 649 are described below.

The second attachment side 612 also may include a spacer slot 650 extending through the second attachment side 612 from the first side 643 to the second side 644 thereof. During use of the device 600, the spacer slot 650 may be configured to receive the spacer 630 of the first attachment side 611 therethrough, as shown. In certain embodiments, as shown, the spacer slot 650 may be defined in the central portion 647 of the second attachment side 612 and may extend to the fourth side 646 thereof, although other positions of the spacer slot 650 may be used. The second attachment side 612 further may include a number of engagement features configured for securely engaging the respective vertebrae. In certain embodiments, as shown, the engagement features may be one or more bone fasteners 651 extending from the second side 644 of the second attachment side 612. The bone fasteners 651 may be formed as spikes or barbs, although other forms and types of bone fasteners 651 may be used for securely engaging the vertebrae. In certain embodiments, one or more of the bone fasteners 651 may extend form the first wing 648, as shown. Various configurations of the bone fasteners 651 of the second attachment side 612 may be used. In certain embodiments, as shown, the bone fasteners 651 may be configured to engage the laminae of the respective vertebrae. In other embodiments, one or more of the bone fasteners 651 may be configured to engage the spinous processes, the laminae, and/or other portions of the respective vertebrae. As shown, the second attachment side 612 also may include a securing aperture 652 configured to receive at least a portion of and cooperate with the securing means 613 for selectively fixing the first attachment side 611 and the second attachment side 612 relative to one another. The securing aperture 652 also may be configured for receiving a portion of and cooperating with an instrument used for positioning the second attachment side 612 during implantation of the device 600. Example instruments for implantation of the device 600 are described in the Prior Applications.

The securing means 613 may be configured for selectively fixing the first attachment side 611 and the second attachment side 612 relative to one another. In certain embodiments, as shown, the securing means 613 may be a fastener, such as a set screw, although other types of fasteners and other types of securing means may be used. As shown, the securing means 613 may be inserted into and at least partially through the securing aperture 652 of the second attachment side 612. In this manner, the securing means 613 may be advanced through the securing aperture 652 until the securing means 613 engages the spacer 630 of the first attachment side 611 positioned within the spacer slot 650 of the second attachment side 612. Upon desired positioning of the first attachment side 611 and the second attachment side 612 with respect to the corresponding vertebrae of the patient, the securing means 613 may be tightened to maintain the spacing and orientation of the first attachment side 611 and the second attachment side 612 relative to one another and relative to the corresponding vertebrae. In certain embodiments, the securing means 613 may be formed of a metal, such as titanium or stainless steel, although other suitable materials, such as polyether ether ketone (PEEK), other polymers, or composites, may be used.

As described above, the device 600 may be configured to allow relative movement of the treated vertebrae upon implantation of the device 600. In particular, the device 600 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 611 and the second attachment side 612 each may include one or more features configured to facilitate such relative movement of the treated vertebrae. In particular, the first attachment side 611 may include a slider 633 (which also may be referred to as a "dynamic slider," a "sliding member," an "engagement member," a "sleeve," or a "cap") that is movably attached to a main body 634 of the first attachment side 611. In certain embodiments, as shown, the main body 634 may include the central portion 627, the first wing 628, and the second wing 629 of the first attachment side 611, although other configurations of the main body 634 may be used. In certain embodiments, as shown, the slider 633 may be movably attached to the second wing 629, although the slider 633 may be movably attached to other features of the first attachment side 611 in other embodiments. The slider 633 may be formed as a sleeve or a cap configured to be movably positioned over or around at least a portion of the second wing 629, although other shapes and configurations of the slider 633 may be used. In certain embodiments, as shown, the slider 633 may include a central opening 635 extending through at least a portion of the slider 633 and configured for receiving at least a portion of the second wing 629 therein. The central opening 635 may be formed as a blind hole, as shown, extending in the direction of the longitudinal axis $A_L$ of the device 600. Alternatively, the central opening 635 may be formed as a thru hole extending in the direction of the longitudinal axis $A_L$ of the device 600.

As shown, the slider 633 also may include a coupling aperture 636 extending from an external surface of the slider 633 to the central opening 635 and configured to receive a coupling member 637 at least partially therein. In certain embodiments, as shown, the coupling member 637 may be formed as a pin configured for extending through the coupling aperture 636 of the slider 633 and at least partially into a channel 638 (which also may be referred to as a "guide channel" or a "guide") defined in the second wing 629. As shown, the channel 638 may have an elongated shape extending in the direction of the longitudinal axis $A_L$ of the device 600. In certain embodiments, the channel 638 may have a straight shape extending in the direction of the longitudinal axis $A_L$ of the device 600. In other embodiments, the channel 638 may have a curved shape extending in the direction of the longitudinal axis $A_L$ of the device 600. For example, the channel 638 may have a curved shape such that a concave shape of the channel faces the fourth side 626 of the first attachment side 611. During assembly of the slider 633 to the second wing 629, the second wing 629 may be positioned at least partially within the central opening 635 of the slider 633, and the coupling member 637 may be passed through the coupling aperture 636 and at least partially into the channel 638. In certain embodiments, as shown, the coupling member 637 may be press fit into the coupling aperture 636, and a portion of the coupling member 637 extending into the central opening 635 may be slidably received within the channel 638. As shown, the channel 638 may have a pair of closed ends positioned opposite one another along the length of the channel 638. In this manner, the connection between the coupling member 637 and the channel 638 may limit relative movement between the slider 633 and the second wing 629 and the overall main body 634. It will be appreciated that the illustrated connection is merely one example and that other mechanisms for movably attaching the slider 633 to the main body 634 may be used.

The slider 633 may be configured to move relative to the main body 634 between an extended position (which also may be referred to as a "first position"), as shown in FIG. 6E, and a retracted position (which also may be referred to as a "second position"), as shown in FIG. 6F. In particular, the slider 633 may be configured to translate or otherwise slide along the second wing 629 between the extended position and the retracted position. In certain embodiments, the slider 633 may move along a linear path between the extended position and the retracted position, in the direction of the longitudinal axis $A_L$ of the device 600, while being guided by the shape of the channel 638 and/or the shape of the second wing 629. For example, the slider 633 may move along a linear path when the channel 638 and/or the second wing 629 have a linear shape in the direction of the longitudinal axis $A_L$ of the device 600. In other embodiments, the slider 633 may move along a curved path between the extended position and the retracted position, in the direction of the longitudinal axis $A_L$ of the device 600, while being guided by the shape of the channel 638 and/or the shape of the second wing 629. For example, the slider 633 may move along a curved path when the channel 638 and/or the second wing 629 have a curved shape in the direction of the longitudinal axis $A_L$ of the device 600. As shown, the slider 633 may include a number of engagement features configured for securely engaging the respective vertebra. In certain embodiments, as shown, the engagement features may be one or more bone fasteners 639 extending from the slider 633 along the first side 623 of the first attachment side 611. The bone fasteners 639 may be formed as spikes or barbs, although other forms and types of bone fasteners 639 may be used for securely engaging the vertebrae. In certain embodiments, as shown, the bone fasteners 639 may be shaped and configured in a manner similar to the bone fasteners 631 extending form the first wing 628. Various configurations of the bone fasteners 639 of the slider 633 may be used. In certain embodiments, as shown, the bone fasteners 639 may be configured to engage the laminae of the respective vertebrae. In other embodiments, one or more of the bone fasteners 639 may be configured to engage the spinous processes, the laminae, and/or other portions of the respective vertebra.

It will be appreciated that the connection between the slider 633 and the main body 634 may be configured to allow portions of the first attachment side 611 to move relative to one another. As described above, the slider 633 may be movably attached to the main body 634, and thus the slider 633 may move relative to the central portion 627, the first wing 628, and the spacer 630 of the main body 634. In particular, the slider 633 may move toward the central portion 627, the first wing 628, and the spacer 630 when the slider 633 moves toward the retracted position, and the slider 633 may move away from the central portion 627, the first wing 628, and the spacer 630 when the slider 633 moves toward the extended position. As a result, the slider 633 and the first wing 628 may be configured to move toward one another and away from one another in the direction of the longitudinal axis $A_L$ of the device 600. In effect, the movable attachment between the slider 633 and the main body 634 may cause the first attachment side 611 to function as a slide which may be extended or retracted in the direction of the longitudinal axis $A_L$ of the device 600.

In a similar manner, the second attachment side 612 may include a slider 653 (which also may be referred to as a "dynamic slider," a "sliding member," an "engagement member," a "sleeve," or a "cap") that is movably attached to a main body 654 of the second attachment side 612. In certain embodiments, as shown, the main body 654 may include the central portion 647, the first wing 648, and the second wing 649 of the second attachment side 612, although other configurations of the main body 654 may be used. In certain embodiments, as shown, the slider 653 may be movably attached to the second wing 649, although the slider 653 may be movably attached to other features of the second attachment side 612 in other embodiments. The slider 653 may be formed as a sleeve or a cap configured to be movably positioned over or around at least a portion of the second wing 649, although other shapes and configurations of the slider 653 may be used. In certain embodiments, as shown, the slider 653 may include a central opening 655 extending through at least a portion of the slider 653 and configured for receiving at least a portion of the second wing 649 therein. The central opening 655 may be formed as a blind hole, as shown, extending in the direction of the longitudinal axis $A_L$ of the device 600. Alternatively, the central opening 655 may be formed as a thru hole extending in the direction of the longitudinal axis $A_L$ of the device 600.

As shown, the slider 653 also may include a coupling aperture 656 extending from an external surface of the slider 653 to the central opening 655 and configured to receive a coupling member 657 at least partially therein. In certain embodiments, as shown, the coupling member 657 may be formed as a pin configured for extending through the coupling aperture 656 of the slider 653 and at least partially into a channel 658 (which also may be referred to as a "guide channel" or a "guide") defined in the second wing 649. As shown, the channel 658 may have an elongated shape extending in the direction of the longitudinal axis $A_L$ of the device 600. In certain embodiments, the channel 658 may have a straight shape extending in the direction of the longitudinal axis $A_L$ of the device 600. In other embodiments, the channel 658 may have a curved shape extending in the direction of the longitudinal axis $A_L$ of the device 600. For example, the channel 658 may have a curved shape such that a concave shape of the channel 658 faces the fourth side 646 of the second attachment side 612. During assembly of the slider 653 to the second wing 649, the second wing 649 may be positioned at least partially within the central opening 655 of the slider 653, and the coupling member 657 may be passed through the coupling aperture 656 and at least partially into the channel 658. In certain embodiments, as shown, the coupling member 657 may be press fit into the coupling aperture 656, and a portion of the coupling member 657 extending into the central opening 655 may be slidably received within the channel 658. As shown, the channel 658 may have a pair of closed ends positioned opposite one another along the length of the channel 658. In this manner, the connection between the coupling member 657 and the channel 658 may limit relative movement between the slider 653 and the second wing 649 and the overall main body 654. It will be appreciated that the illustrated connection is merely one example and that other mechanisms for movably attaching the slider 653 to the main body 654 may be used.

The slider 653 may be configured to move relative to the main body 654 between an extended position (which also may be referred to as a "first position"), as shown in FIG. 6G, and a retracted position (which also may be referred to as a "second position"), as shown in FIG. 6H. In particular, the slider 653 may be configured to translate or otherwise slide along the second wing 649 between the extended position and the retracted position. In certain embodiments, the slider 653 may move along a linear path between the extended position and the retracted position, in the direction of the longitudinal axis $A_L$ of the device 600, while being guided by the shape of the channel 658 and/or the shape of the second wing 649. For example, the slider 653 may move along a linear path when the channel 658 and/or the second wing 649 have a linear shape in the direction of the longitudinal axis $A_L$ of the device 600. In other embodiments, the slider 653 may move along a curved path between the extended position and the retracted position, in the direction of the longitudinal axis $A_L$ of the device 600, while being guided by the shape of the channel 658 and/or the shape of the second wing 649. For example, the slider 653 may move along a curved path when the channel 658 and/or the second wing 649 have a curved shape in the direction of the longitudinal axis $A_L$ of the device 600. As shown, the slider 653 may include a number of engagement features configured for securely engaging the respective vertebra. In certain embodiments, as shown, the engagement features may be one or more bone fasteners 659 extending from the slider 653 along the second side 644 of the second attachment side 612. The bone fasteners 659 may be formed as spikes or barbs, although other forms and types of bone fasteners 659 may be used for securely engaging the vertebrae. In certain embodiments, as shown, the bone fasteners 659 may be shaped and configured in a manner similar to the bone fasteners 651 extending form the first wing 648. Various configurations of the bone fasteners 659 of the slider 653 may be used. In certain embodiments, as shown, the bone fasteners 659 may be configured to engage the laminae of the respective vertebrae. In other embodiments, one or more of the bone fasteners 659 may be configured to engage the spinous processes, the laminae, and/or other portions of the respective vertebra.

It will be appreciated that the connection between the slider 653 and the main body 654 may be configured to allow portions of the second attachment side 612 to move relative to one another. As described above, the slider 653 may be movably attached to the main body 654, and thus the slider 653 may move relative to the central portion 647, the first wing 648, and the spacer slot 650 of the main body 654. In particular, the slider 653 may move toward the central portion 647, the first wing 648, and the spacer slot 650 when the slider 653 moves toward the retracted position, and the slider 653 may move away from the central portion 647, the first wing 648, and the spacer slot 650 when the slider 653 moves toward the extended position. As a result, the slider 653 and the first wing 648 may be configured to move toward one another and away from one another in the direction of the longitudinal axis $A_L$ of the device 600. In effect, the movable attachment between the slider 653 and the main body 654 may cause the second attachment side 612 to function as a slide which may be extended or retracted in the direction of the longitudinal axis $A_L$ of the device 600. In certain embodiments, as shown, the slider 633 of the first attachment side 611 may be formed as a mirror image of the slider 653 of the second attachment side 612. In other embodiments, the shape or configuration of the slider 633 of the first attachment side 611 may be different than the shape or configuration of the slider 653 of the second attachment side 612. Various configurations of the sliders 633, 653 and the features thereof may be used to allow for a desired range of movement of the corresponding vertebrae.

In certain embodiments, the device 600 may include means for preventing or inhibiting the movement of the slider 633 relative to the main body 634 of the first attachment side 611 and for preventing or inhibiting the movement of the slider 653 relative to the main body 654 of the second attachment side 612. FIGS. 6L and 6M illustrate an embodiment in which the device 600 includes a pair of securing means for preventing or inhibiting such movement of the sliders 633, 653. As shown, the first attachment side 611 may include a slider securing means 661 (which also may be referred to as a "fastener" or a "lock") configured for selectively preventing on inhibiting movement of the slider 633 relative to the main body 634. In this manner, the securing means 661 may selectively fix the slider 633 relative to the main body 634. In certain embodiments, as shown, the securing means 661 may be a fastener, such as a set screw, although other types of fasteners and other types of securing means may be used. As shown, the securing means 661 may be inserted into and at least partially through a securing aperture 662 defined in the slider 633. The securing aperture 662 may extend from an external surface of the slider 633 to the central opening 635 thereof and be configured to receive the securing means 661 at least partially therein. In certain embodiments, securing aperture 662 may be threaded, and the securing means 661 may threadably engage the securing aperture 662. When desired, the securing means 661 may be advanced at least partially through the securing aperture 662 and into the central opening 635 to engage the second wing 629. In certain instances, the securing means 661 may engage the second wing 629 such that relative movement between the slider 633 and the main body 634 is inhibited but not entirely prevented. In this manner, the engagement between the securing means 661 and the second wing 629 may generate a frictional force that opposes but does not prevent relative movement between the slider 633 and the main body 634. As an example, when the securing means 661 is threaded, the securing means 661 may be initially tightened against the second wing 629 by applying a lesser amount of torque which inhibits but does not prevent the relative movement. In other instances, the securing means 661 may engage the second wing 629 such that relative movement between the slider 633 and the main body 634 is prevented. In this manner, the engagement between the securing means 661 and the second wing 629 may generate a frictional force that prevents relative movement between the slider 633 and the main body 634. As an example, when the securing means 661 is threaded, the securing means 661 may be further tightened against the second wing 629 by applying a greater amount of torque which prevents the relative movement. Ultimately, the securing means 661 may be used to vary the degree of resistance to the relative movement between the slider 633 and the main body 634, thereby controlling the relative movement between the treated vertebrae, and/or the securing means 661 may be used to prevent relative movement between the slider 633 and the main body 634, thereby preventing relative movement between the treated vertebrae.

In a similar manner, the second attachment side 612 may include a slider securing means 665 (which also may be referred to as a "fastener" or a "lock") configured for selectively preventing on inhibiting movement of the slider 653 relative to the main body 654. In this manner, the securing means 665 may selectively fix the slider 653 relative to the main body 654. In certain embodiments, as shown, the securing means 665 may be a fastener, such as a set screw, although other types of fasteners and other types of securing means may be used. As shown, the securing means 665 may be inserted into and at least partially through a securing aperture 666 defined in the slider 653. The securing aperture 666 may extend from an external surface of the slider 653 to the central opening 655 thereof and be configured to receive the securing means 665 at least partially therein. In certain embodiments, securing aperture 666 may be threaded, and the securing means 665 may threadably engage the securing aperture 666. When desired, the securing means 665 may be advanced at least partially through the securing aperture 666 and into the central opening 655 to engage the second wing 649. In certain instances, the securing means 665 may engage the second wing 649 such that relative movement between the slider 653 and the main body 654 is inhibited but not entirely prevented. In this manner, the engagement between the securing means 665 and the second wing 649 may generate a frictional force that opposes but does not prevent relative movement between the slider 653 and the main body 654. As an example, when the securing means 665 is threaded, the securing means 665 may be initially tightened against the second wing 649 by applying a lesser amount of torque which inhibits but does not prevent the relative movement. In other instances, the securing means 665 may engage the second wing 649 such that relative movement between the slider 653 and the main body 654 is prevented. In this manner, the engagement between the securing means 665 and the second wing 649 may generate a frictional force that prevents relative movement between the slider 653 and the main body 654. As an example, when the securing means 665 is threaded, the securing means 665 may be further tightened against the second wing 649 by applying a greater amount of torque which prevents the relative movement. Ultimately, the securing means 665 may be used to vary the degree of resistance to the relative movement between the slider 653 and the main body 654, thereby controlling the relative movement between the treated vertebrae, and/or the securing means 665 may be used to prevent relative movement between the slider 653 and the main body 654, thereby preventing relative movement between the treated vertebrae.

It will be appreciated that the securing means 661, 665 of the device 600 may be used to control the relative movement between the treated vertebrae, when desired. In particular, the securing means 661, 665 may be used to increase or decrease resistance to the relative movement between the treated vertebrae or to prevent such relative movement. In this manner, the device 600 may be used as a dynamic device or a rigid device, with the ability to convert the device 600 between a dynamic configuration and a rigid configuration, as may be desired in certain applications. The securing means 661, 665 may be used to selectively adjust the resistance to relative movement between the treated vertebrae, or to prevent such relative movement, prior to implantation of the device 600, during initial implantation of the device 600 as a part of an initial surgery, or during a follow-up surgery.

In certain embodiments, the device 600 may include means for varying resistance to the relative movement between the slider 633 and the main body 634 of the first attachment side 611 over at least a portion of the range of motion of the slider 633 and for varying resistance to the relative movement between the slider 653 and the main body 654 of the second attachment side 612 over at least a portion of the range of motion of the slider 653. In this manner, the device 600 may vary the resistance to the relative movement between the treated vertebrae over at least a portion of the range of motion of the vertebrae allowed by the device 600. FIGS. 6N and 6O illustrate an embodiment in which the device 600 includes a pair of resistance means for varying resistance to the movement of the sliders 633, 635, thereby varying resistance to the movement of the treated vertebrae. As shown, the first attachment side 611 may include a slider resistance means 671 (which also may be referred to as a "resistance member" or a "biasing member") configured for varying resistance to movement of the slider 633 relative to the main body 634 over at least a portion of the range of motion of the slider 633 (i.e., between the extended position and the retracted position of the slider 633). In certain embodiments, as shown, the slider resistance means 671 may be formed as a spring, such as a leaf spring, although other configurations may be used. For example, the slider resistance means 671 alternatively may be a member formed of a compressible material, which may function similar to a spring. In certain embodiments, as shown, the slider resistance means 671 may be positioned at least partially between the slider 633 and the central portion 627 and within the path of travel of the slider 633 between the extended position and the retracted position. In this manner, the slider resistance means 671 may engage slider 633 over at least a portion of the range of motion of the slider 633. In certain embodiments, as shown, the slider resistance means 671 may be attached to the central portion 627, although other attachment points may be used.

According to the illustrated embodiment, the slider 633 may be spaced apart from, and unaffected by, the slider resistance means 671 when the slider 633 is in the extended position and during a first portion of the range motion as the slider 633 moves from the extended position toward the retracted position. As the slider 633 continues to move toward the retracted position, the slider 633 may engage the slider resistance means 671, which may resist but not prevent further movement of the slider 633 toward the retracted position. In view of the configuration of the slider resistance means 671, which may be a spring or a compressible material member, the resistance provided by the slider resistance means 671 may increase as the slider 633 continues to move toward the retracted position. In this manner, the slider resistance means 671 may provide a biasing force opposing the movement of the slider 633 toward the retracted position and biasing the slider 633 back toward the extended position. It will be appreciated that illustrated configuration of the slider resistance means 671 is merely one example, and that various other configurations may be used.

In a similar manner, the second attachment side 612 may include a slider resistance means 672 (which also may be referred to as a "resistance member" or a "biasing member") configured for varying resistance to movement of the slider 653 relative to the main body 654 over at least a portion of the range of motion of the slider 653 (i.e., between the extended position and the retracted position of the slider 653). In certain embodiments, as shown, the slider resistance means 672 may be formed as a spring, such as a leaf spring, although other configurations may be used. For example, the slider resistance means 672 alternatively may be a member formed of a compressible material, which may function similar to a spring. In certain embodiments, as shown, the slider resistance means 672 may be positioned at least partially between the slider 653 and the central portion 647 and within the path of travel of the slider 653 between the extended position and the retracted position. In this manner, the slider resistance means 672 may engage slider 653 over at least a portion of the range of motion of the slider 653. In certain embodiments, as shown, the slider resistance means 672 may be attached to the central portion 647, although other attachment points may be used.

According to the illustrated embodiment, the slider 653 may be spaced apart from, and unaffected by, the slider resistance means 672 when the slider 653 is in the extended position and during a first portion of the range motion as the slider 653 moves from the extended position toward the retracted position. As the slider 653 continues to move toward the retracted position, the slider 653 may engage the slider resistance means 672, which may resist but not prevent further movement of the slider 653 toward the retracted position. In view of the configuration of the slider resistance means 672, which may be a spring or a compressible material member, the resistance provided by the slider resistance means 672 may increase as the slider 653 continues to move toward the retracted position. In this manner, the slider resistance means 672 may provide a biasing force opposing the movement of the slider 653 toward the retracted position and biasing the slider 653 back toward the extended position. It will be appreciated that illustrated configuration of the slider resistance means 672 is merely one example, and that various other configurations may be used.

It will be appreciated that the slider resistance means 671, 672 of the device 600 may be used to vary resistance to the relative movement between the treated vertebrae, when desired. In particular, the slider resistance means 671, 672 may be used to increase resistance to the relative movement between the treated vertebrae over at least a portion of the range of motion of the vertebrae allowed by the device 600. In this manner, the device 600 advantageously may function in a manner similar to a native disc, providing minimal resistance to initial relative movement in a direction in the sagittal plane and increasing resistance to further relative movement in the same direction. It will be appreciated that size, shape, configuration, and/or material of the slider resistance means 671, 672 may be selected to provide a desired degree of resistance to the relative motion of the treated vertebrae.

FIGS. 6P and 6Q illustrate another embodiment in which the device 600 includes means for varying resistance to the relative movement between the slider 633 and the main body 634 of the first attachment side 611 over at least a portion of the range of motion of the slider 633 and for varying resistance to the relative movement between the slider 653 and the main body 654 of the second attachment side 612 over at least a portion of the range of motion of the slider 653. In particular, the device 600 may include a plurality of resistance means for varying resistance to the movement of the sliders 633, 635, thereby varying resistance to the movement of the treated vertebrae. As shown, the first attachment side 611 may include a pair of slider resistance means 681 (which also may be referred to as a "resistance member" or a "biasing member") configured for varying resistance to movement of the slider 633 relative to the main body 634 over at least a portion of the range of motion of the slider 633 (i.e., between the extended position and the retracted position of the slider 633). In certain embodiments, as shown, the slider resistance means 681 may be positioned within the channel 638, with a first slider resistance means 681 positioned between the coupling member 637 and one of the closed ends of the channel 638 and a second slider resistance means 681 positioned between the coupling member 637 and the other closed end of the channel 638. In this manner, the first slider resistance means 681 may resist movement of the slider 633 toward the extended position, and the second slider resistance means 681 may resist movement of the slider 633 toward the retracted position. Accordingly, the slider resistance means 681 collectively may tend to bias the coupling member 637 and the slider 633 to a home position, as shown in FIG. 6P, between the extended position and the retracted position. In certain embodiments, as shown, both of the slider resistance means 681 may engage the coupling member 637 when the slider 633 is at the home position. In certain embodiments, as shown, at least one of the slider resistance means 681 may engage the coupling member 637 at a given position along the range of motion between the extended position and the retracted position. In other words, at any position along the range of motion of the slider 633, the first slider resistance means 681, the second slider resistance means 681, or both of the slider resistance means 681 may engage the coupling member 637. In certain embodiments, as shown, each slider resistance means 681 may be formed as a spring, such as a leaf spring, a spring finger, or a compression spring, although other configurations may be used. In view of the configuration of the slider resistance means 681, the resistance provided by the first slider resistance means 681 may increase as the slider 633 moves toward the extended position, and the resistance provided by the second slider resistance means 681 may decrease as the slider 633 moves toward the extended position. Similarly, the resistance provided by the first slider resistance means 681 may decrease as the slider 633 moves toward the retracted position, and the resistance provided by the second slider resistance means 681 may increase as the slider 633 moves toward the retracted position. In this manner, the slider resistance means 681 collectively may provide biasing forces opposing the movement of the slider 633 toward the retracted position or the extended position and biasing the slider 633 back toward the home position. It will be appreciated that illustrated configuration of the slider resistance means 681 is merely one example, and that various other configurations may be used.

In a similar manner, the second attachment side 612 may include a pair of slider resistance means 682 (which also may be referred to as a "resistance member" or a "biasing member") configured for varying resistance to movement of the slider 653 relative to the main body 654 over at least a portion of the range of motion of the slider 653 (i.e., between the extended position and the retracted position of the slider 653). In certain embodiments, as shown, the slider resistance means 682 may be positioned within the channel 658, with a first slider resistance means 682 positioned between the coupling member 657 and one of the closed ends of the channel 658 and a second slider resistance means 682 positioned between the coupling member 657 and the other closed end of the channel 658. In this manner, the first slider resistance means 682 may resist movement of the slider 653 toward the extended position, and the second slider resistance means 682 may resist movement of the slider 653 toward the retracted position. Accordingly, the slider resistance means 682 collectively may tend to bias the coupling member 657 and the slider 653 to a home position, as shown in FIG. 6P, between the extended position and the retracted position. In certain embodiments, as shown, both of the slider resistance means 682 may engage the coupling member 657 when the slider 653 is at the home position. In certain embodiments, as shown, at least one of the slider resistance means 682 may engage the coupling member 657 at a given position along the range of motion between the extended position and the retracted position. In other words, at any position along the range of motion of the slider 653, the first slider resistance means 682, the second slider resistance means 682, or both of the slider resistance means 682 may engage the coupling member 657. In certain embodiments, as shown, each slider resistance means 682 may be formed as a spring, such as a leaf spring, a spring finger, or a compression spring, although other configurations may be used. In view of the configuration of the slider resistance means 682, the resistance provided by the first slider resistance means 682 may increase as the slider 653 moves toward the extended position, and the resistance provided by the second slider resistance means 682 may decrease as the slider 653 moves toward the extended position. Similarly, the resistance provided by the first slider resistance means 682 may decrease as the slider 653 moves toward the retracted position, and the resistance provided by the second slider resistance means 682 may increase as the slider 653 moves toward the retracted position. In this manner, the slider resistance means 682 collectively may provide biasing forces opposing the movement of the slider 653 toward the retracted position or the extended position and biasing the slider 653 back toward the home position. It will be appreciated that illustrated configuration of the slider resistance means 682 is merely one example, and that various other configurations may be used.

It will be appreciated that the slider resistance means 681, 682 of the device 600 may be used to vary resistance to the relative movement between the treated vertebrae, when desired. In particular, the slider resistance means 681, 682 may be used to increase resistance to the relative movement between the treated vertebrae over at least a portion of the range of motion of the vertebrae allowed by the device 600. In this manner, the device 600 advantageously may function in a manner similar to a native disc, providing minimal resistance to initial relative movement in a direction in the sagittal plane and increasing resistance to further relative movement in the same direction. It will be appreciated that size, shape, configuration, and/or material of the slider resistance means 681, 682 may be selected to provide a desired degree of resistance to the relative motion of the treated vertebrae.

FIGS. 6R and 6S illustrate another embodiment in which the device 600 includes means for varying resistance to the relative movement between the slider 633 and the main body 634 of the first attachment side 611 over at least a portion of the range of motion of the slider 633 and for varying resistance to the relative movement between the slider 653 and the main body 654 of the second attachment side 612 over at least a portion of the range of motion of the slider 653. In particular, the device 600 may include a plurality of resistance means for varying resistance to the movement of the sliders 633, 635, thereby varying resistance to the movement of the treated vertebrae. As shown, the first attachment side 611 may include a pair of slider resistance means 691 (which also may be referred to as a "resistance insert," a "resistance member," or a "biasing member") configured for varying resistance to movement of the slider 633 relative to the main body 634 over at least a portion of the range of motion of the slider 633 (i.e., between the extended position and the retracted position of the slider 633). In certain embodiments, as shown, the slider resistance means 691 may be positioned within the channel 638, with a first slider resistance means 691 positioned between the coupling member 637 and one of the closed ends of the channel 638 and a second slider resistance means 691 positioned between the coupling member 637 and the other closed end of the channel 638. In this manner, the first slider resistance means 691 may resist movement of the slider 633 toward the extended position, and the second slider resistance means 691 may resist movement of the slider 633 toward the retracted position. Accordingly, the slider resistance means 691 collectively may tend to bias the coupling member 637 and the slider 633 to a home position, as shown in FIG. 6R, between the extended position and the retracted position. In certain embodiments, as shown, both of the slider resistance means 691 may engage the coupling member 637 when the slider 633 is at the home position. In certain embodiments, as shown, at least one of the slider resistance means 691 may engage the coupling member 637 at a given position along the range of motion between the extended position and the retracted position. In other words, at any position along the range of motion of the slider 633, the first slider resistance means 691, the second slider resistance means 691, or both of the slider resistance means 691 may engage the coupling member 637. In certain embodiments, as shown, each slider resistance means 691 may be formed of a compressible material or a resiliently deformable material, such as a biocompatible polymer or other suitable material, which may be compressed by the movement of the coupling member 637 within the channel 638 but may have a natural tendency to return to a natural state when compression forces are removed. It will be appreciated that a durometer of the compressible material or resiliently deformable material may be selected to provide a desired resistance to the movement of the coupling member 637 within the channel 638. In certain embodiments, as shown, each resistance means 691 may fill or substantially fill the respective portion of the channel 638 between the coupling member 637 and the respective closed end of the channel 638. In other embodiments, each resistance means 691 may partially fill the respective portion of the channel 638 between the coupling member 637 and the respective closed end of the channel 638. In view of the configuration of the slider resistance means 691, the resistance provided by the first slider resistance means 691 may increase as the slider 633 moves toward the extended position, and the resistance provided by the second slider resistance means 691 may decrease as the slider 633 moves toward the extended position. Similarly, the resistance provided by the first slider resistance means 691 may decrease as the slider 633 moves toward the retracted position, and the resistance provided by the second slider resistance means 691 may increase as the slider 633 moves toward the retracted position. In this manner, the slider resistance means 691 collectively may provide biasing forces opposing the movement of the slider 633 toward the retracted position or the extended position and biasing the slider 633 back toward the home position. It will be appreciated that illustrated configuration of the slider resistance means 691 is merely one example, and that various other configurations may be used.

In a similar manner, the second attachment side 612 may include a pair of slider resistance means 692 (which also may be referred to as a "resistance insert," a "resistance member," or a "biasing member") configured for varying resistance to movement of the slider 653 relative to the main body 654 over at least a portion of the range of motion of the slider 653 (i.e., between the extended position and the retracted position of the slider 653). In certain embodiments, as shown, the slider resistance means 692 may be positioned within the channel 658, with a first slider resistance means 692 positioned between the coupling member 657 and one of the closed ends of the channel 658 and a second slider resistance means 692 positioned between the coupling member 657 and the other closed end of the channel 658. In this manner, the first slider resistance means 692 may resist movement of the slider 653 toward the extended position, and the second slider resistance means 692 may resist movement of the slider 653 toward the retracted position. Accordingly, the slider resistance means 692 collectively may tend to bias the coupling member 657 and the slider 653 to a home position, as shown in FIG. 6S, between the extended position and the retracted position. In certain embodiments, as shown, both of the slider resistance means 692 may engage the coupling member 657 when the slider 653 is at the home position. In certain embodiments, as shown, at least one of the slider resistance means 692 may engage the coupling member 657 at a given position along the range of motion between the extended position and the retracted position. In other words, at any position along the range of motion of the slider 653, the first slider resistance means 692, the second slider resistance means 692, or both of the slider resistance means 692 may engage the coupling member 657. In certain embodiments, as shown, each slider resistance means 692 may be formed of a compressible material or a resiliently deformable material, such as a biocompatible polymer or other suitable material, which may be compressed by the movement of the coupling member 657 within the channel 658 but may have a natural tendency to return to a natural state when compression forces are removed. It will be appreciated that a durometer of the compressible material or resiliently deformable material may be selected to provide a desired resistance to the movement of the coupling member 657 within the channel 658. In certain embodiments, as shown, each resistance means 692 may fill or substantially fill the respective portion of the channel 658 between the coupling member 657 and the respective closed end of the channel 658. In other embodiments, each resistance means 692 may partially fill the respective portion of the channel 658 between the coupling member 657 and the respective closed end of the channel 658. In view of the configuration of the slider resistance means 692, the resistance provided by the first slider resistance means 692 may increase as the slider 653 moves toward the extended position, and the resistance provided by the second slider resistance means 692 may decrease as the slider 653 moves toward the extended position. Similarly, the resistance provided by the first slider resistance means 692 may decrease as the slider 653 moves toward the retracted position, and the resistance provided by the second slider resistance means 692 may increase as the slider 653 moves toward the retracted position. In this manner, the slider resistance means 692 collectively may provide biasing forces opposing the movement of the slider 653 toward the retracted position or the extended position and biasing the slider 653 back toward the home position. It will be appreciated that illustrated configuration of the slider resistance means 692 is merely one example, and that various other configurations may be used.

It will be appreciated that the slider resistance means 691, 692 of the device 600 may be used to vary resistance to the relative movement between the treated vertebrae, when desired. In particular, the slider resistance means 691, 692 may be used to increase resistance to the relative movement between the treated vertebrae over at least a portion of the range of motion of the vertebrae allowed by the device 600. In this manner, the device 600 advantageously may function in a manner similar to a native disc, providing minimal resistance to initial relative movement in a direction in the sagittal plane and increasing resistance to further relative movement in the same direction. It will be appreciated that size, shape, configuration, and/or material of the slider resistance means 691, 692 may be selected to provide a desired degree of resistance to the relative motion of the treated vertebrae.

FIGS. 6T and 6U illustrate an embodiment in which the device 600 does not include the bone fasteners 631, 651 described above. In particular, the first wing 628 of the first attachment side 611 may be devoid of any bone fasteners 631, and the first wing 648 of the second attachment side 612 may be devoid of any bone fasteners 651. In this manner, the interior side of the first wing 628 may have a smooth or substantially smooth surface for engaging the respective vertebra, and the only bone fasteners of the first attachment side 611 for securely engaging the treated vertebrae may be the bone fasteners 639 of the slider 633. Such configuration of the first attachment side 611 may facilitate relative movement of the treated vertebrae, while minimizing certain stresses induced in the first attachment side 611. In a similar manner, the interior side of the first wing 648 may have a smooth or substantially smooth surface for engaging the respective vertebra, and the only bone fasteners of the second attachment side 612 for securely engaging the treated vertebrae may be the bone fasteners 659 of the slider 653. Such configuration of the second attachment side 612 may facilitate relative movement of the treated vertebrae, while minimizing certain stresses induced in the second attachment side 612. Such configuration of the second attachment side 612 may facilitate relative movement of the treated vertebrae, while minimizing certain stresses induced in the second attachment side 612.

FIGS. 6V and 6W illustrate an example implantation of the device 600 with respect to a first vertebra $V_1$ and an adjacent second vertebra $V_2$. As shown, the first attachment side 611 and the second attachment side 612 may be positioned relative to the vertebrae $V_1$, $V_2$ such that the spacer 630 is positioned between a first spinous process $SP_1$ of the first vertebra $V_1$ and a second spinous process $SP_2$ of the second vertebra $V_2$. In this manner, the spacer 630 may limit a minimum spacing between the spinous processes $SP_1$, $SP_2$. Additionally, the first attachment side 611 and the second attachment side 612 may be positioned relative to the vertebrae $V_1$, $V_2$ such that the first wing 628 and the slider 633 of the first attachment side 611 and the first wing 648 and the slider 653 of the second attachment side 612 engage a first lamina $L_1$ of the first vertebra $V_1$ and a second lamina $L_2$ of the second vertebra $V_2$. In this manner, the respective bone fasteners 631, 639 of the first attachment side 611 and the respective bone fasteners 651, 659 of the second attachment side 612 may penetrate and securely engage the laminae $L_1$, $L_2$. Accordingly, the implanted device 600 may stabilize the vertebrae $V_1$, $V_2$, although the device 600 may allow relative movement of the vertebrae $V_1$, $V_2$. In particular, the sliders 633, 653 of the device 600 may allow relative movement of the vertebrae $V_1$, $V_2$ in sagittal plane of the patient, thereby allowing flexion and extension of the treated segment of the spine. It will be appreciated that the configuration of the sliders 633, 653, the coupling members 637, 657, the channels 638, 658, and any resistance means of the device 600 may be varied to allow a desired range of motion in the sagittal plane. Further, the material from which the various components and features of the first attachment side 611 and the second attachment side 612 are formed may be selected to achieve the desired range of motion. In certain embodiments, portions of the first attachment side 611 and the second attachment side 612 may be formed of titanium, although other suitable metals, polymers, or other materials may be used in other embodiments. Meanwhile, the device 600 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 600 and the disc D. In other embodiments in which the native disc D is removed, an interbody device, such as a cage or a spacer, may be implanted within the disc space DS (i.e., the intervertebral space) and the loads carried by the treated spinal segment may be shared by the device 600 and the interbody device. As described above, the device 600 may be used in conjunction with other additional hardware, such that the device 600 and the additional hardware collectively stabilize the treated segment of the spine and share loads carried thereby. It will be appreciated that the foregoing description and the corresponding drawings are merely examples of the device 600 and that other configurations and modifications may be made.

Figure 7A:
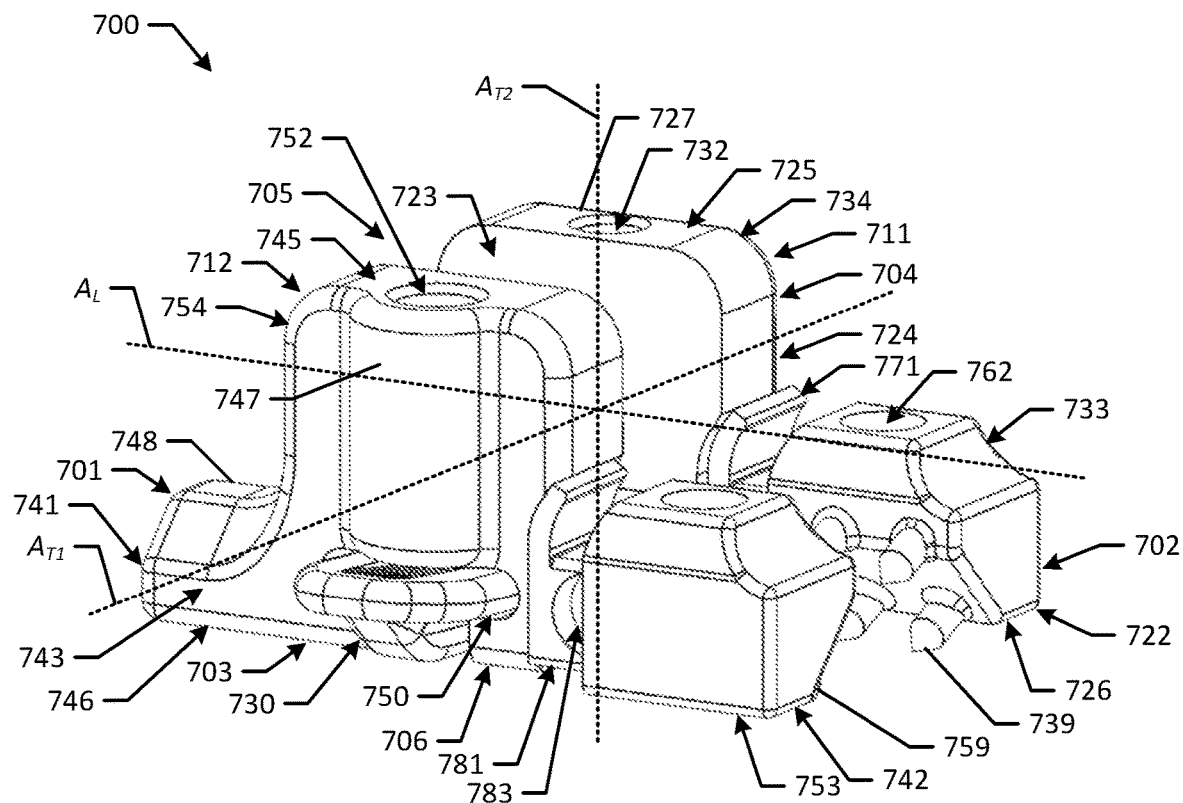
FIG. 7A is a perspective view of a dynamic interspinous process device in accordance with one or more embodiments of the present disclosure, showing a first attachment side and a second attachment side of the dynamic interspinous process device in an assembled state.
Figure 7B:
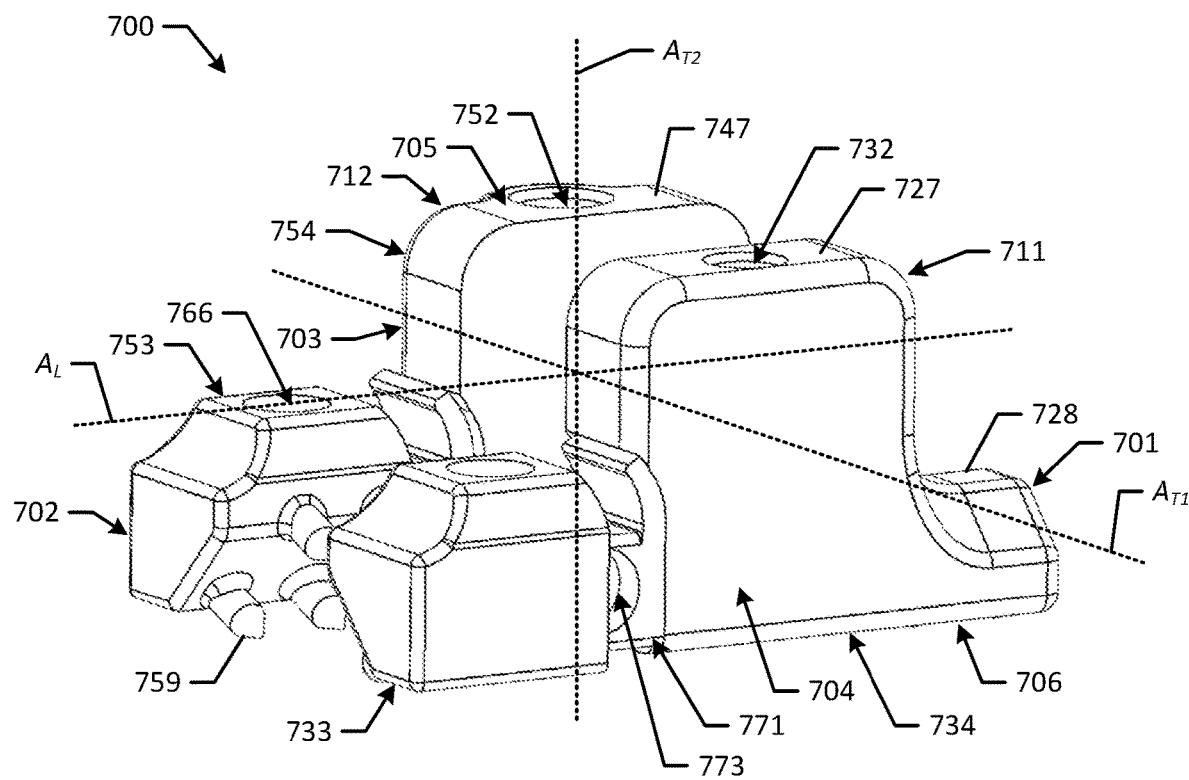
FIG. 7B is a perspective view of the dynamic interspinous process device of FIG. 7A, showing the first attachment side and the second attachment side in the assembled state.
Figure 7C:
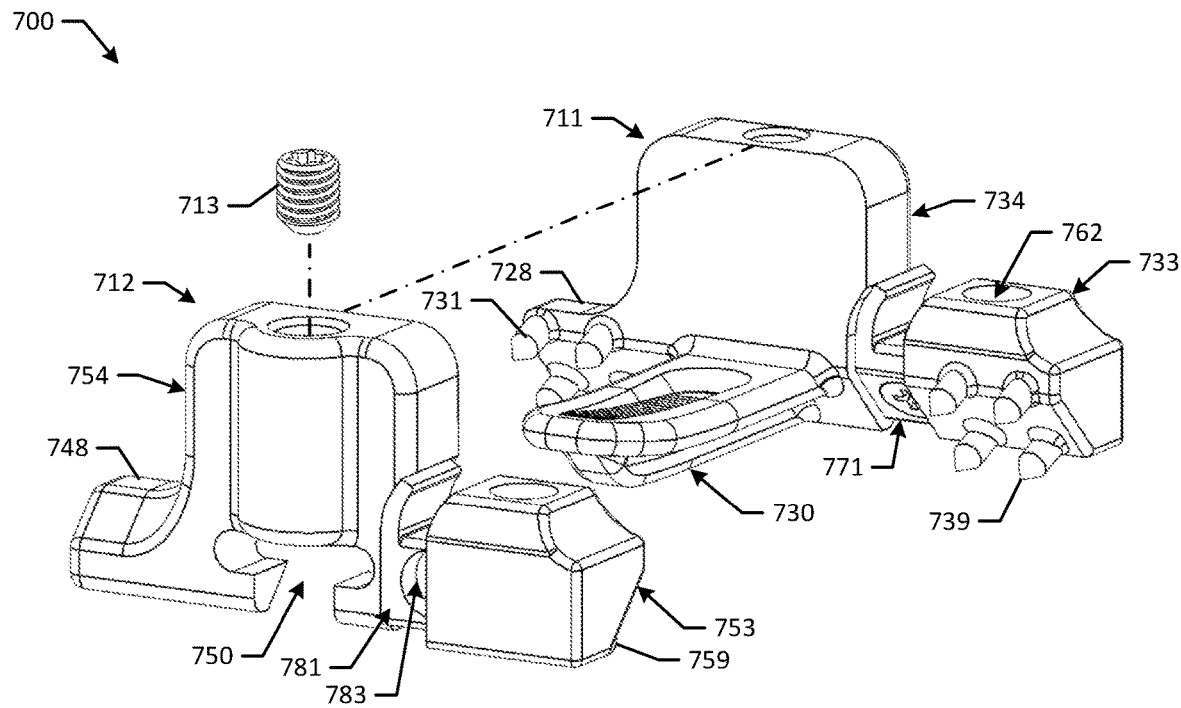
FIG. 7C is a perspective view of the dynamic interspinous process device of FIG. 7A, showing the first attachment side, the second attachment side, and a securing means of the dynamic interspinous process device in a disassembled state.
Figure 7D:
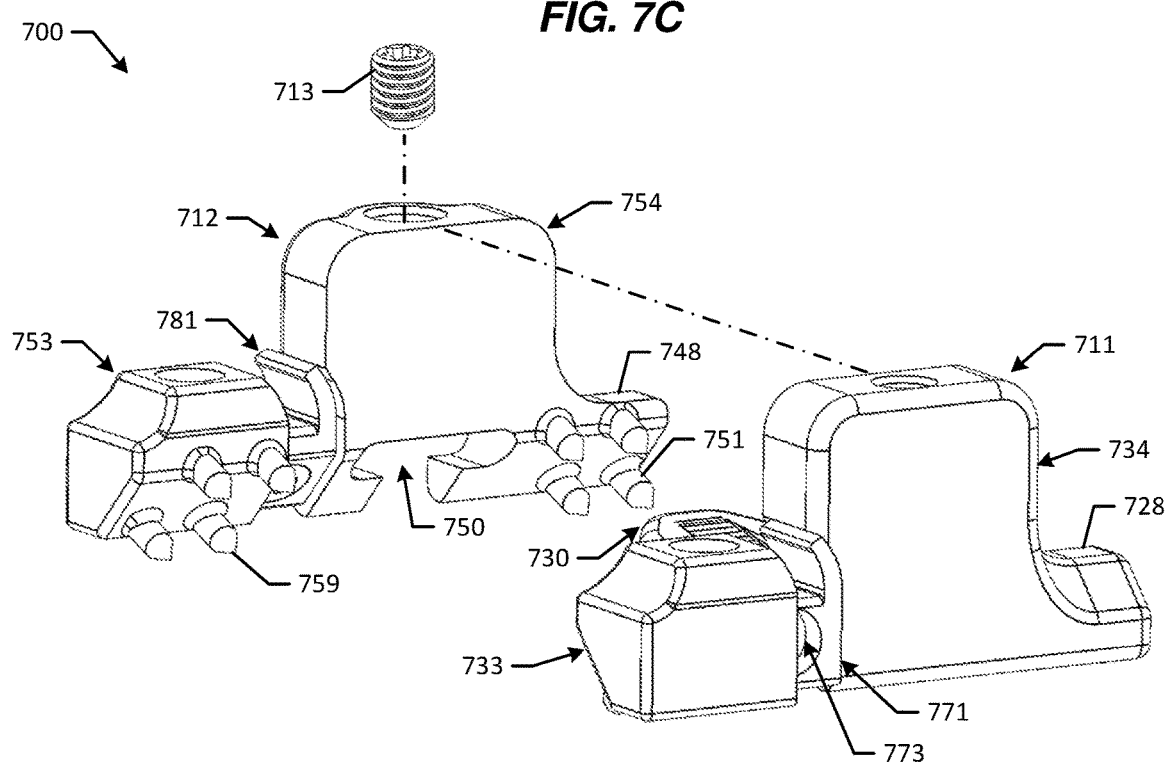
FIG. 7D is a perspective view of the dynamic interspinous process device of FIG. 7A, showing the first attachment side, the second attachment side, and the securing means in the disassembled state.
Figure 7E:
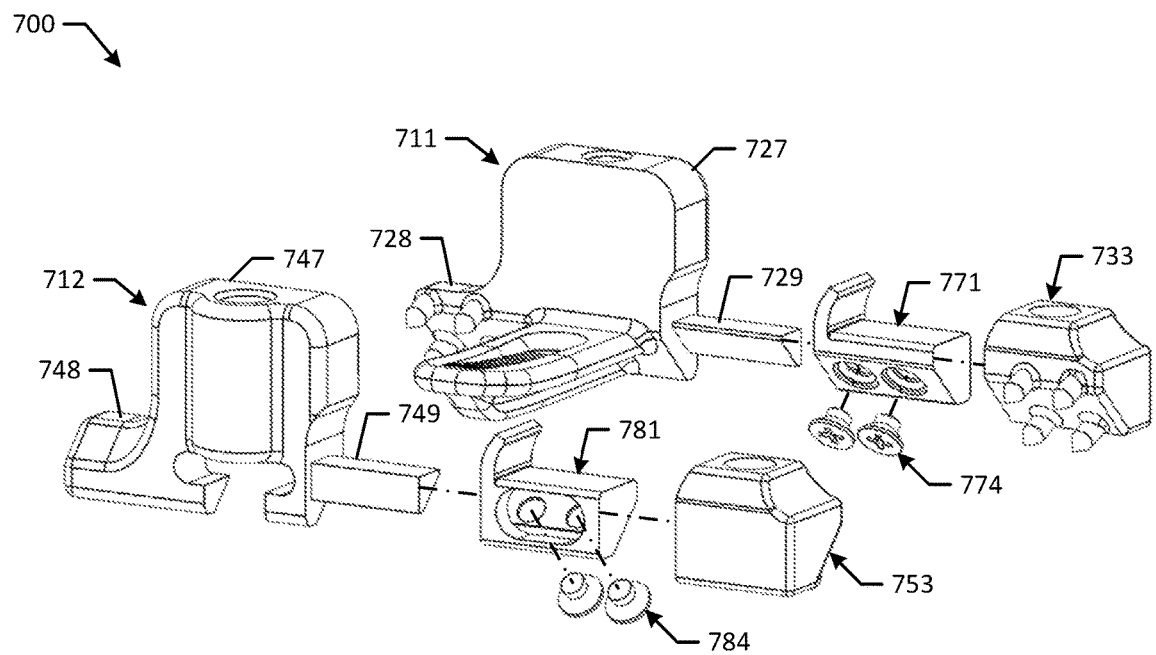
FIG. 7E is a perspective view of the dynamic interspinous process device of FIG. 7A, showing respective sliders and sheaths of the first attachment side and the second attachment side in a disassembled state.
Figure 7F:
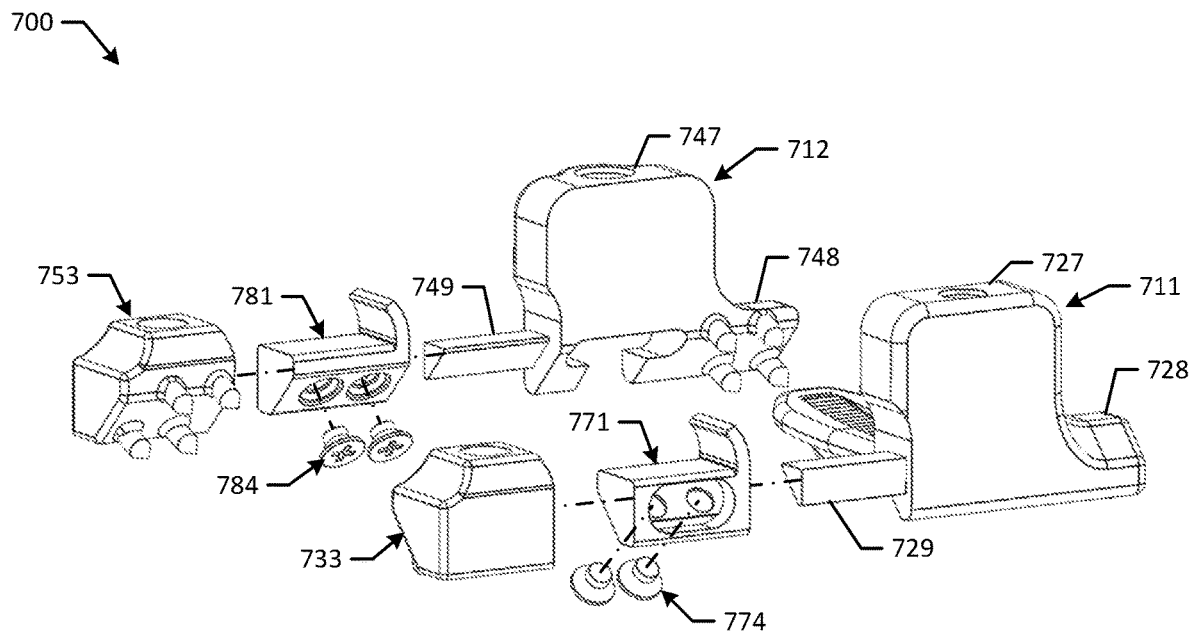
FIG. 7F is a perspective view of the dynamic interspinous process device of FIG. 7A, showing the sliders and the sheaths of the first attachment side and the second attachment side in the disassembled state.
Figure 7G:
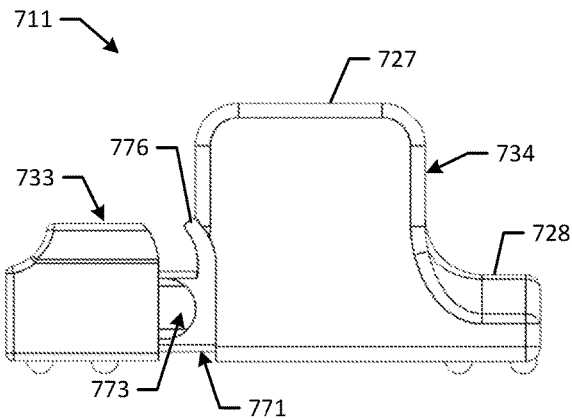
FIG. 7G is a plan view of the first attachment side of the dynamic interspinous process device of FIG. 7A, showing the slider of the first attachment side in an extended position relative to a main body of the first attachment side.
Figure 7H:
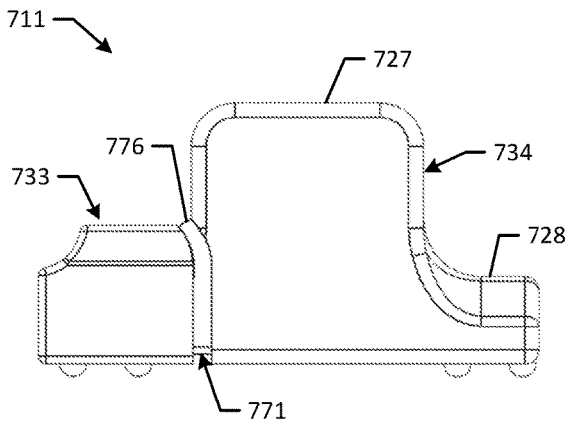
FIG. 7H is a plan view of the first attachment side of the dynamic interspinous process device of FIG. 7A, showing the slider of the first attachment side in a retracted position relative to the main body of the first attachment side.
Figure 7I:
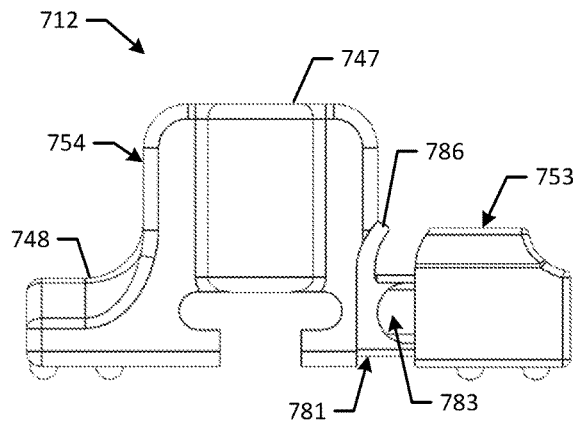
FIG. 7I is a plan view of the second attachment side of the dynamic interspinous process device of FIG. 7A, showing the slider of the second attachment side in an extended position relative to a main body of the second attachment side.
Figure 7J:
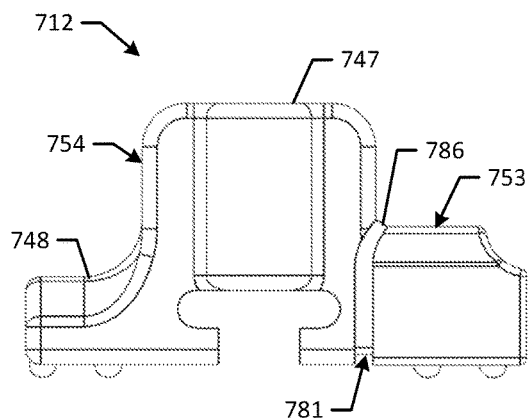
FIG. 7J is a plan view of the second attachment side of the dynamic interspinous process device of FIG. 7A, showing the slider of the second attachment side in a retracted position relative to the main body of the second attachment side.
Figure 7K:
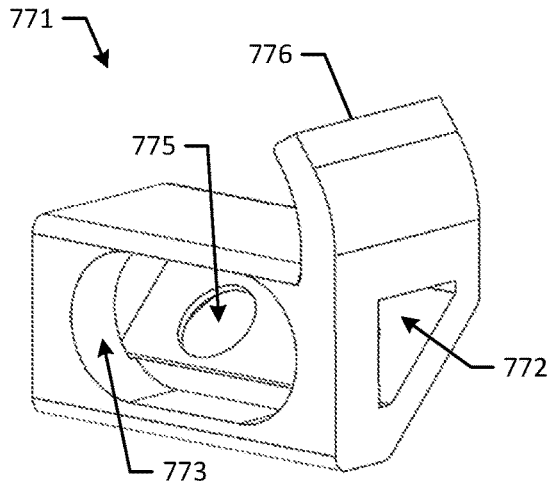
FIG. 7K is a perspective view of the sheath of the first attachment side of the dynamic interspinous process device of FIG. 7A.
Figure 7L:
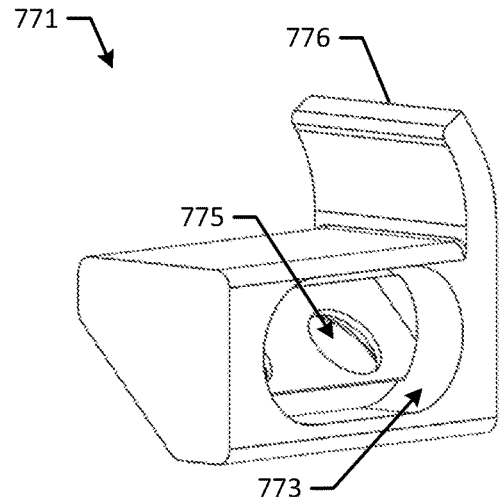
FIG. 7L is a perspective view of the sheath of the first attachment side of the dynamic interspinous process device of FIG. 7A.
Figure 7M:
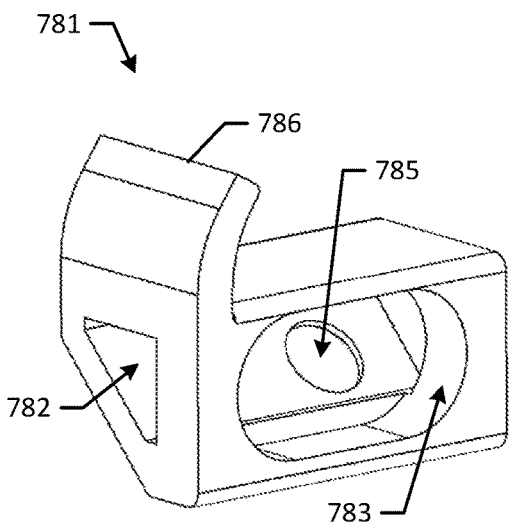
FIG. 7M is a perspective view of the sheath of the second attachment side of the dynamic interspinous process device of FIG. 7A.
Figure 7N:
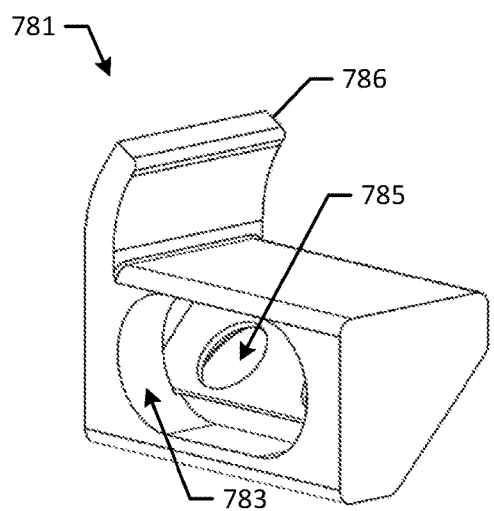
FIG. 7N is a perspective view of the sheath of the second attachment side of the dynamic interspinous process device of FIG. 7A.
Figure 7O:
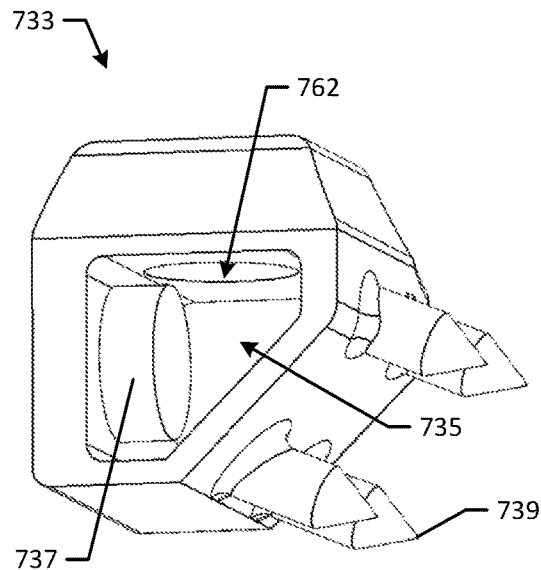
FIG. 7O is a perspective view of the slider of the first attachment side of the dynamic interspinous process device of FIG. 7A.
Figure 7P:
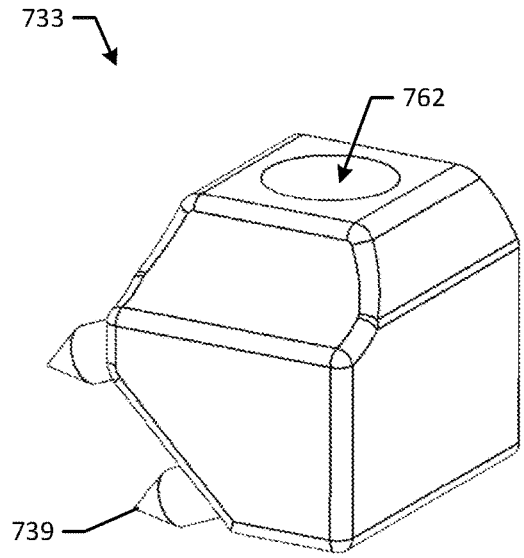
FIG. 7P is a perspective view of the slider of the first attachment side of the dynamic interspinous process device of FIG. 7A.
Figure 7Q:
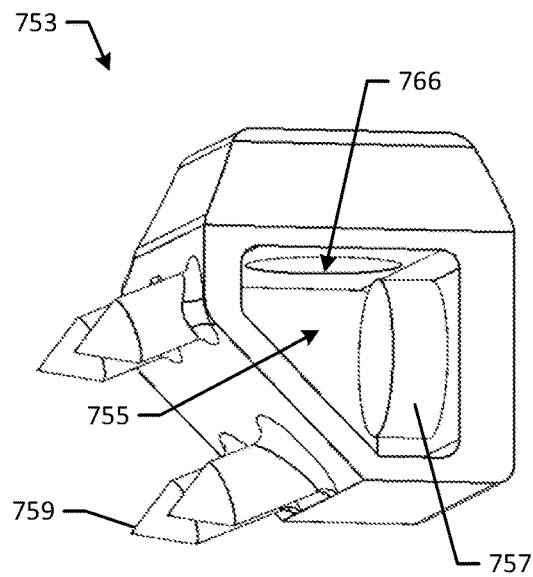
FIG. 7Q is a perspective view of the slider of the second attachment side of the dynamic interspinous process device of FIG. 7A.
Figure 7R:
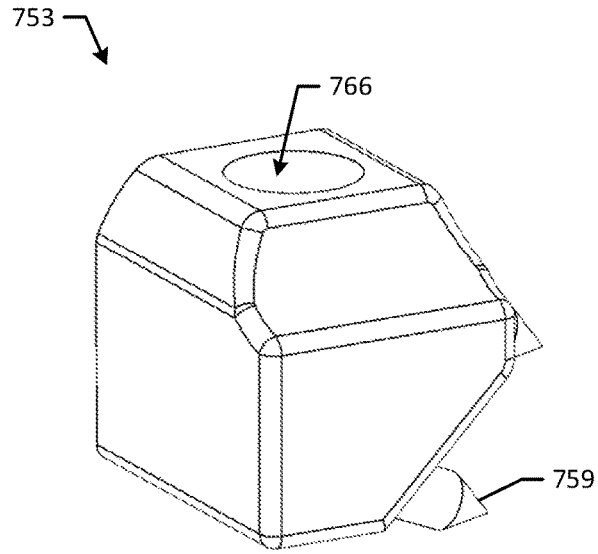
FIG. 7R is a perspective view of the slider of the second attachment side of the dynamic interspinous process device of FIG. 7A.
Figure 7S:
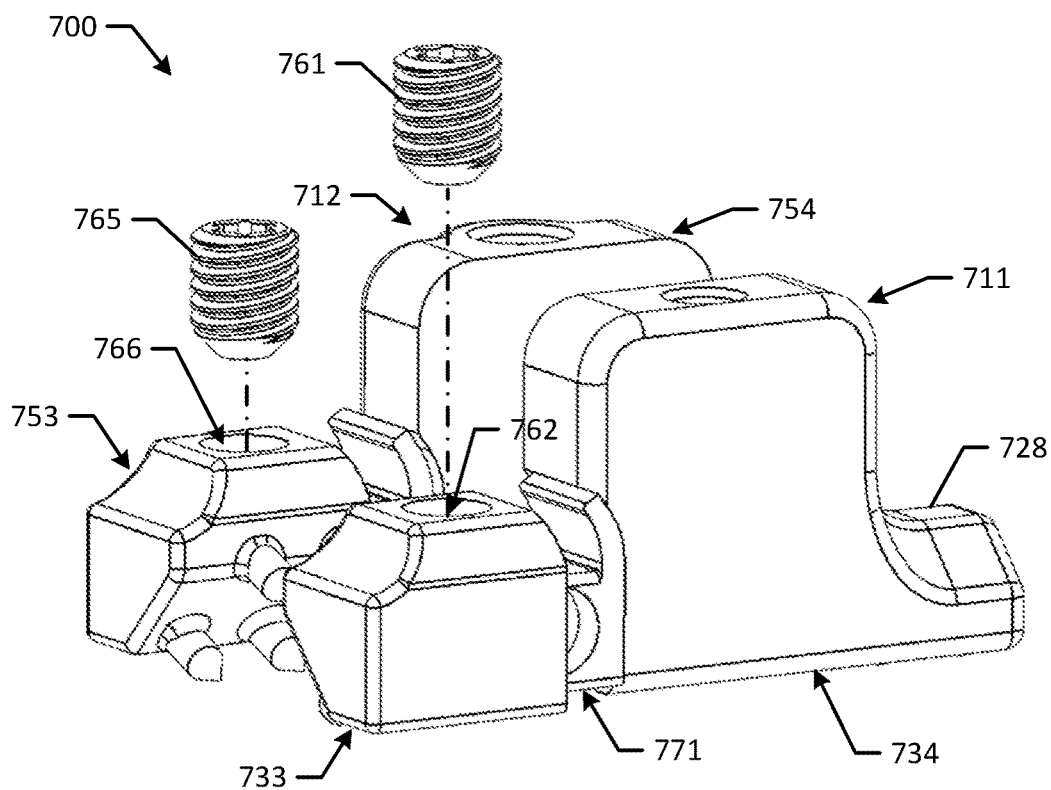
FIG. 7S is a perspective view of the dynamic interspinous process device of FIG. 7A, showing the first attachment side and the second attachment side in an assembled state and a pair of slider securing means in a disassembled state.
Figure 7T:
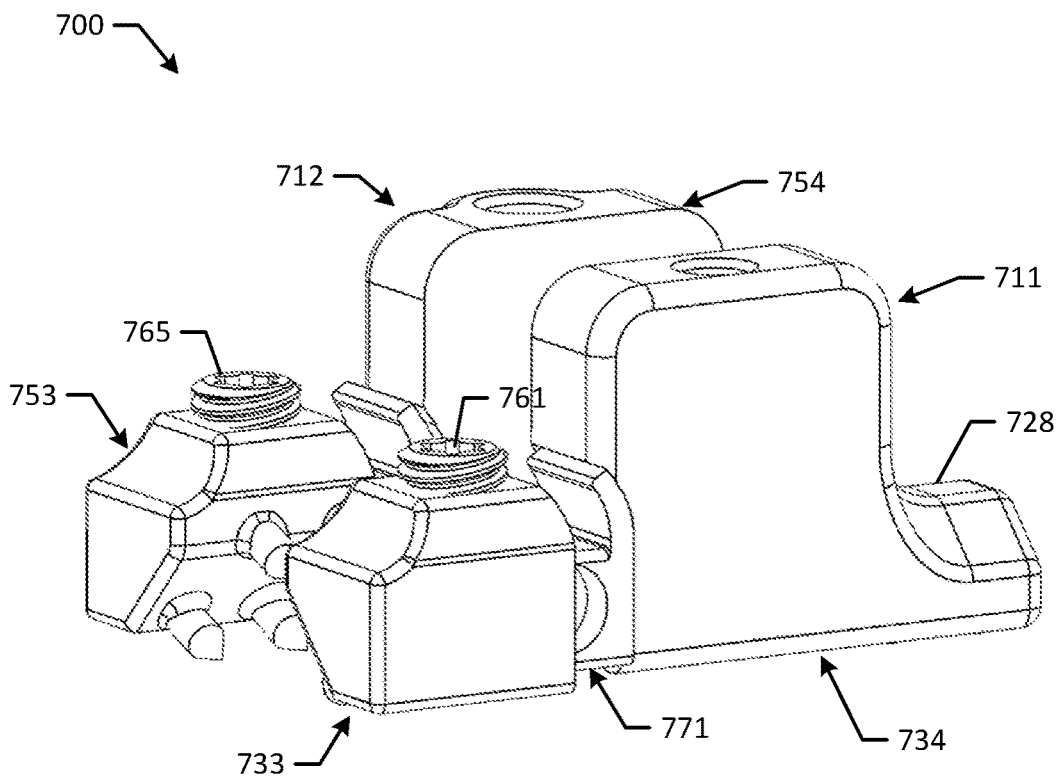
FIG. 7T is a perspective view of the dynamic interspinous process device of FIG. 7A, showing the first attachment side and the second attachment side in the assembled state and the pair of slider securing means in an assembled state.
Figure 7U:
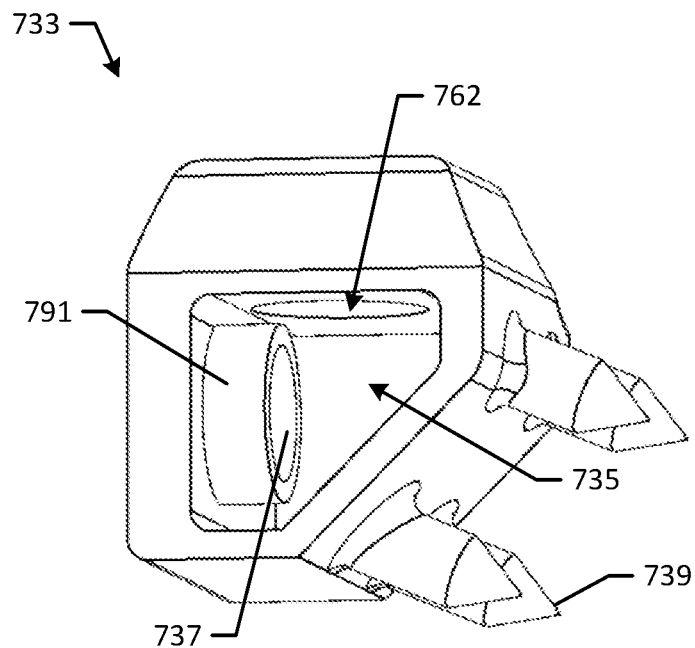
FIG. 7U is a perspective view of the slider of the first attachment side of the dynamic interspinous process device of FIG. 7A in accordance with one or more embodiments of the present disclosure, showing a resistance means attached to a coupling member of the slider.
Figure 7V:
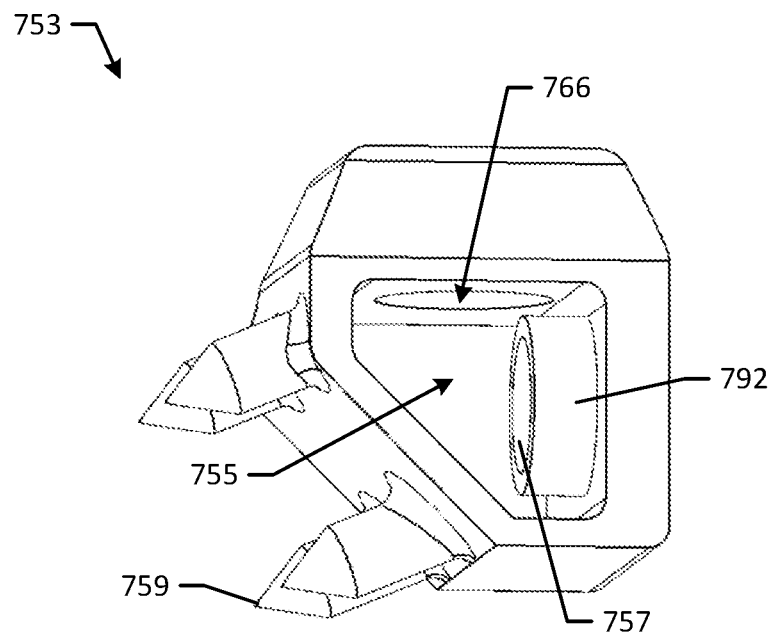
FIG. 7V is a perspective view of the slider of the second attachment side of the dynamic interspinous process device of FIG. 7A in accordance with one or more embodiments of the present disclosure, showing a resistance means attached to a coupling member of the slider.
Figure 7W:
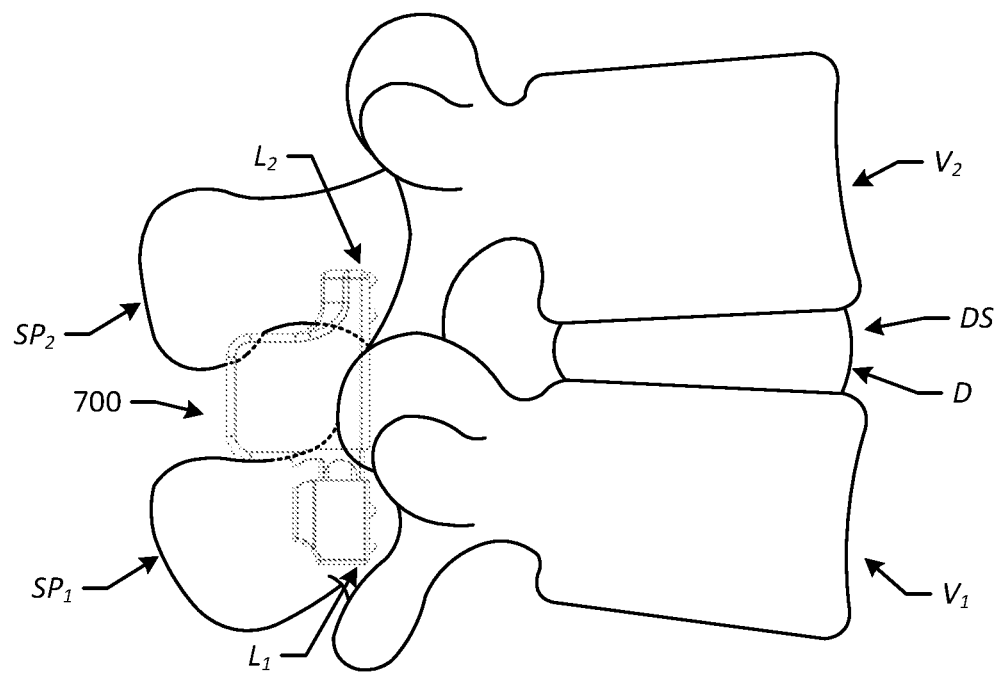
FIG. 7W is a side view of the dynamic interspinous process device of FIG. 7A implanted with respect to a first vertebra and a second vertebra in accordance with one or more embodiments of the present disclosure.
Figure 7X:
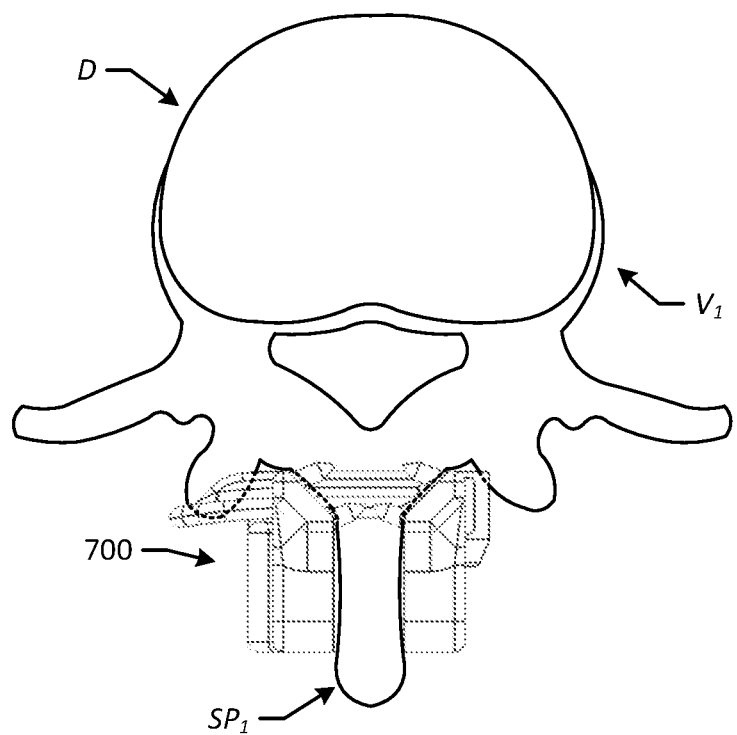
FIG. 7X is a top view of the dynamic interspinous process device of FIG. 7A implanted with respect to the first vertebra, the second vertebra being removed from view for purposes of illustration.

FIGS. 7A-7X illustrate an interspinous process device 700 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 700 may be configured for implantation relative to a first vertebra and an adjacent second vertebra, as described below, specifically with reference to FIGS. 7W and 7X. In particular, a portion of the interspinous process device 700 may be positioned between the spinous process of the first vertebra and the spinous process of the second vertebra, while one or more other portions of the interspinous process device 700 engage the spinous processes, the laminae, and/or other portions of the respective vertebra. As described below, the interspinous process device 700 may allow a desired range of relative movement between the treated vertebrae, which may be desirable in certain treatment applications. Additionally, the interspinous process device 700 may be converted between a dynamic configuration, in which the device 700 allows relative movement between the treated vertebrae, and a rigid configuration, in which the device 700 prevents or substantially inhibits such relative movement. In this manner, the interspinous process device 700 may be adjusted to allow relative motion, when desired, and to inhibit relative motion, when desired, without having to remove or replace the device 700. The interspinous process device 700 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 700, itself or in combination with additional hardware, may provide the structural support necessary to restore and maintain normal spacing and alignment of the treated vertebrae while avoiding certain drawbacks presented by existing interspinous process devices.

The interspinous process device 700 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 700 may include a first end 701 and a second end 702 disposed opposite the first end 701 in the direction of the longitudinal axis $A_L$. As described below, the device 700 may be implanted with the longitudinal axis $A_L$ extending in a direction substantially parallel to the sagittal plane and the coronal plane of the patient and transverse to the transverse plane of the patient. In this manner, depending on the orientation of the device 700 upon implantation thereof, one of the first end 701 and the second end 702 of the device 700 may be referred to as the "superior end" of the device 700, and the other of the first end 701 and the second end 702 of the device 700 may be referred to as the "inferior end" of the device 700. The device 700 also may include a first side 703 extending from the first end 701 to the second end 702, and a second side 704 disposed opposite the first side 703 in the direction of the first transverse axis $A_{T1}$ and extending from the first end 701 to the second end 702. The device 700 may be implanted with the first transverse axis $A_{T1}$ extending in a direction substantially parallel to the coronal plane and the transverse plane of the patient and transverse to the sagittal plane of the patient. In this manner, depending on the orientation of the device 700 upon implantation thereof, one of the first side 703 and the second side 704 of the device 700 may be referred to as the "right side" of the device 700, and the other of the first side 703 and the second side 704 of the device 700 may be referred to as the "left side" of the device 700. The device 700 further may include a third side 705 extending from the first end 701 to the second end 702 and from the first side 703 to the second side 704, and a fourth side 706 disposed opposite the third side 705 in the direction of the second transverse axis $A_{T2}$ and extending from the first end 701 to the second end 702 and from the first side 703 to the second side 704. The device 700 may be implanted with the second transverse axis $A_{T2}$ extending in a direction substantially parallel to the sagittal plane and the transverse plane of the patient and transverse to the coronal plane of the patient. As described below, the device 700 may be oriented upon implantation thereof such that the third side 705 faces posteriorly and the fourth side 706 faces anteriorly with respect to the patient. In this manner, the third side 705 may be referred to as the "posterior side" of the device 700, and the fourth side 706 may be referred to as the "anterior side" of the device 700. The device 700 may have an overall "length" extending from the first end 701 to the second end 702 in the direction of the longitudinal axis $A_L$, an overall "width" extending from the first side 703 to the second side 704 in the direction of the first transverse axis $A_{T1}$, and an overall "height" extending from the third side 705 to the fourth side 706 in the direction of the second transverse axis $A_{T2}$. Further, various components and features of the device 700 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 700 may include a first attachment side 711 (which also may be referred to as a "first attachment portion," a "first attachment assembly," or a "first plate") and a second attachment side 712 (which also may be referred to as a "second attachment portion," a "second attachment assembly," or a "second plate") configured for removably attaching to one another via a securing means 713. During use of the device 700, one of the first attachment side 711 and the second attachment side 712 may be disposed, at least partially, along the right side of the patient's spine, and the other of the first attachment side 711 and the second attachment side 712 may be disposed, at least partially, along the right side of the patient's spine. It will be appreciated that the first attachment side 711 and the second attachment side 712 may include corresponding features that are mirror images of one another, although certain differences between the first attachment side 711 and the second attachment side 712 may exist, as described below. In certain embodiments, the first attachment side 711 and the second attachment side 712 may be formed of a metal, such as titanium or stainless steel, although other suitable materials, such as polyether ether ketone (PEEK), other polymers, or composites, may be used.

The first attachment side 711 may have a first end 721, a second end 722 disposed opposite the first end 721, a first side 723 (which also may be referred to as an "interior side"), a second side 724 (which also may be referred to as an "exterior side") disposed opposite the first side 723, a third side 725 (which also may be referred to as an "posterior side"), and a fourth side 726 (which also may be referred to as an "anterior side") disposed opposite the third side 725. As shown, the first attachment side 711 may include a central portion 727 and a pair of wings 728, 729 disposed on opposite sides of the central portion 727. In particular, the first wing 728 may extend from the central portion 727 to the first end 721 of the first attachment side 711, and the second wing 729 may extend from the central portion 727 toward the second end 722 of the first attachment side 711. In certain embodiments, as shown, the wings 728, 729 may extend in opposite directions from the central portion 727, although other configurations of the wings 728, 729 may be used. In certain embodiments, the wings 728, 729 may be shaped and configured in a manner similar to any one of the wing embodiments described and/or shown in the Prior Applications. Further details regarding the configurations of the wings 728, 729 and differences between the first wing 728 and the second wing 729 are described below.

The first attachment side 711 also may include a spacer 730 extending from the first side 723 thereof. During use of the device 700, the spacer 730 may be positioned between the spinous processes of the respective vertebrae. In certain embodiments, as shown, the spacer 730 may extend from the central portion 727 of the first attachment side 711 and be integrally formed therewith. In other embodiments, the spacer 730 may be separately formed from and attached to the central portion 727 via an attachment mechanism. The first attachment side 711 further may include a number of engagement features configured for securely engaging the respective vertebrae. In certain embodiments, as shown, the engagement features may be one or more bone fasteners 731 extending from the first side 723 of the first attachment side 711. The bone fasteners 731 may be formed as spikes or barbs, although other forms and types of bone fasteners 731 may be used for securely engaging the vertebrae. In certain embodiments, one or more of the bone fasteners 731 may extend form the first wing 728, as shown. Various configurations of the bone fasteners 731 of the first attachment side 711 may be used. In certain embodiments, as shown, the bone fasteners 731 may be configured to engage the laminae of the respective vertebrae. In other embodiments, one or more of the bone fasteners 731 may be configured to engage the spinous processes, the laminae, and/or other portions of the respective vertebrae. As shown, the first attachment side 711 also may include an instrument engagement aperture 732 configured for receiving a portion of and cooperating with an instrument used for positioning the first attachment side 711 during implantation of the device 700. Example instruments for implantation of the device 700 are described in the Prior Applications.

In a similar manner, the second attachment side 712 may have a first end 741, a second end 742 disposed opposite the first end 741, a first side 743 (which also may be referred to as an "exterior side"), a second side 744 (which also may be referred to as an "interior side") disposed opposite the first side 743, a third side 745 (which also may be referred to as an "posterior side"), and a fourth side 746 (which also may be referred to as an "anterior side") disposed opposite the third side 745. As shown, the second attachment side 712 may include a central portion 747 and a pair of wings 748, 749 disposed on opposite sides of the central portion 747. In particular, the first wing 748 may extend from the central portion 747 to the first end 741 of the second attachment side 712, and the second wing 749 may extend from the central portion 747 toward the second end 742 of the second attachment side 712. In certain embodiments, as shown, the wings 748, 749 may extend in opposite directions from the central portion 747, although other configurations of the wings 748, 749 may be used. In certain embodiments, the wings 748, 749 may be shaped and configured in a manner similar to any one of the wing embodiments described and/or shown in the Prior Applications. Further details regarding the configurations of the wings 748, 749 and differences between the first wing 748 and the second wing 749 are described below.

The second attachment side 712 also may include a spacer slot 750 extending through the second attachment side 712 from the first side 743 to the second side 744 thereof. During use of the device 700, the spacer slot 750 may be configured to receive the spacer 730 of the first attachment side 711 therethrough, as shown. In certain embodiments, as shown, the spacer slot 750 may be defined in the central portion 747 of the second attachment side 712 and may extend to the fourth side 746 thereof, although other positions of the spacer slot 750 may be used. The second attachment side 712 further may include a number of engagement features configured for securely engaging the respective vertebrae. In certain embodiments, as shown, the engagement features may be one or more bone fasteners 751 extending from the second side 744 of the second attachment side 712. The bone fasteners 751 may be formed as spikes or barbs, although other forms and types of bone fasteners 751 may be used for securely engaging the vertebrae. In certain embodiments, one or more of the bone fasteners 751 may extend form the first wing 748, as shown. Various configurations of the bone fasteners 751 of the second attachment side 712 may be used. In certain embodiments, as shown, the bone fasteners 751 may be configured to engage the laminae of the respective vertebrae. In other embodiments, one or more of the bone fasteners 751 may be configured to engage the spinous processes, the laminae, and/or other portions of the respective vertebrae. As shown, the second attachment side 712 also may include a securing aperture 752 configured to receive at least a portion of and cooperate with the securing means 713 for selectively fixing the first attachment side 711 and the second attachment side 712 relative to one another. The securing aperture 752 also may be configured for receiving a portion of and cooperating with an instrument used for positioning the second attachment side 712 during implantation of the device 700. Example instruments for implantation of the device 700 are described in the Prior Applications.

The securing means 713 may be configured for selectively fixing the first attachment side 711 and the second attachment side 712 relative to one another. In certain embodiments, as shown, the securing means 713 may be a fastener, such as a set screw, although other types of fasteners and other types of securing means may be used. As shown, the securing means 713 may be inserted into and at least partially through the securing aperture 752 of the second attachment side 712. In this manner, the securing means 713 may be advanced through the securing aperture 752 until the securing means 713 engages the spacer 730 of the first attachment side 711 positioned within the spacer slot 750 of the second attachment side 712. Upon desired positioning of the first attachment side 711 and the second attachment side 712 with respect to the corresponding vertebrae of the patient, the securing means 713 may be tightened to maintain the spacing and orientation of the first attachment side 711 and the second attachment side 712 relative to one another and relative to the corresponding vertebrae. In certain embodiments, the securing means 713 may be formed of a metal, such as titanium or stainless steel, although other suitable materials, such as polyether ether ketone (PEEK), other polymers, or composites, may be used.

As described above, the device 700 may be configured to allow relative movement of the treated vertebrae upon implantation of the device 700. In particular, the device 700 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 711 and the second attachment side 712 each may include one or more features configured to facilitate such relative movement of the treated vertebrae. In particular, the first attachment side 711 may include a slider 733 (which also may be referred to as a "dynamic slider," a "sliding member," an "engagement member," a "sleeve," or a "cap") that is movably attached to a main body 734 of the first attachment side 711. In certain embodiments, as shown, the main body 734 may include the central portion 727, the first wing 728, and the second wing 729 of the first attachment side 711, although other configurations of the main body 734 may be used. In certain embodiments, as shown, the slider 733 may be movably attached to the second wing 729, although the slider 733 may be movably attached to other features of the first attachment side 711 in other embodiments. The slider 733 may be formed as a sleeve or a cap configured to be movably positioned over or around at least a portion of the second wing 729, although other shapes and configurations of the slider 733 may be used. In certain embodiments, as shown, the slider 733 may include a central opening 735 extending through at least a portion of the slider 733 and configured for receiving at least a portion of the second wing 729 therein. The central opening 735 may be formed as a blind hole, as shown, extending in the direction of the longitudinal axis $A_L$ of the device 700. Alternatively, the central opening 735 may be formed as a thru hole extending in the direction of the longitudinal axis $A_L$ of the device 700.

In certain embodiments, as shown, the slider 733 may be movably attached to the second wing 729 via a sheath 771 positioned between the second wing 729 and the slider 733. The sheath 771 may be formed as a sleeve or cap configured to be positioned over or around at least a portion of the second wing 729, although other shapes and configurations of the sheath 771 may be used. In certain embodiments, as shown, the sheath 771 may include a central opening 772 extending through at least a portion of the sheath 771 and configured for receiving at least a portion of the second wing 729 therein. The central opening 772 may be formed as a blind hole, as shown, extending in the direction of the longitudinal axis $A_L$ of the device 700. Alternatively, the central opening 772 may be formed as a thru hole extending in the direction of the longitudinal axis $A_L$ of the device 700. The sheath 771 also may include a channel 773 (which also may be referred to as a "guide channel" or a "guide") defined therein. In certain embodiments, the channel 773 may be in communication with the central opening 772. In other embodiments, the channel 773 and the central opening 772 may be separate and spaced apart from one another by a wall of the sheath 771. As shown, the channel 773 may have an elongated shape extending in the direction of the longitudinal axis $A_L$ of the device 700. In certain embodiments, the channel 773 may have a straight shape extending in the direction of the longitudinal axis $A_L$ of the device 700. In other embodiments, the channel 773 may have a curved shape extending in the direction of the longitudinal axis $A_L$ of the device 700. For example, the channel 773 may have a curved shape such that a concave shape of the channel faces the fourth side 726 of the first attachment side 711. In certain embodiments, the sheath 771 may be fixedly attached to the second wing 729. For example, the sheath 771 may be fixedly attached to the second wing 729 by a pair of sheath securing means 774 (which also may be referred to as a "fastener"). Each of the sheath securing means 774 may extend through a mating securing aperture 775 of the sheath 771 and engage the second wing 729 to fixedly attach the sheath 771 to the second wing 729. In certain embodi-ments, the securing means 774 may engage a mating surface of the second wing 729. In other embodiments, the securing means 774 may engage mating apertures defined in the second wing 729. In certain embodiments, as shown, the sheath 771 also may include a flange 775 configured to engage a mating portion of the central portion 727 when the sheath 771 is attached to the second wing 729.

As shown, the slider 733 also may include a coupling member 737 positioned at least partially within the central opening 735 of the slider 733 and configured to engage the channel 773 of the sheath 771. In certain embodiments, as shown, the coupling member 737 may be formed as a pin configured for extending at least partially into the channel 773. In certain embodiments, the coupling member 737 may be formed of a rigid material, such as a rigid metal or a rigid plastic. In certain embodiments, the coupling member 737 may be formed separately from and attached to a remainder of the slider 733. For example, similar to the embodiment described above with respect to the device 600, the slider 733 may include a coupling aperture extending from an external surface of the slider 733 to the central opening 735 and configured to receive the coupling member 737 at least partially therein. In this manner, the coupling member 737 may be inserted through the coupling aperture and at least partially into the central opening of the slider 733 and the channel 773 of the sheath 771. The coupling member 737 then may be attached, either fixedly or removably, to the remainder of the slider 733. During assembly of the slider 733 to the second wing 729 and the sheath 771, the second wing 729 and the sheath 771 may be positioned at least partially within the central opening 735 of the slider 733, and the coupling member 737 may be passed through the coupling aperture and at least partially into the channel 773. In certain embodiments, the coupling member 737 may be press fit into the coupling aperture, and a portion of the coupling member 737 extending into the central opening 735 may be slidably received within the channel 773. As shown, the channel 773 may have a pair of closed ends positioned opposite one another along the length of the channel 773. In this manner, the connection between the coupling member 737 and the channel 773 may limit relative movement between the slider 733 and the sheath 771, the second wing 729, and the overall main body 734. It will be appreciated that the illustrated connection is merely one example and that other mechanisms for movably attaching the slider 733 to the main body 734 may be used.

The slider 733 may be configured to move relative to the main body 734 between an extended position (which also may be referred to as a "first position"), as shown in FIG. 7G, and a retracted position (which also may be referred to as a "second position"), as shown in FIG. 7H. In particular, the slider 733 may be configured to translate or otherwise slide along the sheath 771 and the second wing 729 between the extended position and the retracted position. In certain embodiments, the slider 733 may move along a linear path between the extended position and the retracted position, in the direction of the longitudinal axis $A_L$ of the device 700, while being guided by the shape of the channel 773 and/or the shape of the sheath 771 or the second wing 729. For example, the slider 733 may move along a linear path when the channel 773, the sheath 771, and/or the second wing 729 have a linear shape in the direction of the longitudinal axis $A_L$ of the device 700. In other embodiments, the slider 733 may move along a curved path between the extended position and the retracted position, in the direction of the longitudinal axis $A_L$ of the device 700, while being guided by the shape of the channel 773, the shape of the sheath 771, and/or the shape of the second wing 729. For example, the slider 733 may move along a curved path when the channel 773, the sheath 771, and/or the second wing 729 have a curved shape in the direction of the longitudinal axis $A_L$ of the device 700. As shown, the slider 733 may include a number of engagement features configured for securely engaging the respective vertebra. In certain embodiments, as shown, the engagement features may be one or more bone fasteners 739 extending from the slider 733 along the first side 723 of the first attachment side 711. The bone fasteners 739 may be formed as spikes or barbs, although other forms and types of bone fasteners 739 may be used for securely engaging the vertebrae. In certain embodiments, as shown, the bone fasteners 739 may be shaped and configured in a manner similar to the bone fasteners 731 extending form the first wing 728. Various configurations of the bone fasteners 739 of the slider 733 may be used. In certain embodiments, as shown, the bone fasteners 739 may be configured to engage the laminae of the respective vertebrae. In other embodiments, one or more of the bone fasteners 739 may be configured to engage the spinous processes, the laminae, and/or other portions of the respective vertebra.

It will be appreciated that the connection between the slider 733 and the main body 734 may be configured to allow portions of the first attachment side 711 to move relative to one another. As described above, the slider 733 may be movably attached to the main body 734, and thus the slider 733 may move relative to the central portion 727, the first wing 728, and the spacer 730 of the main body 734. In particular, the slider 733 may move toward the central portion 727, the first wing 728, and the spacer 730 when the slider 733 moves toward the retracted position, and the slider 733 may move away from the central portion 727, the first wing 728, and the spacer 730 when the slider 733 moves toward the extended position. As a result, the slider 733 and the first wing 728 may be configured to move toward one another and away from one another in the direction of the longitudinal axis $A_L$ of the device 700. In effect, the movable attachment between the slider 733 and the main body 734 may cause the first attachment side 711 to function as a slide which may be extended or retracted in the direction of the longitudinal axis $A_L$ of the device 700.

In certain embodiments, the slider 733, the main body 734, and the sheath 771 may be formed of different materials. For example, the slider 733 and the main body 734 may be formed of a rigid metal, such as titanium, and the sheath 771 may be formed of a rigid or substantially rigid polymer, such as ultra-high-molecular-weight polyethylene (UHMWPE), high-density polyethylene (HDPE), polyethylene high-density (PEHD), PEEK, or similar polymers. In this manner, the sheath 771 may prevent metal-on-metal contact between the slider 733 and the main body 734. During movement of the slider 733 between the extended position and the retracted position, the slider 733 may contact only the sheath 771 and may remain spaced apart from the second wing 729 and the main body 734. In this manner, the configuration of the sheath 771 may prevent wear between the slider 733 and the second wing 729 or the main body 734 during movement of the slider 733.

In a similar manner, the second attachment side 712 may include a slider 753 (which also may be referred to as a "dynamic slider," a "sliding member," an "engagement member," a "sleeve," or a "cap") that is movably attached to a main body 754 of the second attachment side 712. In certain embodiments, as shown, the main body 754 may include the central portion 747, the first wing 748, and the second wing 749 of the second attachment side 712, although other configurations of the main body 754 may be used. In certain embodiments, as shown, the slider 753 may be movably attached to the second wing 749, although the slider 753 may be movably attached to other features of the second attachment side 712 in other embodiments. The slider 753 may be formed as a sleeve or a cap configured to be movably positioned over or around at least a portion of the second wing 749, although other shapes and configurations of the slider 753 may be used. In certain embodiments, as shown, the slider 753 may include a central opening 755 extending through at least a portion of the slider 753 and configured for receiving at least a portion of the second wing 749 therein. The central opening 755 may be formed as a blind hole, as shown, extending in the direction of the longitudinal axis $A_L$ of the device 700. Alternatively, the central opening 755 may be formed as a thru hole extending in the direction of the longitudinal axis $A_L$ of the device 700.

In certain embodiments, as shown, the slider 753 may be movably attached to the second wing 749 via a sheath 781 positioned between the second wing 749 and the slider 753. The sheath 781 may be formed as a sleeve or cap configured to be positioned over or around at least a portion of the second wing 749, although other shapes and configurations of the sheath 781 may be used. In certain embodiments, as shown, the sheath 781 may include a central opening 782 extending through at least a portion of the sheath 781 and configured for receiving at least a portion of the second wing 749 therein. The central opening 782 may be formed as a blind hole, as shown, extending in the direction of the longitudinal axis $A_L$ of the device 700. Alternatively, the central opening 782 may be formed as a thru hole extending in the direction of the longitudinal axis $A_L$ of the device 700. The sheath 781 also may include a channel 783 (which also may be referred to as a "guide channel" or a "guide") defined therein. In certain embodiments, the channel 783 may be in communication with the central opening 782. In other embodiments, the channel 783 and the central opening 782 may be separate and spaced apart from one another by a wall of the sheath 781. As shown, the channel 783 may have an elongated shape extending in the direction of the longitudinal axis $A_L$ of the device 700. In certain embodiments, the channel 783 may have a straight shape extending in the direction of the longitudinal axis $A_L$ of the device 700. In other embodiments, the channel 783 may have a curved shape extending in the direction of the longitudinal axis $A_L$ of the device 700. For example, the channel 783 may have a curved shape such that a concave shape of the channel faces the fourth side 746 of the second attachment side 712. In certain embodiments, the sheath 781 may be fixedly attached to the second wing 749. For example, the sheath 781 may be fixedly attached to the second wing 749 by a pair of sheath securing means 784 (which also may be referred to as a "fastener"). Each of the sheath securing means 784 may extend through a mating securing aperture 785 of the sheath 781 and engage the second wing 749 to fixedly attach the sheath 781 to the second wing 749. In certain embodiments, the securing means 784 may engage a mating surface of the second wing 749. In other embodiments, the securing means 784 may engage mating apertures defined in the second wing 749. In certain embodiments, as shown, the sheath 781 also may include a flange 785 configured to engage a mating portion of the central portion 747 when the sheath 781 is attached to the second wing 749.

As shown, the slider 753 also may include a coupling member 757 positioned at least partially within the central opening 755 of the slider 753 and configured to engage the channel 783 of the sheath 781. In certain embodiments, as shown, the coupling member 757 may be formed as a pin configured for extending at least partially into the channel 783. In certain embodiments, the coupling member 757 may be formed of a rigid material, such as a rigid metal or a rigid plastic. In certain embodiments, the coupling member 757 may be formed separately from and attached to a remainder of the slider 753. For example, similar to the embodiment described above with respect to the device 600, the slider 753 may include a coupling aperture extending from an external surface of the slider 753 to the central opening 755 and configured to receive the coupling member 757 at least partially therein. In this manner, the coupling member 757 may be inserted through the coupling aperture and at least partially into the central opening of the slider 753 and the channel 783 of the sheath 781. The coupling member 757 then may be attached, either fixedly or removably, to the remainder of the slider 753. During assembly of the slider 753 to the second wing 749 and the sheath 781, the second wing 749 and the sheath 781 may be positioned at least partially within the central opening 755 of the slider 753, and the coupling member 757 may be passed through the coupling aperture and at least partially into the channel 783. In certain embodiments, the coupling member 757 may be press fit into the coupling aperture, and a portion of the coupling member 757 extending into the central opening 755 may be slidably received within the channel 783. As shown, the channel 783 may have a pair of closed ends positioned opposite one another along the length of the channel 783. In this manner, the connection between the coupling member 757 and the channel 783 may limit relative movement between the slider 753 and the sheath 781, the second wing 749, and the overall main body 754. It will be appreciated that the illustrated connection is merely one example and that other mechanisms for movably attaching the slider 753 to the main body 754 may be used.

The slider 753 may be configured to move relative to the main body 754 between an extended position (which also may be referred to as a "first position"), as shown in FIG. 7I, and a retracted position (which also may be referred to as a "second position"), as shown in FIG. 7J. In particular, the slider 753 may be configured to translate or otherwise slide along the sheath 781 and the second wing 749 between the extended position and the retracted position. In certain embodiments, the slider 753 may move along a linear path between the extended position and the retracted position, in the direction of the longitudinal axis $A_L$ of the device 700, while being guided by the shape of the channel 783 and/or the shape of the sheath 781 or the second wing 749. For example, the slider 753 may move along a linear path when the channel 783, the sheath 781, and/or the second wing 749 have a linear shape in the direction of the longitudinal axis $A_L$ of the device 700. In other embodiments, the slider 753 may move along a curved path between the extended position and the retracted position, in the direction of the longitudinal axis $A_L$ of the device 700, while being guided by the shape of the channel 783, the shape of the sheath 781, and/or the shape of the second wing 749. For example, the slider 753 may move along a curved path when the channel 783, the sheath 781, and/or the second wing 749 have a curved shape in the direction of the longitudinal axis $A_L$ of the device 700. As shown, the slider 753 may include a number of engagement features configured for securely engaging the respective vertebra. In certain embodiments, as shown, the engagement features may be one or more bone fasteners 759 extending from the slider 753 along the second side 744 of the second attachment side 712. The bone fasteners 759 may be formed as spikes or barbs, although other forms and types of bone fasteners 759 may be used for securely engaging the vertebrae. In certain embodiments, as shown, the bone fasteners 759 may be shaped and configured in a manner similar to the bone fasteners 751 extending form the first wing 748. Various configurations of the bone fasteners 759 of the slider 753 may be used. In certain embodiments, as shown, the bone fasteners 759 may be configured to engage the laminae of the respective vertebrae. In other embodiments, one or more of the bone fasteners 759 may be configured to engage the spinous processes, the laminae, and/or other portions of the respective vertebra.

It will be appreciated that the connection between the slider 753 and the main body 754 may be configured to allow portions of the second attachment side 712 to move relative to one another. As described above, the slider 753 may be movably attached to the main body 754, and thus the slider 753 may move relative to the central portion 747, the first wing 748, and the spacer slot 750 of the main body 754. In particular, the slider 753 may move toward the central portion 747, the first wing 748, and the spacer slot 750 when the slider 753 moves toward the retracted position, and the slider 753 may move away from the central portion 747, the first wing 748, and the spacer slot 750 when the slider 753 moves toward the extended position. As a result, the slider 753 and the first wing 748 may be configured to move toward one another and away from one another in the direction of the longitudinal axis $A_L$ of the device 700. In effect, the movable attachment between the slider 753 and the main body 754 may cause the second attachment side 712 to function as a slide which may be extended or retracted in the direction of the longitudinal axis $A_L$ of the device 700. In certain embodiments, as shown, the slider 733 of the first attachment side 711 may be formed as a mirror image of the slider 753 of the second attachment side 712. In other embodiments, the shape or configuration of the slider 733 of the first attachment side 711 may be different than the shape or configuration of the slider 753 of the second attachment side 712. Various configurations of the sliders 733, 753 and the features thereof may be used to allow for a desired range of movement of the corresponding vertebrae.

In certain embodiments, the slider 753, the main body 754, and the sheath 781 may be formed of different materials. For example, the slider 753 and the main body 754 may be formed of a rigid metal, such as titanium, and the sheath 781 may be formed of a rigid or substantially rigid polymer, such as UHMWPE, HDPE, PEHD, PEEK, or similar polymers. In this manner, the sheath 781 may prevent metal-on-metal contact between the slider 753 and the main body 754. During movement of the slider 753 between the extended position and the retracted position, the slider 753 may contact only the sheath 781 and may remain spaced apart from the second wing 749 and the main body 754. In this manner, the configuration of the sheath 781 may prevent wear between the slider 753 and the second wing 749 or the main body 754 during movement of the slider 753.

In certain embodiments, the device 700 may include means for preventing or inhibiting the movement of the slider 733 relative to the main body 734 of the first attachment side 711 and for preventing or inhibiting the movement of the slider 753 relative to the main body 754 of the second attachment side 712. FIGS. 7S and 7T illustrate an embodiment in which the device 700 includes a pair of securing means for preventing or inhibiting such movement of the sliders 733, 753. As shown, the first attachment side 711 may include a slider securing means 761 (which also may be referred to as a "fastener" or a "lock") configured for selectively preventing on inhibiting movement of the slider 733 relative to the main body 734. In this manner, the securing means 761 may selectively fix the slider 733 relative to the main body 734. In certain embodiments, as shown, the securing means 761 may be a fastener, such as a set screw, although other types of fasteners and other types of securing means may be used. As shown, the securing means 761 may be inserted into and at least partially through a securing aperture 762 defined in the slider 733. The securing aperture 762 may extend from an external surface of the slider 733 to the central opening 735 thereof and be configured to receive the securing means 761 at least partially therein. In certain embodiments, securing aperture 762 may be threaded, and the securing means 761 may threadably engage the securing aperture 762. When desired, the securing means 761 may be advanced at least partially through the securing aperture 762 and into the central opening 735 to engage the sheath 771. In certain instances, the securing means 761 may engage the sheath 771 such that relative movement between the slider 733 and the main body 734 is inhibited but not entirely prevented. In this manner, the engagement between the securing means 761 and the sheath 771 may generate a frictional force that opposes but does not prevent relative movement between the slider 733 and the main body 734. As an example, when the securing means 761 is threaded, the securing means 761 may be initially tightened against the sheath 771 by applying a lesser amount of torque which inhibits but does not prevent the relative movement. In other instances, the securing means 761 may engage the sheath 771 such that relative movement between the slider 733 and the main body 734 is prevented. In this manner, the engagement between the securing means 761 and the sheath 771 may generate a frictional force that prevents relative movement between the slider 733 and the main body 734. As an example, when the securing means 761 is threaded, the securing means 761 may be further tightened against the sheath 771 by applying a greater amount of torque which prevents the relative movement. Ultimately, the securing means 761 may be used to vary the degree of resistance to the relative movement between the slider 733 and the main body 734, thereby controlling the relative movement between the treated vertebrae, and/or the securing means 761 may be used to prevent relative movement between the slider 733 and the main body 734, thereby preventing relative movement between the treated vertebrae.

In a similar manner, the second attachment side 712 may include a slider securing means 765 (which also may be referred to as a "fastener" or a "lock") configured for selectively preventing on inhibiting movement of the slider 753 relative to the main body 754. In this manner, the securing means 765 may selectively fix the slider 753 relative to the main body 754. In certain embodiments, as shown, the securing means 765 may be a fastener, such as a set screw, although other types of fasteners and other types of securing means may be used. As shown, the securing means 765 may be inserted into and at least partially through a securing aperture 766 defined in the slider 753. The securing aperture 766 may extend from an external surface of the slider 753 to the central opening 755 thereof and be configured to receive the securing means 765 at least partially therein. In certain embodiments, securing aperture 766 may be threaded, and the securing means 765 may threadably engage the securing aperture 766. When desired, the securing means 765 may be advanced at least partially through the securing aperture 766 and into the central opening 755 to engage the sheath 781. In certain instances, the securing means 765 may engage the sheath 781 such that relative movement between the slider 753 and the main body 754 is inhibited but not entirely prevented. In this manner, the engagement between the securing means 765 and the sheath 781 may generate a frictional force that opposes but does not prevent relative movement between the slider 753 and the main body 754. As an example, when the securing means 765 is threaded, the securing means 765 may be initially tightened against the sheath 781 by applying a lesser amount of torque which inhibits but does not prevent the relative movement. In other instances, the securing means 765 may engage the sheath 781 such that relative movement between the slider 753 and the main body 754 is prevented. In this manner, the engagement between the securing means 765 and the sheath 781 may generate a frictional force that prevents relative movement between the slider 753 and the main body 754. As an example, when the securing means 765 is threaded, the securing means 765 may be further tightened against the sheath 781 by applying a greater amount of torque which prevents the relative movement. Ultimately, the securing means 765 may be used to vary the degree of resistance to the relative movement between the slider 753 and the main body 754, thereby controlling the relative movement between the treated vertebrae, and/or the securing means 765 may be used to prevent relative movement between the slider 753 and the main body 754, thereby preventing relative movement between the treated vertebrae.

It will be appreciated that the securing means 761, 765 of the device 700 may be used to control the relative movement between the treated vertebrae, when desired. In particular, the securing means 761, 765 may be used to increase or decrease resistance to the relative movement between the treated vertebrae or to prevent such relative movement. In this manner, the device 700 may be used as a dynamic device or a rigid device, with the ability to convert the device 700 between a dynamic configuration and a rigid configuration, as may be desired in certain applications. The securing means 761, 765 may be used to selectively adjust the resistance to relative movement between the treated vertebrae, or to prevent such relative movement, prior to implantation of the device 700, during initial implantation of the device 700 as a part of an initial surgery, or during a follow-up surgery.

In certain embodiments, the device 700 may include means for varying resistance to the relative movement between the slider 733 and the main body 734 of the first attachment side 711 over at least a portion of the range of motion of the slider 733 and for varying resistance to the relative movement between the slider 753 and the main body 754 of the second attachment side 712 over at least a portion of the range of motion of the slider 753. In this manner, the device 700 may vary the resistance to the relative movement between the treated vertebrae over at least a portion of the range of motion of the vertebrae allowed by the device 700. As described above, in certain embodiments, the coupling members 737, 757 of the sliders 733, 753 may be formed of a rigid material, such as a rigid metal or a rigid plastic. In this manner, the respective retracted positions and extended positions of the sliders 733, 753 may be defined by hard stops when the coupling members 737, 757 engage the respective closed ends of the channels 773, 783. In other embodiments, at least a portion of the coupling members 737, 757 may be formed of a flexible or substantially flexible material, such as a flexible plastic. For example, at least the portion of the coupling members 737, 757 that resides within the respective channels 773, 783 may be formed of a flexible material. In this manner, when the coupling members 737, 757 engage the respective closed ends of the channels 773, 783, the coupling members 737, 757 may flex or bend. As a result, the flexible portions of the coupling members 737, 757 may be used to increase resistance to the relative movement between the treated vertebrae over at least a portion of the range of motion of the vertebrae allowed by the device 700. In this manner, the device 700 advantageously may function in a manner similar to a native disc, providing minimal resistance to initial relative movement in a direction in the sagittal plane and increasing resistance to further relative movement in the same direction. It will be appreciated that size, shape, configuration, and/or material of the flexible portions of the coupling members 737, 757 may be selected to provide a desired degree of resistance to the relative motion of the treated vertebrae.

In other embodiments, the device 700 may include alternative or additional means for varying resistance to the relative movement between the slider 733 and the main body 734 of the first attachment side 711 over at least a portion of the range of motion of the slider 733 and for varying resistance to the relative movement between the slider 753 and the main body 754 of the second attachment side 712 over at least a portion of the range of motion of the slider 753. FIGS. 7U and 7V illustrate an embodiment in which the device 700 includes a pair of resistance means for varying resistance to the movement of the sliders 733, 753, thereby varying resistance to the movement of the treated vertebrae. As shown in FIG. 7U, the slider 733 may include a slider resistance means 791 (which also may be referred to as a "resistance member," a "compressible member," a "biasing member") configured for varying resistance to movement of the slider 733 relative to the main body 734 over at least a portion of the range of motion of the slider 733 (i.e., between the extended position and the retracted position of the slider 733). In a similar manner, as shown in FIG. 7V, the slider 753 may include a slider resistance means 792 (which also may be referred to as a "resistance member," a "compressible member," a "biasing member") configured for varying resistance to movement of the slider 753 relative to the main body 754 over at least a portion of the range of motion of the slider 753 (i.e., between the extended position and the retracted position of the slider 753). In certain embodiments, as shown, the slider resistance means 791, 792 may be formed as a ring-shaped member surrounding the portion of the respective coupling member 737, 757 that resides within the respective channel 773, 783. In certain embodiments, the slider resistance means 791, 792 may be attached to the respective coupling member 737, 757 as a coating. In other embodiments, the slider resistance means 791, 792 may be formed as a separate component and positioned over the respective coupling member 737, 757. The slider resistance means 791, 792 may be formed of a compressible material, such as an elastomeric material. In this manner, when the slider resistance means 791, 792 engage the respective closed ends of the channels 773, 783, the slider resistance means 791, 792 may compress. As a result, the slider resistance means 791, 792 may be used to increase resistance to the relative movement between the treated vertebrae over at least a portion of the range of motion of the vertebrae allowed by the device 700. In this manner, the device 700 advantageously may function in a manner similar to a native disc, providing minimal resistance to initial relative movement in a direction in the sagittal plane and increasing resistance to further relative movement in the same direction. It will be appreciated that size, shape, configuration, and/or material of the flexible portions of the slider resistance means 791, 792 may be selected to provide a desired degree of resistance to the relative motion of the treated vertebrae. In certain embodiments, the slider resistance means 791, 792 may be used with the coupling members 737, 757 formed of a rigid material, as described above. In other embodiments, the slider resistance means 791, 792 may be used with the coupling members 737, 757 formed of a flexible material to provide additional resistance to the relative movement between the sliders 733, 753.

FIGS. 7W and 7X illustrate an example implantation of the device 700 with respect to a first vertebra $V_1$ and an adjacent second vertebra $V_2$. As shown, the first attachment side 711 and the second attachment side 712 may be positioned relative to the vertebrae $V_1$, $V_2$ such that the spacer 730 is positioned between a first spinous process $SP_1$ of the first vertebra $V_1$ and a second spinous process $SP_2$ of the second vertebra $V_2$. In this manner, the spacer 730 may limit a minimum spacing between the spinous processes $SP_1$, $SP_2$. Additionally, the first attachment side 711 and the second attachment side 712 may be positioned relative to the vertebrae $V_1$, $V_2$ such that the first wing 728 and the slider 733 of the first attachment side 711 and the first wing 748 and the slider 753 of the second attachment side 712 engage a first lamina $L_1$ of the first vertebra $V_1$ and a second lamina $L_2$ of the second vertebra $V_2$. In this manner, the respective bone fasteners 731, 739 of the first attachment side 711 and the respective bone fasteners 751, 759 of the second attachment side 712 may penetrate and securely engage the laminae $L_1$, $L_2$. Accordingly, the implanted device 700 may stabilize the vertebrae $V_1$, $V_2$, although the device 700 may allow relative movement of the vertebrae $V_1$, $V_2$. In particular, the sliders 733, 753 of the device 700 may allow relative movement of the vertebrae $V_1$, $V_2$ in sagittal plane of the patient, thereby allowing flexion and extension of the treated segment of the spine. It will be appreciated that the configuration of the sliders 733, 753, the coupling members 737, 757, the channels 773, 783, and any resistance means of the device 700 may be varied to allow a desired range of motion in the sagittal plane. Further, the material from which the various components and features of the first attachment side 711 and the second attachment side 712 are formed may be selected to achieve the desired range of motion. In certain embodiments, portions of the first attachment side 711 and the second attachment side 712 may be formed of titanium, although other suitable metals, polymers, or other materials may be used in other embodiments. Meanwhile, the device 700 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 700 and the disc D. In other embodiments in which the native disc D is removed, an interbody device, such as a cage or a spacer, may be implanted within the disc space DS (i.e., the intervertebral space) and the loads carried by the treated spinal segment may be shared by the device 700 and the interbody device. As described above, the device 700 may be used in conjunction with other additional hardware, such that the device 700 and the additional hardware collectively stabilize the treated segment of the spine and share loads carried thereby. It will be appreciated that the foregoing description and the corresponding drawings are merely examples of the device 700 and that other configurations and modifications may be made.

FIGS. 8A-8X illustrate an interspinous process device 800 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 800 may be configured for implantation relative to a first vertebra and an adjacent second vertebra, as described below, specifically with reference to FIGS. 8W and 8X. In particular, a portion of the interspinous process device 800 may be positioned between the spinous process of the first vertebra and the spinous process of the second vertebra, while one or more other portions of the interspinous process device 800 engage the spinous processes, the laminae, and/or other portions of the respective vertebra. As described below, the interspinous process device 800 may allow a desired range of relative movement between the treated vertebrae, which may be desirable in certain treatment applications. Additionally, the interspinous process device 800 may be converted between a dynamic configuration, in which the device 800 allows relative movement between the treated vertebrae, and a rigid configuration, in which the device 800 prevents or substantially inhibits such relative movement. In this manner, the interspinous process device 800 may be adjusted to allow relative motion, when desired, and to inhibit relative motion, when desired, without having to remove or replace the device 800. The interspinous process device 800 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 800, itself or in combination with additional hardware, may provide the structural support necessary to restore and maintain normal spacing and alignment of the treated vertebrae while avoiding certain drawbacks presented by existing interspinous process devices.

The interspinous process device 800 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 800 may include a first end 801 and a second end 802 disposed opposite the first end 801 in the direction of the longitudinal axis $A_L$. As described below, the device 800 may be implanted with the longitudinal axis $A_L$ extending in a direction substantially parallel to the sagittal plane and the coronal plane of the patient and transverse to the transverse plane of the patient. In this manner, depending on the orientation of the device 800 upon implantation thereof, one of the first end 801 and the second end 802 of the device 800 may be referred to as a the "superior end" of the device 800, and the other of the first end 801 and the second end 802 of the device 800 may be referred to as the "inferior end" of the device 800. The device 800 also may include a first side 803 extending from the first end 801 to the second end 802, and a second side 804 disposed opposite the first side 803 in the direction of the first transverse axis $A_{T1}$ and extending from the first end 801 to the second end 802. The device 800 may be implanted with the first transverse axis $A_{T1}$ extending in a direction substantially parallel to the coronal plane and the transverse plane of the patient and transverse to the sagittal plane of the patient. In this manner, depending on the orientation of the device 800 upon implantation thereof, one of the first side 803 and the second side 804 of the device 800 may be referred to as the "right side" of the device 800, and the other of the first side 803 and the second side 804 of the device 800 may be referred to as the "left side" of the device 800. The device 800 further may include a third side 805 extending from the first end 801 to the second end 802 and from the first side 803 to the second side 804, and a fourth side 806 disposed opposite the third side 805 in the direction of the second transverse axis $A_{T2}$ and extending from the first end 801 to the second end 802 and from the first side 803 to the second side 804. The device 800 may be implanted with the second transverse axis $A_{T2}$ extending in a direction substantially parallel to the sagittal plane and the transverse plane of the patient and transverse to the coronal plane of the patient. As described below, the device 800 may be oriented upon implantation thereof such that the third side 805 faces posteriorly and the fourth side 806 faces anteriorly with respect to the patient. In this manner, the third side 805 may be referred to as the "posterior side" of the device 800, and the fourth side 806 may be referred to as the "anterior side" of the device 800. The device 800 may have an overall "length" extending from the first end 801 to the second end 802 in the direction of the longitudinal axis $A_L$, an overall "width" extending from the first side 803 to the second side 804 in the direction of the first transverse axis $A_{T1}$, and an overall "height" extending from the third side 805 to the fourth side 806 in the direction of the second transverse axis $A_{T2}$. Further, various components and features of the device 800 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 800 may include a first attachment side 811 (which also may be referred to as a "first attachment portion," a "first attachment assembly," or a "first plate") and a second attachment side 812 (which also may be referred to as a "second attachment portion," a "second attachment assembly," or a "second plate") configured for removably attaching to one another via a securing means 813. During use of the device 800, one of the first attachment side 811 and the second attachment side 812 may be disposed, at least partially, along the right side of the patient's spine, and the other of the first attachment side 811 and the second attachment side 812 may be disposed, at least partially, along the right side of the patient's spine. It will be appreciated that the first attachment side 811 and the second attachment side 812 may include corresponding features that are mirror images of one another, although certain differences between the first attachment side 811 and the second attachment side 812 may exist, as described below. In certain embodiments, the first attachment side 811 and the second attachment side 812 may be formed of a metal, such as titanium or stainless steel, although other suitable materials, such as polyether ether ketone (PEEK), other polymers, or composites, may be used.

The first attachment side 811 may have a first end 821, a second end 822 disposed opposite the first end 821, a first side 823 (which also may be referred to as an "interior side"), a second side 824 (which also may be referred to as an "exterior side") disposed opposite the first side 823, a third side 825 (which also may be referred to as an "posterior side"), and a fourth side 826 (which also may be referred to as an "anterior side") disposed opposite the third side 825. As shown, the first attachment side 811 may include a central portion 827 and a pair of wings 828, 829 disposed on opposite sides of the central portion 827. In particular, the first wing 828 may extend from the central portion 827 to the first end 821 of the first attachment side 811, and the second wing 829 may extend from the central portion 827 toward the second end 822 of the first attachment side 811. In certain embodiments, as shown, the wings 828, 829 may extend in opposite directions from the central portion 827, although other configurations of the wings 828, 829 may be used. In certain embodiments, the wings 828, 829 may be shaped and configured in a manner similar to any one of the wing embodiments described and/or shown in the Prior Applications. Further details regarding the configurations of the wings 828, 829 and differences between the first wing 828 and the second wing 829 are described below.

The first attachment side 811 also may include a spacer 830 extending from the first side 823 thereof. During use of the device 800, the spacer 830 may be positioned between the spinous processes of the respective vertebrae. In certain embodiments, as shown, the spacer 830 may extend from the central portion 827 of the first attachment side 811 and be integrally formed therewith. In other embodiments, the spacer 830 may be separately formed from and attached to the central portion 827 via an attachment mechanism. The first attachment side 811 further may include a number of engagement features configured for securely engaging the respective vertebrae. In certain embodiments, as shown, the engagement features may be one or more bone fasteners 831 extending from the first side 823 of the first attachment side 811. The bone fasteners 831 may be formed as spikes or barbs, although other forms and types of bone fasteners 831 may be used for securely engaging the vertebrae. In certain embodiments, one or more of the bone fasteners 831 may extend form the first wing 828, as shown. Various configurations of the bone fasteners 831 of the first attachment side 811 may be used. In certain embodiments, as shown, the bone fasteners 831 may be configured to engage the laminae of the respective vertebrae. In other embodiments, one or more of the bone fasteners 831 may be configured to engage the spinous processes, the laminae, and/or other portions of the respective vertebrae. As shown, the first attachment side 811 also may include an instrument engagement aperture 832 configured for receiving a portion of and cooperating with an instrument used for positioning the first attachment side 811 during implantation of the device 800. Example instruments for implantation of the device 800 are described in the Prior Applications.

In a similar manner, the second attachment side 812 may have a first end 841, a second end 842 disposed opposite the first end 841, a first side 843 (which also may be referred to as an "exterior side"), a second side 844 (which also may be referred to as an "interior side") disposed opposite the first side 843, a third side 845 (which also may be referred to as an "posterior side"), and a fourth side 846 (which also may be referred to as an "anterior side") disposed opposite the third side 845. As shown, the second attachment side 812 may include a central portion 847 and a pair of wings 848, 849 disposed on opposite sides of the central portion 847. In particular, the first wing 848 may extend from the central portion 847 to the first end 841 of the second attachment side 812, and the second wing 849 may extend from the central portion 847 toward the second end 842 of the second attachment side 812. In certain embodiments, as shown, the wings 848, 849 may extend in opposite directions from the central portion 847, although other configurations of the wings 848, 849 may be used. In certain embodiments, the wings 848, 849 may be shaped and configured in a manner similar to any one of the wing embodiments described and/or shown in the Prior Applications. Further details regarding the configurations of the wings 848, 849 and differences between the first wing 848 and the second wing 849 are described below.

The second attachment side 812 also may include a spacer slot 850 extending through the second attachment side 812 from the first side 843 to the second side 844 thereof. During use of the device 800, the spacer slot 850 may be configured to receive the spacer 830 of the first attachment side 811 therethrough, as shown. In certain embodiments, as shown, the spacer slot 850 may be defined in the central portion 847 of the second attachment side 812 and may extend to the fourth side 846 thereof, although other positions of the spacer slot 850 may be used. The second attachment side 812 further may include a number of engagement features configured for securely engaging the respective vertebrae. In certain embodiments, as shown, the engagement features may be one or more bone fasteners 851 extending from the second side 844 of the second attachment side 812. The bone fasteners 851 may be formed as spikes or barbs, although other forms and types of bone fasteners 851 may be used for securely engaging the vertebrae. In certain embodiments, one or more of the bone fasteners 851 may extend form the first wing 848, as shown. Various configurations of the bone fasteners 851 of the second attachment side 812 may be used. In certain embodiments, as shown, the bone fasteners 851 may be configured to engage the laminae of the respective vertebrae. In other embodiments, one or more of the bone fasteners 851 may be configured to engage the spinous processes, the laminae, and/or other portions of the respective vertebrae. As shown, the second attachment side 812 also may include a securing aperture 852 configured to receive at least a portion of and cooperate with the securing means 813 for selectively fixing the first attachment side 811 and the second attachment side 812 relative to one another. The securing aperture 852 also may be configured for receiving a portion of and cooperating with an instrument used for positioning the second attachment side 812 during implantation of the device 800. Example instruments for implantation of the device 800 are described in the Prior Applications.

The securing means 813 may be configured for selectively fixing the first attachment side 811 and the second attachment side 812 relative to one another. In certain embodiments, as shown, the securing means 813 may be a fastener, such as a set screw, although other types of fasteners and other types of securing means may be used. As shown, the securing means 813 may be inserted into and at least partially through the securing aperture 852 of the second attachment side 812. In this manner, the securing means 813 may be advanced through the securing aperture 852 until the securing means 813 engages the spacer 830 of the first attachment side 811 positioned within the spacer slot 850 of the second attachment side 812. Upon desired positioning of the first attachment side 811 and the second attachment side 812 with respect to the corresponding vertebrae of the patient, the securing means 813 may be tightened to maintain the spacing and orientation of the first attachment side 811 and the second attachment side 812 relative to one another and relative to the corresponding vertebrae. In certain embodiments, the securing means 813 may be formed of a metal, such as titanium or stainless steel, although other suitable materials, such as polyether ether ketone (PEEK), other polymers, or composites, may be used.

As described above, the device 800 may be configured to allow relative movement of the treated vertebrae upon implantation of the device 800. In particular, the device 800 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 811 and the second attachment side 812 each may include one or more features configured to facilitate such relative movement of the treated vertebrae. In particular, the first attachment side 811 may include a slider 833 (which also may be referred to as a "dynamic slider," a "sliding member," an "engagement member," a "sleeve," or a "cap") that is movably attached to a main body 834 of the first attachment side 811. In certain embodiments, as shown, the main body 834 may include the central portion 827, the first wing 828, and the second wing 829 of the first attachment side 811, although other configurations of the main body 834 may be used. In certain embodiments, as shown, the slider 833 may be movably attached to the second wing 829, although the slider 833 may be movably attached to other features of the first attachment side 811 in other embodiments. The slider 833 may be formed as a sleeve or a cap configured to be movably positioned over or around at least a portion of the second wing 829, although other shapes and configurations of the slider 833 may be used. In certain embodiments, as shown, the slider 833 may include a central opening 835 extending through at least a portion of the slider 833 and configured for receiving at least a portion of the second wing 829 therein. The central opening 835 may be formed as a blind hole, as shown, extending in the direction of the longitudinal axis $A_L$ of the device 800. Alternatively, the central opening 835 may be formed as a thru hole extending in the direction of the longitudinal axis $A_L$ of the device 800.

In certain embodiments, as shown, the slider 833 may be movably attached to the second wing 829 via a sheath 871 positioned between the second wing 829 and the slider 833. The sheath 871 may be formed as a sleeve configured to be positioned over or around at least a portion of the second wing 829, although other shapes and configurations of the sheath 871 may be used. In certain embodiments, as shown, the sheath 871 may include a central opening 872 extending through at least a portion of the sheath 871 and configured for receiving at least a portion of the second wing 829 therein. The central opening 872 may be formed as a thru hole extending in the direction of the longitudinal axis $A_L$ of the device 800. The sheath 871 also may include a channel 873 (which also may be referred to as a "guide channel" or a "guide") defined therein. In certain embodiments, the channel 873 may be in communication with the central opening 872. In other embodiments, the channel 873 and the central opening 872 may be separate and spaced apart from one another by a wall of the sheath 871. As shown, the channel 873 may have an elongated shape extending in the direction of the longitudinal axis $A_L$ of the device 800. In certain embodiments, the channel 873 may have a straight shape extending in the direction of the longitudinal axis $A_L$ of the device 800. In other embodiments, the channel 873 may have a curved shape extending in the direction of the longitudinal axis $A_L$ of the device 800. For example, the channel 873 may have a curved shape such that a concave shape of the channel faces the fourth side 826 of the first attachment side 811. In certain embodiments, the sheath 871 may be fixedly attached to the second wing 829. For example, the sheath 871 may be fixedly attached to the second wing 829 by a pair of sheath securing means 874 (which also may be referred to as a "fastener"). Each of the sheath securing means 874 may extend through a mating securing aperture 875 of the sheath 871 and engage the second wing 829 to fixedly attach the sheath 871 to the second wing 829. In certain embodiments, the securing means 874 may engage a mating surface of the second wing 829. In other embodiments, the securing means 874 may engage mating apertures defined in the second wing 829. In certain embodiments, as shown, the sheath 871 also may include a flange 875 configured to correspond to a mating portion of the central portion 827 when the sheath 871 is attached to the second wing 829.

In other embodiments, as shown, the sheath 871 may be movably attached to the second wing 829. For example, the sheath 871 may be configured to translate along the second wing 829 in the direction of the longitudinal axis $A_L$ of the device 800. In particular, the sheath 871 may be positioned over the second wing 829 and configured to translate between the central portion 827 and a flange 877 positioned about the free end of the second wing 829. In this manner, movement of the sheath 871 relative to the second wing 829 may be limited by the central portion 827 and the flange 877. As shown, the first attachment side 811 also may include a pair of resistance means (which also may be referred to as a "resistance member," a "compressible member," a "biasing member") positioned over the second wing 829 at opposite ends of the sheath 871. In particular, a first resistance means 878 may be positioned between the central portion 827 and the sheath 871, and a second resistance means 879 may be positioned between the flange 877 and the sheath 871. The resistance means 878, 879 may be formed as ring-shaped members surrounding respective portions of the second wing 829. The resistance means 878, 879 may be formed of a compressible material, such as an elastomeric material. In this manner, the resistance means 878, 879 may be compressed when the sheath 871 moves relative to the second wing 829 and engages the respective resistance means 878, 879.

As shown, the slider 833 also may include a coupling member 837 positioned at least partially within the central opening 835 of the slider 833 and configured to engage the channel 873 of the sheath 871. In certain embodiments, as shown, the coupling member 837 may be formed as a pin configured for extending at least partially into the channel 873. In certain embodiments, the coupling member 837 may be formed of a rigid material, such as a rigid metal or a rigid plastic. In certain embodiments, the coupling member 837 may be formed separately from and attached to a remainder of the slider 833. For example, similar to the embodiment described above with respect to the device 600, the slider 833 may include a coupling aperture extending from an external surface of the slider 833 to the central opening 835 and configured to receive the coupling member 837 at least partially therein. In this manner, the coupling member 837 may be inserted through the coupling aperture and at least partially into the central opening of the slider 833 and the channel 873 of the sheath 871. The coupling member 837 then may be attached, either fixedly or removably, to the remainder of the slider 833. During assembly of the slider 833 to the second wing 829 and the sheath 871, the second wing 829 and the sheath 871 may be positioned at least partially within the central opening 835 of the slider 833, and the coupling member 837 may be passed through the coupling aperture and at least partially into the channel 873. In certain embodiments, the coupling member 837 may be press fit into the coupling aperture, and a portion of the coupling member 837 extending into the central opening 835 may be slidably received within the channel 873. As shown, the channel 873 may have a pair of closed ends positioned opposite one another along the length of the channel 873. In this manner, the connection between the coupling member 837 and the channel 873 may limit relative movement between the slider 833 and the sheath 871, the second wing 829, and the overall main body 834. It will be appreciated that the illustrated connection is merely one example and that other mechanisms for movably attaching the slider 833 to the main body 834 may be used.

The slider 833 may be configured to move relative to the main body 834 between an extended position (which also may be referred to as a "first position"), as shown in FIG. 8I, and a retracted position (which also may be referred to as a "second position"), as shown in FIG. 8J. In particular, the slider 833 may be configured to translate or otherwise slide along the sheath 871 and the second wing 829 between the extended position and the retracted position. In certain embodiments, the slider 833 may move along a linear path between the extended position and the retracted position, in the direction of the longitudinal axis $A_L$ of the device 800, while being guided by the shape of the channel 873 and/or the shape of the sheath 871 or the second wing 829. For example, the slider 833 may move along a linear path when the channel 873, the sheath 871, and/or the second wing 829 have a linear shape in the direction of the longitudinal axis $A_L$ of the device 800. In other embodiments, the slider 833 may move along a curved path between the extended position and the retracted position, in the direction of the longitudinal axis $A_L$ of the device 800, while being guided by the shape of the channel 873, the shape of the sheath 871, and/or the shape of the second wing 829. For example, the slider 833 may move along a curved path when the channel 873, the sheath 871, and/or the second wing 829 have a curved shape in the direction of the longitudinal axis $A_L$ of the device 800. As shown, the slider 833 may include a number of engagement features configured for securely engaging the respective vertebra. In certain embodiments, as shown, the engagement features may be one or more bone fasteners 839 extending from the slider 833 along the first side 823 of the first attachment side 811. The bone fasteners 839 may be formed as spikes or barbs, although other forms and types of bone fasteners 839 may be used for securely engaging the vertebrae. In certain embodiments, as shown, the bone fasteners 839 may be shaped and configured in a manner similar to the bone fasteners 831 extending form the first wing 828. Various configurations of the bone fasteners 839 of the slider 833 may be used. In certain embodiments, as shown, the bone fasteners 839 may be configured to engage the laminae of the respective vertebrae. In other embodiments, one or more of the bone fasteners 839 may be configured to engage the spinous processes, the laminae, and/or other portions of the respective vertebra.

It will be appreciated that the connection between the slider 833 and the main body 834 may be configured to allow portions of the first attachment side 811 to move relative to one another. As described above, the slider 833 may be movably attached to the main body 834, and thus the slider 833 may move relative to the central portion 827, the first wing 828, and the spacer 830 of the main body 834. In particular, the slider 833 may move toward the central portion 827, the first wing 828, and the spacer 830 when the slider 833 moves toward the retracted position, and the slider 833 may move away from the central portion 827, the first wing 828, and the spacer 830 when the slider 833 moves toward the extended position. As a result, the slider 833 and the first wing 828 may be configured to move toward one another and away from one another in the direction of the longitudinal axis $A_L$ of the device 800. In effect, the movable attachment between the slider 833 and the main body 834 may cause the first attachment side 811 to function as a slide which may be extended or retracted in the direction of the longitudinal axis $A_L$ of the device 800.

In a similar manner, the second attachment side 812 may include a slider 853 (which also may be referred to as a "dynamic slider," a "sliding member," an "engagement member," a "sleeve," or a "cap") that is movably attached to a main body 854 of the second attachment side 812. In certain embodiments, as shown, the main body 854 may include the central portion 847, the first wing 848, and the second wing 849 of the second attachment side 812, although other configurations of the main body 854 may be used. In certain embodiments, as shown, the slider 853 may be movably attached to the second wing 849, although the slider 853 may be movably attached to other features of the second attachment side 812 in other embodiments. The slider 853 may be formed as a sleeve or a cap configured to be movably positioned over or around at least a portion of the second wing 849, although other shapes and configurations of the slider 853 may be used. In certain embodiments, as shown, the slider 853 may include a central opening 855 extending through at least a portion of the slider 853 and configured for receiving at least a portion of the second wing 849 therein. The central opening 855 may be formed as a blind hole, as shown, extending in the direction of the longitudinal axis $A_L$ of the device 800. Alternatively, the central opening 855 may be formed as a thru hole extending in the direction of the longitudinal axis $A_L$ of the device 800.

In certain embodiments, as shown, the slider 853 may be movably attached to the second wing 849 via a sheath 881 positioned between the second wing 849 and the slider 853. The sheath 881 may be formed as a sleeve or cap configured to be positioned over or around at least a portion of the second wing 849, although other shapes and configurations of the sheath 881 may be used. In certain embodiments, as shown, the sheath 881 may include a central opening 882 extending through at least a portion of the sheath 881 and configured for receiving at least a portion of the second wing 849 therein. The central opening 882 may be formed as a thru hole extending in the direction of the longitudinal axis $A_L$ of the device 800. The sheath 881 also may include a channel 883 (which also may be referred to as a "guide channel" or a "guide") defined therein. In certain embodiments, the channel 883 may be in communication with the central opening 882. In other embodiments, the channel 883 and the central opening 882 may be separate and spaced apart from one another by a wall of the sheath 881. As shown, the channel 883 may have an elongated shape extending in the direction of the longitudinal axis $A_L$ of the device 800. In certain embodiments, the channel 883 may have a straight shape extending in the direction of the longitudinal axis $A_L$ of the device 800. In other embodiments, the channel 883 may have a curved shape extending in the direction of the longitudinal axis $A_L$ of the device 800. For example, the channel 883 may have a curved shape such that a concave shape of the channel faces the fourth side 846 of the second attachment side 812. In certain embodiments, the sheath 881 may be fixedly attached to the second wing 849. For example, the sheath 881 may be fixedly attached to the second wing 849 by a pair of sheath securing means 884 (which also may be referred to as a "fastener"). Each of the sheath securing means 884 may extend through a mating securing aperture 885 of the sheath 881 and engage the second wing 849 to fixedly attach the sheath 881 to the second wing 849. In certain embodiments, the securing means 884 may engage a mating surface of the second wing 849. In other embodiments, the securing means 884 may engage mating apertures defined in the second wing 849. In certain embodiments, as shown, the sheath 881 also may include a flange 885 configured to correspond to a mating portion of the central portion 847 when the sheath 881 is attached to the second wing 849.

In other embodiments, as shown, the sheath 881 may be movably attached to the second wing 849. For example, the sheath 881 may be configured to translate along the second wing 849 in the direction of the longitudinal axis $A_L$ of the device 800. In particular, the sheath 881 may be positioned over the second wing 849 and configured to translate between the central portion 847 and a flange 887 positioned about the free end of the second wing 849. In this manner, movement of the sheath 881 relative to the second wing 849 may be limited by the central portion 847 and the flange 887. As shown, the second attachment side 812 also may include a pair of resistance means (which also may be referred to as a "resistance member," a "compressible member," a "biasing member") positioned over the second wing 849 at opposite ends of the sheath 881. In particular, a first resistance means 888 may be positioned between the central portion 847 and the sheath 881, and a second resistance means 889 may be positioned between the flange 887 and the sheath 881. The resistance means 888, 889 may be formed as ring-shaped members surrounding respective portions of the second wing 849. The resistance means 888, 889 may be formed of a compressible material, such as an elastomeric material. In this manner, the resistance means 888, 889 may be compressed when the sheath 881 moves relative to the second wing 849 and engages the respective resistance means 888, 889.

As shown, the slider 853 also may include a coupling member 857 positioned at least partially within the central opening 855 of the slider 853 and configured to engage the channel 883 of the sheath 881. In certain embodiments, as shown, the coupling member 857 may be formed as a pin configured for extending at least partially into the channel 883. In certain embodiments, the coupling member 857 may be formed of a rigid material, such as a rigid metal or a rigid plastic. In certain embodiments, the coupling member 857 may be formed separately from and attached to a remainder of the slider 853. For example, similar to the embodiment described above with respect to the device 600, the slider 853 may include a coupling aperture extending from an external surface of the slider 853 to the central opening 855 and configured to receive the coupling member 857 at least partially therein. In this manner, the coupling member 857 may be inserted through the coupling aperture and at least partially into the central opening of the slider 853 and the channel 883 of the sheath 881. The coupling member 857 then may be attached, either fixedly or removably, to the remainder of the slider 853. During assembly of the slider 853 to the second wing 849 and the sheath 881, the second wing 849 and the sheath 881 may be positioned at least partially within the central opening 855 of the slider 853, and the coupling member 857 may be passed through the coupling aperture and at least partially into the channel 883. In certain embodiments, the coupling member 857 may be press fit into the coupling aperture, and a portion of the coupling member 857 extending into the central opening 855 may be slidably received within the channel 883. As shown, the channel 883 may have a pair of closed ends positioned opposite one another along the length of the channel 883. In this manner, the connection between the coupling member 857 and the channel 883 may limit relative movement between the slider 853 and the sheath 881, the second wing 849, and the overall main body 854. It will be appreciated that the illustrated connection is merely one example and that other mechanisms for movably attaching the slider 853 to the main body 854 may be used.

The slider 853 may be configured to move relative to the main body 854 between an extended position (which also may be referred to as a "first position"), as shown in FIG. 8K, and a retracted position (which also may be referred to as a "second position"), as shown in FIG. 8L. In particular, the slider 853 may be configured to translate or otherwise slide along the sheath 881 and the second wing 849 between the extended position and the retracted position. In certain embodiments, the slider 853 may move along a linear path between the extended position and the retracted position, in the direction of the longitudinal axis $A_L$ of the device 800, while being guided by the shape of the channel 883 and/or the shape of the sheath 881 or the second wing 849. For example, the slider 853 may move along a linear path when the channel 883, the sheath 881, and/or the second wing 849 have a linear shape in the direction of the longitudinal axis $A_L$ of the device 800. In other embodiments, the slider 853 may move along a curved path between the extended position and the retracted position, in the direction of the longitudinal axis $A_L$ of the device 800, while being guided by the shape of the channel 883, the shape of the sheath 881, and/or the shape of the second wing 849. For example, the slider 853 may move along a curved path when the channel 883, the sheath 881, and/or the second wing 849 have a curved shape in the direction of the longitudinal axis $A_L$ of the device 800. As shown, the slider 853 may include a number of engagement features configured for securely engaging the respective vertebra. In certain embodiments, as shown, the engagement features may be one or more bone fasteners 859 extending from the slider 853 along the second side 844 of the second attachment side 812. The bone fasteners 859 may be formed as spikes or barbs, although other forms and types of bone fasteners 859 may be used for securely engaging the vertebrae. In certain embodiments, as shown, the bone fasteners 859 may be shaped and configured in a manner similar to the bone fasteners 851 extending form the first wing 848. Various configurations of the bone fasteners 859 of the slider 853 may be used. In certain embodiments, as shown, the bone fasteners 859 may be configured to engage the laminae of the respective vertebrae. In other embodiments, one or more of the bone fasteners 859 may be configured to engage the spinous processes, the laminae, and/or other portions of the respective vertebra.

It will be appreciated that the connection between the slider 853 and the main body 854 may be configured to allow portions of the second attachment side 812 to move relative to one another. As described above, the slider 853 may be movably attached to the main body 854, and thus the slider 853 may move relative to the central portion 847, the first wing 848, and the spacer slot 850 of the main body 854. In particular, the slider 853 may move toward the central portion 847, the first wing 848, and the spacer slot 850 when the slider 853 moves toward the retracted position, and the slider 853 may move away from the central portion 847, the first wing 848, and the spacer slot 850 when the slider 853 moves toward the extended position. As a result, the slider 853 and the first wing 848 may be configured to move toward one another and away from one another in the direction of the longitudinal axis $A_L$ of the device 800. In effect, the movable attachment between the slider 853 and the main body 854 may cause the second attachment side 812 to function as a slide which may be extended or retracted in the direction of the longitudinal axis $A_L$ of the device 800. In certain embodiments, as shown, the slider 833 of the first attachment side 811 may be formed as a mirror image of the slider 853 of the second attachment side 812. In other embodiments, the shape or configuration of the slider 833 of the first attachment side 811 may be different than the shape or configuration of the slider 853 of the second attachment side 812. Various configurations of the sliders 833, 853 and the features thereof may be used to allow for a desired range of movement of the corresponding vertebrae.

In certain embodiments, the device 800 may include means for preventing or inhibiting the movement of the slider 833 relative to the main body 834 of the first attachment side 811 and for preventing or inhibiting the movement of the slider 853 relative to the main body 854 of the second attachment side 812. FIGS. 8U and 8V illustrate an embodiment in which the device 800 includes a pair of securing means for preventing or inhibiting such movement of the sliders 833, 853. As shown, the first attachment side 811 may include a slider securing means 861 (which also may be referred to as a "fastener" or a "lock") configured for selectively preventing on inhibiting movement of the slider 833 relative to the main body 834. In this manner, the securing means 861 may selectively fix the slider 833 relative to the main body 834. In certain embodiments, as shown, the securing means 861 may be a fastener, such as a set screw, although other types of fasteners and other types of securing means may be used. As shown, the securing means 861 may be inserted into and at least partially through a securing aperture 862 defined in the slider 833. The securing aperture 862 may extend from an external surface of the slider 833 to the central opening 835 thereof and be configured to receive the securing means 861 at least partially therein. In certain embodiments, securing aperture 862 may be threaded, and the securing means 861 may threadably engage the securing aperture 862. When desired, the securing means 861 may be advanced at least partially through the securing aperture 862 and into the central opening 835 to engage the sheath 871. In certain instances, the securing means 861 may engage the sheath 871 such that relative movement between the slider 833 and the main body 834 is inhibited but not entirely prevented. In this manner, the engagement between the securing means 861 and the sheath 871 may generate a frictional force that opposes but does not prevent relative movement between the slider 833 and the main body 834. As an example, when the securing means 861 is threaded, the securing means 861 may be initially tightened against the sheath 871 by applying a lesser amount of torque which inhibits but does not prevent the relative movement. In other instances, the securing means 861 may engage the sheath 871 such that relative movement between the slider 833 and the main body 834 is prevented. In this manner, the engagement between the securing means 861 and the sheath 871 may generate a frictional force that prevents relative movement between the slider 833 and the main body 834. As an example, when the securing means 861 is threaded, the securing means 861 may be further tightened against the sheath 871 by applying a greater amount of torque which prevents the relative movement. Ultimately, the securing means 861 may be used to vary the degree of resistance to the relative movement between the slider 833 and the main body 834, thereby controlling the relative movement between the treated vertebrae, and/or the securing means 861 may be used to prevent relative movement between the slider 833 and the main body 834, thereby preventing relative movement between the treated vertebrae.

In a similar manner, the second attachment side 812 may include a slider securing means 865 (which also may be referred to as a "fastener" or a "lock") configured for selectively preventing on inhibiting movement of the slider 853 relative to the main body 854. In this manner, the securing means 865 may selectively fix the slider 853 relative to the main body 854. In certain embodiments, as shown, the securing means 865 may be a fastener, such as a set screw, although other types of fasteners and other types of securing means may be used. As shown, the securing means 865 may be inserted into and at least partially through a securing aperture 866 defined in the slider 853. The securing aperture 866 may extend from an external surface of the slider 853 to the central opening 855 thereof and be configured to receive the securing means 865 at least partially therein. In certain embodiments, securing aperture 866 may be threaded, and the securing means 865 may threadably engage the securing aperture 866. When desired, the securing means 865 may be advanced at least partially through the securing aperture 866 and into the central opening 855 to engage the sheath 881. In certain instances, the securing means 865 may engage the sheath 881 such that relative movement between the slider 853 and the main body 854 is inhibited but not entirely prevented. In this manner, the engagement between the securing means 865 and the sheath 881 may generate a frictional force that opposes but does not prevent relative movement between the slider 853 and the main body 854. As an example, when the securing means 865 is threaded, the securing means 865 may be initially tightened against the sheath 881 by applying a lesser amount of torque which inhibits but does not prevent the relative movement. In other instances, the securing means 865 may engage the sheath 881 such that relative movement between the slider 853 and the main body 854 is prevented. In this manner, the engagement between the securing means 865 and the sheath 881 may generate a frictional force that prevents relative movement between the slider 853 and the main body 854. As an example, when the securing means 865 is threaded, the securing means 865 may be further tightened against the sheath 881 by applying a greater amount of torque which prevents the relative movement. Ultimately, the securing means 865 may be used to vary the degree of resistance to the relative movement between the slider 853 and the main body 854, thereby controlling the relative movement between the treated vertebrae, and/or the securing means 865 may be used to prevent relative movement between the slider 853 and the main body 854, thereby preventing relative movement between the treated vertebrae.

It will be appreciated that the securing means 861, 865 of the device 800 may be used to control the relative movement between the treated vertebrae, when desired. In particular, the securing means 861, 865 may be used to increase or decrease resistance to the relative movement between the treated vertebrae or to prevent such relative movement. In this manner, the device 800 may be used as a dynamic device or a rigid device, with the ability to convert the device 800 between a dynamic configuration and a rigid configuration, as may be desired in certain applications. The securing means 861, 865 may be used to selectively adjust the resistance to relative movement between the treated vertebrae, or to prevent such relative movement, prior to implantation of the device 800, during initial implantation of the device 800 as a part of an initial surgery, or during a follow-up surgery.

In certain embodiments, the device 800 may include means for varying resistance to the relative movement between the slider 833 and the main body 834 of the first attachment side 811 over at least a portion of the range of motion of the slider 833 and for varying resistance to the relative movement between the main body 853 and the main body 854 of the second attachment side 812 over at least a portion of the range of motion of the slider 853. In this manner, the device 800 may vary the resistance to the relative movement between the treated vertebrae over at least a portion of the range of motion of the vertebrae allowed by the device 800. As described above, the device 800 may include the resistance means 878, 879 of the first attachment side 811 and the resistance means 888, 889 of the second attachment side 812, which may be formed of a compressible material. In this manner, when the coupling members 837, 857 engage the respective closed ends of the channels 873, 883, the coupling members 837, 857 may cause the respective sheath 871, 881 to translate relative to the respective second wing 829, 849. Such translation of the sheath 871, 881 relative to the second wing 829, 849 may cause the respective resistance means 878, 879, 888, 889 to be compressed by the sheath 871, 881. As a result, the compressible resistance means 878, 879, 888, 889 may be used to increase resistance to the relative movement between the treated vertebrae over at least a portion of the range of motion of the vertebrae allowed by the device 800. In this manner, the device 800 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 878, 879, 888, 889 may be selected to provide a desired degree of resistance to the relative motion of the treated vertebrae.

FIGS. 8W and 8X illustrate an example implantation of the device 800 with respect to a first vertebra $V_1$ and an adjacent second vertebra $V_2$. As shown, the first attachment side 811 and the second attachment side 812 may be positioned relative to the vertebrae $V_1$, $V_2$ such that the spacer 830 is positioned between a first spinous process $SP_1$ of the first vertebra $V_1$ and a second spinous process $SP_2$ of the second vertebra $V_2$. In this manner, the spacer 830 may limit a minimum spacing between the spinous processes $SP_1$, $SP_2$. Additionally, the first attachment side 811 and the second attachment side 812 may be positioned relative to the vertebrae $V_1$, $V_2$ such that the first wing 828 and the slider 833 of the first attachment side 811 and the first wing 848 and the slider 853 of the second attachment side 812 engage a first lamina $L_1$ of the first vertebra $V_1$ and a second lamina $L_2$ of the second vertebra $V_2$. In this manner, the respective bone fasteners 831, 839 of the first attachment side 811 and the respective bone fasteners 851, 859 of the second attachment side 812 may penetrate and securely engage the laminae $L_1$, $L_2$. Accordingly, the implanted device 800 may stabilize the vertebrae $V_1$, $V_2$, although the device 800 may allow relative movement of the vertebrae $V_1$, $V_2$. In particular, the sliders 833, 853 of the device 800 may allow relative movement of the vertebrae $V_1$, $V_2$ in sagittal plane of the patient, thereby allowing flexion and extension of the treated segment of the spine. It will be appreciated that the configuration of the sliders 833, 853, the coupling members 837, 857, the channels 873, 883, and any resistance means of the device 800 may be varied to allow a desired range of motion in the sagittal plane. Further, the material from which the various components and features of the first attachment side 811 and the second attachment side 812 are formed may be selected to achieve the desired range of motion. In certain embodiments, portions of the first attachment side 811 and the second attachment side 812 may be formed of titanium, although other suitable metals, polymers, or other materials may be used in other embodiments. Meanwhile, the device 800 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 800 and the disc D. In other embodiments in which the native disc D is removed, an interbody device, such as a cage or a spacer, may be implanted within the disc space DS (i.e., the intervertebral space) and the loads carried by the treated spinal segment may be shared by the device 800 and the interbody device. As described above, the device 800 may be used in conjunction with other additional hardware, such that the device 800 and the additional hardware collectively stabilize the treated segment of the spine and share loads carried thereby. It will be appreciated that the foregoing description and the corresponding drawings are merely examples of the device 800 and that other configurations and modifications may be made.

FIGS. 9A-9M illustrate an interspinous process device 900 (which also may be referred to as a "dynamic interspinous process device," a "convertible dynamic interspinous process device," an "interspinous process spacing device," an "interspinous process stabilization device," an "ISP device," or simply a "device") according to one or more embodiments of the disclosure. The interspinous process device 900 may be configured for implantation relative to a first vertebra and an adjacent second vertebra, as described below, specifically with reference to FIGS. 9L and 9M. In particular, a portion of the interspinous process device 900 may be positioned between the spinous process of the first vertebra and the spinous process of the second vertebra, while one or more other portions of the interspinous process device 900 engage the spinous processes, the laminae, and/or other portions of the respective vertebra. As described below, the interspinous process device 900 may allow a desired range of relative movement between the treated vertebrae, which may be desirable in certain treatment applications. The interspinous process device 900 may be used for treatment of various spinal conditions, such as those described above, to stabilize the treated vertebrae while allowing controlled motion of the vertebrae in one or more anatomical directions and inhibiting motion of the vertebrae in one or more other anatomical directions. Ultimately, the interspinous process device 900, itself or in combination with additional hardware, may provide the structural support necessary to restore and maintain normal spacing and alignment of the treated vertebrae while avoiding certain drawbacks presented by existing interspinous process devices.

The interspinous process device 900 may have an elongated shape defining a longitudinal axis $A_L$, a first transverse axis $A_{T1}$ that is perpendicular to the longitudinal axis $A_L$, and a second transverse axis $A_{T2}$ that is perpendicular to each of the longitudinal axis $A_L$ and the first transverse axis $A_{T1}$. As shown, the device 900 may include a first end 901 and a second end 902 disposed opposite the first end 901 in the direction of the longitudinal axis $A_L$. As described below, the device 900 may be implanted with the longitudinal axis $A_L$ extending in a direction substantially parallel to the sagittal plane and the coronal plane of the patient and transverse to the transverse plane of the patient. In this manner, depending on the orientation of the device 900 upon implantation thereof, one of the first end 901 and the second end 902 of the device 900 may be referred to as a the "superior end" of the device 900, and the other of the first end 901 and the second end 902 of the device 900 may be referred to as the "inferior end" of the device 900. The device 900 also may include a first side 903 extending from the first end 901 to the second end 902, and a second side 904 disposed opposite the first side 903 in the direction of the first transverse axis $A_{T1}$ and extending from the first end 901 to the second end 902. The device 900 may be implanted with the first transverse axis $A_{T1}$ extending in a direction substantially parallel to the coronal plane and the transverse plane of the patient and transverse to the sagittal plane of the patient. In this manner, depending on the orientation of the device 900 upon implantation thereof, one of the first side 903 and the second side 904 of the device 900 may be referred to as a the "right side" of the device 900, and the other of the first side 903 and the second side 904 of the device 900 may be referred to as the "left side" of the device 900. The device 900 further may include a third side 905 extending from the first end 901 to the second end 902 and from the first side 903 to the second side 904, and a fourth side 906 disposed opposite the third side 905 in the direction of the second transverse axis $A_{T2}$ and extending from the first end 901 to the second end 902 and from the first side 903 to the second side 904. The device 900 may be implanted with the second transverse axis $A_{T2}$ extending in a direction substantially parallel to the sagittal plane and the transverse plane of the patient and transverse to the coronal plane of the patient. As described below, the device 900 may be oriented upon implantation thereof such that the third side 905 faces posteriorly and the fourth side 906 faces anteriorly with respect to the patient. In this manner, the third side 905 may be referred to as the "posterior side" of the device 900, and the fourth side 906 may be referred to as the "anterior side" of the device 900. The device 900 may have an overall "length" extending from the first end 901 to the second end 902 in the direction of the longitudinal axis $A_L$, an overall "width" extending from the first side 903 to the second side 904 in the direction of the first transverse axis $A_{T1}$, and an overall "height" extending from the third side 905 to the fourth side 906 in the direction of the second transverse axis $A_{T2}$. Further, various components and features of the device 900 may have a respective "length" in the direction of the longitudinal axis $A_L$, a respective "width" in the direction of the first transverse axis $A_{T1}$, and a respective "height" in the direction of the second transverse axis $A_{T2}$.

As shown, the interspinous process device 900 may include a first attachment side 911 (which also may be referred to as a "first attachment portion," a "first attachment assembly," or a "first plate") and a second attachment side 912 (which also may be referred to as a "second attachment portion," a "second attachment assembly," or a "second plate") configured for removably attaching to one another via a securing means 913. During use of the device 900, one of the first attachment side 911 and the second attachment side 912 may be disposed, at least partially, along the right side of the patient's spine, and the other of the first attachment side 911 and the second attachment side 912 may be disposed, at least partially, along the right side of the patient's spine. It will be appreciated that the first attachment side 911 and the second attachment side 912 may include corresponding features that are mirror images of one another, although certain differences between the first attachment side 911 and the second attachment side 912 may exist, as described below. In certain embodiments, the first attachment side 911 and the second attachment side 912 may be formed of a metal, such as titanium or stainless steel, although other suitable materials, such as polyether ether ketone (PEEK), other polymers, or composites, may be used.

The first attachment side 911 may have a first end 921, a second end 922 disposed opposite the first end 921, a first side 923 (which also may be referred to as an "interior side"), a second side 924 (which also may be referred to as an "exterior side") disposed opposite the first side 923, a third side 925 (which also may be referred to as an "posterior side"), and a fourth side 926 (which also may be referred to as an "anterior side") disposed opposite the third side 925. As shown, the first attachment side 911 may include a central portion 927 and a pair of wings 928, 929 disposed on opposite sides of the central portion 927. In particular, the first wing 928 may extend from the central portion 927 to the first end 921 of the first attachment side 911, and the second wing 929 may extend from the central portion 927 to the second end 922 of the first attachment side 911. In certain embodiments, the wings 928, 929 may extend in opposite directions from the central portion 927 and may be formed as mirror images of one another. In other embodiments, as shown, the wings 928, 929 may extend in opposite directions from the central portion 927, but the first wing 928 may have a different shape or configuration than the second wing 929 such that the wings 928, 929 are not mirror images of one another. In certain embodiments, the wings 928, 929 may be shaped and configured in a manner similar to any one of the wing embodiments described and/or shown in the Prior Applications. Various other configurations of the wings 928, 929 may be used.

The first attachment side 911 also may include a spacer 930 extending from the first side 923 thereof. During use of the device 900, the spacer 930 may be positioned between the spinous processes of the respective vertebrae. In certain embodiments, as shown, the spacer 930 may extend from the central portion 927 of the first attachment side 911 and be integrally formed therewith. In other embodiments, the spacer 930 may be separately formed from and attached to the central portion 927 via an attachment mechanism. The first attachment side 911 further may include a number of engagement features configured for securely engaging the respective vertebrae. In certain embodiments, as shown, the engagement features may be one or more bone fasteners 931 extending from the first side 923 of the first attachment side 911. The bone fasteners 931 may be formed as spikes or barbs, although other forms and types of bone fasteners 931 may be used for securely engaging the vertebrae. In certain embodiments, one or more of the bone fasteners 931 may extend form the first wing 928, and one or more bone fasteners 931 may extend from the second wing 929. In certain embodiments, the first wing 928 may include a first number of bone fasteners 931 extending therefrom, and the second wing 929 may include a second number of bone fasteners 931 extending therefrom, wherein the first number is different than the second number. In this manner, the degree of engagement between the bone fasteners 931 of the first wing 928 and the corresponding vertebra may be different from the degree of engagement between the bone fasteners 931 of the second wing 929 and the corresponding vertebra. Such an arrangement may facilitate relative movement of the treated vertebrae, while minimizing certain stresses induced in the device 900. In certain embodiments, one of the first wing 928 and the second wing 929 may not include any bone fasteners 931 extending therefrom, and the other of the first wing 928 and the second wing 929 may include one or more of the bone fasteners 931 extending therefrom. Such an arrangement also may facilitate relative movement of the treated vertebrae, while minimizing certain stresses induced in the device 900. Various configurations of the bone fasteners 931 of the first attachment side 911 may be used. In certain embodiments, as shown, the bone fasteners 931 may be configured to engage the laminae of the respective vertebrae. In other embodiments, one or more of the bone fasteners 931 may be configured to engage the spinous processes, the laminae, and/or other portions of the respective vertebrae. As shown, the first attachment side 911 also may include an instrument engagement aperture 932 configured for receiving a portion of and cooperating with an instrument used for positioning the first attachment side 911 during implantation of the device 900. Example instruments for implantation of the device 900 are described in the Prior Applications.

In a similar manner, the second attachment side 912 may have a first end 941, a second end 942 disposed opposite the first end 941, a first side 943 (which also may be referred to as an "exterior side"), a second side 944 (which also may be referred to as an "interior side") disposed opposite the first side 943, a third side 945 (which also may be referred to as an "posterior side"), and a fourth side 946 (which also may be referred to as an "anterior side") disposed opposite the third side 945. As shown, the second attachment side 912 may include a central portion 947 and a pair of wings 948, 949 disposed on opposite sides of the central portion 947. In particular, the first wing 948 may extend from the central portion 947 to the first end 941 of the second attachment side 912, and the second wing 949 may extend from the central portion 947 to the second end 942 of the second attachment side 912. In certain embodiments, the wings 948, 949 may extend in opposite directions from the central portion 947 and may be formed as mirror images of one another. In other embodiments, as shown, the wings 948, 949 may extend in opposite directions from the central portion 947, but the first wing 948 may have a different shape or configuration than the second wing 949 such that the wings 948, 949 are not mirror images of one another. In certain embodiments, the wings 948, 949 may be shaped and configured in a manner similar to any one of the wing embodiments described and/or shown in the Prior Applications. Various other configurations of the wings 948, 949 may be used.

The second attachment side 912 also may include a spacer slot 950 extending through the second attachment side 912 from the first side 943 to the second side 944 thereof. During use of the device 900, the spacer slot 950 may be configured to receive the spacer 930 of the first attachment side 911 therethrough, as shown. In certain embodiments, as shown, the spacer slot 950 may be defined in the central portion 947 of the second attachment side 912 and may extend to the fourth side 946 thereof, although other positions of the spacer slot 950 may be used. The second attachment side 912 further may include a number of engagement features configured for securely engaging the respective vertebrae. In certain embodiments, as shown, the engagement features may be one or more bone fasteners 951 extending from the second side 944 of the second attachment side 912. The bone fasteners 951 may be formed as spikes or barbs, although other forms and types of bone fasteners 951 may be used for securely engaging the vertebrae. In certain embodiments, one or more of the bone fasteners 951 may extend form the first wing 948, and one or more bone fasteners 951 may extend from the second wing 949. In certain embodiments, the first wing 948 may include a first number of bone fasteners 951 extending therefrom, and the second wing 959 may include a second number of bone fasteners 951 extending therefrom, wherein the first number is different than the second number. In this manner, the degree of engagement between the bone fasteners 951 of the first wing 948 and the corresponding vertebra may be different from the degree of engagement between the bone fasteners 951 of the second wing 949 and the corresponding vertebra. Such an arrangement may facilitate relative movement of the treated vertebrae, while minimizing certain stresses induced in the device 900. In certain embodiments, one of the first wing 948 and the second wing 949 may not include any bone fasteners 951 extending therefrom, and the other of the first wing 948 and the second wing 949 may include one or more of the bone fasteners 951 extending therefrom. Such an arrangement also may facilitate relative movement of the treated vertebrae, while minimizing certain stresses induced in the device 900. Various configurations of the bone fasteners 951 of the second attachment side 912 may be used. In certain embodiments, as shown, the bone fasteners 951 may be configured to engage the laminae of the respective vertebrae. In other embodiments, one or more of the bone fasteners 951 may be configured to engage the spinous processes, the laminae, and/or other portions of the respective vertebrae. As shown, the second attachment side 912 also may include a securing aperture 952 configured to receive at least a portion of and cooperate with the securing means 913 for selectively fixing the first attachment side 911 and the second attachment side 912 relative to one another. The securing aperture 952 also may be configured for receiving a portion of and cooperating with an instrument used for positioning the second attachment side 912 during implantation of the device 900. Example instruments for implantation of the device 900 are described in the Prior Applications.

The securing means 913 may be configured for selectively fixing the first attachment side 911 and the second attachment side 912 relative to one another. In certain embodiments, as shown, the securing means 913 may be a fastener, such as a set screw, although other types of fasteners and other types of securing means may be used. As shown, the securing means may be inserted into and at least partially through the securing aperture 952 of the second attachment side 912. In this manner, the securing means 913 may be advanced through the securing aperture 952 until the securing means 913 engages the spacer 930 of the first attachment side 911 positioned within the spacer slot 950 of the second attachment side 912. Upon desired positioning of the first attachment side 911 and the second attachment side 912 with respect to the corresponding vertebrae of the patient, the securing means 913 may be tightened to maintain the spacing and orientation of the first attachment side 911 and the second attachment side 912 relative to one another and relative to the corresponding vertebrae. In certain embodiments, the securing means 913 may be formed of a metal, such as titanium or stainless steel, although other suitable materials, such as polyether ether ketone (PEEK), other polymers, or composites, may be used.

As described above, the device 900 may be configured to allow relative movement of the treated vertebrae upon implantation of the device 900. In particular, the device 900 may allow relative movement of the treated vertebrae in the sagittal plane of the patient, thereby allowing flexion and extension of the treated segment of the spine, while substantially preventing or at least inhibiting relative movement of the treated vertebrae in the coronal plane and the transverse plane of the patient. As shown, the first attachment side 911 and the second attachment side 912 each may include one or more features configured to facilitate such relative movement of the treated vertebrae. In particular, the first attachment side 911 may include one or more slots 933

(which also may be referred to as a "dynamic slot," a "cutout," an "opening," or a "slit") defined therein and configured to allow relative movement of portions of the first attachment side 911. In certain embodiments, as shown, the first attachment side 911 may include a single slot 933. In certain embodiments, the slot 933 may be defined between the central portion 927 and an arm 934 of the first wing 928. In other embodiments, the first attachment side 911 may include a pair of the slots 933 spaced apart from one another in the direction of the longitudinal axis $A_L$ of the device 900. For example, according to embodiments in which the first wing 928 and the second wing 929 are mirror images of one another, a first slot 933 may be defined between the central portion 927 and the arm 934 of the first wing 928, and a second slot 933 may be defined between the central portion 927 and a corresponding arm of the second wing 929. Each slot 933 may have an elongated shape extending in the direction of the second transverse axis $A_{T2}$ of the device 900. In certain embodiments, as shown, each slot 933 may extend from the first side 923 to the second side 924 of the first attachment side 911. Further, in certain embodiments, as shown, each slot 933 may extend from the third side 925 of the first attachment side 911 toward, but not to, the fourth side 926 of the first attachment side 911. In other words, the slot 933 may be open along the third side 925 and may terminate at a location spaced apart from the fourth side 926. In certain embodiments, the slot 933 may have a straight shape extending in a linear manner in the direction of the second transverse axis $A_{T2}$ of the device 900. In other embodiments, the slot 933 may have a curved or otherwise contoured shape extending transverse to the second transverse axis $A_{T2}$ of the device 900. In certain embodiments, the slot 933 may have a first portion 935 positioned closer to the third side 925 of the first attachment side 911 and a second portion 936 positioned closer to the fourth side 926 of the first attachment side 911. In certain embodiments, as shown, the first portion 935 may be larger than the second portion 936 in the direction of the longitudinal axis $A_L$ of the device 900. In certain embodiments, the portions of the arm 934 of the first wing 928 and the central portion 927 defining the first portion 935 of the slot 933 may be threaded and configured to engage a threaded fixation member, as described below. In certain embodiments, the portions of the arm 934 of the first wing 928 and the central portion 927 defining the second portion 936 of the slot 933 may include one or more grooves 937 configured to receive a resistance means, as described below.

It will be appreciated that the one or more slots 933 may be configured to allow portions of the first attachment side 911 to move relative to one another. In particular, the illustrated slot 933 may be configured to allow a portion of the first wing 928 to move toward the central portion 927 and the spacer 930, in the direction of the longitudinal axis $A_L$ of the device 900, as the arm 934 of the first wing 928 and the central portion 927 compress the slot 933, and also to allow a portion of the first wing 928 to move away from the central portion 927 and the spacer 930, in the direction of the longitudinal axis $A_L$ of the device 900, as the arm 934 of the first wing 928 and the central portion 927 expand the slot 933. In a similar manner, according to embodiments in which another slot 933 is provided between an arm of the second wing 929 and the central portion 927, the slot 933 may be configured to allow a portion of the second wing 929 to move toward the central portion 927 and the spacer 930, in the direction of the longitudinal axis $A_L$ of the device 900, as the arm of the second wing 929 and the central portion 927 compress the slot 933, and also to allow a portion of the second wing 929 to move away from the central portion 927 and the spacer 930, in the direction of the longitudinal axis $A_L$ of the device 900, as the arm of the second wing 929 and the central portion expand the slot 933. As a result, the first wing 928 and the second wing 929 may be configured to move toward one another as one or both of the slots 933 are compressed, and to move away from one another as one or both of the slots 933 are expanded. It will be appreciated that, during such movement of the wings 928, 929, one or more regions of the first attachment side 911 surrounding the slots 933, such as the regions of the respective wings 928, 929 surrounding the terminal ends of the slots 933, may flex or may be compressed to accommodate the compression or expansion of the slots 933. In effect, the slots 933 may cause the first attachment side 911 to function as a spring which may be compressed or extended in the direction of the longitudinal axis $A_L$ of the device 900 but has a natural tendency to return to a natural state as shown in FIG. 9E.

In a similar manner, the second attachment side 912 may include one or more slots 953 (which also may be referred to as a "dynamic slot," a "cutout," an "opening," or a "slit") defined therein and configured to allow relative movement of portions of the second attachment side 912. In certain embodiments, as shown, the second attachment side 912 may include a single slot 953. In certain embodiments, the slot 953 may be defined between the central portion 947 and an arm 954 of the first wing 948. In other embodiments, the second attachment side 912 may include a pair of the slots 953 spaced apart from one another in the direction of the longitudinal axis $A_L$ of the device 900. For example, according to embodiments in which the first wing 948 and the second wing 949 are mirror images of one another, a first slot 953 may be defined between the central portion 947 and the arm 954 of the first wing 948, and a second slot 953 may be defined between the central portion 947 and a corresponding arm of the second wing 949. Each slot 953 may have an elongated shape extending in the direction of the second transverse axis $A_{T2}$ of the device 900. In certain embodiments, as shown, each slot 953 may extend from the first side 943 to the second side 944 of the second attachment side 912. Further, in certain embodiments, as shown, each slot 953 may extend from the third side 925 of the second attachment side 912 toward, but not to, the fourth side 926 of the second attachment side 912. In other words, the slot 953 may be open along the third side 925 and may terminate at a location spaced apart from the fourth side 926. In certain embodiments, the slot 953 may have a straight shape extending in a linear manner in the direction of the second transverse axis $A_{T2}$ of the device 900. In other embodiments, the slot 953 may have a curved or otherwise contoured shape extending transverse to the second transverse axis $A_{T2}$ of the device 900. In certain embodiments, the slot 953 may have a first portion 955 positioned closer to the third side 925 of the second attachment side 912 and a second portion 956 positioned closer to the fourth side 926 of the second attachment side 912. In certain embodiments, as shown, the first portion 955 may be larger than the second portion 956 in the direction of the longitudinal axis $A_L$ of the device 900. In certain embodiments, the portions of the arm 954 of the first wing 948 and the central portion 947 defining the first portion 955 of the slot 953 may be threaded and configured to engage a threaded fixation member, as described below. In certain embodiments, the portions of the arm 954 of the first wing 948 and the central portion 947 defining the second portion 956 of the slot 953 may include one or more grooves 957 configured to receive a resistance means, as described below.

It will be appreciated that the one or more slots 953 may be configured to allow portions of the second attachment side 912 to move relative to one another. In particular, the illustrated slot 953 may be configured to allow a portion of the first wing 948 to move toward the central portion 947 and the spacer slot 950, in the direction of the longitudinal axis $A_L$ of the device 900, as the arm 954 of the first wing 948 and the central portion 947 compress the slot 953, and also to allow a portion of the first wing 948 to move away from the central portion 947 and the spacer slot 950, in the direction of the longitudinal axis $A_L$ of the device 900, as the arm 954 of the first wing 948 and the central portion 947 expand the slot 953. In a similar manner, according to embodiments in which another slot 953 is provided between an arm of the second wing 949 and the central portion 947, the slot 953 may be configured to allow a portion of the second wing 949 to move toward the central portion 947 and the spacer slot 950, in the direction of the longitudinal axis $A_L$ of the device 900, as the arm of the second wing 949 and the central portion 947 compress the slot 953, and also to allow a portion of the second wing 949 to move away from the central portion 947 and the spacer slot 950, in the direction of the longitudinal axis $A_L$ of the device 900, as the arm of the second wing 949 and the central portion 947 expand the slot 953. As a result, the first wing 948 and the second wing 949 may be configured to move toward one another as one or both of the slots 953 are compressed, and to move away from one another as one or both of the slots 953 are expanded. It will be appreciated that, during such movement of the wings 948, 949, one or more regions of the second attachment side 912 surrounding the slots 953, such as the regions of the respective wings 948, 949 surrounding the terminal ends of the slots 953, may flex or may be compressed to accommodate the compression or expansion of the slots 953. In effect, the slots 953 may cause the second attachment side 912 to function as a spring which may be compressed or extended in the direction of the longitudinal axis $A_L$ of the device 900 but has a natural tendency to return to a natural state as shown in FIG. 9F. In certain embodiments, as shown, the slots 933 of the first attachment side 911 may be formed as a mirror image of the slots 953 of the second attachment side 912. In other embodiments, the number, shape, or configuration of the slots 933 of the first attachment side 911 may be different than the number, shape, or configuration of the slots 953 of the second attachment side 912. Various configurations of the slots 933 and the slots 953 may be used to allow for a desired range of movement of the corresponding vertebrae.

In certain embodiments, the device 900 may include means for varying resistance to the relative movement between the first wing 928 and the second wing 929 of the first attachment side 911 over at least a portion of the range of motion of the wings 928, 929 and for varying resistance to the relative movement between the first wing 948 and the second wing 949 of the second attachment side 912 over at least a portion of the range of motion of the wings 948, 949. In this manner, the device 900 may vary the resistance to the relative movement between the treated vertebrae over at least a portion of the range of motion of the vertebrae allowed by the device 100. FIGS. 9F and 9G illustrate an embodiment in which the device 900 includes a pair of resistance means for varying resistance to the relative movement between the wings 928, 929 and between the wings 948, 949. As shown, the first attachment side 911 may include a resistance means 961 (which also may be referred to as a "resistance insert," a "resistance member" or a "biasing member") configured for varying resistance to movement of the first wing 928 relative to the central portion 927 and the second wing 929 over at least a portion of the range of motion of these features as may be allowed by the slot 933. In certain embodiments, as shown, the resistance means 961 may be an elongated insert configured to be inserted into and retained within the slot 933. In certain embodiments, the resistance means 961 may be inserted into the second portion 936 of the slot 933 and retained therein by the grooves 937 thereof. In certain embodiments, the resistance means 961 may be press-fit into the second portion 936 of the slot 933. In certain embodiments, the resistance means 961 may be removably received within the slot 933, such that the resistance means 961 may be placed therein when resistance is desired and may be removed therefrom when resistance is not desired. In other embodiments, the resistance means 961 may be securely fixed within the slot 933, such that the resistance means 961 is not removable therefrom. In certain embodiments, the resistance means 961 may be formed of a compressible material or a resiliently deformable material, such as a biocompatible polymer or other suitable material, which may be compressed by the relative movement of surrounding portions of the first attachment side 911 but may have a natural tendency to return to a natural state when compression forces are removed. It will be appreciated that a durometer of the compressible material or resiliently deformable material may be selected to provide a desired resistance to the relative movement of surrounding portions of the first attachment side 911. According to the illustrated embodiment, the resistance means 961 may be configured to resist movement of the first wing 928 toward the central portion 927. In particular, as the first wing 928 moves toward the central portion 927 and the slot 933 is compressed, the resistance means 961 may be compressed, thereby resisting, but not preventing, further movement of the first wing 928 toward the central portion 927. Further, the resistance means 961 may provide a biasing force acting on the portions of the first attachment side 911 surrounding the slot 933, biasing the first wing 928 and the central portion 927 toward their home or natural position and the slot 933 to its home or natural state.

In a similar manner, the second attachment side 912 may include a resistance means 962 (which also may be referred to as a "resistance insert," a "resistance member" or a "biasing member") configured for varying resistance to movement of the first wing 948 relative to the central portion 947 and the second wing 949 over at least a portion of the range of motion of these features as may be allowed by the slot 953. In certain embodiments, as shown, the resistance means 962 may be an elongated insert configured to be inserted into and retained within the slot 953. In certain embodiments, the resistance means 962 may be inserted into the second portion 956 of the slot 953 and retained therein by the grooves 957 thereof. In certain embodiments, the resistance means 962 may be press-fit into the second portion 956 of the slot 953. In certain embodiments, the resistance means 962 may be removably received within the slot 953, such that the resistance means 962 may be placed therein when resistance is desired and may be removed therefrom when resistance is not desired. In other embodiments, the resistance means 962 may be securely fixed within the slot 953, such that the resistance means 962 is not removable therefrom. In certain embodiments, the resistance means 962 may be formed of a compressible material or a resiliently deformable material, such as a biocompatible polymer or other suitable material, which may be compressed by the relative movement of surrounding portions of the second attachment side 912 but may have a natural tendency to return to a natural state when compression forces are removed. It will be appreciated that a durometer of the compressible material or resiliently deformable material may be selected to provide a desired resistance to the relative movement of surrounding portions of the second attachment side 912. According to the illustrated embodiment, the resistance means 962 may be configured to resist movement of the first wing 948 toward the central portion 947. In particular, as the first wing 948 moves toward the central portion 947 and the slot 953 is compressed, the resistance means 962 may be compressed, thereby resisting, but not preventing, further movement of the first wing 948 toward the central portion 947. Further, the resistance means 962 may provide a biasing force acting on the portions of the second attachment side 912 surrounding the slot 953, biasing the first wing 948 and the central portion 947 toward their home or natural position and the slot 953 to its home or natural state.

It will be appreciated that the resistance means 961, 962 of the device 900 may be used to vary resistance to the relative movement between the treated vertebrae, when desired. In particular, the resistance means 961, 962 may be used to increase resistance to the relative movement between the treated vertebrae over at least a portion of the range of motion of the vertebrae allowed by the device 900. In this manner, the device 900 advantageously may function in a manner similar to a native disc, providing minimal resistance to initial relative movement in a direction in the sagittal plane and increasing resistance to further relative movement in the same direction. It will be appreciated that size, shape, configuration, and/or material of the resistance means 961, 962 may be selected to provide a desired degree of resistance to the relative motion of the treated vertebrae.

In certain embodiments, the device 900 may include means for preventing or inhibiting the relative movement between the first wing 928 and the second wing 929 of the first attachment side 911 and for preventing or inhibiting the relative movement between the first wing 948 and the second wing 949 of the second attachment side 912. In this manner, the device 900 may prevent or inhibit the relative movement between the treated vertebrae. FIGS. 9F and 9G illustrate embodiments in which the device 900 includes one or more fixation means for preventing or inhibiting the relative movement between the wings 928, 929 and between the wings 948, 949. As shown, the first attachment side 911 may include one or more fixation means 971 (which also may be referred to as a "fixation insert," a "fixation member," a "fastener," or a "lock") configured for preventing or inhibiting movement of the first wing 928 relative to the central portion 927 and the second wing 929 as may be allowed by the slot 933. In certain embodiments, the fixation means 971 may be removably attached to the central portion 927 and/or the first wing 928. In certain embodiments, as shown, the fixation means 971 may be formed as a fastener, such as a threaded fastener, configured to be received within the first portion 935 of the slot 933. In this manner, the fixation means 971 may engage the respective threaded portions of the arm 934 of the first wing 928 and the central portion 927. In certain embodiments, the fixation means 971 may have a reverse angle thread for threadably engaging and retaining the mating threaded portions of the arm 934 of the first wing 928 and the central portion 927. In certain embodiments, the fixation means 971 also may engage a mating portion of the resistance means 961, as shown. Other types and configurations of the fixation means 971 may be used herein. When positioned within the first portion 935 of the slot 933, the fixation means 971 may prevent or inhibit compression and expansion of at least a portion of the slot 933.

In a similar manner, the second attachment side 912 may include one or more fixation means 972 (which also may be referred to as a "fixation insert," a "fixation member," a "fastener," or a "lock") configured for preventing or inhibiting movement of the first wing 948 relative to the central portion 947 and the second wing 949 as may be allowed by the slot 953. In certain embodiments, the fixation means 972 may be removably attached to the central portion 947 and/or the first wing 948. In certain embodiments, as shown, the fixation means 972 may be formed as a fastener, such as a threaded fastener, configured to be received within the first portion 955 of the slot 953. In this manner, the fixation means 972 may engage the respective threaded portions of the arm 954 of the first wing 948 and the central portion 947. In certain embodiments, the fixation means 972 may have a reverse angle thread for threadably engaging and retaining the mating threaded portions of the arm 954 of the first wing 948 and the central portion 947. In certain embodiments, the fixation means 972 also may engage a mating portion of the resistance means 962, as shown. Other types and configurations of the fixation means 972 may be used herein. When positioned within the first portion 955 of the slot 953, the fixation means 972 may prevent or inhibit compression and expansion of at least a portion of the slot 953.

It will be appreciated that the fixation means 971, 972 of the device 900 may be used to control the relative movement between the treated vertebrae, when desired. In particular, the fixation means 971, 972 may be used to prevent or inhibit relative movement between the treated vertebrae. In this manner, the device 900 may be used as a dynamic device or a rigid device, with the ability to convert the device 900 between a dynamic configuration and a rigid configuration, as may be desired in certain applications. The fixation means 971, 972 may be used to convert the device 900 between the dynamic configuration and the rigid configuration prior to implantation of the device 900, during initial implantation of the device 100 as a part of an initial surgery, or during a follow-up surgery.

In certain embodiments, the device 900 may include additional means for resisting deformation of the first attachment side 911 and the second attachment side 912 during loading of the device 900. FIGS. 9H-9K illustrate an embodiment in which the device 900 includes a pair of resistance means for resisting deformation of the attachment sides 911, 921 during torsion or lateral bending of the device 900. As shown, the first attachment side 911 may include a resistance means 981 (which also may be referred to as a "resistance band," a "resistance member" or a "biasing member") configured for resisting deformation of the first wing 928 relative to the central portion 927 during torsional or lateral loading of the device 900. In certain embodiments, as shown, the resistance means 981 may be an elongated band positioned within the slot 933 and attached to the arm 934 of the first wing 928 and the central portion 927 at respective ends of the resistance means 981. In this manner, the resistance means 981 may extend across the slot in the direction of the longitudinal axis $A_L$ of the device 900. In certain embodiments, the resistance means 981 may be formed of a flexible material. In this manner, the resistance means 981 may be configured to bend or flex during torsional or lateral loading of the device 900 but may limit a degree of deformation of the arm 934 of the first wing 928 relative to the central portion 927 during such loading. In a similar manner, the second attachment side 912 may include a resistance means 982 (which also may be referred to as a "resistance band," a "resistance member" or a "biasing member") configured for resisting deformation of the first wing 948 relative to the central portion 947 during torsional or lateral loading of the device 900. In certain embodiments, as shown, the resistance means 982 may be an elongated band positioned within the slot 953 and attached to the arm 954 of the first wing 948 and the central portion 947 at respective ends of the resistance means 982. In this manner, the resistance means 982 may extend across the slot in the direction of the longitudinal axis $A_L$ of the device 900. In certain embodiments, the resistance means 982 may be formed of a flexible material. In this manner, the resistance means 982 may be configured to bend or flex during torsional or lateral loading of the device 900 but may limit a degree of deformation of the arm 954 of the first wing 948 relative to the central portion 947 during such loading.

FIGS. 9L and 9M illustrate an example implantation of the device 900 with respect to a first vertebra $V_1$ and an adjacent second vertebra $V_2$. As shown, the first attachment side 911 and the second attachment side 912 may be positioned relative to the vertebrae $V_1$, $V_2$ such that the spacer 930 is positioned between a first spinous process $SP_1$ of the first vertebra $V_1$ and a second spinous process $SP_2$ of the second vertebra $V_2$. In this manner, the spacer 930 may limit a minimum spacing between the spinous processes $SP_1$, $SP_2$. Additionally, the first attachment side 911 and the second attachment side 912 may be positioned relative to the vertebrae $V_1$, $V_2$ such that the respective wings 928, 929 of the first attachment side 911 and the respective wings 948, 949 of the second attachment side 912 engage a first lamina $L_1$ of the first vertebra $V_1$ and a second lamina $L_2$ of the second vertebra $V_2$. In this manner, the respective bone fasteners 931 of the first attachment side 911 and the respective bone fasteners 951 of the second attachment side 912 may penetrate and securely engage the laminae $L_1$, $L_2$. Accordingly, the implanted device 900 may stabilize the vertebrae $V_1$, $V_2$, although the device 900 may allow relative movement of the vertebrae $V_1$, $V_2$. In particular, the slots 933, 953 of the device 900 may allow relative movement of the vertebrae $V_1$, $V_2$ in sagittal plane of the patient, thereby allowing flexion and extension of the treated segment of the spine. It will be appreciated that the configuration of the slots 933, 953 may be varied, for example, by varying the number, size, and/or shape the slots 933, 953 to allow a desired range of motion in the sagittal plane. Further, the material from which the first attachment side 911 and the second attachment side 912 are formed may be selected to achieve the desired range of motion. In certain embodiments, the first attachment side 911 and the second attachment side 912 may be formed of titanium, although other suitable metals, polymers, or other materials may be used in other embodiments. Meanwhile, the device 900 may prevent or substantially inhibit relative movement of the treated vertebrae $V_1$, $V_2$ in coronal plane (i.e., lateral bending) and the transverse plane (i.e., axial rotation) of the patient. In certain embodiments, a native disc D positioned between the vertebral bodies of the vertebrae $V_1$, $V_2$ may be left intact, such that loads carried by the treated spinal segment may be shared by the device 900 and the disc D. In other embodiments in which the native disc D is removed, an interbody device, such as a cage or a spacer, may be implanted within the disc space DS (i.e., the intervertebral space) and the loads carried by the treated spinal segment may be shared by the device 900 and the interbody device. As described above, the device 900 may be used in conjunction with other additional hardware, such that the device 900 and the additional hardware collectively stabilize the treated segment of the spine and share loads carried thereby. It will be appreciated that the foregoing description and the corresponding drawings are merely examples of the device 900 and that other configurations and modifications may be made.

As explained above, the interspinous process devices described herein may be used in various types of spinal procedures. It will be appreciated that the interspinous process devices of the present invention can be used individually or in tandem with additional interspinous process devices and other dynamic or fusion spinal stabilization rods, interbody spacers, braces, plates, and/or vertebral implant systems. For example, the interspinous process devices of the present invention can be implanted above a spinal fusion system to create a transition between the rigid construct and the un-instrumented spine to treat or prevent Proximal Junctional Kyphosis (PJK), which can occur following a long (e.g., 4+ level) posterior fusion of the spine.

Many modifications of the embodiments of the present disclosure will come to mind to one skilled in the art to which the disclosure pertains upon having the benefit of the teachings presented herein through the foregoing descriptions and the associated drawings. Therefore, it is to be understood that the present invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A dynamic interspinous process device comprising:
   a first attachment side comprising:
   a central portion;
   a first wing extending from the central portion;
   a second wing extending from the central portion;
   a slider movably attached to the second wing and configured to move relative to the second wing between an extended position and a retracted position; and
   one or more resistance means, wherein the slider is configured to interact with the one or more resistance means to provide dynamic movement; and
   a second attachment side comprising:
   a central portion;
   a first wing extending from the central portion;
   a second wing extending from the central portion;
   a slider movably attached to the second wing and configured to move relative to the second wing between an extended position and a retracted position; and
   one or more resistance means, wherein the slider is configured to interact with the one or more resistance means to provide dynamic movement,
   wherein the dynamic interspinous process device is configured for implantation with respect to a first vertebra and an adjacent second vertebra.

2. The dynamic interspinous process device of claim 1, wherein the slider of the first attachment side is configured to move relative to the second wing of the first attachment side in a direction of a longitudinal axis of the dynamic interspinous process device, and wherein the slider of the second attachment side is configured to move relative to the second wing of the second attachment side in the direction of the longitudinal axis of the dynamic interspinous process device.

3. The dynamic interspinous process device of claim 1, wherein the slider of the first attachment side is configured to move along a linear path relative to the second wing of the first attachment side, and wherein the slider of the second attachment side is configured to move along a linear path relative to the second wing of the second attachment side.

4. The dynamic interspinous process device of claim 1, wherein the slider of the first attachment side is configured to move along a curved path relative to the second wing of the first attachment side, and wherein the slider of the second attachment side is configured to move along a curved path relative to the second wing of the second attachment side.

5. The dynamic interspinous process device of claim 1, wherein the slider of the first attachment side is movably attached to the second wing of the first attachment side by a pin extending through a portion of the slider of the first attachment side and at least partially received within a channel defined in the second wing of the first attachment side, and wherein the slider of the second attachment side is movably attached to the second wing of the second attachment side by a pin extending through a portion of the slider of the second attachment side and at least partially received within a channel defined in the second wing of the second attachment side.

6. The dynamic interspinous process device of claim 5, wherein the one or more resistance means on the first attachment side are positioned at least partially within the channel of the second wing of the first attachment side and configured to provide dynamic movement by resisting the relative movement between the slider and the second wing of the first attachment side, and wherein the one or more resistance means on the second attachment side are positioned at least partially within the channel of the second wing of the first attachment side and configured to provide dynamic movement by resisting the relative movement between the slider and the second wing of the first attachment side.

7. The dynamic interspinous process device of claim 6, wherein the one or more resistance means of the first attachment side comprises one or more springs, and wherein the one or more resistance means of the second attachment side comprises one or more springs.

8. The dynamic interspinous process device of claim 7, wherein the one or more springs of the first attachment side comprises a first spring positioned between the pin and a first end of the channel of the second wing of the first attachment side and a second spring positioned between the pin and a second end of the channel of the second wing of the first attachment side, and wherein the one or more springs of the second attachment side comprises a first spring positioned between the pin and a first end of the channel of the second wing of the second attachment side and a second spring positioned between the pin and a second end of the channel of the second wing of the second attachment side.

9. The dynamic interspinous process device of claim 6, wherein the one or more resistance means of the first attachment side comprises one or more members formed of a compressible material, and wherein the one or more resistance means of the second attachment side comprises one or more members formed of a compressible material.

10. The dynamic interspinous process device of claim 9, wherein the one or more compressible members of the first attachment side comprises a first compressible member positioned between the pin and a first end of the channel of the second wing of the first attachment side and a second compressible member positioned between the pin and a second end of the channel of the second wing of the first attachment side, and wherein the one or more compressible member of the second attachment side comprises a first compressible member positioned between the pin and a first end of the channel of the second wing of the second attachment side and a second compressible member positioned between the pin and a second end of the channel of the second wing of the second attachment side.

11. The dynamic interspinous process device of claim 5, wherein the pin extending through a portion of the slider of the first attachment side and at least partially received within a channel defined in the second wing of the first attachment side is secured by a gasket or flange, and wherein the a pin extending through a portion of the slider of the second attachment side and at least partially received within a channel defined in the second wing of the second attachment side is secured by a gasket or flange.

12. The dynamic interspinous process device of claim 5, wherein the channel defined in the second wing of the first attachment side is not threaded and the channel defined in the second wing of the second attachment side is not threaded.

13. The dynamic interspinous process device of claim 1, wherein the first attachment side further comprises one or more securing means configured for positioning at least partially through the slider of the first attachment side and engaging the second wing of the first attachment side to inhibit the relative movement between the slider and the second wing of the first attachment side, and wherein the second attachment side further comprises one or more securing means configured for positioning at least partially through the slider of the second attachment side and engaging the second wing of the second attachment side to inhibit the relative movement between the slider and the second wing of the second attachment side.

14. The dynamic interspinous process device of claim 13, wherein the one or more securing means of the first attachment side comprises one or more fasteners, and wherein the one or more securing means of the second attachment side comprises one or more fasteners.

15. The dynamic interspinous process device of claim 1, wherein the first attachment side further comprises one or more bone fasteners extending from an interior side of the first wing of the first attachment side and one or more bone fasteners extending from an interior side of the slider of the first attachment side, and wherein the second attachment side further comprises one or more bone fasteners extending from an interior side of the first wing of the second attachment side and one or more bone fasteners extending from an interior side of the slider of the second attachment side.

16. The dynamic interspinous process device of claim 1, wherein the first attachment side further comprises one or more bone fasteners extending from an interior side of the slider of the first attachment side, wherein an interior side of the first wing of the first attachment side is devoid of any bone fasteners, wherein the second attachment side further comprises one or more bone fasteners extending from an interior side of the slider of the second attachment side, and wherein an interior side of the first wing of the second attachment side is devoid of any bone fasteners.

17. The dynamic interspinous process device of claim 1, wherein the first attachment side further comprises a spacer extending from an interior side of the first attachment side, and wherein the second attachment side further comprises a spacer slot extending from an interior side of the second attachment side to an exterior side of the second attachment side and configured to receive the spacer therein.

18. The dynamic interspinous process device of claim 1, wherein the first attachment side further comprises a sheath positioned between the second wing and the slider of the first attachment side, and wherein the second attachment side further comprises a sheath positioned between the second wing and the slider of the second attachment side.

19. The dynamic interspinous process device of claim 18, wherein second wings and the sliders of the first attachment side and the second attachment side are formed of a metal, and wherein the sheaths of the first attachment side and the second attachment side are formed of a polymer.

* * * * *